US006734186B1

(12) United States Patent
Maw et al.

(10) Patent No.: US 6,734,186 B1
(45) Date of Patent: May 11, 2004

(54) COMPOUNDS FOR THE TREATMENT OF FEMALE SEXUAL DYSFUNCTION

(75) Inventors: Graham Nigel Maw, Sandwich (GB); Christopher Peter Wayman, Sandwich (GB)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/708,392

(22) Filed: Nov. 8, 2000

Related U.S. Application Data

(60) Provisional application No. 60/221,093, filed on Jul. 27, 2000, provisional application No. 60/221,014, filed on Jul. 27, 2000, provisional application No. 60/217,479, filed on Jul. 11, 2000, provisional application No. 60/192,962, filed on Mar. 29, 2000, and provisional application No. 60/175,161, filed on Jan. 7, 2000.

(30) Foreign Application Priority Data

| Nov. 8, 1999 | (GB) | 9926437 |
| Feb. 18, 2000 | (GB) | 0004021 |
| May 26, 2000 | (GB) | 0013001 |
| Jul. 5, 2000 | (GB) | 0016563 |
| Jul. 12, 2000 | (GB) | 0017141 |

(51) Int. Cl.[7] .................. A01N 43/90; A61K 31/52; C07D 237/00; C07D 237/02; C07D 239/00
(52) U.S. Cl. ............... 514/263.1; 544/224; 544/242
(58) Field of Search ............... 514/258, 263.1; 544/262, 224, 242

(56) References Cited

U.S. PATENT DOCUMENTS

| 4,666,908 A | * | 5/1987 | Hamilton ............... 514/229 |
| 5,574,068 A | | 11/1996 | Stamler et al. .......... 514/562 |
| 5,612,314 A | | 3/1997 | Stamler et al. .......... 514/13 |
| 5,861,396 A | * | 1/1999 | Niewohner et al. ...... 514/234.2 |
| 5,981,527 A | | 11/1999 | Daugan et al. .......... 514/250 |
| 6,043,252 A | | 3/2000 | Bombrun |
| 6,235,742 B1 | * | 5/2001 | Bell et al. ............. 514/258 |
| 6,294,550 B1 | * | 9/2001 | Place et al. ............ 514/302 |
| 6,306,841 B1 | | 10/2001 | Place et al. ............ 514/149 |
| 6,316,457 B1 | | 11/2001 | Garvey et al. .......... 514/263 |
| 2001/0051656 A1 | * | 12/2001 | Place et al. ............ 514/530 |
| 2002/0019405 A1 | * | 2/2002 | Garvey et al. .......... 514/258 |
| 2002/0028846 A1 | * | 3/2002 | Yeager et al. ........... 514/513 |
| 2002/0052370 A1 | * | 5/2002 | Barber et al. ........... 514/237.5 |
| 2002/0169101 A1 | * | 11/2002 | Gonzalez et al. ........ 514/1 |

FOREIGN PATENT DOCUMENTS

| EP | 0274434 | 7/1988 | C07D/409/06 |
| EP | 0771799 | 7/1997 | C07D/473/00 |
| EP | 0911333 | 4/1999 | C07D/487/04 |
| WO | WO9104042 | 4/1991 | A61K/37/02 |
| WO | WO9720821 | 6/1997 | C07D/239/95 |
| WO | WO9735989 | 10/1997 | C12N/15/55 |
| WO | WO9739760 | 10/1997 | A61K/33/26 |
| WO | WO9803492 | 1/1998 | C07D/295/18 |
| WO | WO9920266 | 4/1999 | A61K/31/19 |
| WO | WO9921562 | 5/1999 | A61K/31/557 |
| WO | WO9922731 | 5/1999 | A61K/31/44 |
| WO | WO0015228 | 3/2000 | A61K/31/4985 |
| WO | WO0015639 | 3/2000 | C07D/471/04 |

OTHER PUBLICATIONS

Traish, A., Moreland, R. B., Huang, Y., et al., *Mol. Cell Biol. Res. Comm.*, 2, 131–137 (1999).
Palle, Bredkjaer, Ottesen and Fahrenkrug 1990 Clinical and Experimental Pharmacology and Physiology vol. 17, 61–68.
Beavo JA and Reifsnyder DH, *Trends Pharmacol. Sci.* 11:150 (1990).
Beavo J and Housley MD (Eds.)., *Cyclic Nucleotide Phosphodiesterases: Structure, Regulation and Drug Action* John Wiley & Sons, Chichester, pp. 3–15 (1990).
Wieshar RE et al., *J. Med. Chem.*, 28, 537 (1985).
Giembycz MA, *Biochem. Pharm.*, 43:2041 (1992).
Lowe JA and Cheng JB, *Drugs for the Future*, 17, 799–807 (1992).
Ashur–Fabian, O., Perl, O., Lilling, G., et al.,. "SNV, a lipophilic superative VIP analog, acts through cGMP to promote neuronal survival,"*Peptides*, 20, 629–633 (1999).
Berman, J.R., Berman, L. & Goldstein, I., "Female sexual dysfunction: Incidence, pathophysiology, evaluation, and treatment options," *Urology*, 54, 385–391 (1999).
Berman, J., Goldstein, I., Werbin, T. et al., "Double blind placebo controlled study with crossover to assess effect of slidenafil on physiological parameters of the female sexual response," *J. Urol.*, 161, 805 (1999).
Burnett, A, Calvin, D., Silver, R. et al. "Immunohistochemical description of nitric oxide synthase isoforms in human clitoris," *J. Urol.*, 158, 75–78 (1997).
*Diagnostic and statistical manual of mental disorders–IV*, American Psychiatric Association: Washington, DC., pp. 493–518 (1987).
Fan, Y.P., Chakder, S. & Ratton, S., "Inhibitory effect of zinc protoporphyrin IX on lower esophageal sphincter smooth muscle relaxation by vasoactive intestinal polypeptide and other receptor agonists," *J. Pharmacol. Exp. Ther.*, 285, 468–474 (1998).
Foda, H.D., Sharaf, H.H. Absood, A. et al., "Pituitary adenylate cyclase–activating peptide (PACAP), a VIP–like peptide, has prolonged airway smooth muscle relaxant activity," *Peptides*, 16, 1057–1061 (1995).
Frank, E., Anderson, C. & Rubinstein, D. "Frequency of sexual dysfunction in "normal" couples," *N. Engl. J. Med.*, 229, 111–115 (1978).

(List continued on next page.)

Primary Examiner—Sreeni Padmanabhan
Assistant Examiner—Lauren Q. Wells
(74) *Attorney, Agent, or Firm*—Peter C. Richardson; Gregg C. Benson; Arlene K. Musser

(57) ABSTRACT

A method of treating a female suffering from FSD, in particular FSAD, is described. The method comprises delivering to the female an agent that is capable of potentiating cAMP in the sexual genitalia; wherein the agent is in an amount to cause potentiation of cAMP in the sexual genitalia of the female. The agent may be admixed with a pharmaceutically acceptable carrier, diluent or excipient.

24 Claims, 13 Drawing Sheets

OTHER PUBLICATIONS

Goldstein, I. & Berman, J.R. "Vasculogenic female sexual dysfunction: vaginal engorgement and clitoral erectile insufficiency syndromes," *Int. J. Impot. Res.*, 10, S84–S90 (1998).

Gu, Z.F., Jensen, R.T. & Maton, P.N. "A primary role for protein kinase A in smooth muscle relaxation induced by adrenergic agonists and neuropeptides,". *Am. J. Physiol.*, 263, G360–G364 (1992).

Hauser–Kronberger, C., Cheung, A., Hacker, G. et al., "Peptidergic innervation of the human clitoris," *Peptides*, 20, 539–543 (1999).

Hoyle, C.H.V., Stones, R.W., Robson, T. et al., "Innervation of vasculature and microvasculature of the human vagina by NOS and neuropeptide containing nerves," *J. Anat.*, 188, 633–644 (1996).

Ingenhoven, N. & Beck–Sickinger, A.G. "Fluorescent labelled analogues of neuropeptide Y for the characterisation of cells expressing NPY receptor subtypes," *J. Recept. Signal Transduct. Res.*, 17, 407–418 (1997).

Jovanovic, A., Jovanovic, S., Tulic,. I. et al., "Predominant role for nitric oxide in the relaxation induced by vasoactive intestinal polypeptide in human uterine artery," *Mol. Human Reprod.*, 4, 71–76 (1998).

Kaplan, S.A., Reis, R.B., Kohm, I.J. et al., "Safety and efficacy of sildenafil in postmenopausal women with sexual dysfunction," *Urology*, 53, 481–486 (1999).

Kim, Y.C., Choi, H.K., Ahn, Y.S., et al. "The effect of vasoactive intestinal polypeptide (VIP) on rabbit cavernosal smooth muscle contractility," *J. Androl.*, 15. 392–397 (1994).

Laan, E. & Everaerd, W. "Physiological measures of vaginal vasocongestion,". *Int. J. Impot. Res.*, 10, S107–S110 (1998).

Leiblum, S.R. "Definition and classification of female sexual disorders," *Int. J. Impotence Res.*, 10, S104–S106 (1998).

Levin,R.J., "The physiology of sexual function in women," *Clin. Obstet. Gynecol.*, 7, 213–252 (1980).

Levin, R.J., "VIP, vagina, clitoral and preurethral gians.: An update on female genital arousal," *Exp. Clin.*

Levin, R.J., "The mechanisms of human female sexual arousal," *Ann. Rev. Sex Res.*, 3, 1–48 (1992).

Levin, R.J., & Wagner, G.) "TRH and vaginal blood flow-effects in conscious women and anaesthetized sheep," *J. Physiol.*, 378, 83P (1986.

Lundberg, J.M., Modin, A. & Malmstrom, R.E. "Recent developments with neuropeptide Y receptor antagonists," *Trends. Pharmacol. Sci.*, 17, 301–304 (1996).

Ottesen, B., Gerstenberg, T. Ulrichsen, H. et al., "Vasoactive intestinal oplypeptide (VIP) increases vaginal blood flow and inhibits smooth muslce activity in women," *Eur. J. Clin. Invest.*, 13, 321–324 (1983).

Ottesen, B., Wagner, G & Fahrenkrug, J., *Peptide innervation of the sexual organs.* In: Handbook of Sexology, vol. 6, The Pharmacological and Endocrinology of Sexual Function, Sitsen, J.M.A. (eds), Amsterdam: Elsevier Science Publishers, chapter 4, pp 66–97. (1988).

Ottensen, B. Pedersen, B,, Nielsen, J. et al., "Vasoactive polypeptide (VIP) provokes vaginal lubrication in normal women," *Peptides*, 8, 797–800 (1987).

Park, K., Goldstein, I., Andry, C., et al.,. "Vasculogenic female sexual dysfunction: The hemodynamic basis for vaginal engorgement insufficiency and clitoral erectile insufficiency," *Int. J. Impotence Res.*, 9, 27–37 (1997).

Rosen, R. Taylor, J., Leiblum, S. et al., "Prevalence of sexual dysfunction in women: results of a survey of 329 women in an outpatient gynecological clinic," *J. Sex Marital Ther.*, 19, 171–188 (1993).

Schiavi, R.C. & Seagraves, R.T., "The biology of sexual function," *Psychiat. Clin. North. Am.*, 18, 7–23 (1995).

Schoeffter, P. & Stoclet, J.C., "Effect of vasoactive intestinal polypeptide (VIP) on cyclic AMP level and relaxation in rat isolated aorta," *Eur. J. Pharmacol.*, 109, 275–279 (1985).

Serradeil–Le Gal, C., Valette, G., Rouby, P.E. et al., "SR 120819A, an orally–active and selective neuropeptide Y Y1 recptor antagonist," *FEBS Letters*, 3, 192–196 (1995).

Sjoberg, I. "The vagina: Morphological, functional and ecological aspects," *Acta Obst. Gynecol. Scand.*, 71, 84–85 (1992).

Spector, I.P. & Carey, M.P. "Incidence and prevalence of sexual dysfunctions: a critical review of the empirical literature," *Arch. Sex. Behav.*, 19, 389–408 (1990).

Wagner, G. "Aspects of genital physiology and pathology," *Sem. Neurol.*, 12, 87–97 (1992).

Werbin, T., Salimpour, P., Berman, L., et al., "Effect of sexual stimulation and age on genital blood flow in women and sexual stimulation," *J. Urol.*, 161, 688 (1999).

Wincze, J.P., Albert, a. & Bansal, S. "Sexual arousal in diabetic females: Physiological and self–report measures," *Arch. Sex Behav.*, 22, 587–601 (1993).

Wieland, H.A., Willim, K.D., Entzeroth, M. et al., "Subtype selectivity and antagonist profile of the nonpeptide Y1 receptor antagonist BIBP 3226," *J Pharmcol Exp Ther.*, 275, 143–9 (1995).

Ottesen, B. "Vasoactive intestinal peptide as a neurotransmitter in the female genital tract", *American Journal of Obstetrics & Gynecology*, vol. 147, 1983, pp. 208–224.

Clark, J. T., et al., "Neuropeptide Y stimulates feeding but inhibits sexual behaviour in rats", *Endocrinology*, vol. 117, No. 6, 1985, pp. 2435–2442.

Suzuki, H., et al., "Neutral endopeptridase modulates VIP–induced vasodilatation in hamster cheek pouch vessels in situ", *American Journal of Physiology*, vol. 271, No. 2 Part 2, 1996, pp. R393–R397.

Erdös, E. G., et al., "Neutral metalloendopeptidase in human male genital tract", *Laboratory Investigation*, vol. 52, No. 4, 1985, pp. 737–447.

United States non–provisional patent application No. 09/708,344, filed Nov. 8, 2000; Maw, et al., "Compounds for the Treatment of Female Sexual Dysfunction". (Our docket No. PC10931AAKM).

United States non–provisional patent application No. 09/708,365, filed Nov. 8, 2000; Maw, et al., "Compounds for the Treatment of Female Sexual Dysfunction". (Our docket No. PC10932AAKM).

United States non–provisional patent application No. 09/708,393, filed Nov. 8, 2000; Maw, et al., "Compounds for the Treatment of Female Sexual Dysfunction". (Our docket No. PC10930AAKM).

Hedlund, et al. *PNAS*, "Erectile Dysfunction in Cyclin GMP–Dependent Kinase I–Deficient Mice" 97 (5) 2349–2354 (2000).

\* cited by examiner

Effect of VIP (Sequence No. 8), an NEP$_{cAMP}$ Inhibitor, a PDE inhibitor or Pelvic Nerve Stimulation on Mean Arterial Pressure in the Anaesthetised Rabbit Effect of a NEPi on pelvic nerve stimulated increases in clitoral blood flow

COMPOUNDS FOR THE TREATMENT OF FEMALE SEXUAL DYSFUNCTION

This application claims the benefit of United Kingdom Provisional Patent Application Nos. 0017141.3, filed Jul. 12, 2000; 0016563.9, filed Jul. 5, 2000; 0013001.3, filed May 26, 2000; 0004021.2, filed Feb. 18, 2000; and 9926437.6, filed Nov. 8, 1999; and U.S. Provisional Patent Application Nos. 60/221,093, filed Jul. 27, 2000; 60/221,014, filed Jul. 27, 2000; 60/217,479, filed Jul. 11, 2000; 60/192,962, filed Mar. 29, 2000; and 601175,161, filed Jan. 7, 2000; all of which are incorporated in their entirety herein by reference.

FIELD OF INVENTION

The present invention relates to a pharmaceutical that is useful for the treatment of female sexual dysfunction (FSD), in particular female sexual arousal disorder (FSAD). The present invention also relates to a method of treatment of FSD, in particular FSAD. The present invention also relates to assays to screen for compounds useful in the treatment of FSD, in particular FSAD.

For convenience, a list of abbreviations that are used in the following text is presented before the Claims section.

Female Sexual Response

The female sexual response phase of arousal is not easily distinguished from the phase of desire until physiological changes begin to take place in the vagina and clitoris as well as other sexual organs. Sexual excitement and pleasure are accompanied by a combination of vascular and neuromuscular events which lead to engorgement of the clitoris, labia and vaginal wall, increased vaginal lubrication and dilatation of the vaginal lumen (Levin, 1980; Ottesen, 1983; Levin, 1991; Levin, 1992; Sjoberg, 1992; Wagner, 1992; Schiavi et al., 1995; Masters et al., 1996; Berman et al., 1999).

Vaginal engorgement enables transudation to occur and this process is responsible for increased vaginal lubrication. Transudation allows a flow of plasma through the epithelium and onto the vaginal surface, the driving force for which is increased blood flow in the vaginal capillary bed during the aroused state. In addition engorgement leads to an increase in vaginal length and luminal diameter, especially in the distal $2/3$ of the vaginal canal. The luminal dilatation of the vagina is due to a combination of smooth muscle relaxation of its wall and skeletal muscle relaxation of the pelvic floor muscles. Some sexual pain disorders such as vaginismus are thought to be due, at least in part, by inadequate relaxation preventing dilatation of the vagina; it has yet to be ascertained if this is primarily a smooth or skeletal muscle problem. (Levin, 1980; Oltesen, 1983; Levin, 1991; Levin, 1992; Sjoberg, 1992; Wagner, 1992; Schiavi et al., 1995; Master et al., 1996; Berman et al., 1999).

The vasculature and micro vasculature of the vagina are innervated by nerves containing neuropeptides and other neurotransmitter candidates. These include calcitonin gene-related peptide (CGRP), neuropeptide Y (NPY; Sequence No. 4), nitric oxide synthase (NOS), substance P and vasoactive intestinal peptide (VIP; Sequence No. 8) (Hoyle et al., 1996). Peptides that are present in the clitoris are discussed infra. Nitric oxide synthase, which is often colocalised with VIP (Sequence No. 8), displays a greater expression, immunologically, in the deep arteries and veins rather than in the blood vessels of the propria (Hoyle et al., 1996).

Female Sexual Dysfunction

It is known that some individuals can suffer from female sexual dysfunction (FSD). FSD is best defined as the difficulty or inability of a woman to find satisfaction in sexual expression. FSD is a collective term for several diverse female sexual disorders (Leiblum, 1998, Berman et al., 1999). The woman may have lack of desire, difficulty with arousal or orgasm, pain with intercourse or a combination of these problems. Several types of disease, medications, injuries or psychological problems can cause FSD.

Studies investigating sexual dysfunction in couples reveals that up to 76% of women have complaints of sexual dysfunction and that 30–50% of women in the USA experience FSD.

Sub-types of FSD include hypoactive sexual desire disorder, female sexual arousal disorder, orgasmic disorder and sexual desire disorder.

Treatments in development are targeted to treat specific subtypes of FSD, predominantly desire and arousal disorders.

The categories of FSD are best defined by contrasting them to the phases of normal female sexual response: desire, arousal and orgasm (Leiblum 1998). Desire or libido is the drive for sexual expression—and manifestations often include sexual thoughts either when in the company of an interested partner or when exposed to other erotic stimuli. In contrast, sexual arousal is the vascular response to sexual stimulation, an important component of which is vaginal lubrication and elongation of the vagina. Thus, sexual arousal, in contrast to sexual desire, is a response relating to genital (e.g. vaginal and clitoral) blood flow and not necessarily sensitivity. Orgasm is the release of sexual tension that has culminated during arousal. Hence, FSD typically occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders.

Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

Female sexual arousal disorder (FSAD) is characterised by inadequate genital response to sexual stimulation. The genitalia (e.g. the vagina and/or the clitoris) do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants eg SSRIs or antihypertensive agents. FSAD is discussed in more detail infra.

Sexual pain disorders (which include dyspareunia and vaginismus) are characterised by pain resulting from penetration and may be caused by medications which reduce lubrication, endometriosis, pelvic inflammatory disease, inflammatory bowel disease or urinary tract problems.

The prevalence of FSD is difficult to gauge because the term covers several types of problem, some of which are difficult to measure, and because the interest in treating FSD is relatively recent. Many women's sexual problems are associated either directly with the female ageing process or with chronic illnesses such as diabetes and hypertension.

There are wide variations in the reported incidence and prevalence of FSD, in part explained by the use of differing evaluation criteria, but most investigators report that a significant proportion of otherwise healthy women have symptoms of one or more of the FSD subgroups. By way of example, studies comparing sexual dysfunction in couples reveal that 63% of women had arousal or orgasmic dysfunction compared with 40% of men have erectile or ejaculatory dysfunction (Frank et al., 1978).

However, the prevalence of female sexual arousal disorder varies considerably from survey to survey. In a recent National Health and Social Life Survey 19% of women reported lubrication difficulties whereas 14% of women in an outpatient gynaecological clinic reported similar difficulties with lubrication (Rosen et al., 1993).

Several studies have also reported dysfunction with sexual arousal in diabetic women (up to 47%), this included reduced vaginal lubrication (Wincze et al., 1993). There was no association between neuropathy and sexual dysfunction.

Numerous studies have also shown that between 11–48% of women overall may have reduced sexual desire with age. Similarly, between 11–50% of women report problems with arousal and lubrication, and therefore experience pain with intercourse. Vaginismus is far less common, affecting approximately 1% of women.

Studies of sexually experienced women have detailed that 5–10% have primary anorgasmia. Another 10% have infrequent orgasms and a further 10% experience them inconsistently (Spector et al., 1990).

Because FSD consists of several subtypes that express symptoms in separate phases of the sexual response cycle, there is not a single therapy. Current treatment of FSD focuses principally on psychological or relationship issues. Treatment of FSD is gradually evolving as more clinical and basic science studies are dedicated to the investigation of this medical problem. Female sexual complaints are not all psychological in pathophysiology, especially for those individuals who may have a component of vasculogenic dysfunction (eg FSAD) contributing to the overall female sexual complaint. There are at present no drugs licensed for the treatment of FSD. Empirical drug therapy includes oestrogen administration (topically or as hormone replacement therapy), androgens or mood-altering drugs such as buspirone or trazodone. These treatment options are often unsatisfactory due to low efficacy or unacceptable side effects.

Since interest is relatively recent in treating FSD pharmacologically, therapy consists of the following:- psychological counselling, over-the-counter sexual lubricants, and investigational candidates, including drugs approved for other conditions. These medications consist of hormonal agents, either testosterone or combinations of oestrogen and testosterone and more recently vascular drugs, that have proved effective in male erectile dysfunction. None of these agents has been demonstrated to be very effective in treating FSD.

Female Sexual Arousal Disorder (FSAD)

The sexual arousal response consists of vasocongestion in the pelvis, vaginal lubrication and expansion and swelling of the external genitalia. The disturbance causes marked distress and/or interpersonal difficulty. Studies investigating sexual dysfunction in couples reveals that there is a large number of females who suffer from sexual arousal dysfunction; otherwise known as female sexual arousal disorder (FSAD).

The Diagnostic and Statistical Manual (DSM) IV of the American Psychiatric Association defines Female Sexual Arousal Disorder (FSAD) as being:

"a persistent or recurrent inability to attain or to maintain until completion of the sexual activity adequate lubrication-swelling response of sexual excitement. The disturbance must cause marked distress or interpersonal difficulty."

FSAD is a highly prevalent sexual disorder affecting pre-, peri- and post menopausal (±HRT) women. It is associated with concomitant disorders such as depression, cardiovascular diseases, diabetes and UG disorders.

The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

It has recently been hypothesised that there is a vascular basis for at least a proportion of patients with symptoms of FSAD (Goldstein et al., 1998) with animal data supporting this view (Park et al., 1997).

Drug candidates for treating FSAD, which are under investigation for efficacy, are primarily erectile dysfunction therapies that promote circulation to the male genitalia. They consist of two types of formulation, oral or sublingual medications (Apomorphine, Phentolamine, Sildenafil), and prostaglandin ($PGE_1$-Alprostadil) that are injected or administered transurethrally in men, and topically to the genitalia in women.

The present invention seeks to provide an effective means of treating FSD, and in particular FSAD.

SUMMARY

The present invention is based on findings that FSAD is associated with reduced genital blood flow—in particular reduced blood flow in the vagina and/or the clitoris. Hence, treatment of women with FSAD can be achieved by enhancement of genital blood flow with vasoactive agents. In our studies, we have shown that cAMP mediates vaginal and clitoral vasorelaxation and that genital (e.g. vaginal and clitoral) blood flow can be enhanced/potentiated by elevation of cAMP levels. This is a seminal finding.

In this respect, no one has previously proposed that FSAD can be treated in such a way—i.e. by direct or indirect elevation of cAMP levels. Moreover, there are no teachings in the art to suggest that FSAD was associated with a detrimental modulation of cAMP activity and/or levels or that cAMP is responsible for mediating vaginal and clitoral vasorelaxation. Hence, the present invention is even further surprising.

In addition, we have found that by using agents of the present invention it is possible to increase genital engorgement and treat FSAD—e.g. increased lubrication in the vagina and increased sensitivity in the vagina and clitoris. Thus, in a broad aspect, the present invention relates to the use of a cAMP potentiator to treat FSD, in particular FSAD.

The present invention is advantageous as it provides a means for restoring a normal sexual arousal response—namely increased genital blood flow leading to vaginal, clitoral and labial engorgement. This will result in increased vaginal lubrication via plasma transudation, increased vaginal compliance and increased genital (e.g. vaginal and clitoral) sensitivity. Hence, the present invention provides a means to restore, or potentiate, the normal sexual arousal response.

More particularly, the present invention relates to:

A pharmaceutical composition for use (or when in use) in the treatment of FSD, in particular FSAD; the pharmaceutical composition comprising an agent capable of potentiating cAMP in the sexual genitalia of a female suffering from FSD, in particular FSAD; wherein the agent is optionally admixed with a pharmaceutically acceptable carrier, diluent or excipient.

The use of an agent in the manufacture of a medicament (such as a pharmaceutical composition) for the treatment of FSD, in particular FSAD; wherein the agent is capable of potentiating cAMP in the sexual genitalia of a female suffering from FSD, in particular FSAD.

A method of treating a female suffering from FSD, in particular FSAD; the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient.

An assay method for identifying an agent that can be used to treat FSD, in particular FSAD, the assay method comprising: determining whether an agent can directly or indirectly potentiate cAMP; wherein a potentiation of cAMP in the presence of the agent is indicative that the agent may be useful in the treatment of FSD, in particular FSAD.

In other embodiments, the present invention relates to:

A pharmaceutical composition for use (or when in use) in the treatment of FSD, in particular FSAD; the pharmaceutical composition comprising an agent capable of treating a female suffering from FSD, in particular FSAD; wherein the agent is optionally admixed with a pharmaceutically acceptable carrier, diluent or excipient; wherein the agent is selected from any one or more of:

a cAMP mimetic
I:$PDE_{cAMP}$
I:$PDEn_{cAMP}$
I:NPY
I:NPY $Y_n$
I:NEP
U: $A_{cAMP}$
A:AC
A:VIPr
A:$VIP_n$
I:I:VIPr
l:I:$VIP_n$
$P_{cAMP}$.

The use of an agent in the manufacture of a medicament (such as a pharmaceutical composition) for the treatment of FSD, in particular FSAD; wherein the agent is capable of treating a female suffering from FSD, in particular FSAD; wherein the agent is selected from any one or more of:

a cAMP mimetic
I:$PDE_{cAMP}$
I:$PDEn_{cAMP}$
I:NPY
I:NPY $Y_n$
I:NEP
A:$A_{cAMP}$
A:VIPr
A:$VIP_n$
I:I:VIPr
I:I:$VIP_n$
$P_{cAMP}$.

A method of treating a female suffering from FSD, in particular FSAD; the method comprising delivering to the female an agent that is capable of treating a female suffering from FSD, in particular FSAD, wherein the agent is optionally admixed with a pharmaceutically acceptable carrier, diluent or excipient, wherein the agent is selected from any one or more of:

a cAMP mimetic
I:$PDE_{cAMP}$
I:$PDEn_{cAMP}$
I:NPY
I:NPY $Y_n$
I:NEP
U:$A_{cAMP}$
A:AC
A:VIPr
A:$VIP_n$
I:I:VIPr
I:I:$VIP_n$
$P_{cAMP}$.

An assay method for identifying an agent that treat a female suffering from FSD, in particular FSAD, the assay method comprising determining whether or not a putative agent is capable of acting as any one or more of:

a cAMP mimetic
I:$PDE_{cAMP}$
I:$PDEn_{cAMP}$
I:NPY
I:NPY $Y_n$
I:NEP
U: $A_{cAMP}$
A:AC
A:VIPr
A:$VIP_n$
I:I:VIPr
I:I:$VIP_n$
$P_{cAMP}$ wherein if the putative agent is capable of acting as any one or more of a cAMP mimetic
I:$PDE_{cAMP}$
I:$PDEn_{cAMP}$
I:NPY
I:NPY $Y_n$
I:NEP
U:$A_{cAMP}$
A:AC
A:VIPr
A:$VIP_n$
I:I:VIPr
I:I:$VIP_n$
$P_{cAMP}$ then the agent may be useful in the treatment of FSD, in particular FSAD.

In other embodiments, the present invention relates to:

A pharmaceutical composition for use (or when in use) in enhancing genital (e.g. vaginal or clitoral) blood flow; the pharmaceutical composition comprising an agent capable of enhancing cAMP signalling in the sexual genitalia of a female; wherein the agent is optionally admixed with a pharmaceutically acceptable carrier, diluent or excipient.

The use of an agent in the manufacture of a medicament (such as a pharmaceutical composition) for enhancing genital (e.g. vaginal or clitoral) blood flow; wherein the agent is capable of enhancing cAMP signalling in the sexual genitalia of a female.

A method of treating a female; the method comprising delivering to the female an agent that is capable of enhancing cAMP signalling in the sexual genitalia of the female so as to cause enhanced genital (e.g. vaginal or clitoral) blood flow.

BRIEF DESCRIPTION OF THE FIGURES

FIG. 2:—Vasoactive intestinal peptide (VIP)(Sequence No. 8)-induces increases in vaginal blood flow in the anaesthetised rabbit model of sexual arousal.

FIG. 4:—Activation of the cAMP/adenylate cyclase pathway mimics VIP (Sequence No. 8) mediated vasorelaxation and smooth muscle relaxation in vaginal tissue.

DETAILED DESCRIPTION

Figure 1:
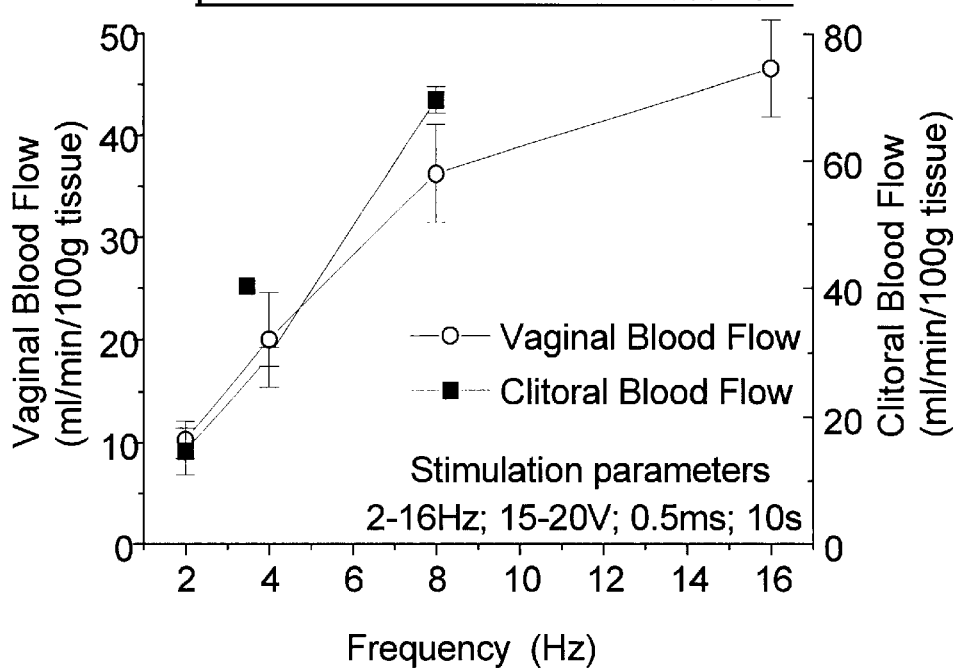
FIG. 1:—Electrical stimulation of the pelvic nerve induces a frequency-dependent increase in vaginal blood flow in the anaesthetised rabbit model of sexual arousal. Increasing the stimulation frequency induces larger increases in blood flow. Changes were monitored using laser Doppler technologies.

In one aspect, the present invention relates to a pharmaceutical composition for use (or when in use) in the treatment of FSD, in particular FSAD; the pharmaceutical composition comprising an agent capable of potentiating cAMP in the sexual genitalia of a female suffering from FSD, in particular FSAD; wherein the agent is optionally admixed with a pharmaceutically acceptable carrier, diluent or excipient. Here, the composition (like any of the other compositions mentioned herein) may be packaged for subsequent use in the treatment of FSD, in particular FSAD.

In another aspect, the present invention relates to the use of an agent in the manufacture of a medicament (such as a pharmaceutical composition) for the treatment of FSD, in particular FSAD; wherein the agent is capable of potentiating cAMP in the sexual genitalia of a female suffering from FSD, in particular FSAD.

In a further aspect, the present invention relates to a method of treating a female suffering from FSD, in particular FSAD; the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient.

In a further aspect, the present invention relates to an assay method for identifying an agent that can be used to treat FSD, in particular FSAD, the assay method comprising: determining whether an agent can directly or indirectly potentiate cAMP; wherein a potentiation of cAMP in the presence of the agent is indicative that the agent may be useful in the treatment of FSD, in particular FSAD.

By way of example, the present invention relates to an assay method for identifying an agent that can directly or indirectly potentiate cAMP in order to treat FSD, in particular FSAD, the assay method comprising: contacting an agent with a moeity capable of affecting cAMP activity and/or levels; and measuring the activity and/or levels of cAMP; wherein a potentiation of cAMP in the presence of the agent is indicative that the agent may be useful in the treatment of FSD, in particular FSAD.

By way of further example, the present invention relates to an assay method for identifying an agent that can directly or indirectly potentiate cAMP in order to treat FSD, in particular FSAD, the assay method comprising: contacting an agent with cAMP; and measuring the activity of cAMP; wherein a potentiation of cAMP in the presence of the agent is indicative that the agent may be useful in the treatment of FSD, in particular FSAD.

In a further aspect, the present invention relates to a process comprising the steps of: (a) performing the assay according to the present invention; (b) identifying one or more agents that can directly or indirectly potentiate cAMP activity; and (c) preparing a quantity of those one or more identified agents.

With this aspect, the agent identified in step (b) may be modified so as to, for example, maximise activity and then step (a) may be repeated. These steps may be repeated until the desired activity or pharmacokinetic profile has been achieved.

Thus, in a further aspect, the present invention relates to a process comprising the steps of: (a1) performing the assay according to the present invention; (b1) identifying one or more agents that can directly or indirectly potentiate cAMP activity, (b2) modifying one or more of said identified agents; (a2) optionally repeating step (a1); and (c) preparing a quantity of those one or more identified agents (i.e. those that have been modified).

In a further aspect, the present invention relates to a method of treating FSD, in particular FSAD, by potentiating in vivo cAMP with an agent; wherein the agent is capable of directly or indirectly potentiating cAMP in an in vitro assay method; wherein the in vitro assay method is the assay method according to the present invention.

In a further aspect, the present invention relates to the use of an agent in the preparation of a pharmaceutical composition for the treatment of FSD, in particular FSAD, wherein the agent is capable of directly or indirectly potentiating cAMP when assayed in vitro by the assay method according to the present invention.

In a further aspect, the present invention relates to an animal model used to identify agents capable of treating FSD (in particular FSAD), said model comprising an anaesthetised female animal including means to measure changes in vaginal and/or clitoral blood flow of said animal following stimulation of the pelvic nerve thereof.

In a further aspect, the present invention relates to an assay method for identifying an agent that can directly or indirectly potentiate cAMP in order to treat FSAD, the assay method comprising: administering an agent to the animal model of the present invention; and measuring any potentiation of cAMP and/or increase in blood flow in the vagina and/or clitoris of said animal.

For ease of reference, these and further aspects of the present invention are now discussed under appropriate section headings. However, the teachings under each section are not necessarily limited to each particular section.

Preferable Aspects

Preferably, the agent is for the treatment of FSAD.

Preferably, the agent is a mediator of female genital (e.g. vaginal or clitoral) vasorelaxation.

In one embodiment, preferably the agent is for oral administration.

In another embodiment, the agent may be for topical administration.

For some applications, preferably the agent has an indirect potentiating effect on cAMP. Examples of such agents include I:NEP and/or I:NPY. Alternatively expressed, for some applications, preferably the agent does not have a direct potentiating effect on cAMP. It is to be understood that the agent may have an indirect potentiating effect on cAMP by acting on naturally found and laturally located directly acting agents—such as naturally found and located VIP (Sequence No. 8).

For some applications, preferably the agent has a direct potentiating effect on cAMP. Examples of such agents include I:PDE.

For some applications the agent of the present invention may be administered in conjunction with another pharmaceutically active agent. Here the co-administration need not be done at the same time, let alone by the same route. An example of a co-administration composition could be a composition that comprises an agent according to the present invention and an additional agent, wherein the additional agent could have a direct potentiating effect on cAMP. Combination examples are discussed infra.

For some applications, preferably the agent is an inhibitor—i.e. it is capable of exhibiting an inhibitory function.

For some applications, preferably the agent is an I:PDE (sometimes written as PDEi).

For some applications, preferably the agent is an I:PDE1 or I:PDE2 (sometimes written as I:PDEII or PDEIIi or PDE21 or I:PDE type 2 or PDE type 2i) or I:PDE3 or I:PDE4 or I:PDE7 or I:PDE8, more preferably the agent is an I:PDE2.

For some applications, preferably the agent is a I:NEP (sometimes written as NEPi).

For some applications, preferably the agent is a I:NPY (sometimes written as NPYi).

For some applications, preferably the agent is an I:NPY Y1 or I:NPY Y2 or I:NPY Y5 (sometimes written as NPY $Y_n I$ or NPY Yni where n is the receptor subtype), more preferably the agent is an I:NPY Y1.

For some applications, preferably the agent is a selective I:PDEII.

For some applications, preferably the agent is a selective I:NEP.

For some applications, preferably the agent is a selective I:NPY.

Preferably, said agent is selected from one or more of: an I:PDE 2 (I:PDE II), an I:NEP wherein said NEP is EC 3.4.24.11 (Sequence No. 1), an I:NPY Y1.

More preferably, said agent is selected from one or more of: a selective I:PDE 2 (I:PDE II), a selective I:NEP wherein said NEP is EC 3.4.24.11 (Sequence No. 1), a selective I:NPY Y1.

For some applications, preferably the agent does not cause—or is administered in such a fashion so that it does not cause—a prolonged drop in blood pressure (e.g. over a period of about 5 minutes or more). In this embodiment, if the agent is to be delivered topically then that agent may have the ability to cause a drop in blood pressure (such as if it were to be delivered intraveneously), provided that in the topical application minimal levels of the agent pass into the blood stream. For an oral agent, it is preferred that the agent does not cause a prolonged drop in blood pressure.

In a preferred aspect, the agent does not cause—or is administered in such a fashion so that it does not cause—a large change in heart rate.

Treatment

It is to be appreciated that all references herein to treatment include one or more of curative, palliative and prophylactic treatment. Preferably, the term treatment includes at least curative treatment and/or palliative tretament.

Female Genitalia

The term "female genitalia" is used in accordance with the definition provided in Gray's Anatomy, C. D. Clemente, 13th American Edition—viz.

"The genital organs consist of an internal and external group. The internal organs are situated within the pelvis and consist of ovaries, the uterine tubes, uterus and the vagina. The external organs are superficial to the urogenital diaphragm and below the pelvic arch. They comprise the mons pubis, the labia majora and minora pudendi, the clitoris, the vestibule, the bulb of the vestibule, and the greater vestibular glands".

Endogenous Camp

In a highly preferred embodiment the agent of the present invention potentiates endogenous cAMP—such as potentiates endogenous cAMP levels.

Here, the term "endogenous cAMP" means cAMP that arises from sexual stimulation (sexual arousal). Hence, the term does not encompass cAMP levels that will be elevated independent of sexual drive.

Thus, according to the present invention, treatment of FSAD is achieved by directly or indirectly potentiating endogenous cAMP signalling which, in turn, increases vaginal blood flow/lubrication and/or clitoral blood flow; thus enhancing the natural sexual arousal response. Thus, the treatment method of the present invention restores or potentiates the normal arousal response. In the treatment method of the present invention, this result may be achieved by use of an inhibitor of NEP (EC 3.4.24.1 1; Sequence No. 1) or a cAMP-hydrolysing PDE inhibitor or a NPY (Sequence No. 4) receptor antagonist.

If the agent of the present invention is an I:PDE then said PDE a cAMP hydrolysing PDE (and optionally cGMP hydrolysing). The term "hydrolysing cAMP" also includes metabolising and/or breaking down cAMP. The term "hydrolysing cAMP (and optionally cGMP)" means that the agent of the present invention may be able to hydrolyse cGMP in addition to cAMP. Here, the term "hydrolyse cGMP" also includes metabolising and/or breaking down cGMP. However, for some embodiments of the present invention, it is to be understood that the agent of the present invention need not necessarily be able to hydrolyse cGMP.

An animal test model is provided herein. This animal test model may be used to determine increases of genital blood flow as a result of cAMP potentiation. In this animal model a pelvic nerve is stimulated—which brings on an effect that mimics the physiology of a sexual arousal/response. In these experiments, agents according to the present invention cause an increase in blood flow, above control increases, after the nerve has been stimulated. In the absence of stimulation, the agents have no (or a negligible) effect in causing an increase in blood flow. Typically, in these experiments, the nerve is stimulated in order to obtain a base line increase in blood flow. Then a candidate (or actual) agent is delivered to the animal systemically or locally, such as by the intravenous, topical or oral route. An increase in blood flow, compared to control increases, is then indicative of an agent according to the present invention.

Sexual Stimulation

The present invention also encompasses administration of the agent of the present invention before and/or during sexual stimulation. Here the term "sexual stimulation" may be synonymous with the term "sexual arousal". This aspect of the present invention is advantageous because it provides systemic selectivity. The natural cascade only occurs at the genitalia and not in other locations—e.g. in the heart etc. Hence, it would be possible to achieve a selective effect on the genitalia.

Thus, for some aspects of the present invention it is highly desirable that there is a sexual stimulation step. We have found that this step can provide systemic selectivity. Here, "sexual stimulation" may be one or more of a visual stimulation, a physical stimulation, an auditory stimulation, or a thought stimulation.

Thus, preferably the agents of the present invention are delivered before or during sexual stimulation, particulaly when those agents are for oral delivery.

Hence, for this preferred aspect, the present invention provides for the use of an agent in the manufacture of a medicament for the treatment of FSAD; wherein the agent is capable of potentiating cAMP in the sexual genitalia of a female suffering from FSAD; and wherein said female is sexually stimulated before or during administration of said medicament.

Preferably, the present invention provides for the use of an agent in the manufacture of a medicament for the treatment of FSAD; wherein the agent is capable of potentiating cAMP in the sexual genitalia of a female suffering from FSAD; wherein said female is sexually stimulated before or during administration of said medicament; and wherein said medicament is delivered orally to said female.

In addition, for this preferred aspect, the present invention provides for a method of treating a female suffering from FSAD; the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient; and wherein said female is sexually stimulated before or during administration of said agent.

Preferably, the present invention provides for a method of treating a female suffering from FSAD; the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient; wherein said female is sexually stimulated before or during administration of said agent; and wherein said agent is delivered orally to said female.

Potentiating cAMP

As used herein with reference to cAMP, the term "potentiating" includes any one or more of: increasing the effectiveness of cAMP, increasing the levels of cAMP, increasing the activity of cAMP, decreasing the level of cAMP degradation, decreasing the level of cAMP inhibition.

The potentiating effect can be a direct effect. An example of a direct effect would be upregulation of cAMP levels by an agent that increases the expression thereof.

Alternatively, the potentiating effect could be an indirect effect. An example of such an effect would be action on a substance that would otherwise inhibit and/or reduce the levels and/or activity of cAMP. Another example of such an effect would be increasing the action of a substance that increases the effectiveness of cAMP, increases the levels of cAMP, increases the activity of cAMP, decreases the level of cAMP degradation, or decreases the level of cAMP inhibition.

An example of a PcAMP would be I:PDE, such as I:PDEII.

cAMP Mimetic

For some aspects of the present invention, the agent may act as a cAMP mimetic.

As used herein, the term "cAMP mimetic" means an agent that can act in a similar fashion (e.g. have a similar biological profile and effect) to cAMP in the female sexual genitalia and, in doing so, does any one or more of: increases the effectiveness of cAMP like moieties, increases the levels of cAMP like moieties, increases the activity of cAMP like moieties, decreases the level of degradation of cAMP like moieties, decreases the level of inhibition of cAMP like moieties.

Thus, in one aspect, the present invention relates to a pharmaceutical composition for use (or when in use) in the treatment of FSAD; the pharmaceutical composition comprising an agent capable of acting as a cAMP mimetic in the sexual genitalia of a female suffering from FSAD; wherein the agent is optionally admixed with a pharmaceutically acceptable carrier, diluent or excipient.

Thus, in another aspect, the present invention relates to the use of an agent in the manufacture of a medicament (such as a pharmaceutical composition) for the treatment of FSAD; wherein the agent is capable of acting as a cAMP mimetic in the sexual genitalia of a female suffering from FSAD.

Thus, in a further aspect, the present invention relates to a method of treating a female suffering from FSAD; the method comprising delivering to the female an agent that is capable of acting as a cAMP mimetic in the sexual genitalia; wherein the agent is in an amount to potentiate cAMP levels in the sexual genitalia of the female; wherein the agent is optionally admixed with a pharmaceutically acceptable carrier, diluent or excipient.

An example of a cAMP mimetic would be forskolin. Here we have found that forskolin increases vaginal and clitoral blood flow and it can also act as a vaginal relaxant.

In a preferred aspect, the cAMP mimetic is administered orally.

Activator of cAMP

As used herein, the term "activator of cAMP" means a substance that controls or releases cAMP in the female sexual genitalia. The control may be direct (e.g. on cAMP itself) or indirect (e.g. via activation of cAMP). For ease of reference, we refer to these substances as $A_{cAMP}$.

Target

The term "target" as used herein with reference to the present invention means any substance that is cAMP, an $A_{cAMP}$, an $I_{cAMP}$, or an $AM_{cAMP}$. Otherwise expressed, the target can be referred to as a $P_{cAMP}$ target.

The target for the agent of the present invention may be an amino acid sequence and/or a nucleotide sequence encoding same and/or an expression unit responsible for the expression of same and/or a modulator of same.

The target may even be a combination of such targets.

Agent

The agent may be any suitable agent that can act as a $P_{cAMP}$.

The agent can be an amino acid sequence or a chemical derivative thereof. The substance may even be an organic compound or other chemical. The agent may even be a nucleotide sequence—which may be a sense sequence or an antisense sequence. The agent may even be an antibody.

Thus, the term "agent" includes, but is not limited to, a compound which may be obtainable from or produced by any suitable source, whether natural or not.

The agent may be designed or obtained from a library of compounds which may comprise peptides, as well as other compounds, such as small organic molecules, such as lead compounds.

By way of example, the agent may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetics, a derivatised agent, a peptide cleaved from a whole protein, or a peptides synthesised synthetically (such as, by way of example, either using a peptide synthesizer or by recombinant techniques or combinations thereof, a recombinant agent, an antibody, a natural or a non-natural agent, a fusion protein or equivalent thereof and mutants, derivatives or combinations thereof.

As used herein, the term "agent" may be a single entity or it may be a combination of agents.

If the agent is an organic compound then for some applications—such as if the agent is an I:NEP—that organic compound may typically comprise an amide group (i.e. —N(H)—C(O)— or even —C(O)—N(H)—) and one or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the agent comprises at least one cyclic group. For some applications, preferably the agent comprises at least one cyclic group linked to another hydrocarbyl group via an amide bond. Examples of such compounds are presented in the Examples section herein.

If the agent is an organic compound then for some applications—such as if the agent is an I:PDE—that organic compound may typically comprise two or more linked hydrocarbyl groups. For some applications, preferably the agent comprises at least two cyclic groups—wherein one of which cyclic groups may be a fused cyclic ring structure. For some applications, preferably at least one of the cyclic groups is a heterocyclic group. For some applications, preferably the heterocyclic group comprises at least one N in the ring. Examples of such compounds are presented in the Examples section herein.

If the agent is an organic compound then for some applications—such as if the agent is an I:NPY—that organic compound may typically comprise two or more linked hydrocarbyl groups. For some applications, preferably the agent comprises at least two cyclic groups—optionally wherein one of which cyclic groups may be a fused cyclic ring structure. For some applications, at least one of the cyclic groups is a heterocyclic group. For some applications, preferably the heterocyclic group comprises at least one N in the ring. Examples of such compounds are presented in the Examples section herein.

The agent may contain halo groups. Here, "halo" means fluoro, chloro, bromo or iodo.

The agent may contain one or more of alkyl, alkoxy, alkenyl, alkylene and alkenylene groups—which may be unbranched- or branched-chain.

The agent may be in the form of a pharmaceutically acceptable salt—such as an acid addition salt or a base salt—or a solvate thereof, including a hydrate thereof. For a review on suitable salts see Berge et al, J. Pharm. Sci., 1977, 66, 1–19.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases which form non-toxic salts and examples are the sodium, potassium, aluminium, calcium, magnesium, zinc and diethanolamine salts.

A pharmaceutically acceptable salt of an agent of the present invention may be readily prepared by mixing together solutions of the agent and the desired acid or base, as appropriate. The salt may precipitate from solution and be collected by filtration or may be recovered by evaporation of the solvent.

The agent of the present invention may exisit in polymorphic form.

The agent of the present invention may contain one or more asymmetric carbon atoms and therefore exists in two or more stereoisomeric forms. Where an agent contains an alkenyl or alkenylene group, cis (E) and trans (Z) isomerism may also occur. The present invention includes the individual stereoisomers of the agent and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the agent or a suitable salt or derivative thereof. An individual enantiomer of the agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

It will be appreciated by those skilled in the art that the agent of the present invention may be derived from a prodrug. Examples of prodrugs include entities that have certain protected group(s) and which may not possess pharmacological activity as such, but may, in certain instances, be administered (such as orally or parenterally) and thereafter metabolised in the body to form the agent of the present invention which are pharmacologically active.

It will be further appreciated that certain moieties known as "pro-moieties", for example as described in "Design of Prodrugs" by H. Bundgaard, Elsevier, 1985 (the disclosured of which is hereby incorporated by reference), may be placed on appropriate functionalities of the agents. Such prodrugs are also included within the scope of the invention.

The $P_{cAMP}$ may do any one or more of: directly or indirectly increase the effectiveness of cAMP, directly or indirectly increase the levels of cAMP, directly or indirectly increase the activity of cAMP, directly or indirectly decrease the level of cAMP degradation, directly or indirectly decrease the level of cAMP inhibition.

Preferably, the agent directly or indirectly increases cAMP levels in the sexual genitalia of a female suffering from FSAD.

More preferably, the agent directly or indirectly selectively increases cAMP levels in the sexual genitalia of a female suffering from FSAD.

More preferably, the agent directly or indirectly selectively increases cAMP levels wherein said cAMP is sexually arousal induced cAMP.

In a highly preferred aspect, the agent of the present invention increases the relative amount of sexual arousal induced cAMP.

For some applications, the agent selectively treats FSAD.

In one aspect, the agent may inhibit or antagonise a suitable target and in doing so potentiate cAMP levels in the female sexual genitalia. In the text, we have used the term inhibitor to mean an inhibitor and/or antagonist.

In another aspect, the agent may activate or agonise a suitable target and in doing so potentiate cAMP levels in the female sexual genitalia. In the text, we have used the terms activator and upregulator inhibitor to mean activator and/or upregulator and/or agonist.

Thus, the agent may agonise, antagonise, upregulate, or inhibit a suitable target.

The agent may be a single entity that is capable of exhibiting two or more of these properties. Alternatively, or in addition, the agent can be a combination of agents that are capable of exhibiting one or more of these properties.

Preferably, the agent may selectively agonise, selectively antagonise, selectively upregulate, or selectively inhibit a suitable target.

Preferably, the agent may selectively agonise, selectively antagonise, selectively upregulate, or selectively inhibit a selective, suitable target.

The agent of the present invention may also be capable of displaying one or more other beneficial functional properties. By way of example, the agent of the present invention may potentiate cAMP as well as potentiating cAMP.

For some applications (such as a topical application), the agent may also display an ACE (angiotensin converting enzyme) inhibitory action. An ACE assay is presented in the Experimental Section herein. For some applications (such as with particular patient types), such agents (i.e. those that also display ACE inhibitory action) may not be suitable for oral administration.

For some applications, the agent may also display an ECE (endothelium converting enzyme) inhibitory action. ECE assays are well known in the art.

Pharmaceutical Combinations

The agent may be used in combination with one or more other pharmaceutically active agents, such as a $P_{cGMP}$ (such a phosphodiesterase type 5 inhibitor eg Sildenafil, or a nitric oxide donor, or a nitric oxide precursor eg L-arginine or inhibitors of arginase) and/or a centrally acting pharmaceutical (e.g. a dopamine receptor agonist such as apomorphine or a dopamine D2 receptor agonist such as PNU-95666 or a melanocortin receptor agonist, such as melanotan II). Teachings on the use of apomorphine as a pharmaceutical may be found in U.S. Pat. No. 5,945,117. In that particular document, apomorphine is delivered sub-lingually. In addition, or in the alternative, the agent may be used in combination with one or more of: a PDE5 inhibitor (eg sildenafil, vardenafil (Bayer BA 38-9456) and IC351 (Cialis, Icos Lilly)), one or more of a nitric oxide donor (eg NMI-921), one or more of a dopamine receptor agonist (eg apomorphine, Uprima, Ixsene), one or more of a heterocyclic amine such as generically and specifically disclosed in WO 00/40226, in particular examples number 7, 8 and 9, one or more of a melanocortin receptor agonist (eg Melanotan II or PT14), one or more of a potassium channel opener (eg a $K_{ATP}$ channel opener (eg minoxidil, nicorandil) and/or a calcium activated potassium channel opener (eg BMS-204352), one or more of a α1-adrenoceptor antagonist (eg phentolamine, Vasofem, Vasomax), one or more of a VIP receptor agonist or a VIP analogue (eg Ro-125-1553) or a VIP fragment, one or more of a α-adrenoceptor antagonist with VIP combination (eg Invicorp, Aviptadil), one or more of a α2-adrenoceptor antagonist (eg yohimbine), one or more of a estrogen, estrogen and medroxyprogesterone or medroxyprogesterone acetate (MPA) or oestrogen and methyl testosterone hormone replacement therapy agent (eg HRT especially Premarin, Cenestin, Oestrofeminal, Equin, Estrace, Estrofem, Elleste Solo, Estring, Eastraderm, Eastraderm TTS, Eastraderm Matrix, Dermestril, Premphase, Prempro, Prempak, Premique, Estratest, Estratest HS, Tibolone), one or more of a testosterone replacement agent (inc DHEA (dehydroandrostendione), testosterone (Tostrelle) or a testosterone implant (Organon)), one or more of a testosterone/oestradiol agent one or more of an estrogen agonists eg Lasofoxifene, one or more of a serotonin receptor agonist or antagonist (eg 5HT1A, 5HT2C, 5HT2A and 5HT3 receptor agonists and antagonists; as described in WO2000/28993), one or more of a prostanoid receptor agonist (eg Muse, alprostadil, misoprostol), one or more of a purinergic receptor agonist (especially P2Y2 and P2Y4) one or more antidepressant agents (eg bupropion (Wellbutrin), mirrtazapine, nefazodone).

The structure of IC351 is:

IC351 (Icos Lilly)

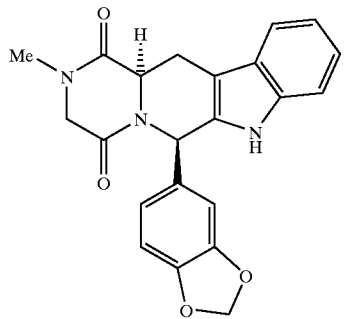

If a combination of active agents are administered, then they may be administered simultaneously, separately or sequentially.

VIP (Sequence No. 8) Combination

According to the present invention, the agent is not VIP (Sequence No. 8)(or preferably not an analogue thereof or a fragment thereof). However, for some embodiments, the agent of the present invention may be co-administered with VIP (Sequence No. 8) or an analogue thereof or a fragment thereof.

In a highly preferred aspect, VIP (Sequence No. 8) or an analogue thereof or a fragment thereof is not administered. This is because there has been a report that VIP (Sequence No. 8) infusions lead to significant cardiovascular adverse effects such as increases in heart rate and a decrease in diastolic arterial blood pressure (Ottesen 1983, 1987, 1995)

In addition, and even though, Ottesen and co-workers have demonstrated that VIP (Sequence No. 8) induces increases in vaginal blood flow and lubrication in healthy volunteers, the mechanism by which VIP (Sequence No. 8) is exerting it's effects are unclear. In the literature, there are a number of examples of VIP (Sequence No. 8) signalling through different second messenger systems eg cGMP/ guanylate cyclase (Ashur-Fabian, 1999); carbon monoxide (CO)/heme oxygenase (Fan et al.,1998) and cAMP/ adenylate cyclase (Foda, 1995; Schoeffter, 1985; Gu, 1992). This is exemplified by a recent report which describes how the vasorelaxant effects of VIP (Sequence No. 8) in the uterine artery can be explained by the release of nitric oxide. (Jovanovic, 1998). Again, there is also evidence for VIP (Sequence No. 8) modulating nitric oxide (NO)/cGMP in male urogenital function (Kim, 1994).

Furthermore, in the literature it has been reported that VIP (Sequence No. 8) has no effect on cAMP levels in vaginal smooth muscle cell cultures (see Traish, A., Moreland, R. B., Huang, Y., et al. (1999). Development of human and rabbit vaginal smooth muscle cell cultures: Effects of vasoactive agents on intracellular levels of cyclic nucleotides. Mol. Cell Biol. Res. Comm., 2, 131–137).

Moreover, in follow up studies, Ottesen and co-workers (see Palle, Bredkjaer, Ottesen and Fahrenkrug 1990 Clinical and Experimental Pharmacology and Physiology vol 17 61–68), report that the effect of VIP (Sequence No. 8) on vaginal blood flow irrespective of the route of administration is part of a systemic vasodilatory effect rather than a local response. In addition, they report on a number of vascular side effects associated with VIP (Sequence No. 8)—viz flushing, hypotension and tachycardia.

$K_i$ Values

For some applications, preferably the agent of the present invention has a $K_i$ value of less than about 100 nM, preferably less than about 75 nM, preferably less than about 50 nM, preferably less than about 25 nM, preferably less than about 20 nM, preferably less than about 15 nM, preferably less than about 10 nM, preferably less than about 5 nM.

$K_b$ Values

For some applications, preferably the agent of the present invention has a $K_b$ value of less than about 100 nM, preferably less than about 75 nM, preferably less than about 50 nM, preferably less than about 25 nM, preferably less than about 20 nM, preferably less than about 15 nM, preferably less than about 10 nM, preferably less than about 5 nM.

$K_a$ Values

For some applications, preferably the agent of the present invention has a $K_a$ value of less than about 100 nM, preferably less than about 75 nM, preferably less than about 50 nM, preferably less than about 25 nM, preferably less than about 20 nM, preferably less than about 15 nM, preferably less than about 10 nM, preferably less than about 5 nM.

Pharmacokinetics

For some embodiments of the present invention, preferably the agents of the present invention (e.g. I:NEP) have a log D of −2 to +4, more preferably −1 to +2. The log D can be determined by standard procedures known in the art such as described in J. Pharm. Pharmacol. 1990, 42:144.

In addition, or in the alternative, for some embodiments preferably the agents of the present invention (e.g. I:NEP) have a caco-2 flux of greater than $2 \times 10^{-6}$ cms$^{-1}$, more preferably greater than $5 \times 10^{-6}$ cms$^{-1}$. The caco flux value can be determined by standard procedures known in the art such as described in J. Pharm. Sci 79, 7, p595–600 (1990), and Pharm. Res. vol 14, no. 6 (1997).

Selectivity

For some applications, preferably the agent of the present invention has at least about a 100 fold selectivity to the desired target, preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

For some applications, preferably the agent of the present invention has at least about a 400 fold selectivity to the desired target, preferably at least about a 500 fold selectivity to the desired target, preferably at least about a 600 fold selectivity to the desired target, preferably at least about a 700 fold selectivity to the desired target, preferably at least about a 800 fold selectivity to the desired target, preferably at least about a 900 fold selectivity to the desired target, preferably at least about a 1000 fold selectivity to the desired target.

Chemical Synthesis Methods

Typically the agent of the present invention will be prepared by chemical synthesis techniques.

The agent or target of the present invention or variants, homologues, derivatives, fragments or mimetics thereof may be produced using chemical methods to synthesize the agent in whole or in part. For example, peptides can be synthesized by solid phase techniques, cleaved from the resin, and purified by preparative high performance liquid chromatography (e.g., Creighton (1983) Proteins Structures And Molecular Principles, WH Freeman and Co, New York, N.Y.). The composition of the synthetic peptides may be confirmed by amino acid analysis or sequencing (e.g., the Edman degradation procedure; Creighton, supra).

Direct synthesis of the agent or variants, homologues, derivatives, fragments or mimetics thereof can be performed using various solid-phase techniques (Roberge J Y et al (1995) Science 269: 202–204) and automated synthesis may be achieved, for example, using the ABI 43 1 A Peptide Synthesizer (Perkin Elmer) in accordance with the instructions provided by the manufacturer. Additionally, the amino acid sequences comprising the agent or any part thereof, may be altered during direct synthesis and/or combined using chemical methods with a sequence from other subunits, or any part thereof, to produce a variant agent or target, such as, for example, a variant PDE, NEP (Sequence No. 1) or NPY (Sequence No. 4).

In an alternative embodiment of the invention, the coding sequence of the agent target or variants, homologues, derivatives, fragments or mimetics thereof may be synthesized, in whole or in part, using chemical methods well known in the art (see Caruthers M H et al (1980) Nuc Acids Res Symp Ser 215–23, Horn T et al (1980) Nuc Acids Res Symp Ser 225–232).

Mimetic

As used herein, the term "mimetic" relates to any chemical which includes, but is not limited to, a peptide, polypeptide, antibody or other organic chemical which has the same qualitative activity or effect as a reference agent to a target.

Chemical Derivative

The term "derivative" or "derivatised" as used herein includes chemical modification of an agent. Illustrative of such chemical modifications would be replacement of hydrogen by a halo group, an alkyl group, an acyl group or an amino group.

Chemical Modification

In one embodiment of the present invention, the agent may be a chemically modified agent.

The chemical modification of an agent of the present invention may either enhance or reduce hydrogen bonding interaction, charge interaction, hydrophobic interaction, Van Der Waals interaction or dipole interaction between the agent and the target.

In one aspect, the identified agent may act as a model (for example, a template) for the development of other compounds.

Recombinant Methods

Typically the target of the present invention for use in the assay of the present invention may be prepared by recombinant DNA techniques.

Potentiating cGMP

As used herein with reference to cGMP, the term "potentiating" includes any one or more of: increasing the effectiveness of cGMP, increasing the levels of cGMP, increasing the activity of cGMP, decreasing the level of cGMP degradation, decreasing the level of cGMP inhibition.

The potentiating effect can be a direct effect. Alternatively, it could be a secondary effect and/or a downstream effect.

Here, preferably, the agent that potentiates cGMP acts on a $I_{cGMP}$ and/or an $AM_{cGMP}$ wherein the modulator of cGMP has an adverse effect on cGMP, such that the agent reduces and/or eliminates and/or masks and/or diverts the detrimental effect of the $I_{cGMP}$ and/or the $AM_{cGMP}$ towards cGMP.

Hence, the present invention encompasses a combination of one or more I:$I_{cAMP}$ and one or more I:$I_{cGMP}$.

In one aspect, the I:$I_{cGMP}$ is a I:$PDE_{cGMP}$.

$I_{cAMP}$ and/or $AM_{cAMP}$

We have shown that cAMP mediates genital (e.g. vaginal or clitoral) blood flow and by enhancing cAMP signalling we can enhance genital (e.g. vaginal or clitoral) blood flow in an animal model. Thus, an agent that upregulates/enhances cAMP-mediated vasorelaxation will be efficacious in the treatment of FSAD. For ease of reference, we refer to these substances as $I_{cAMP}$ and/or an $AM_{cAMP}$. Here, the $I_{cAMP}$ and the $AM_{cAMP}$ have an adverse effect on cAMP levels or activity. Thus, the agent may be any one of more of: an I:$I_{cAMP}$ and/or an I:$AM_{cAMP}$.

The agent may be a single entity that is capable of exhibiting two or more of these properties. Alternatively, or in addition, the agent can be a combination of agents that are capable of exhibiting one or more of these properties.

Examples of $I_{cAMP}$ and the $AM_{cAMP}$ include one or more of PDE(s), NPY (Sequence No. 4) and NEP (Sequence No. 1), or any component associated therewith. The associated component may be, for example, a receptor and/or a co-factor.

Thus, preferably the agent may be any one of more of: an I:$PDE_{cAMP}$, an I:NPY (sometimes written as NPYi), an I:NPY $Y_n$ (sometimes written as NPY $Y_n$i), and I:NEP.

Likewise, the agent may be a single entity that is capable of exhibiting two or more of these properties. Alternatively, or in addition, the agent can be a combination of agents that are capable of exhibiting one or more of these properties.

I:$I_{cAMP}$ and/or I:$AM_{cAMP}$

In accordance with the present invention we have found that it is possible to treat and/or prevent FSAD by using an agent that reduces and/or eliminates and/or masks and/or diverts and/or prevents the detrimental effect of the $I_{cAMP}$ and/or the $AM_{cAMP}$ towards cAMP. The agent may even restore cAMP levels that were decreased by the a $I_{cAMP}$ and/or a $AM_{cAMP}$. For ease, we refer to these substances as I:$I_{cAMP}$ and/or a I:$AM_{cAMP}$. Here, the I:$I_{cAMP}$ and the I:$AM_{cAMP}$ prevent or reduce the adverse effect on cAMP levels or activity.

Thus, in one preferred aspect, the agent is an I:$I_{cAMP}$ and/or an I:$AM_{cAMP}$ wherein the $AM_{cAMP}$ has a detrimental effect on $AM_{cAMP}$.

In a preferred aspect, the agent may be one or more of:

I:$PDE_{cAMP}$

I:$PDEn_{cAMP}$ (where n denotes an appropriate class or sub-class)

I:NPY

I:NPY $Y_n$ (where n denotes an appropriate class or sub-class)

I:NEP $A_{cAMP}$

In accordance with the present invention, we have found that one of the important causes of FSAD is due to low levels or low activity of cAMP in the female genitalia. Thus, the agent may be a U:$A_{cAMP}$.

Examples of $A_{cAMP}$ include VIP (Sequence No. 8) and AC, or any component associated therewith. The associated component may be, for example, a receptor and/or a co-factor. Thus, preferably the agent may be any one of more of: A:AC, A:VIPr, A:$VIP_n$, I:I:VIPr or I:I:$VIP_n$.

The agent may be a single entity that is capable of exhibiting two or more of these properties. Alternatively, or in addition, the agent can be a combination of agents that are capable of exhibiting one or more of these properties.

U:$A_{cAMP}$

In another respect, preferably, the target is a component that increases the level of cAMP. Hence, the agent can be an U:AC.

By way of example, the target could be cAMP itself or AC or VIP (Sequence No. 8) (or combinations thereof). Hence, by way of example, the agent can be any one of: an U:$A_{cAMP}$, an A:AC, an A:VIPr, an A:$VIP_n$, an I:I:VIPr or an I:$VIP_n$.

Combination of I:$I_{cAMP}$ and/or I:$M_{cAMP}$ and/or U:$A_{cAMP}$

In another aspect, the agent of the present invention may even be a combination of cAMP potentiators. By way of example, the agent of the present invention may be two or more of:

I:$PDE_{cAMP}$

I:$PDEn_{cAMP}$

I:NPY

I:NPY $Y_n$

I:NEP

U:$A_{cAMP}$

A:AC

A:VIPr

A:$VIP_n$

I:I:VIPr

I:I:$VIP_n$.

Combination of cAMP Mimetic and I:$I_{cAMP}$ and/or I:$M_{cAMP}$ and/or U:$A_{cAMP}$ In another aspect, the agent of the present invention may even be a combination of a cAMP mimetic and one or more cAMP potentiators. By way of example, the agent of the present invention may be a cAMP mimetic and one or more of:

I:$PDE_{cAMP}$

I:$PDEn_{cAMP}$

I:NPY

I:NPY $Y_n$

I:NEP

U:$A_{cAMP}$

A:AC

A:VIPr

A:$VIP_n$

I:I:VIPr

I:I:$VIP_n$.

Inhibitor

The term "inhibitor" as used herein with respect to the agent of the present invention means an agent that can reduce and/or eliminate and/or mask and/or prevent the detrimental action of a $I_{cAMP}$ and/or a detrimental $M_{cAMP}$ towards cAMP. The inhibitor may act as an antagonist.

Activator

The term "activator" as used herein with respect to the agent of the present invention means an agent that can increase and/or produce and/or unmask and/or elevate and/or ensure action of cAMP and/or an $A_{cAMP}$. The activator may act as an agonist.

Other Active Components

In another aspect, the agent of the present invention may even be in combination with one or more other active components—such as one or more agents capable of potentiating cGMP.

Amino Acid Sequence

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "protein".

The amino acid sequence may be prepared isolated from a suitable source, or it may be made synthetically or it may be prepared by use of recombinant DNA techniques.

In one aspect, the present invention provides an amino acid sequence that is capable of acting as a target in an assay for the identification of one or more agents and/or derivatives thereof capable of affecting the amino acid sequence in order to potentiate cAMP to treat FSAD.

Nucleotide Sequence

As used herein, the term "nucleotide sequence" is synonymous with the term "polynucleotide".

The nucleotide sequence may be DNA or RNA of genomic or synthetic or of recombinant origin. The nucleotide sequence may be double-stranded or single-stranded whether representing the sense or antisense strand or combinations thereof.

For some applications, preferably, the nucleotide sequence is DNA.

For some applications, preferably, the nucleotide sequence is prepared by use of recombinant DNA techniques (e.g. recombinant DNA).

For some applications, preferably, the nucleotide sequence is cDNA.

For some applications, preferably, the nucleotide sequence may be the same as the naturally occurring form for this aspect.

In one aspect, the present invention provides a nucleotide sequence encoding a substance capable of acting as a target in an assay (such as a yeast two hybrid assay) for the identification of one or more agents and/or derivatives thereof capable of affecting the substance in order to potentiate cAMP to treat FSAD.

It will be understood by a skilled person that numerous different nucleotide sequences can encode the targets of the present invention as a result of the degeneracy of the genetic code. In addition, it is to be understood that skilled persons may, using routine techniques, make nucleotide substitutions that do not substantially affect the activity encoded by the nucleotide sequence of the present invention to reflect the codon usage of any particular host organism in which the target of the present invention is to be expressed. Thus, the terms "variant", "homologue" or "derivative" in relation to the nucleotide sequence set out in the attached sequence listings include any substitution of, variation of, modification of, replacement of, deletion of or addition of one (or more) nucleic acid from or to the sequence providing the resultant nucleotide sequence encodes a functional target according the present invention (or even an agent according to the present invention if said agent comprises a nucleotide sequence or an amino acid sequence).

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

The present invention also encompasses nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length. These sequences could be used a probes, such as in a diagnostic kit.

Variants/Homoloques/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which may be at least 75, 85 or 90% identical, preferably at least 95 or 98% identical. In particular, homology should typically be considered with respect to those regions of the sequence known to be essential for an activity. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However it is preferred to use the GCG Bestfit program. A new tool, called BLAST 2 Sequences is also available for comparing protein and nucleotide sequence (see FEMS Microbiol Lett 1999 174(2): 247–50; FEMS Microbiol Left 1999 177(1): 187–8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone#, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydro-isoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367–9371 and Horwell D C, Trends Biotechnol. (1995) 13(4), 132–134.

Hybridisation

The present invention also encompasses the use of sequences that can hybridise to the target sequences presented herein—such as if the agent is an antisense sequence.

The term "hybridization" as used herein shall include "the process by which a strand of nucleic acid joins with a complementary strand through base pairing" as well as the process of amplification as carried out in polymerase chain reaction (PCR) technologies.

Nucleotide sequences of the invention capable of selectively hybridising to the nucleotide sequences presented herein, or to their complement, will be generally at least 75%, preferably at least 85 or 90% and more preferably at least 95% or 98% homologous to the corresponding complementary nucleotide sequences presented herein over a region of at least 20, preferably at least 25 or 30, for instance at least 40, 60 or 100 or more contiguous nucleotides. Preferred nucleotide sequences of the invention will comprise regions homologous to the-nucleotide sequence set out in SEQ ID No 2 of the sequence listings of the present invention preferably at least 80 or 90% and more preferably at least 95% homologous to the nucleotide sequence set out in SEQ ID No 2 of the sequence listings of the present invention.

The term "selectively hybridizable" means that the nucleotide sequence, when used as a probe, is used under conditions where a target nucleotide sequence of the invention is found to hybridize to the probe at a level significantly above background. The background hybridization may occur because of other nucleotide sequences present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}$P.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm–5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC {1×SSC=0.15 M NaCl, 0.015 M $Na_3$ Citrate pH 7.0). Where the nucleotide sequence of the invention is double-stranded, both strands of the duplex, either individually or in combination, are encompassed by the present invention. Where the nucleotide sequence is single-stranded, it is to be understood that the complementary sequence of that nucleotide sequence is also included within the scope of the present invention.

Nucleotide sequences which are not 100% homologous to the sequences of the present invention but fall within the scope of the invention can be obtained in a number of ways. Other variants of the sequences described herein may be obtained for example by probing DNA libraries made from a range of sources. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the nucleotide sequence set out in herein under conditions of medium to high stringency. Similar considerations apply to obtaining species homologues and allelic variants of the amino acid and/or nucleotide sequences of the present invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used. The primers used in degenerate PCR will contain one or more degenerate positions and will be used at stringency conditions lower than those used for cloning sequences with single sequence primers against known sequences.

Alternatively, such nucleotide sequences may be obtained by site directed mutagenesis of characterised sequences, such as the nucleotide sequence set out in SEQ ID No 2 of the sequence listings of the present invention. This may be useful where for example silent codon changes are required to sequences to optimise codon preferences for a particular host cell in which the nucleotide sequences are being expressed. Other sequence changes may be desired in order to introduce restriction enzyme recognition sites, or to alter the activity of the protein encoded by the nucleotide sequences.

The nucleotide sequences of the present invention may be used to produce a primer, e.g. a PCR primer, a primer for an alternative amplification reaction, a probe e.g. labelled with a revealing label by conventional means using radioactive or non-radioactive labels, or the nucleotide sequences may be cloned into vectors. Such primers, probes and other fragments will be at least 15, preferably at least 20, for example at least 25, 30 or 40 nucleotides in length, and are also encompassed by the term nucleotide sequence of the invention as used herein.

The nucleotide sequences such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer nucleotide sequences will generally be produced using recombinant means, for example using a PCR (polymerase chain reaction) cloning techniques. This will involve making a pair of primers (e.g. of about 15 to 30 nucleotides) flanking a region of the targeting sequence which it is desired to clone, bringing the primers into contact with mRNA or cDNA obtained from an animal or human cell, performing a polymerase chain reaction (PCR) under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Due to the inherent degeneracy of the genetic code, other DNA sequences which encode substantially the same or a functionally equivalent amino acid sequence, may be used to clone and express the target sequences. As will be understood by those of skill in the art, for certain expression systems, it may be advantageous to produce the target sequences with non-naturally occurring codons. Codons preferred by a particular prokaryotic or eukaryotic host (Murray E et al (1989) Nuc Acids Res 17:477–508) can be selected, for example, to increase the rate of the target expression or to produce recombinant RNA transcripts having desirable properties, such as a longer half-life, than transcripts produced from naturally occurring sequence.

Expression Vectors

The nucleotide sequence for use as the target or for expressing the target can be incorporated into a recombinant replicable vector. The vector may be used to replicate and express the nucleotide sequence in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The protein produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence may be produced as a fusion protein, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the target.

The fusion protein may comprise an antigen or an antigenic determinant fused to the substance of the present invention. In this embodiment, the fusion protein may be a non-naturally occurring fusion protein comprising a substance which may act as an adjuvant in the sense of providing a generalized stimulation of the immune system. The antigen or antigenic determinant may be attached to either the amino or carboxy terminus of the substance.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognized by a commercially available antibody.

Antibodies

In one embodiment of the present invention, the agent of the present invention may be an antibody. In addition, or in the alternative, the target of the present invention may be an antibody. In addition, or in the alternative, the means for detecting the target of the present invention may be an antibody.

Antibodies may be produced by standard techniques, such as by immunisation with the substance of the invention or by using a phage display library.

For the purposes of this invention, the term "antibody", unless specified to the contrary, includes but is not limited to, polyclonal, monoclonal, chimeric, single chain, Fab fragments, fragments produced by a Fab expression library, as well as mimetics thereof. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the antigen-binding site of the antibody. Furthermore, the antibodies and fragments thereof may be humanised antibodies. Neutralizing antibodies, i.e., those which inhibit biological activity of the substance polypeptides, are especially preferred for diagnostics and therapeutics.

If polyclonal antibodies are desired, a selected mammal (e.g., mouse, rabbit, goat, horse, etc.) is immunised with an immunogenic polypeptide bearing a epitope(s) obtainable from an identified agent and/or substance of the present invention. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guefin) and *Corynebacterium parvum* are potentially useful human adjuvants which may be employed if purified the substance polypeptide is administered to immunologically compromised individuals for the purpose of stimulating systemic defence.

Serum from the immunised animal is collected and treated according to known procedures. If serum containing polyclonal antibodies to an epitope obtainable from an identifed agent and/or substance of the present invention contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals or humans.

Monoclonal antibodies directed against epitopes obtainable from an identified agent and/or substance of the present invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against orbit epitopes can be screened for various properties; i.e., for isotype and epitope affinity.

Monoclonal antibodies to the substance and/or identified agent of the present invention may be prepared using any technique which provides for the production of antibody molecules by continuous cell lines in culture. These include, but are not limited to, the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452454). Alternatively, techniques described for the production of single chain antibodies (U.S. Pat. No. 4,946,779) can be adapted to produce the substance specific single chain antibodies.

Antibodies, both monoclonal and polyclonal, which are directed against epitopes obtainable from an identifed agent and/or substance of the present invention are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the substance and/or agent against which protection is desired. Techniques for raising anti-idiotype antibodies are known in the art. These anti-idiotype antibodies may also be useful in therapy.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for the substance may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al (1989) Science 256:1275–1281).

Reporters

A wide variety of reporters may be used in the assay methods (as well as screens) of the present invention with preferred reporters providing conveniently detectable signals (eg. by spectroscopy). By way of example, a reporter gene may encode an enzyme which catalyses a reaction which alters light absorption properties.

Examples of reporter molecules include but are not limited to β-galactosidase, invertase, green fluorescent protein, luciferase, chloramphenicol, acetyltransferase, β-glucuronidase, exo-glucanase and glucoamylase. Alternatively, radiolabelled or fluorescent tag-labelled nucleotides can be incorporated into nascent transcripts which are then identified when bound to oligonucleotide probes.

In one preferred embodiment, the production of the reporter molecule is measured by the enzymatic activity of the reporter gene product, such as β-galactosidase.

A variety of protocols for detecting and measuring the expression of the target, such as by using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes on polypeptides is preferred, but a competitive binding assay may be employed. These and other assays are described, among other places, in Hampton R et al (1990, Serological Methods, A Laboratory Manual, APS Press, St Paul, Minn.) and Maddox D E et al (1983, J Exp Med 15 8:1211).

A wide variety of labels and conjugation techniques are known by those skilled in the art and can be used in various nucleic and amino acid assays. Means for producing labelled hybridisation or PCR probes for detecting the target polynucleotide sequences include oligolabelling, nick translation, end-labelling or PCR amplification using a labelled nucleotide. Alternatively, the coding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241. Also, recombinant immunoglobulins may be produced as shown in U.S. Pat. No. 4,816,567.

Additional methods to quantify the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantification of multiple samples may be speeded up by running the assay in an ELISA format where the oligomer of interest is presented in various dilutions and a spectrophotometric or calorimetric response gives rapid quantification.

Although the presence/absence of marker gene expression suggests that the gene of interest is also present, its presence and expression should be confirmed. For example, if the nucleotide sequence is inserted within a marker gene sequence, recombinant cells containing the same may be identified by the absence of marker gene function. Alternatively, a marker gene can be placed in tandem with a target coding sequence under the control of a single promoter. Expression of the marker gene in response to induction or selection usually indicates expression of the target as well.

Alternatively, host cells which contain the coding sequence for the target and express the target coding regions may be identified by a variety of procedures known to those of skill in the art. These procedures include, but are not limited to, DNA-DNA or DNA-RNA hybridisation and protein bioassay or immunoassay techniques which include membrane-based, solution-based, or chip-based technologies for the detection and/or quantification of the nucleic acid or protein.

General Assays For cAMP Activity/Levels

The ability of a test agent to potentiate cAMP may be determined by measuring a relevant increase or decrease of a target level. In addition, or in the alternative, the ability of a test agent to potentiate cAMP may be determined by measuring a relevant increase in cAMP levels. By way of example, one may adapt the teachings of Smith et al 1993 (Appl. Biochem. Biotechnol. 41:189–218). There are also commercially available immunoassay kits for the measurement of cAMP (eg Amersham International, Arlington Heights, Ill, and DuPont, Boston, Mass.). Details on a suitable cAMP assay are provided in the Experimental Section.

Screens

Any one or more of appropriate targets—such as an amino acid sequence and/or nucleotide sequence—may be used for identifying a $P_{cAMP}$ in any of a variety of drug screening techniques. The target employed in such a test may be free in solution, affixed to a solid support, borne on a cell surface, or located intracellularly. The target may even be within an animal model, wherein said target may be an exogenous target or an introduced target. The animal model will be a non-human animal model. The abolition of target activity or the formation of binding complexes between the target and the agent being tested may be measured.

Techniques for drug screening may be based on the method described in Geysen, European Patent Application 84/03564, published on Sep. 13, 1984. In summary, large numbers of different small peptide test compounds are synthesized on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Thus, the present invention also relates to a method of identifying agents that potentiate cAMP, the method comprising contacting a suitable target with the agent and then measuring the activity and/or levels of cAMP.

The present invention also relates to a method of identifying agents that selectively potentiate cAMP in female sexual genitalia, the method comprising contacting a suitable target from female sexual genitalia and then measuring the activity and/or levels of cAMP.

The present invention also relates to a method of identifying agents that potentiate cAMP, the method comprising contacting a suitable target with the agent and then measuring the activity and/or levels of the target.

The present invention also relates to a method of identifying agents that selectively potentiate cAMP in female sexual genitalia, the method comprising contacting a suitable target from female sexual genitalia and then measuring the activity and/or levels of the target.

In a preferred aspect, the screen of the present invention comprises at least the following steps (which need not be in this same consecutive order): (a) conducting an in vitro screen to determine whether a candidate agent has the relevant activity (such as modulation of PDEII and/or NEP (Sequence No. 1), such as NEP (Sequence No. 1) from dog kidney); (b) conducting one or more selectivity screens to determine the selectivity of said candidate agent (e.g. to see if said agent is also an ACE inhibitor—such as by using the assay protocol presented herein); and (c) conducting an in vivo screen with said candidate agent (e.g. using a functional animal model). Typically, if said candidate agent passes screen (a) and screen (b) then screen (c) is performed.

Diagnostics

The present invention also provides a diagnostic composition or kit for the detection of a pre-disposition for FSAD. In this respect, the composition or kit will comprise an entity that is capable of indicating the presence of one or more—or even the absence of one or more—of the targets in a test sample. Preferably, the test sample is obtained from the female sexual genitalia or a secretion thereof or therefrom.

By way of example, the diagnostic composition may comprise any one of the nucleotide sequences mentioned herein or a variant, homologue, fragment or derivative thereof, or a sequence capable of hybridising to all or part of any one of the nucleotide sequence.

In order to provide a basis for the diagnosis of disease, normal or standard values from a target should be established. This may be accomplished by combining body fluids or cell extracts taken from normal subjects, either animal or human, with an antibody to a target under conditions suitable for complex formation which are well known in the art. The amount of standard complex formation may be quantified by comparing it to a dilution series of positive controls where a known amount of antibody is combined with known concentrations of a purified target. Then, standard values obtained from normal samples may be compared with values obtained from samples from subjects potentially affected by FSAD. Deviation between standard and subject values establishes the presence of the disease state.

A target itself, or any part thereof, may provide the basis for a diagnostic and/or a therapeutic compound. For diagnostic purposes, target polynucleotide sequences may be used to detect and quantify gene expression in conditions, disorders or diseases in which FSAD may be implicated.

The target encoding polynucleotide sequence may be used for the diagnosis of FSAD resulting from expression of the target. For example, polynucleotide sequences encoding a target may be used in hybridisation or PCR assays of tissues from biopsies or autopsies or biological fluids, to detect abnormalities in target expression. The form of such qualitative or quantitative methods may include Southern or northern analysis, dot blot or other membrane-based technologies; PCR technologies; dip stick, pin or chip technologies; and ELISA or other multiple sample format technologies. All of these techniques are well known in the art and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for target expression should be established. This is accomplished by combining body fluids or cell extracts taken from normal subjects, either animal or human, with the target or a portion thereof, under conditions suitable for hybridisation or amplification. Standard hybridisation may be quantified by comparing the values obtained for normal subjects with a dilution series of positive controls run in the same experiment where a known amount of purified target is used. Standard values obtained from normal samples may be compared with values obtained from samples from subjects potentially affected by a disorder or disease related to expression of the target coding sequence. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

Thus, in one aspect, the present invention relates to the use of a target polypeptide, or variant, homologue, fragment or derivative thereof, to produce anti-target antibodies which can, for example, be used diagnostically to detect and quantify target levels in an FSAD states.

The present invention further provides diagnostic assays and kits for the detection of a target in cells and tissues comprising a purified target which may be used as a positive control, and anti-target antibodies. Such antibodies may be used in solution-based, membrane-based, or tissue-based technologies to detect any disease state or condition related to the expression of target protein or expression of deletions or a variant, homologue, fragment or derivative thereof.

Assay Methods

The diagnostic compositions and/or methods and/or kits may be used in the following techniques which include but are not limited to; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, immunohistochemistry and immunocytochemistry.

By way of example, an immunohistochemistry kit may also be used for localization of NEP (Sequence No. 1), PDE or NPY (Sequence No. 4) activity in genital tissue. This immunohistochemistry kit permits localization of NEP (Sequence No. 1), PDE or NPY (Sequence No. 4) in tissue sections and cultured cells using both light and electron microscopy which may be used for both research and clinical purposes. Such information may be useful for diagnostic and possibly therapeutic purposes in the detection and/or prevention and/or treatment of a FSD, such as FSAD. For each kit the range, sensitivity, precision, reliability, specificity and reproducibility of the assay are established. Intraassay and interassay variation is established at 20%, 50% and 80% points on the standard curves of displacement or activity.

Probes

Another aspect of the subject invention is the provision of nucleic acid hybridisation or PCR probes which are capable of detecting (especially those that are capable of selectively selecting) polynucleotide sequences, including genomic sequences, encoding a target coding region or closely related molecules, such as alleles. The specificity of the probe, i.e., whether it is derived from a highly conserved, conserved or non-conserved region or domain, and the stringency of the hybridisation or amplification (high, intermediate or low) will determine whether the probe identifies only naturally occurring target coding sequence, or related sequences. Probes for the detection of related nucleic acid sequences are selected from conserved or highly conserved nucleotide regions of target family members and such probes may be used in a pool of degenerate probes. For the detection of identical nucleic acid sequences, or where maximum specificity is desired, nucleic acid probes are selected from the non-conserved nucleotide regions or unique regions of the target polynucleotides. As used herein, the term "non-conserved nucleotide region" refers to a nucleotide region that is unique to a target coding sequence disclosed herein and does not occur in related family members.

PCR as described in U.S. Pat. No. 4,683,195, U.S. Pat. No. 4,800,195 and U.S. Pat. No. 4,965,188 provides additional uses for oligonucleotides based upon target sequences. Such oligomers are generally chemically synthesized, but they may be generated enzymatically or produced from a recombinant source. Oligomers generally comprise two nucleotide sequences, one with sense orientation (5'–>3') and one with antisense (3'<–5') employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

The nucleic acid sequence for a target can also be used to generate hybridisation probes as previously described, for mapping the endogenous genomic sequence. The sequence may be mapped to a particular chromosome or to a specific region of the chromosome using well known techniques. These include in situ hybridisation to chromosomal spreads (Verma et al (1988) Human Chromosomes: A Manual of Basic Techniques, Pergamon Press, New York City), flow-sorted chromosomal preparations, or artificial chromosome constructions such as YACs, bacterial artificial chromosomes (BACs), bacterial PI constructions or single chromosome cDNA libraries.

In situ hybridisation of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome has been crudely localised by genetic linkage to a particular genomic region any sequences mapping to that area may represent associated or regulatory genes for further investigation. The nucleotide sequence of the subject invention may also be used to detect differences in the chromosomal location due to translocation, inversion, etc. between normal, carrier or affected individuals.

Host Cells

The term "host cell"—in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and may for example be prokaryotic (for example bacterial), fungal, yeast or plant cells.

The gram-negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus Bacillus are very suitable as heterologous hosts because of their capability to secrete proteins into the culture medium. Other bacteria suitable as hosts are those from the genera Streptomyces and Pseudomonas.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as Aspergillus species (such as those described in EP-A-0184438 and EP-A-0284603) and Trichoderma species; bacteria such as Bacillus species (such as those described in EP-A-0134048 and EP-A-0253455), Streptomyces species and Pseudomonas species; and yeasts such as Kluyveromyces species (such as those described in EP-A-0096430 and EP-A-0301670) and Saccharomyces species. By way of example, typical expression hosts may be selected from *Aspergillus niger, Aspergillus niger* var. tubigenis, *Aspergillus niger* var. awamofi, *Aspergillus aculeatis, Aspergillus nidulans, Aspergillus orvzae, Trichoderma reesei, Bacillus subtilis, Bacillus* licheniformis, Bacillus amyloliquefaciens, Kluyveromyces lactis and Saccharomyces cerevisiae.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the target according to the present invention and/or products obtained therefrom. Examples of organisms may include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include E. coli and Bacillus subtilis. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species Saccharomyces cerevisiae has a long history of industrial use, including its use for heterologous gene expression. Expression of heterologous genes in Saccharomyces cerevisiae has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons Saccharomyces cerevisiae is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of Saccharomyces cerevisiae.

A review of the principles of heterologous gene expression in Saccharomyces cerevisiae and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GALL promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104), and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27). Further teachings on plant transformation may be found in EP-A-0449375.

Thus, the present invention also provides a method of transforming a host cell with a nucleotide sequence that is to be the target or is to express the target. Host cells transformed with the nucleotide sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441–53).

Pharmaceutical Compositions

The present invention also provides a pharmaceutical composition comprising a therapeutically effective amount of the agent of the present invention and a pharmaceutically acceptable carrier, diluent or excipients (including combinations thereof.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

In a preferred embodiment, the asents of the present invention are delivered systemically (such as orally, buccally, sublingually), more preferably orally.

Hence, preferably the agent is in a form that is suitable for oral delivery.

For some embodiments, preferably the agent—when in use—does not act on the central nervous system.

For some embodiments, preferably the agent—when in use—is peripherally acting.

Administration

The term "administered" includes delivery by viral or non-viral techniques. Viral delivery mechanisms include but are not limited to adenoviral vectors, adeno-associated viral (AAV) vectos, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The agents of the present invention may be administered alone but will generally be administered as a pharmaceutical composition—e.g. when the agent is in admixture with a suitable pharmaceutical excipient, diluent or carrier selected with regard to the intended route of administration and standard pharmaceutical practice.

For example, the agent can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

It is to be understood that not all of the agent need be administered by the same route. Likewise, if the composition comprises more than one active component, then those components may be administered by different routes.

If the agent of the present invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the agent; and/or by using infusion techniques.

For parenteral administration, the agent is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the agent of the present invention can be administered intranasally or by inhalation and is conveniently delivered in the form of a dry powder inhaler or an aerosol spray presentation from a pressurized container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurized aerosol, the dosage unit may be determined by providing a valve to deliver a metered amount. The pressurized container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insulator may be formulated to contain a powder mix of the agent and a suitable powder base such as lactose or starch.

Alternatively, the agent of the present invention can be administered in the form of a suppository or pessary, or it may be applied topically in the form of a gel, hydrogel, lotion, solution, cream, ointment or dusting powder. The agent of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compositions of the present invention may be administered by direct injection.

For some applications, preferably the agent is administered orally.

For some applications, preferably the agent is administered topically.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The agent and/or the pharmaceutical composition of the present invention may be administered in accordance with a regimen of from 1 to 10 times per day, such as once or twice per day.

For oral and parenteral administration to human patients, the daily dosage level of the agent may be in single or divided doses.

Depending upon the need, the agent may be administered at a dose of from 0.01 to 30 mg/kg body weight, such as from 0.1 to 10 mg/kg, more preferably from 0.1 to 1 mg/kg body weight. Naturally, the dosages mentioned herein are exemplary of the average case. There can, of course, be individual instances where higher or lower dosage ranges are merited.

Formulation

The agents of the present invention may be formulated into a pharmaceutical composition, such as by mixing with one or more of a suitable carrier, diluent or excipient, by using techniques that are known in the art.

The following present some non-limiting examples of formulations. Formulation 1: A tablet is prepared using the following ingredients:

|  | weight/mg |
|---|---|
| Agent | 250 |
| Cellulose, microcrystalline | 400 |
| Silicon dioxide, fumed | 10 |
| Stearic acid | 5 |
| Total | 665 | the components are blended and compressed to form tablets each weighing 665 mg.

Formulation 2: An intravenous formulation may be prepared as follows:

| Agent | 100 mg |
|---|---|
| Isotonic saline | 1,000 ml |

Pharmaceutically Active Salt

The agent of the present invention may be administered as a pharmaceutically acceptable salt. Typically, a pharmaceutically acceptable salt may be readily prepared by using a desired acid or base, as appropriate. The salt may precipitate from solution and be collected by filtration or may be recovered by evaporation of the solvent.

Animal Test Models

In vivo models may be used to investigate and/or design therapies or therapeutic agents to treat FSAD. The models could be used to investigate the effect of various tools/lead compounds on a variety of parameters which indicate the sexual arousal response. These animal test models can be used as, or in, the assay of the present invention. The animal test model will be a non-human animal test model.

There are a number of animal models for vasculogenic female sexual dysfunction (FSAD) available that could be used.

By way of example, reference may be made to invasive animal models (e.g. see Park et al., 1997). Here, vaginal and clitoral haemodynamic responses can be directly recorded following pelvic nerve stimulation in normal and atherosclerotic female rabbits. The in vivo effects of cAMP potentiators—such as vasodilatory agents such as NPY (Sequence No. 4) antagonist or VIP agonists—can be investigated either in normal or FSAD animals.

By way of further example, reference may be made to non-invasive animal models (e.g. see the review of Goldstein et al., 1998; Laan et al., 1998). Here, pulsed wave Doppler ultrasonography provides a means of detecting blood flow changes in the vaginal and clitoral arteries. This model can be used to investigate vasculogenic effects during pharmacological administration of vasodilators.

Other non-invasive techniques that can be used include vaginal photoplethysmography, which provides a quantitative measure of vaginal mucosa engorgement, and vaginal thermal clearance techniques, which are based on the principle that vaginal blood flow changes can be recorded by measuring the heat transfer away from an intravaginal probe kept at a constant temperature.

An Animal Model of Sexual Arousal

In our studies we have developed a robust reproducible model of the physiology of sexual arousal. This model uses an anaesthetised rabbit and employs Laser Doppler technologies to monitor genital blood flow whilst routinely recording cardiovascular parameters. We are capable of measuring small changes in vaginal (and even clitoral) blood flow induced by pelvic nerve stimulation or infusion of VIP (Sequence No. 8) in the absence and presence of test agents.

We believe that our animal model directly reflects the clinical data. Hence, this model can be used to study candidate agents for the treatment of FSAD, such as measuring enhancement of vaginal or clitoral blood flow.

Physiological Measurement of Female Sexual Arousal

In accordance with the present invention, a number of different techniques may be used for measuring clitoral and vaginal blood flow. By way of example, use may be made of vaginal photoplethysmography, vaginal heat washout technique, clitoral and vaginal contrast-enhanced MRI, clitoral/vulval laser Doppler pulsed imaging, and clitoral ultrasonography.

Quantification of vaginal lubrication may also be measured by techniques known in the art—such as (a) pre- and post-stimulation weighing of vaginal tampons, and (b) measuring the pH of vaginal fluid. With respect to the latter aspect, the normal resting acid medium in the vagina becomes more alkaline as it approaches blood pH when transudation of fluid occurs during sexual stimulation.

PDE (Phosphodiesterase)

According to one aspect of the present invention, a $P_{cAMP}$ target is a PDE (phosphodiesterase).

It is known that cyclic nucleotides, such as cAMP and cGMP, are important intracellular second messengers. Cyclic nucleotide phosphodiesterases—otherwise known as PDEs—are a family of enzymes that catalyse the degradation of cyclic nucleotides and, in doing so, are one of the cellular components that regulate the concentration of cyclic nucleotides.

In recent years, at least seven PDE enzymes (such as PDEI-PDEVII), as well as many subtypes of these enzymes, have been defined based on substrate affinity and cofactor requirements (Beavo J A and Reifsnyder D H, Trends Pharmacol. Sci. 11:150[1990]; Beavo J, In: Cyclic Nucleotide Phosphodiesterases: Structure, Regulation and Drug Action., Beavo J and Housley M D (Eds.). Wiley:Chichester, pp. 3–15[ 1990]).

Examples of PDEs include: PDEI (Sequence No. 2) which is a $Ca^{2+}$/Calmodulin-dependent PDE; PDEII (Sequence No. 3) which is a cAMP and cGMP stimulated PDE; PDEIII which is a cGMP inhibited PDE; PDEIV which is a high affinity cAMP-specific PDE; and PDEV which is a cGMP specific PDE. PDEI (Sequence No. 2) etc. are sometimes called PDE type I (Sequence No. 2) etc. or PDE type 1 etc.

Each PDE family may contain two or more isoforms (i.e. there may be two or more PDE isoenzymes). By way of example, mammalian PDE IV, the homologue of the Drosophila Dunce gene (Chen C N et al., Proc. Nat. Acad. Sci. (USA) 83:9313[1986]), is known to have four isoforms in the rat (Swinnen J V et al., Proc. Nat. Acad. Sci. (USA) 86:5325[1989]). Human PDEs are also known to occur as isoforms and have splice variants. For example, the cloning of one human isoform of PDEIV from monocytes was reported in 1990 (Livi G P et al., Mol. Cell. Bio., 10:2678 [1990]). By way of further example, other workers have independently cloned three splice variants of PDEIV, which are now designated hPDEIV-B1, hPDEIV-B2, and hPDEIV-B3.

Teachings on cyclic nucleotide phosphodiesterases can also be found in U.S. Pat. No. 5,932,423 and U.S. Pat. No. 5,932,465.

Teachings on a further cyclic nucleotide phosphodiesterase—namely CN PCDE8—can be found in WO-A-97/35989. According to WO-A-97/35989, CN PCDE8 has two isozymes—which were designated CN PCDE8A and CN PCDE8B. The term "isozyme" is sometimes referred to in the art as "isoform".

According to WO-A-97/35989, many inhibitors of different PDEs have been identified and some have undergone clinical evaluation. For example, PDEIII inhibitors are being developed as antithrombotic agents, as antihypertensive agents and as cardiotonic agents useful in the treatment of congestive heart failure. Rolipram, a PDEIII inhibitor, has been used in the treatment of depression and other inhibitors of PDEIII are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel et al 1995 AIDS 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al, 1995 Nat Med 1:244–248) and may be effective in the treatment of tardive dyskinesia (Sasaki et al, 1995 Eur J Phamacol 282:71–76).

According to WO-A-97/35989, there are also non-specific PDE inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immunomodulatory capacity in the treatment of respiratory diseases (Banner et al 1995 Respir J 8:996–1000) where it is thought to act by inhibiting both CN PDE cAMP and cGMP hydrolysis (Banner et al 1995 Monaldi Arch Chest Dis 50:286–292). Pentoxifylline, also known to block TNF-alpha production, may inhibit HIV-1 replication (Angel et al supra). A list of CN PDE inhibitors is given in Beavo 1995 supra.

It has been suggested that selective inhibitors of PDEs, in addition to their isozymes and their subtypes, will lead to more effective therapy with fewer side effects. For example, see the teachings in the reviews of Wieshaar R E et al, (J. Med. Chem., 28:537[1985]), Giembycz M A (Biochem. Pharm., 43:2041[1992]) and Lowe J A and Cheng J B (Drugs of the Future, 17:799–807[1992]).

Thus, for some applications it is desirable to have a selective inhibition of an individual type of PDE.

Background teachings on PDEs have been presented by Victor A. McKusick et al on http://www3.ncbi.nlm.nlh.gov/Omim/searchomim.htm. The following information concerning PDE2 (Sequence No. 3) or cGMP-stimulated PDE, has been extracted from that source.

"Cyclic nucleotides serve as second messengers that mediate a variety of cellular responses to extracellular signals such as hormones, light, and neurotransmitters. Cyclic nucleotide phosphodiesterases (PDEs) play a role in signal transduction by regulating the cellular concentrations of cyclic nucleotides. Mammalian cells contain multiple PDEs that are distinguished into at least 7 families based on their substrate affinity and on their selective sensitivity to cofactors and inhibitory drugs. These families are: (I) Ca(2+)/calmodulin-dependent PDEs; (II) cGMP-stimulated PDEs; (III) cGMP-inhibited PDEs; (IV) cAMP-specific PDEs; (V) cGMP-specific PDEs; (VI) photoreceptor PDEs; and (VII) high-affinity, cAMP-specific. From the amino acid sequences, it is evident that all these PDE families contain a related domain, thought to be the catalytic domain, with approximately 30% sequence identity between families. Members of the same family are more closely related; they share 60 to 80% sequence identity throughout the entire coding region.

Michaeli et al. (1993) established a highly sensitive functional screen for the isolation of cDNAs encoding cAMP phosphodiesterases by complementation of defects in the *Saccharomyces cerevisiae* strain lacking both endogenous cAMP PDE genes, PDE1 and PDE2. Three groups of cDNAs corresponding to 3 distinct human genes encoding cAMP-specific PDEs were isolated from a human glioblastoma cDNA library using this functional screen. Two of the genes were closely related to the Drosophila 'dunce' cAMP-specific PDE. The third gene, which Michaeli et al. (1993) referred to as HCP1, encoded a novel cAMP-specific PDE. HCP1 had an amino acid sequence related to the sequences of the catalytic domains of all cyclic nucleotide PDEs. It is a high-affinity cAMP-specific PDE that does not share other properties of the cAMP-specific PDE family, however. The PDE activity of HCP1 was not sensitive to cGMP or other inhibitors of the cGMP-inhibitable PDEs. The biochemical and pharmacologic properties of HCP1 suggested to Michaeli et al. (1993) that it is a member of a previously undiscovered cyclic nucleotide PDE family, which they designated as family VII. Northern blot analysis indicated the presence of high levels of an HCP1 RNA in human skeletal muscle. By Southern blot analysis of somatic cell hybrid lines, Milatovich et al. (1994) mapped the HCP1 locus to chromosome 8; by study of somatic cell hybrid lines that contained different regions of chromosome 8, they regionalized the assignment to 8q13–q22. Han et al. (1998) mapped the PDE7A gene to 8q13 by fluorescence in situ hybridization. By interspecific backcross analysis, they mapped the mouse Pde7A gene to the proximal region of chromosome 3."

Background teachings on PDE2 (Sequence No. 3) have been presented by Jennifer P. Macke et al on http://www3.ncbi.nlm.nih.gov/Omim/searchomim.htm. The following information concerning PDE2 cGMP-stimulated has been extracted from that source.

"Rosman et al. (1997) cloned a cDNA corresponding to human PDE2A. The PDE2A gene encodes a 941 amino acid polypeptide with a predicted molecular mass of 106 kD. The protein sequence is 90% identical to bovine and rat PDE2A sequences. Northern blot analysis showed that PDE2A was expressed as a 4.2-kb mRNA at varying levels in all human tissues tested, with greatest expression in brain. Expression studies revealed that PDE2A hydrolyzes cAMP and cGMP and is inhibited by the PDE2A-specific inhibitor EHNA."

Nucleotide sequences and amino acid sequences for PDEs are available in the literature. Some sequences are presented in the Sequence Listings provided herein.

In one aspect, the PDE target is selected from any one or more of the following PDE enzymes: $PDE_{cAMP}$ 1, $PDE_{cAMP}$ 2, $PDE_{cAMP}$ 3, $PDE_{cAMP}$ 4, $PDE_{cAMP}$ 7 and $PDE_{cAMP}$ 8.

In a more preferred aspect, the PDE target is selected from any one or more of the following PDE enzymes: $PDE_{cAMP}$ 1, $PDE_{cAMP}$ 2, $PDE_{cAMP}$ 3, and $PDE_{cAMP}$ 4.

Preferably, for the present invention, the PDE to target is at least PDE 2 (Sequence No. 3).

I:PDE

As indicated above, the agent may be any suitable agent that can act as an I:PDE.

Broad aspects of this aspect of the present invention therefore relate to:

a) A pharmaceutical composition for use (or when in use) in the treatment of FSD (preferably FSAD); the pharmaceutical composition comprising an agent; wherein the agent is optionally admixed with a pharmaceutically acceptable carrier, diluent or excipient; and wherein said agent is an I:PDE.

b) The use of an agent in the manufacture of a medicament (such as a pharmaceutical composition) for the treatment of FSD (preferably FSAD); wherein said agent is an I:PDE.

c) A method of treating a female suffering from FSD (preferably FSAD); the method comprising delivering to the female an agent; wherein the agent is optionally admixed with a pharmaceutically acceptable carrier, diluent or excipient; and wherein said agent is an I:PDE.

d) A pharmaceutical composition for use (or when in use) in enhancing genital (e.g. vaginal or clitoral) blood flow; the pharmaceutical composition comprising an agent; wherein the agent is optionally admixed with a pharmaceutically acceptable carrier, diluent or excipient; and wherein said agent is an I:PDE.

e) The use of an agent in the manufacture of a medicament (such as a pharmaceutical composition) for enhancing genital (e.g. vaginal or clitoral) blood flow; wherein the agent is an I:PDE.

f) A method of treating a female for FSD (preferably FSAD) or to prevent FSD (preferably FSAD); the method comprising delivering to the female an I:PDE.

Other aspects of the present invention encompass:

A) A pharmaceutical composition for use (or when in use) in the treatment of FSAD; the pharmaceutical composition comprising an agent capable of potentiating cAMP in the sexual genitalia of a female suffering from FSAD; wherein the agent is optionally admixed with a pharmaceutically acceptable carrier, diluent or excipient; and wherein said agent is an I:PDE.

B) The use of an agent in the manufacture of a medicament (such as a pharmaceutical composition) for the treatment of FSAD; wherein the agent is capable of potentiating cAMP in the sexual genitalia of a female suffering from FSAD, and wherein said agent is an I:PDE.

C) A method of treating a female suffering from FSAD; the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient; and wherein said agent is an I:PDE.

D) An assay method for identifying an agent that can be used to treat FSD, in particular FSAD, the assay method comprising: determining whether an agent can directly or indirectly potentiate cAMP; wherein a potentiation of cAMP in the presence of the agent is indicative that the agent may be useful in the treatment of FSD, in particular FSAD; and wherein said agent is an I:PDE.

E) A pharmaceutical composition for use (or when in use) in enhancing genital (e.g. vaginal or clitoral) blood flow; the pharmaceutical composition comprising an agent capable of enhancing cAMP signalling in the sexual genitalia of a female; wherein the agent is optionally admixed with a pharmaceutically acceptable carrier, diluent or excipient; and wherein said agent is an I:PDE.

F) The use of an agent in the manufacture of a medicament (such as a pharmaceutical composition) for enhancing genital (e.g. vaginal or clitoral) blood flow; wherein the agent is capable of enhancing cAMP signalling in the sexual genitalia of a female; and wherein said agent is an I:PDE.

G) A method of treating a female; the method comprising delivering to the female an agent that is capable of enhancing cAMP signalling in the sexual genitalia of the female so as to cause enhanced genital (e.g. vaginal or clitoral) blood flow; and wherein said agent is an I:PDE.

Examples of I:PDE are disclosed in EP-A-091133 and EP-A-0771799.

Preferably, the I:PDE is an I:PDE2. Thus, preferred example compounds are those presented in EP-A-0771799. For convenience, claim 1 of EP-A-0771799 is now repeated:

A purin-6-one derivative with general formula (I):

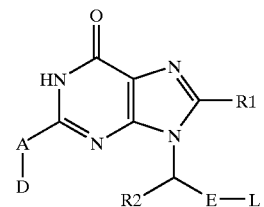

wherein:

| | |
|---|---|
| $R^1$ | represents hydrogen or a linear or branched alkyl containing up to 8 carbon atoms; |
| $R^2$ | represents a linear or branched acyl containing up to 4 carbon atoms, or a linear or branched alkyl containing up to 8 carbon atoms optionally substituted by hydroxyl, azido or a group with formula —$NR^3R^4$ or —$OSO_2R^5$; wherein |
| $R^3$ and $R^4$ | are identical or different and represent a cycloalkyl containing 3 to 6 carbon atoms, hydrogen, formyl, or a linear or branched alkyl containing up to 6 carbon atoms, optionally substituted by a linear or branched alkoxy or alkoxycarbonyl respectively containing up to 6 carbon atoms or by a group with formula —$(CO)_a$—$NR^6R^7$, wherein |
| a | is the number 0 or 1; |
| $R^6$ and $R^7$ | are identical or different and represent hydrogen, formyl, hydroxyl, phenyl or a linear or branched alkyl containing up to 6 carbon atoms, optionally substituted by hydroxyl or a linear or branched alkoxy containing up to 5 carbon atoms; or |
| $R^3$ and/or $R^4$ | represent a linear or branched alkoxycarbonyl containing up to 6 carbon atoms, carboxyl or a linear or branched acyl containing up to 6 carbon atoms optionally substituted by hydroxyl or a linear or branched alkoxy containing up to 4 carbon atoms; or |
| $R^3$ and/or $R^4$ | represent a residue with formula —$(CO)_b$—T—$NR^8R^9$, —$CO$—$R^{10}$, —$SO_2R^{11}$ or —$SO_2NR^{12}R^{13}$, wherein |
| b | has the meaning given above for a and is identical thereto or different therefrom; |
| T | can represent a linear or branched alkyl containing up to 5 carbon atoms, or when b ≠ 0 it can also represent a bond; |
| $R^8$ and $R^9$ | have the meaning given for $R^6$ and $R^7$ above and are identical thereto or different therefrom; |
| $R^{10}$ | represents a saturated, partially unsaturated or unsaturated 5- to 7-membered heterocycle containing up to 3 heteroatoms selected from S, N and/or O, which can optionally also be substituted on the N function by a linear or branched alkyl, alkoxy or alkoxycarbonyl containing up to 4 carbon atoms, carboxyl, benzyloxycarbonyl or hydroxyl; |
| $R^{11}$ | represents a linear or branched alkyl containing up to 5 carbon atoms, benzyl or phenyl; |
| $R^{12}$ and $R^{13}$ | are identical or different and represent hydrogen, phenyl or a linear or branched alkyl containing up to 6 carbon atoms; or |
| $R^3$ and $R^4$ | together with the nitrogen atom form a 5- or 6-membered saturated, partially unsaturated or unsaturated heterocycle which can contain up to 3 heteroatoms selected from N, S and/or O or a —$NR^{14}$ residue, and which is optionally substituted by carbonyl, a linear or branched alkoxycarbonyl containing up to 5 carbon atoms or a linear or branched alkyl containing up to 5 carbon atoms which in its turn can be substituted by hydroxyl, carboxy or a linear or branched acyl, alkoxy or alkoxycarbonyl respectively containing up to 6 carbon atoms; wherein |
| $R^{14}$ | represents hydrogen, carbonyl or a linear or branched alkyl or alkoxycarbonyl respectively containing up to 5 carbon atoms; and |
| $R^5$ | represents phenyl or a linear or branched alkyl containing up to 5 carbon atoms; |
| A | represents a linear or branched alkylene or alkenylene chain respectively containing up to 6 carbon atoms; |
| D and L | are identical or different and represent an aryl containing 6 to 10 carbon atoms or a 5- to 7-membered aromatic, optionally benzocondensed heterocycle containing up to 3 heteroatoms selected from S, N and/or O, optionally substituted up to 3 times, identically or differently, by a halogen, hydroxyl, nitro, |

-continued

A purin-6-one derivative with general formula (I):

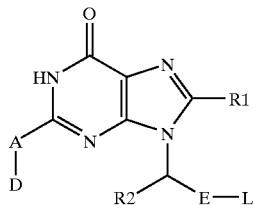

wherein:

| | |
|---|---|
| | trifluoromethyl, carboxy, a linear or branched alkyl, alkoxy or alkoxycarbonyl respectively containing up to 6 carbon atoms or by a group with formula —(V)$_c$—NR$^{15}$R$^{16}$ and/or —OR$^{17}$; wherein |
| c | is the number 0 or 1; |
| V | represents a residue with formula —CO or —SO$_2$; |
| R$^{15}$ and R$^{16}$ | are identical or different and have the meaning given for R$^3$ and R$^4$ above; |
| R$^{17}$ | represents hydrogen, a linear or branched alkenyl containing up to 8 carbon atoms or a linear or branched alkyl containing up to 8 carbon atoms, optionally substituted up to 3 times, identically or differently, with hydroxyl, carbonyl or linear or branched alkoxycarbonyl containing up to 5 carbon atoms; and/or the cycles are optionally substituted by an aryl containing 6 to 10 carbon atoms or by a 5- to 7-membered aromatic, optionally benzocondensed heterocycle containing up to 3 heteroatoms selected from S, N and/or O, which in its turn is optionally substituted up to two times, identically or differently, by a halogen, hydroxyl, nitro, carboxyl, trifluoromethyl or a linear or branched alkyl, alkoxy or alkoxycarbonyl respectively containing up to 5 carbon atoms or with a group with formula(V')$_d$—NR$^{18}$R$^{19}$; wherein |
| d | has the meaning given above for a and is identical thereto or different therefrom; |
| R$^{18}$ and R$^{19}$ | have the meaning given above for R$^3$ and R$^4$ and are identical thereto or different therefrom; |
| V' | has the meaning given above for V and is identical thereto or |

-continued

A purin-6-one derivative with general formula (I):

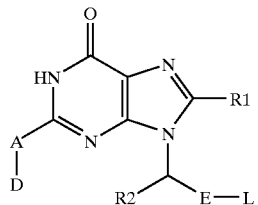

wherein:

| | |
|---|---|
| | different therefrom; and/or represents the ring system given below for D, optionally substituted by a linear or branched acyl containing up to 5 carbon atoms, optionally substituted by hydroxyl, a linear or branched alkoxy containing up to 5 carbon atoms or by a group with formula —NR$^{20}$R$^{21}$; wherein |
| R$^{20}$ and R$^{21}$ | are identical or different and have the meaning given above for R$^3$ and R$^4$; or |
| E | Represents a residue with formula —CH$_2$—Y—Z—; wherein |
| Y | Represents a bond or an oxygen or sulphur atom or the group —NH—; |
| Z | Represents a linear or branched alkyl chain containing up to 5 carbon atoms; |
| D | represents a residue with formula |

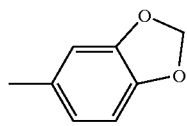

and tautomers and salts thereof.

Preferred I:PDEs are selected from the following structures:

| Compound | Structure | Mode of action References |
|---|---|---|
| FIa | 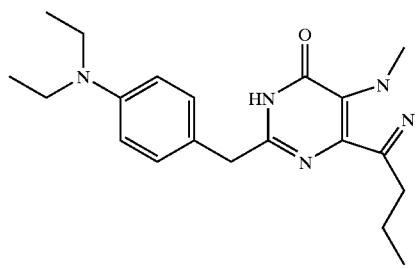 | I:PDE1 EP-A-0911333 (Example 50) |
| FIb | 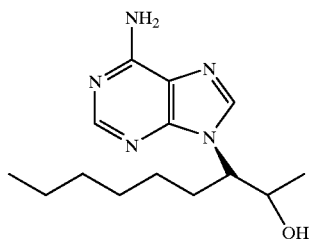 | I:PDE2 EHNA (also an inhibitor of Adenosinedeaminase) |

-continued

| Compound | Structure | Mode of action References |
|---|---|---|
| FII | 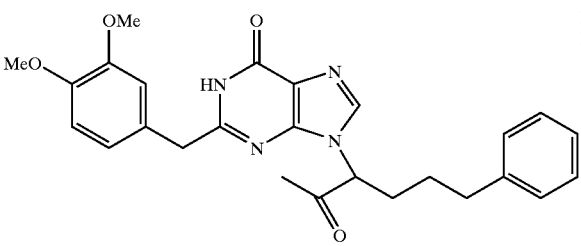 | I:PDE2<br>EP-A-0771799<br>(Example 100) |
| FIII | 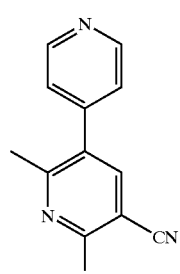 | I:PDE3<br>Milrinone<br>(which is commercially available) |
| FIV | 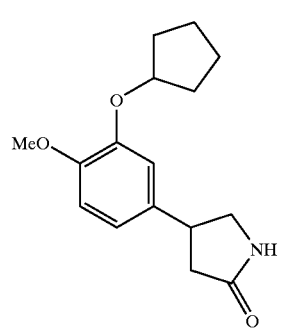 | I:PDE4<br>Rolipram<br>(which is commercially available) |

NEP (Neutral Endopeptidase)(Sequence No. 1)

According to one aspect of the present invention, a $P_{cAMP}$ target is NEP (Sequence No. 1).

Nucleotide sequences and amino acid sequences for NEP (Sequence No. 1) is available in the literature. Some sequences are presented in the Sequence Listings provided herein.

In one aspect, the NEP is NEP (EC 3.4.24.11; Sequence No. 1) (also known as enkephalinase or endopeptidase-2). Here, we have found NEP EC 3.4.24.11 (Sequence No. 1) mRNA and expressed protein in human and rabbit vagina.

Here, we believe that in females including those suffering from FSAD, VIP (Sequence No. 8) is degraded by NEP EC3.4.24.11 (Sequence No. 1). Thus, NEP inhibitors will potentiate the endogenous vasorelaxant effect of VIP (Sequence No. 8) released during arousal. This will lead to a treatment of FSAD, such as through enhanced vaginal engorgement. We have shown that selective inhibitors of NEP EC 3.4.24.11 (Sequence No. 1) enhance pelvic nerve-stimulated and VIP(Sequence No. 8)-induced increases in genital (e.g. vaginal or clitoral) blood flow. In addition that selective NEP inhibitors enhance VIP (Sequence No. 8) and nerve-mediated relaxations of isolated vagina wall.

Background teachings on NEP (Sequence No. 1) have been presented by Victor A. McKusick et al on http://www3.ncbi.nlm.nih.gov/Omim/searchomim.htm. The following information concerning NEP (Sequence No. 1) has been extracted from that source.

"Common acute lymphocytic leukemia antigen is an important cell surface marker in the diagnosis of human acute lymphocytic leukemia (ALL). It is present on leukemic cells of pre-B phenotype, which represent 85% of cases of ALL. CALLA is not restricted to leukemic cells, however, and is found on a variety of normal tissues. CALLA is a glycoprotein that is particularly abundant in kidney, where it is present on the brush border of proximal tubules and on glomerular epithelium. Letarte et al. (1988) cloned a cDNA coding for CALLA and showed that the amino acid sequence deduced from the cDNA sequence is identical to that of human membrane-associated neutral endopeptidase (NEP; EC 3.4.24.11), also known as enkephalinase. NEP cleaves peptides at the amino side of hydrophobic residues and inactivates several peptide hormones including glucagon, enkephalins, substance P, neurotensin, oxytocin, and bradykinin. By cDNA transfection analysis, Shipp et al. (1989) confirmed that CALLA is a functional neutral endopeptidase of the type that has previously been called enkephalinase. Barker et al. (1989) demonstrated that the CALLA gene, which encodes a 100-kD type II transmembrane glycoprotein, exists in a single copy of greater than 45 kb which is not rearranged in malignancies expressing cell surface CALLA. The gene was located to human chromosome 3 by study of somatic cell hybrids and in situ hybridization regionalized the location to 3q21–q27. Tran-Paterson et al. (1989) also assigned the gene to chromosome 3 by Southern blot analysis of DNA from human-rodent somatic cell hybrids. D'Adamio et al. (1989) demonstrated that the CALLA gene spans more than 80 kb and is composed of 24 exons."

I:NEP

As indicated above, the agent may be any suitable agent that can act as an I:NEP.

Broad aspects of this aspect of the present invention therefore relate to:

a) A pharmaceutical composition for use (or when in use) in the treatment of FSD (preferably FSAD); the pharmaceutical composition comprising an agent; wherein the agent is optionally admixed with a pharmaceutically acceptable carrier, diluent or excipient; and wherein said agent is an I:NEP.

b) The use of an agent in the manufacture of a medicament (such as a pharmaceutical composition) for the treatment of FSD (preferably FSAD); wherein said agent is an I:NEP.

c) A method of treating a female suffering from FSD (preferably FSAD); the method comprising delivering to the female an agent; wherein the agent is optionally admixed with a pharmaceutically acceptable carrier, diluent or excipient; and wherein said agent is an I:NEP.

d) A pharmaceutical composition for use (or when in use) in enhancing genital (e.g. vaginal or clitoral) blood flow; the pharmaceutical composition comprising an agent; wherein the agent is optionally admixed with a pharmaceutically acceptable carrier, diluent or excipient; and wherein said agent is an I:NEP.

e) The use of an agent in the manufacture of a medicament (such as a pharmaceutical composition) for enhancing genital (e.g. vaginal or clitoral) blood flow; wherein the agent is an I:NEP.

f) A method of treating a female for FSD (preferably FSAD) or to prevent FSD (preferably FSAD); the method comprising delivering to the female an I:NEP.

Other preferred aspects of the present invention encompass:

A) A pharmaceutical composition for use (or when in use) in the treatment of FSAD; the pharmaceutical composition comprising an agent capable of potentiating cAMP in the sexual genitalia of a female suffering from FSAD; wherein the agent is optionally admixed with a pharmaceutically acceptable carrier, diluent or excipient; and wherein said agent is an I:NEP.

B) The use of an agent in the manufacture of a medicament (such as a pharmaceutical composition) for the treatment of FSAD; wherein the agent is capable of potentiating cAMP in the sexual genitalia of a female suffering from FSAD, and wherein said agent is an I:NEP.

C) A method of treating a female suffering from FSAD; the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient; and wherein said agent is an I:NEP.

D) An assay method for identifying an agent that can be used to treat FSD, in particular FSAD, the assay method comprising: determining whether an agent can directly or indirectly potentiate cAMP; wherein a potentiation of cAMP in the presence of the agent is indicative that the agent may be useful in the treatment of FSD, in particular FSAD; and wherein said agent is an I:NEP.

E) A pharmaceutical composition for use (or when in use) in enhancing genital (e.g. vaginal or clitoral) blood flow; the pharmaceutical composition comprising an agent capable of enhancing cAMP signalling in the sexual genitalia of a female; wherein the agent is optionally admixed with a pharmaceutically acceptable carrier, diluent or excipient; and wherein said agent is an I:NEP.

F) The use of an agent in the manufacture of a medicament (such as a pharmaceutical composition) for enhancing genital (e.g. vaginal or clitoral) blood flow; wherein the agent is capable of enhancing cAMP signalling in the sexual genitalia of a female; and wherein said agent is an I:NEP.

G) A method of treating a female; the method comprising delivering to the female an agent that is capable of enhancing cAMP signalling in the sexual genitalia of the female so as to cause enhanced genital (e.g. vaginal or clitoral) blood flow; and wherein said agent is an I:NEP.

Details on a suitable assay system for identifying and/or studying an I:NEP are presented in the following section. I:NEPs are discussed in the following review articles:

Pathol. Biol., 46(3), 1998, 191.
Current Pharm. Design, 2(5), 1996, 443.
Biochem. Soc. Trans., 21(3), 1993, 678.
Handbook Exp. Pharmacol., 104/1, 1993, 547.
TIPS, 11, 1990, 245.
Pharmacol. Rev., 45(1), 1993, 87.
Curr. Opin. Inves. Drugs, 2(11), 1993, 1175.
Antihypertens. Drugs, (1997), 113.
Chemtracts, (1997), 10(11), 804.
Zinc Metalloproteases Health Dis. (1996), 105.
Cardiovasc. Drug Rev., (1996), 14(2), 166.
Gen. Pharmacol., (1996), 27(4), 581.
Cardiovasc. Drug Rev., (1994), 12(4), 271.
Clin. Exp. Pharmacol. Physiol., (1995), 22(1), 63.
Cardiovasc. Drug Rev., (1991), 9(3), 285.
Exp. Opin. Ther. Patents (1996), 6(11), 1147.

I:NEPs are disclosed in the following documents:

EP-509442A
U.S. Pat. No. 192,435
U.S. Pat. No. 492,9641
EP-599444B
U.S. Pat. No. 884,664
EP-544620A
U.S. Pat. No. 798,684
J. Med. Chem. 1993, 3821.
Circulation 1993, 88(4), 1.
EP-136883
JP-85136554

U.S. Pat. No. 4,722,810
Curr. Pharm. Design, 1996, 2, 443.
EP-640594
J. Med. Chem. 1993, 36(1), 87.
EP-738711-A
JP-270957
CAS # 115406-23-0
DE-19510566
DE-19638020
EP-830863
JP-98101565
EP-733642
WO9614293
JP-08245609
JP-96245609
WO9415908
JP05092948
WO-9309101
WO-9109840
EP-519738
EP-690070
J. Med. Chem. (1993), 36, 2420.
JP-95157459
Bioorg. Med. Chem. Letts., 1996, 6(1), 65.

Preferred I:NEPs are disclosed in the following documents:
EP-A-0274234
JP-88165353
Biochem.Biophys.Res. Comm.,1989, 164, 58
EP-629627-A
U.S. Pat. No. 77,978
Perspect. Med. Chem. (1993), 45.
EP-358398-B Preferred examples of I:NEPs are selected from the following structures:

| Compound | Structure | Mode of Action References |
|---|---|---|
| FXII | 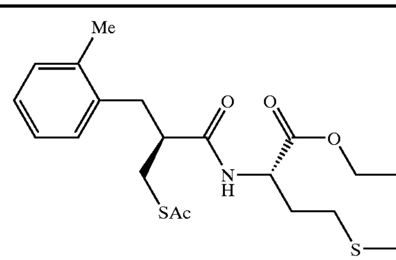 | I:NEP EP-509442A U.S. Pat. No. 192435 U.S. Pat. No. 4929641 |
| FXIII | 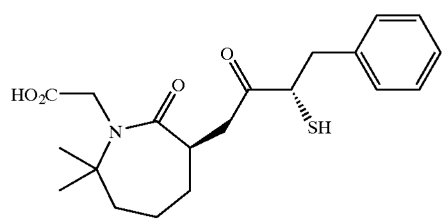 | I:NEP (also an ACE inhibitor) EP-599444B U.S. Pat. No. 884664 |
| FXIV | 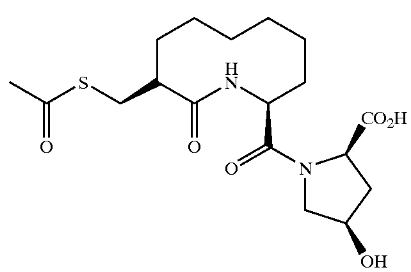 | I:NEP EP-544620A U.S. Pat. No. 798684 J. Med. Chem. 1993, 3821. |
| FXV | 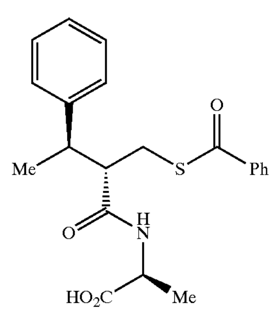 | I:NEP (also an ACE inhibitor) Mixanpril Circulation 1993, 88(4), 1. |

| Compound | Structure | Mode of Action References |
|---|---|---|
| FXVI | 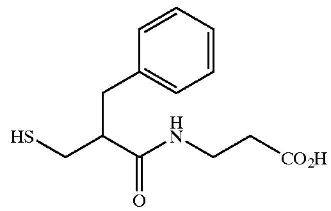 | I:NEP<br>EP-136883<br>JP-85136554<br>U.S. Pat. No. 4722810 |
| FXVII | 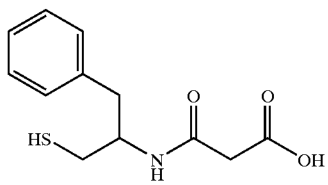 | I:NEP<br>Retrothiorphan<br>Curr. Pharm. Design, 1996, 2, 443. |
| FXVIII | 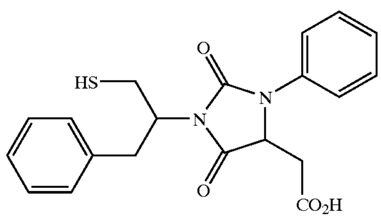 | I:NEP<br>(also an ACE inhibitor)<br>EP-640594 |
| FXIX | 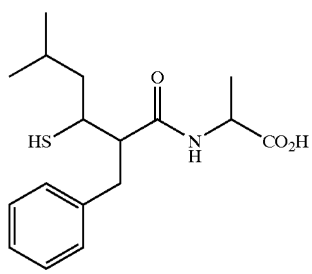 | I:NEP<br>J. Med. Chem.<br>1993, 36(1), 87. |
| FXX | 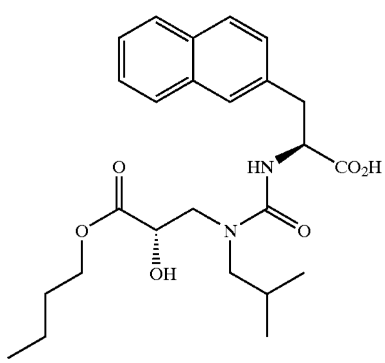 | I:NEP<br>(also an ACE inhibitor)<br>EP-738711-A<br>JP-2780957 |
| FXXI | 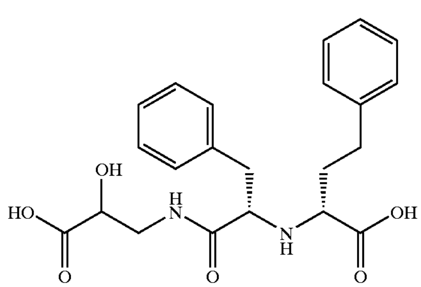 | I:NEP<br>CAS #<br>115406-23-0 |

-continued

| Compound | Structure | Mode of Action References |
|---|---|---|
| FXXII | 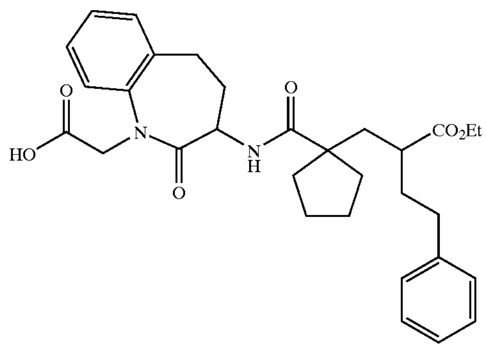 | I:NEP (also an ECE inhibitor) DE-19510566 DE-19638020 EP-830863 JP-98101565 |
| FXXIII | 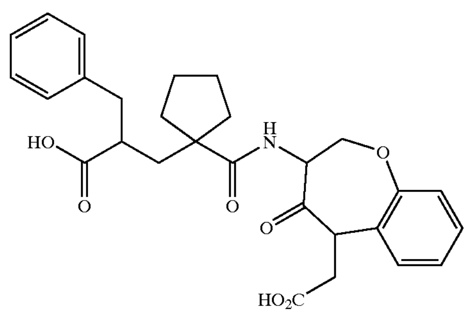 | I:NEP (also an ECE inhibitor) EP-733642 |
| FXXIV | 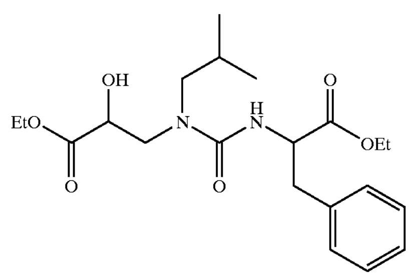 | I:NEP WO96/14293 |
| FXXV | 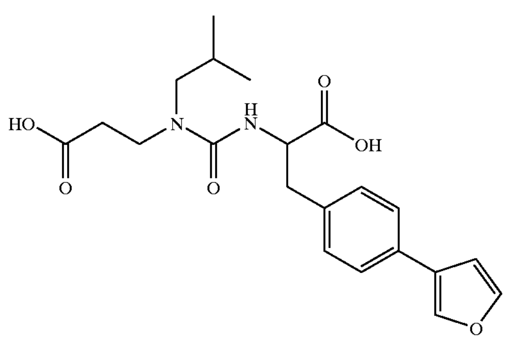 | I:NEP JP-08245609 JP-96245609 |
| FXXVI | 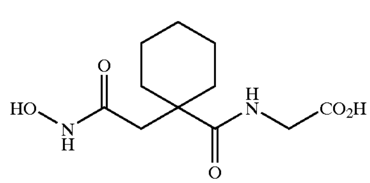 | I:NEP WO9415908 |

-continued

| Compound | Structure | Mode of Action References |
|---|---|---|
| FXXVII | 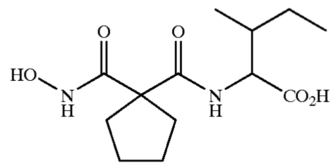 | I:NEP<br>JP05092948 |
| FXXVIII | 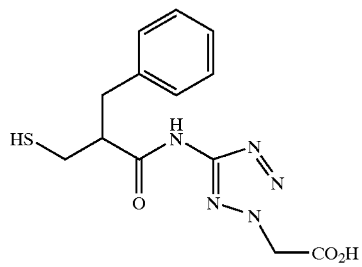 | I:NEP<br>WO-9309101 |
| FXXIX | 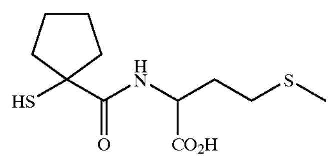 | I:NEP<br>WO-9109840 |
| FXXXI | 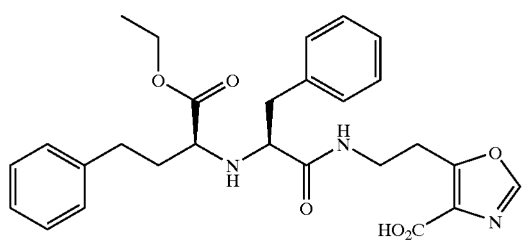 | I:NEP<br>EP-519738<br>EP-690070 |
| FXXXII | 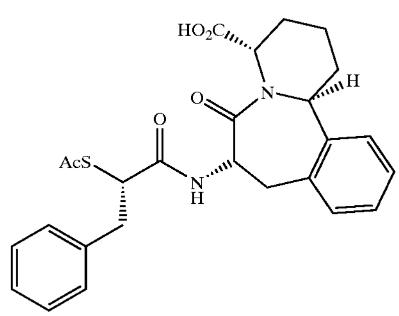 | I:NEP<br>(also an ACE inhibitor)<br>J. Med. Chem. (1993),<br>36, 2420. |
| FXXXIII | 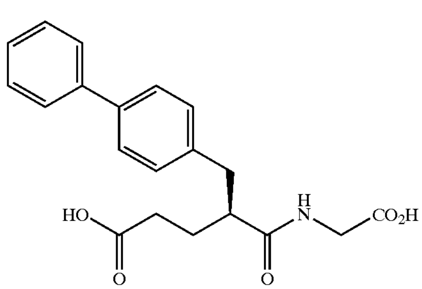 | I:NEP<br>JP-95157459<br>Bioorg. Med. Chem.<br>Letts., 1996, 6(1), 65. |

More preferred I:NEPs are selected from the following structures:

| Compound | Structure | Mode of Action References |
|---|---|---|
| FV | 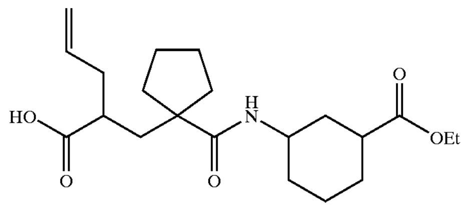 | I:NEP<br>EP-A-0274234<br>(Example 300) |
| FVI | 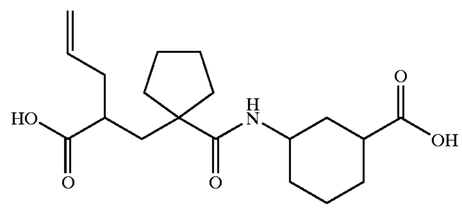 | I:NEP<br>EP-A-0274234<br>(Example 379) |
| FVII | 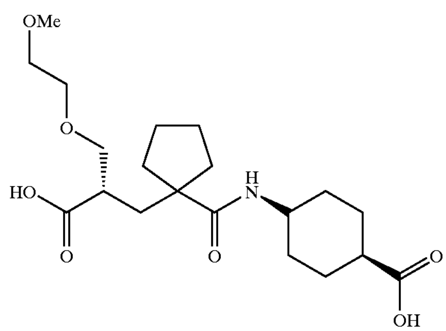 | I:NEP<br>Candoxatrilat<br>EP-274234<br>JP-88165353<br>Biochem. Biophys. Res. Comm., 1989, 164, 58 |
| FVIII | 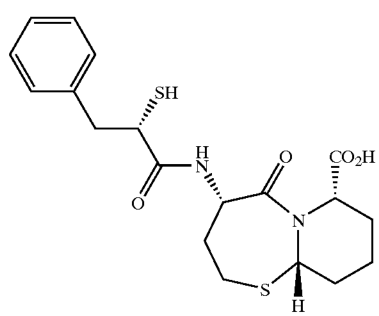 | I:NEP<br>Omapatrilat<br>(also an inhibitor of ACE)<br>EP-0629627-A<br>U.S. Pat. No. 77978 |
| FIX | 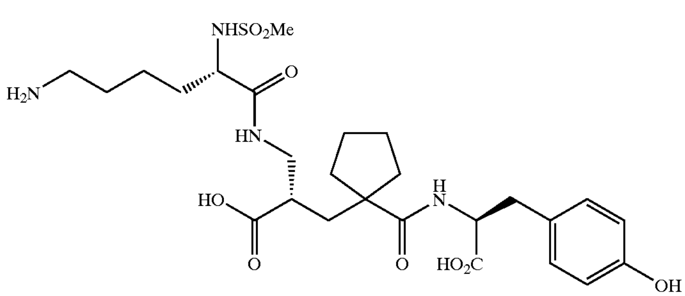 | I:NEP<br>Sampatrilat<br>(also an inhibitor of ACE)<br>Perspect. Med. Chem. (1993), 45.<br>EP-0358398-B |

-continued

| Compound | Structure | Mode of Action References |
|---|---|---|
| FX | 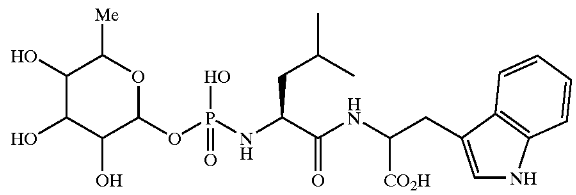 | I:NEP Phosphoramidon (which is commercially available) |
| FXI | 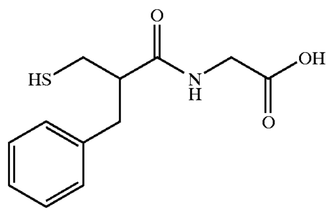 | I:NEP Thiorphan (which is commercially available) |

More preferred I:NEPs are selected from the following structures:

| COMPOUND | STRUCTURE |
|---|---|
| F57 | 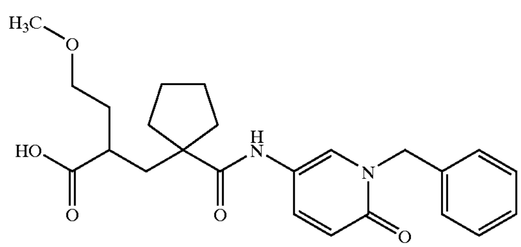 |
| F58 | 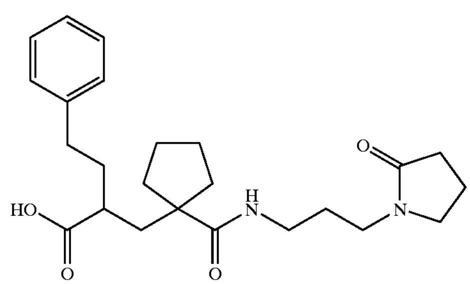 |
| F59 | 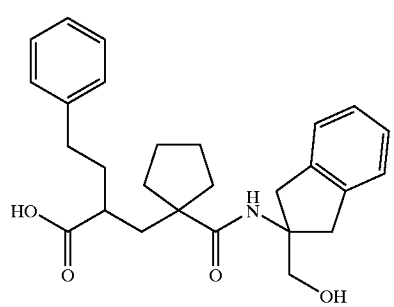 |

-continued

| COMPOUND | STRUCTURE |
| --- | --- |
| F60 | 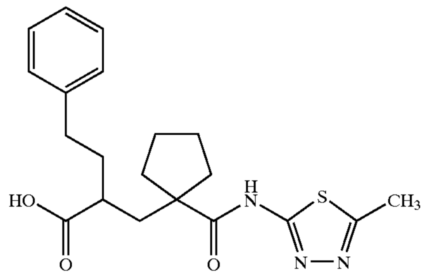 |
| F61 | 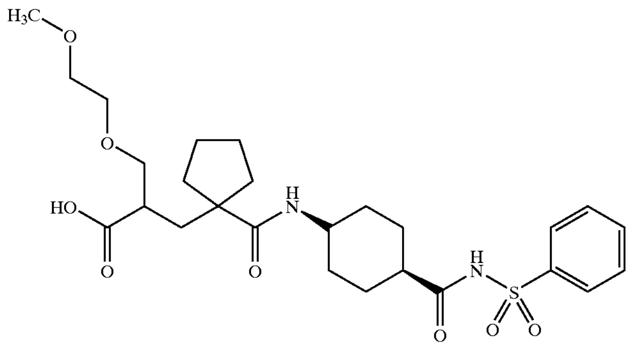 |
| F62 | 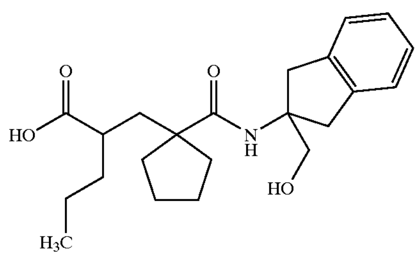 |
| F63 | 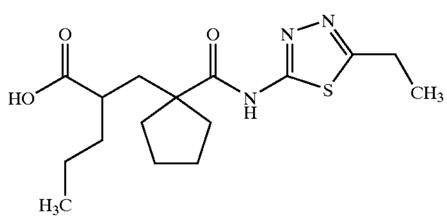 |
| F64 | 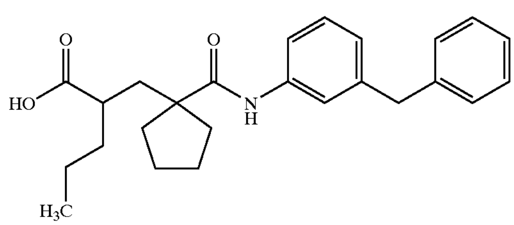 |
| F65 | 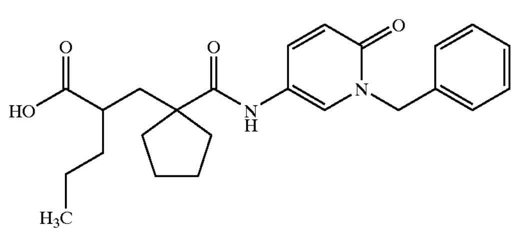 |

| COMPOUND | STRUCTURE |
|---|---|
| F66 | (Ic) |

These compounds were prepared according to the teachings presented in the Experimental section (infra). These compounds were tested as agents according to the present invention and were found to be useful in potentiating cAMP, and thereby being useful in the treatment of FSAD. Some of the experimental data concerning these compounds are presented in the Experimental section (infra).

NEP (Sequence No. 1) Assay

The Preparation and Assay of Souluble (NEP) Neutral Endopeptidase from Canine, Rat, Rabbit and Human Kidney Cortex Soluble NEP is obtained from the kidney cortex and activity is assayed by measuring the rate of cleavage of the NEP substrate Abz-D-Arg-Arg-Leu-EDDnp to generate its fluorescent product, Abz-D-Arg-Arg.

EXPERIMENTAL PROCEDURE

1. Materials
All water is double deionised.
1.1 Tissues
Human Kidney IIAM (Pennsylvania. U.S.A.)
Rat Kidney
Rabbit Kidney
Canine Kidney
1.2 Homogenisation medium
100 mM Mannitol and 20 mM Tris @ pH 7.1 2.42 g Tris (Fisher T/P630/60) is diluted in 1 liter of water and the pH adjusted to 7.1 using 6M HCl at room temperature. To this 18.22 g Mannitol (Sigma M-9546) is added.
1.3 Tris buffer (NEP buffer).
50 ml of 50 mM Tris pH 7.4 (Sigma T2663) is diluted in 950 ml of water.
1.4 Substrate (Abz-D-Arg-Arg-Leu-EDDnp)
Made to order from SNPE, and is stored as a powder at −20° C. A 2 mM stock is made by gently re-suspending the substrate in Tris buffer, this should not be vortexed or sonicated. 600 μl aliquots of the 2 mM stock are stored at −20 for up to one month. (Medeiros, M. A. S., Franca, M. S. F. et al., (1997), Brazilian Journal of Medical and Biological Research, 30, 1157–1162).
1.5 Total product
Samples corresponding to 100% substrate to product conversion are included on the plate to enable the % substrate turnover to be determined. The total product is generated by incubating 1 ml of 2 mM substrate with 20 μl of enzyme stock for 24 hours at 37° C.
1.6 Stop solution.
A 300 μM stock of Phosphoramidon (Sigma R7385) is made up in NEP buffer and stored in 50 μl aliquots at −20.
1.7 Dimethyl sulphoxide (DMSO).
1.8 Magnesium Chloride—$MgCl_2.6H_2O$ (Fisher M0600/53).
1.9 Black 96 well flat bottom assay plates (Costar 3915).
1.10 Topseal A (Packard 6005185).
1.11 Centrifuge tubes
2. Specific Equiptment
2.1 Sorvall RC-5B centrifuge (SS34 GSA rotor, pre-cooled to 4° C.).
2.2 Braun miniprimer mixer.
2.3 Beckman CS-6R centrifuge.
2.4 Fluostar galaxy.
2.5 Wesbart 1589 shaking incubator.
3. Methods
3.1 TISSUE PREPARATION
3.2 Dog, rat, rabbit, and human NEP is obtained from the kidney cortex using a method adapted from Booth, A. G. & Kenny, A. J. (1974) Biochem. J. 142, 575–581.
3.3 Frozen kidneys are allowed to thaw at room temperature and the cortex is dissected away from the medulla.
3.4 The cortex is finely chopped and homogenised in approximately 10 volumes of homogenisation buffer (1.2) using a Braun miniprimer (2.2).
3.5 Magnesium chloride (1.8) (20.3 mg/gm tissue) is added to the homogenate and stirred in an ice-water bath for 15 minutes.
3.6 The homogenate is centrifuged at 1,500 g (3,820 rpm) for 12 minutes in a Beckman centrifuge (2.3) before removing the supernatant to a fresh centrifuge tube and discarding the pellet.
3.7 The supernatant is centrifuged at 15,000 g (12,100 rpm) for 12 minutes in a Sovall centrifuge (2.1) and the supernatant is discarded.
3.8 The pale pink layer on the top of the remaining pellet is removed and re-suspended in homogenisation buffer containing magnesium chloride (9 mg MgCl in 5 ml buffer per 1 g tissue).
3.9 The suspension is centrifuged at 2,200 g (4,630 rpm) for 12 minutes in a Beckman centrifuge (2.3) before discarding the pellet.
3.10 The supernatant is centrifuged at 15,000 g (12,100 rpm) for 12 minutes using the Sorvall centrifuge (2.1) and the supernatant is discarded.
3.11 The final pellet is resuspended in homogenisation buffer containing magnesium chloride (0.9 mg MgCl in 0.5 ml buffer per 1 g tissue). A homogenous suspension is obtained using a Braun miniprimer (2.2). This is then frozen down in 100 μl aliquots to be assayed for NEP activity.
4.0 Determination of NEP (Sequence No. 1) Activity
The activity of the previously aliquoted NEP (Sequence No. 1) is measured by its ability to cleave the NEP (Sequence No. 1) specific peptide substrate.

4.1 A 4% DMSO/NEP buffer solution is made (4 mls DMSO in 96 mls NEP buffer).

4.2 Substrate, total product, enzyme, and Phosphoramidon stocks are left on ice to thaw.

4.3 50 μl of 4% DMSO/NEP buffer solution is added to each well.

4.4 The 2 mM substrate stock is diluted 1:40 to make a 50 μM solution. 100 μp of 50 μM substrate is added to each well (final concentration 25 μM). 4.5 50 μl of a range of enzyme dilutions is added to initiate the reaction (usually 1:100, 1:200, 1:400, 1:800, 1:1600, and 1:3200 are used). 50 μl of NEP buffer is added to blank wells.

4.6 The 2 mM total product is diluted 1:80 to make a 25 μM solution. 200 μl of 25 μM product is added to the first four wells of a new plate.

4.7 Plates are incubated at 37° C. in a shaking incubator for 60 minutes.

4.8 The 300 μM Phosphoramidon stock is diluted 1:100 to 300 nM. The reaction is stopped by the addition of 100 μl 300 nM Phosphoramidon and incubated at 37° C. in a shaking incubator for 20 minutes before being read on the Fluostar (ex320/em420).

5. NEP (Sequence No. 1) Inhibition Assays 5.1 Substrate, total product, enzyme and Phoshoramidon stocks are left on ice to thaw.

5.2 Compound stocks are made up in 100% DMSO and diluted 1:25 in NEP buffer to give a 4% DMSO solution. All further dilutions are carried out in a 4% DMSO solution (4 mls DMSO in 96 mls NEP buffer).

5.3 50 μl of compound in duplicate is added to the 96 well plate and 50 μl of 4% DMSO/NEP buffer is added to control and blank wells.

5.4 The 2 mM substrate stock is diluted 1:40 in NEP buffer to make a 50 μM solution (275 μl 2 mM substrate to 10.73 ml buffer is enough for 1 plate).

5.5 The enzyme stock diluted in NEP buffer (determined from activity checks).

5.6 The 2 mM total product stock is diluted 1:80 in NEP buffer to make a 25 μM solution. 200 μl is added to the first four wells of a separate plate.

5.7 The 300 μM Phosphoramidon stock is diluted 1:1000 to make a 300 nM stock (11 μl Phosphoramidon to 10.99 ml NEP buffer.

5.8 To each well in the 96 well plate the following is added:

Table Reagents to be added to 96 well plate.

|  | Compound/DMSO | Tris Buffer | Substrate | NEP enzyme | Total product |
|---|---|---|---|---|---|
| Samples | 2 μl compound | 50 μl | 100 μl | 50 μl | None |
| Blanks | 2 μl DMSO | 50 μl | 100 μl | 50 μl | None |
| Controls | 2 μl DMSO | 100 μl | 100 μl | None | None |
| Totals | 2 μl DMSO | None | None | None | 200 μl |

5.9 The reaction is initiated by the addition of the NEP enzyme before incubating at 37° C. for 1 hour in a shaking incubator.

5.10 The reaction is stopped with 100 μl 300 nM Phosphoramidon and incubated at 37° C. for 20 minutes in a shaking incubator before being read on the Fluostar (ex320/em420).

6. Calculations

The activity of the NEP enzyme is determined in the presence and absence of compound and expressed as a percentage.

% Control Activity (Turnover of Enzyme):

Mean FU of controls−Mean FU of blanks ×100/Mean FU of totals−Mean FU of blanks

% Activity with inhibitor:

Mean FU of compound−Mean FU of blanks ×100/Mean FU of totals−Mean FU of blanks

Activity expressed as % of control:

$$\frac{\% \text{ Activity with inhibitor}}{\% \text{ Control activity}} \times 100$$

A sigmoidal dose-response curve is fitted to the % activities (% of control) vs compound concentration and IC50 values calculated using LabStats fit-curve in Excel.

NPY (Neuropeptide Y; Sequence No. 4)

According to one aspect of the present invention, a $P_{cAMP}$ target is NPY (Sequence No. 4) or one of its associated receptors.

Nucleotide sequences and amino acid sequences for NPY (Sequence No. 4) and its receptors are available in the literature. Some sequences are presented in the Sequence Listings provided herein.

Here, we have found that neuropeptide Y (NPY; Sequence No. 4) exerts an inhibitory regulatory influence over vasoactive intestinal peptide (VIP)(Sequence No. 8)-mediated vasorelaxation. Thus, inhibition of NPY (Sequence No. 4) receptors will result in an increased pelvic nerve and VIP (Sequence No. 8)-mediated increases in genital (e.g. vaginal or clitoral) blood flow. Clinically this will lead to increased vaginal and/or clitoral engorgement which will ultimately lead to increased lubrication via plasma transudation and increased vaginal compliance. Hence, a suitable target for the treatment of FSAD is NPY (Sequence No. 4) or one of its associated receptors.

Thus, in one preferred aspect, the agent is an NPY $Y_1$ $Y_2$ or $Y_5$ antagonist, preferably an oral NPY $Y_1$ $Y_2$ or $Y_5$ antagonist. This agent will treat FSAD by increasing genital (e.g. vaginal or clitoral) blood flow and increasing lubrication.

The NPY(Sequence No. 4)-mediated antagonism of VIP (Sequence No. 8)-induced increases in blood flow therefore represents a potential therapeutic target by which blood flow in the female genital tract can be influenced. The mechanism through which this antagonism occurs is most likely through NPY $Y_1$ receptor(Sequence No. 5)-induced $G_{i/o}$ activation. In other physiological systems NPY $Y_1$ receptors (Sequence No. 5) have been implicated in mediating vasoconstriction and inhibiting sympathetic transmitter release (Lundberg et al., 1996; a NPY $Y_2$ (Sequence No. 6) effect can not be excluded). We believe in the female genital tract that NPY (Sequence No. 4) inhibits vasorelaxation via direct inhibition of adenylate cyclase direct inhibiting VIP (Sequence No. 8) release or sympathetic neurotransmission.

As indicated, a $P_{cAMP}$ target is one of the NPY receptors.

The neuronal release of NPY (Sequence No. 4) regulates the VIP(Sequence No. 8)-induced vasorelaxation of the vaginal vascular bed. This most likely occurs via a presynaptic mechanism involving NPY $Y_1$ receptors (Sequence No. 5), although a post-synaptic mode of action can not be excluded. An NPY antagonist will potentiate VIP(Sequence No. 8)-induced vasodilation of the vaginal vascular beds.

Clinically this will lead to increased vaginal lubrication and compliance via vaginal wall engorgement.

NPY (Sequence No. 4) receptor expression studies performed by us have identified NPY $Y_1$ $Y_2$ and $Y_5$ receptor subtypes (Sequence Nos. 5, 6, and 7 respectively) within the human vagina.

Hence, in one aspect, the $P_{cAMP}$ target is one or more of the NPY $Y_1$ $Y_2$ and $Y_5$ receptor subtypes (Sequence Nos. 5, 6 and 7 respectively).

Background teachings on NPY (Sequence No. 4) and it associated receptors have been prepared by Victor A. McKusick et al on http://www3.ncbi.nlm.nih.gov/Omim/searchomim.htm. The following text concerning NPY (Sequence No. 4) has been extracted from that source.

"Neuropeptide Y (NPY) is an abundant and widespread peptide in the mammalian nervous system. It shows sequence homology to peptide YY and over 50% homology in amino acid and nucleotide sequence to pancreatic polypeptide (PNP; 167780). NPY is a 36-amino acid peptide. Minth et al. (1984) cloned the NPY gene starting from mRNA of a pheochromocytoma. Takeuchi et al. (1985, 1986) isolated cDNA clones of the NPY and PNP genes from a pheochromocytoma and a pancreatic endocrine tumor, respectively. Using these cDNA probes to analyze genomic DNA from chromosome assignment panels of human-mouse somatic cell hybrids, they then examined the question of whether the genes are syntenic. The studies showed nonsynteny, with NPY on 7pter–7q22 and PNP on 17p11.1–17qter. By studies of a backcross with Mus spretus, Bahary et al. (1991) mapped the homologous NPY gene to mouse chromosome 6. Since mouse chromosome 6 has homology to human 7q, it is likely that the NPY gene in man is located in the region 7cen–q22. Meisler et al. (1987) excluded close linkage between the loci for cystic fibrosis (219700) and neuropeptide Y. Terenghi et al. (1987) determined the distribution of mRNA encoding NPY in neurons of the cerebral cortex in surgical biopsy specimens and postmortem brain by means of in situ hybridization techniques. They showed consistent localization of NPY gene transcription and expression in normal mature cortical neurons. Baker et al. (1995) showed by fluorescence in situ hybridization that the NPY gene is located on 7p15.1 and exists in single copy. They commented that NPY is one of the most highly conserved peptides known, with, for example, only 3 amino acid differences between human and shark. Neuropeptide Y is a neuromodulator implicated in the control of energy balance and is overproduced in the hypothalamus of ob/ob mice. To determine the role of NPY in the response to leptin (164160) deficiency, Erickson et al. (1996) generated ob/ob mice deficient in NPY. In the absence of NPY, ob/ob mice were less obese because of reduced food intake and increased energy expenditure, and were less severely affected by diabetes, sterility, and somatotropic defects. These results were interpreted as indicating that NPY is a central effector of leptin deficiency. Genetic linkage analysis of rats that were selectively bred for alcohol preference identified a chromosomal region that included the NPY gene (Carr et al., 1998). Alcohol-preferring rats had lower levels of NPY in several brain regions compared with alcohol-nonpreferring rats. Thiele et al. (1998) therefore studied alcohol consumption by mice that completely lacked NPY as a result of targeted gene disruption (Erickson et al., 1996). They found that NPY-deficient mice showed increased consumption, compared with wildtype mice, of solutions containing 6%, 10%, and 20% (by volume) ethanol. NPY-deficient mice were also less sensitive to the sedative/hypnotic effects of ethanol, as shown by more rapid recovery from ethanol-induced sleep, even though plasma ethanol concentrations did not differ significantly from those of controls. In contrast, transgenic mice that overexpressed a labeled NPY gene in neurons that usually express it had a lower preference for ethanol and were more sensitive to the sedative/hypnotic effects of ethanol than controls. These data provided direct evidence that alcohol consumption and resistance are inversely related to NPY levels in the brain. As part of an on-going study of the genetic basis of obesity, Karvonen et al. (1998) identified a 1128T-C polymorphism that resulted in substitution of leucine by proline at residue 7 in the signal peptide part of pre-pro-NPY. This polymorphism was not associated with obesity or energy metabolism, but was significantly and consistently associated with high serum total and LDL cholesterol levels both in normal-weight and obese Finns and in obese Dutch subjects. Uusitupa et al. (1998) found the pro7 polymorphism in 14%of Finns but in only 6% of Dutchmen. Subjects with pro7 in NPY had, on average, 0.6 to 1.4 mmol/L higher serum total cholesterol levels than those without this gene variant. As the impact of pro7 NPY on serum cholesterol levels could not be found in normal-weight Dutchmen, it can be assumed that obese persons may be more susceptible to the effect of the gene variant. It was calculated that the probability of having the pro7 in NPY could be as high as 50 to 60% in obese subjects with a total serum cholesterol equal to or higher than 8 mmol/L. At least among Finns, the pro7 form of NPY is one of the strongest genetic factors affecting serum cholesterol levels. SEE ALSO Allen and Bloom (1986); Dockray (1986); Maccarrone and Jarrott (1986); Minth et al. (1986)."

As indicated background teachings on NPY (Sequence No. 4) and it associated receptors have been prepared by Victor A. McKusick et al (ibid). The following text concerning NPYR1 (Sequence No. 5) has been extracted from that source.

"Neuropeptide Y (NPY; 162640) is one of the most abundant neuropeptides in the mammalian nervous system and exhibits a diverse range of important physiologic activities, including effects on psychomotor activity, food intake, regulation of central endocrine secretion, and potent vasoactive effects on the cardiovascular system. Two major subtypes of NPY (Y1 and Y2) have been defined by pharmacologic criteria. The NPY Y1 receptors have been identified in a variety of tissues, including brain, spleen, small intestine, kidney, testis, placenta, and aortic smooth muscle. The Y2 receptor is found mainly in the central nervous system. Herzog et al. (1992) reported cloning of a cDNA encoding a human NPY receptor which they confirmed to be a member of the G protein-coupled receptor superfamily. When expressed in Chinese hamster ovary (CHO) or human embryonic kidney cells, the receptor exhibited characteristic ligand specificity. In the kidney cell line, the receptor was coupled to a pertussis toxin-sensitive G protein that mediated the inhibition of cyclic cAMP accumulation. In the CHO cell line, on the other hand, the receptor was coupled not to inhibition of adenylate cyclase but rather to the elevation of intracellular calcium. Thus the second messenger coupling of the NPY receptor was cell type specific, depending on the specific repertoire of G proteins and effector systems present in the cell type. Larhammar et al. (1992) independently cloned and characterized the neuropeptide Y receptor. Herzog et al. (1993) determined the molecular organization and regulation of the human NPY Y1 receptor gene. In contrast to the contiguous structure of most G protein-coupled receptor genes, they found that the NPY Y1 receptor gene has 3 exons. They also identified a common PstI polymorphism in the first intron of the gene. By high resolution fluorescence in situ hybridization, they localized the gene to 4q31.3–q32. Herzog et al. (1997) found that the NPY1R and NPY5R (602001) genes are colocalized on chromosome 4q31–q32. The 2 genes are transcribed in opposite directions from a common promoter region. One of the alternately spliced 5-prime exons of the Y1 receptor gene is a part of the coding sequence of the Y5 receptor. This unusual arrangement suggested to Herzog et al. (1997) that the 2 genes arose by a gene duplication event and that they may be coordinately expressed. By interspecific backcross analysis, Lutz et al. (1997) mapped the Npy1r and Npy2r genes to conserved linkage groups on mouse chromosomes 8 and 3, respectively, which correspond to the distal region of human chromosome 4q."

As indicated background teachings on NPY (Sequence No. 4) and it associated receptors has been prepared by Victor A. McKusick et al (ibid). The following text concerning NPYR2 (Sequence No. 6) has been extracted from that source.

"Neuropeptide Y (NPY) signals through a family of G protein-coupled receptors present in the brain and sympathetic neurons. At least 3 types of neuropeptide Y receptor have been defined on the basis of pharmacologic criteria, tissue distribution, and structure of the encoding gene; see 162641 and 162643. Rose et al. (1995) reported the expression cloning in COS cells of a cDNA for the human type 2 receptor, NPY2R. Transfected cells showed high affinity for NPY (162640), peptide YY (PYY; 600781), and a fragment of NPY including amino acids 13 to 36. The predicted 381-amino acid protein has 7 transmembrane domains characteristic of G protein-coupled receptors and is only 31% identical to the human Y1 receptor (NPY1 R; 162641). A 4-kb mRNA was detected on Northern blots of tissue samples from several regions of the nervous system. Gerald et al. (1995) cloned the cDNA corresponding to the human Y2 receptor from a human hippocampal cDNA expression library using a radiolabeled PYY-binding assay. They expressed the Y2 gene in COS-7 cells and performed a hormone-binding assay which showed that the Y2 receptor binds (from highest to lowest affinity) PYY, NPY, and pancreatic polypeptide (PP; 167780) hormones. Ammar et al. (1996) cloned and characterized the human gene encoding the type 2 NPY receptor. The transcript spans 9 kb of genomic sequence and is encoded in 2 exons. As in the type 1 NPY receptor gene, the 5-prime untranslated region of NPY2R is interrupted by a 4.5-kb intervening sequence. Ammar et al. (1996) demonstrated by Southern analysis of rodent-human cell hybrids followed by fluorescence in situ hybridization (FISH) that the NPY2R gene maps to 4q31, the same region containing the NPY1R gene, suggesting that these subtypes may have arisen by gene duplication despite their structural differences. By interspecific backcross analysis, Lutz et al. (1 997) mapped the Npy1r and Npy2r genes to conserved linkage groups on mouse chromosomes 8 and 3, respectively, which correspond to the distal region of human chromosome 4q."

An assay for determining whether a putative or actual agent according to the present invention can bind to NPY (Sequence No. 4) is presented in WO-A-98/52890 (see page 96 thereof, lines 2 to 28).

I:NPY

As indicated above, the agent may be any suitable agent that can act as an I:NPY (sometimes referred to as an NPY antagonist).

Broad aspects of this aspect of the present invention therefore relate to:

a) A pharmaceutical composition for use (or when in use) in the treatment of FSD (preferably FSAD); the pharmaceutical composition comprising an agent; wherein the agent is optionally admixed with a pharmaceutically acceptable carrier, diluent or excipient; and wherein said agent is an I:NPY.

b) The use of an agent in the manufacture of a medicament (such as a pharmaceutical composition) for the treatment of FSD (preferably FSAD); wherein said agent is an I:NPY.

c) A method of treating a female suffering from FSD (preferably FSAD); the method comprising delivering to the female an agent; wherein the agent is optionally admixed with a pharmaceutically acceptable carrier, diluent or excipient; and wherein said agent is an I:NPY.

d) A pharmaceutical composition for use (or when in use) in enhancing genital (e.g. vaginal or clitoral) blood flow; the pharmaceutical composition comprising an agent; wherein the agent is optionally admixed with a pharmaceutically acceptable carrier, diluent or excipient; and wherein said agent is an I:NPY.

e) The use of an agent in the manufacture of a medicament (such as a pharmaceutical composition) for enhancing genital (e.g. vaginal or clitoral) blood flow; wherein the agent is an I:NPY.

f) A method of treating a female for FSD (preferably FSAD) or to prevent FSD (preferably FSAD); the method comprising delivering to the female an I:NPY.

Other aspects of the present invention encompass:

A) A pharmaceutical composition for use (or when in use) in the treatment of FSAD; the pharmaceutical composition comprising an agent capable of potentiating cAMP in the sexual genitalia of a female suffering from FSAD; wherein the agent is optionally admixed with a pharmaceutically acceptable carrier, diluent or excipient; and wherein said agent is an I:NPY.

B) The use of an agent in the manufacture of a medicament (such as a pharmaceutical composition) for the treatment of FSAD; wherein the agent is capable of potentiating cAMP in the sexual genitalia of a female suffering from FSAD, and wherein said agent is an I:NPY.

C) A method of treating a female suffering from FSAD; the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient; and wherein said agent is an I:NPY.

D) An assay method for identifying an agent that can be used to treat FSD, in particular FSAD, the assay method comprising: determining whether an agent can directly or indirectly potentiate cAMP; wherein a potentiation of cAMP in the presence of the agent is indicative that the agent may be useful in the treatment of FSD, in particular FSAD; and wherein said agent is an I:NPY.

E) A pharmaceutical composition for use (or when in use) in enhancing genital (e.g. vaginal or clitoral) blood flow; the pharmaceutical composition comprising an agent capable of enhancing cAMP signalling in the sexual genitalia of a female; wherein the agent is optionally admixed with a pharmaceutically acceptable carrier, diluent or excipient; and wherein said agent is an I:NPY.

F) The use of an agent in the manufacture of a medicament (such as a pharmaceutical composition) for enhancing genital (e.g. vaginal or clitoral) blood flow; wherein the agent is capable of enhancing cAMP signalling in the sexual genitalia of a female; and wherein said agent is an I:NPY.

G) A method of treating a female; the method comprising delivering to the female an agent that is capable of enhancing cAMP signalling in the sexual genitalia of the female so as to cause enhanced genital (e.g. vaginal or clitoral) blood flow; and wherein said agent is an I:NPY.

I:NPYs (in particular NPY antagonists) are discussed in the following review articles:

Dunlop J, Rosenzweig-Lipson S: Therapeutic approaches to obestity Exp Opin Ther Pat 1999 8 12 1683–1694

Wang S, Ferguson K C, Burris T P, Dhurandhar N V: 8th annual international conference on obesity and-non-insulin dependent diabetes mellitus: novel drug developments. Exp Opin Invest Drugs 1999 8 7 1117–1125

Ling A L: Neuropeptide Y receptor antagonists Exp Opin Ther Pat 1999 9 4 375–384 Adham N, Tamm J, Du P, Hou C, et al: Identification of residues involved in the binding of the antagonist SNAP 6608 to the Y5 receptor Soc Neurosci Abstr 1998 24 part 2 626.9

Shu Y Z, Cutrone J Q, Klohr S E, Huang S: BMS-192548, a tetracyclic binding inhibitor of neuropeptide Y receptors, from Aspergillus niger WB2346. II. Physicochemical properties and structural characterization J Antibiot 1995 48 10 1060–1065

Rigollier P, Rueger H, Whitebread S, Yamaguchi Y, Chiesi M, Schilling W, Criscione L: Synthesis and SAR of CGP 71683A, a potent and selective antagonist of the neuropeptide Y Y5 receptor. Int Symp Med Chem 1998 15th Edinburgh 239

Criscione L, Rigollier P, Batzl-Hartmann C, Rueger H, Stricker-Krongrad A, et al: Food intake in free-feeding and energy-deprived lean rats is mediated by the neuropeptide Y5 receptor. J Clin Invest 1998 102 12 2136–2145

Neurogen Corp: NGD 95-1 Clin Trials Monitor 1996 5 10 Ab 19244

Buttle L A: Anti-obesity drugs: on target for huge market sales. Exp Opin Invest Drugs 1996 5 12 1583–1587

Gehlert D R, Hipskind P A: Neuropeptide Y receptor antagonists in obesity. Exp Opin Invest Drugs 1996 7 9 1827–1838

Goldstein D J, Trautmann M E: Treatments for obesity. Emerging Drugs 1997 2-1–27

Hipskind P A, Lobb K L, Nixon J A, Britton T C, Bruns R F, Catlow J, Dieckman McGinty D K, Gackenheimer S L, Gitter B D, Iyengar S, Schober D A, et al. : Potent and selective 1,2,3-trisubstituted indole NPY Y-1 antagonists. J Med Chem 1997 40 3712–3714

Zimmerman D M, Cantrall B E, Smith E C R, Nixon J A, Bruns R F, Gitter B, Hipskind P A, Ornstein P L, Zarrinmayeh H, Britton T C, Schober D A, Gehlert D R: Structure-activity relationships of a series of 1-substituted-4-methylbenzimidazole neuropeptide Y-1 receptor antagonists Bioorganic Med Chem Lett 1998 8 5 473–476

Zarrinmayeh H, Nunes A, Omstein P, Zimmerman D, Arnold M B, et al : Synthesis and evaluation of a series of novel 2-[(4-chlorophenoxy)methy]benzimidazoles as selectiveneuropeptide Y Y1 receptor antagonists J Med Chem 1998 41 15 2709–2719

Britton T C, Spinazze P G, Hipskind P A, Zimmerman D M, Zarrinmayeh H, Schober D A, Gehlert D R, Bruns R F: Structure-activity relationships of a series of benzothiophene-dervied NPY-Y1 antagonists: optimization of the C2 side chain Bioorganic Med Chem Lett 1999 9 3 475–480

Zarrinmayeh H, Zimmerman D M, Cantrell B E, Schober D A, Bruns R F, Gackenheimer S L, Omstein P L, Hipskind P A, Britton T C, Gehlert D R: Structure-activity relationship of a series of diaminoalkyl substituted benzimidazole as neuropeptide Y Y1 receptor antagonists Bioorganic Med Chem Lett 1999 9 5 647–652

Murakami Y, Hara H, Okada T, Hashizume H, Kii M, Ishihara Y, Ishikawa M, Mihara S-I, Kato G, Hanasaki K, Hagishita S, Fujimoto M: 1,3-disubstituted benzazepines as novel, potent, selective neurpeptide Y Y1 receptor antagonists J Med Chem 1999 42 14 2621–2632

Rudolf K, Eberlein W, Engel W, Wieland H A, Willim K D, Entzeroth M, Wienen W, Beck Sickinger A G, Doods H N: The first highly potent and selective non-peptide neuropeptide YY1 receptor antagonist: BIBP3226 Eur J Pharmacol 1994 271 2–3 R11–R13

Wieland H A, Willim K D, Entzeroth M, Wienen W, Rudolf K, Eberlein W, Engel W, Doods H N: Subtype selectivity and antagonbist profile of the nonpeptide neuropeptide Y1 receptor antagonist BIBP 3226 J Pharmacol Exp Ther 1995 275 1 143–149.

Wright J, Bolton G, Creswell M, Downing D, Georgic L, Heffner T, Hodges J, MacKenzie R, Wise L: 8-amino-6-(arylsulphonyl)-5-nitroquinolones: novel nonpeptide neuropeptide Y1 receptor antagonists Bioorganic Med Chem Lett 1996 6 15 1809–1814

Capurro D, Huidobro-Toro J P: The involvement of neyropeptide Y Y1 receptors in the blood pressure baroreflex:studies with BIBP 3226 and BIB 3304. Eur J Pharmacol 1999 376 3 251–255

Dumont Y, Cadieux A, Doods H, Quirion R: New tools to investigate neuropeptide Y receptors in the central and peripheral nervous systems: BIBO-3304 (Y1), BIIE-246 (Y2) and [125I]-GR-231118 (Y1/Y4). Soc Neurosci Abstr 1999 25 Part 1 Abs 74.11

Hegde S S, Bonhaus D W, Stanley W, Eglen R M, Moy T M, Loeb M, et al: Pharmacological evaluation of 1229U91, a high affinity and selective neuropeptide Y(NPY)-Y1 receptor antagonist Pharmacol Res 1995 31 190

Matthews J E, Chance W T, Grizzle M K, Heyer D, Daniels A J: Food intake inhibition and body weight loss in rats treated with GI 264879A, an NPY-Y1 receptor. Soc Neurosci Abstr 1997 23 Pt 2 1346

Doods H N, Willim K-D, Smith S J: BIBP 3226: a selective and highly potent NPY-Y1 antagonist Proc Br Pharmacol Soc 1994 13–16 Dec. C47

Rudolf K, Eberlein W, Engel W, Wieland H A, Willim K D, Entzeroth M, Wienen W, Beck Sickinger A G, Doods H N: The first highly potent and selective non-peptide neuropeptide YY1 receptor antagonist: BIBP3226 Eur J Pharmacol 1994 271 2–3 R11–R13

Serradelil-Le-Gal C, Valette G, Rouby P E, Pellet A, Villanova G, Foulon L, Lespy L, Neliat G, Chambon J P, Maffrand J P, Le-Fur G: SR 120107A and SR 120819A: Two potent and selective, orally-effective antagonists for NPY Y1 receptors Soc Neurosci Abstr 1994 20 Pt 1 907 -Abs 376.14

Hong Y, Gregor V, Ling A L, Tompkins E V, Porter J, Chou T S, Paderes G, Peng Z, Hagaman C, Anderes K, Luthin D, May J: Synthesis and biological evaluation of novel guanylurea compounds as potent NPY Y1 receptor antagonist Acs 1999 217 Anaheim MEDI 108

I:NPYs (in particular NPY antagonists) are disclosed in the following documents:

WO-98/07420
WO-94/00486
WO-96/22305
WO-97/20821
WO-97/20822
WO-96/14307
JP-07267988
WO-96/12489
U.S. Pat. No. 5,552,422
WO-98/35957
WO-96/14307
WO-94/17035
EP-0614911
WO-98/40356
EP-0448765
EP-0747356
WO-98/35941
WO-97/46250
EP-0747357

Preferred examples of I:NPYs are selected from the following structures. These compounds were tested as agents according to the present invention and were found to be useful in potentiating cAMP, and thereby being useful in the treatment of FSAD. Some of the experimental data concerning these compounds are presented in the Experimental section (infra).

| Compound | Structure | Mode of Action References |
|---|---|---|
| F34 | 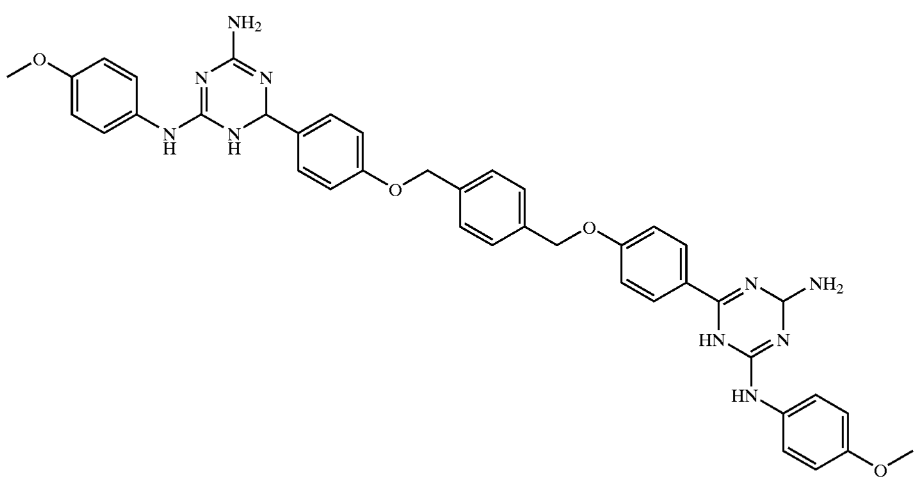 | I:NPY Y1 WO-98/07420 Ref 3 |
| F35 | 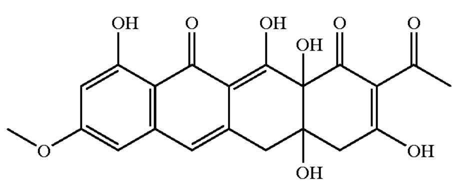 | I:NPY Ref 5 |
| F36 | 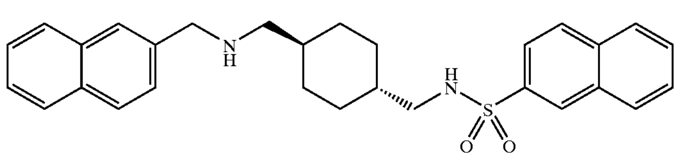 | I:NPY Y5 Ref 1, 4 |

-continued

| Compound | Structure | Mode of Action References |
|---|---|---|
| F37 | Ile-Cys-Pro-Cys-Tyr-Arg-Leu-Arg-Tyr-NH2 cyclic (2,2'), (4,4')-disulfide dimer | I:PNY Y1<br>WO-94/00486<br>WO-96/22305<br>Ref 1, 2, 23 |
| F38 | 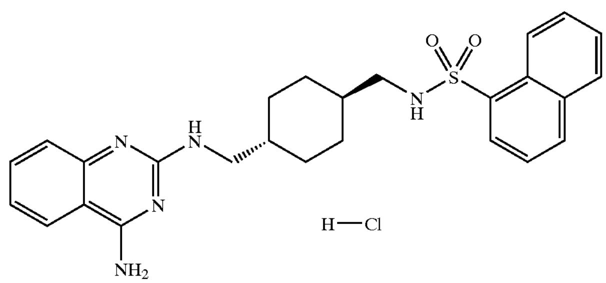 | I:NPY Y5<br>WO-97/20821<br>WO-97/20822<br>Ref 1, 3, 6, 7 |
| F39 | 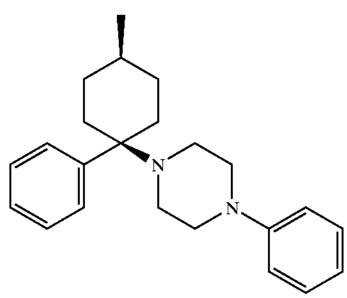 | I:NPY Y1<br>WO-96/14307<br>Ref 1, 8, 9, 10, 11 |
| F40 | 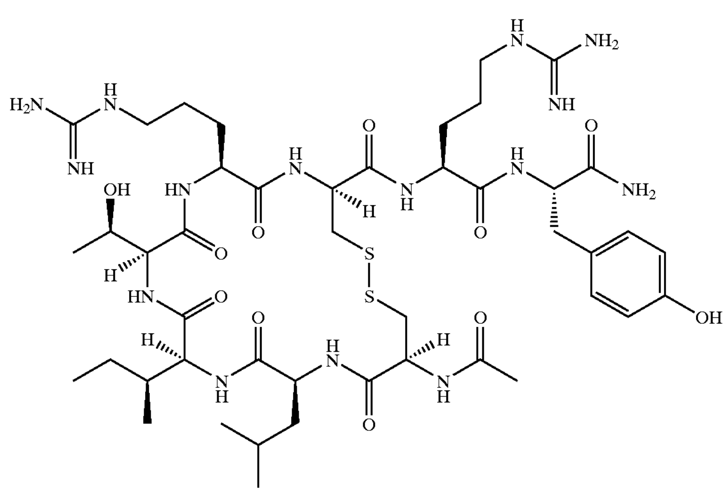 | I:NPY Y1<br>JP-07267988<br>Ref 1 |
| F41 | 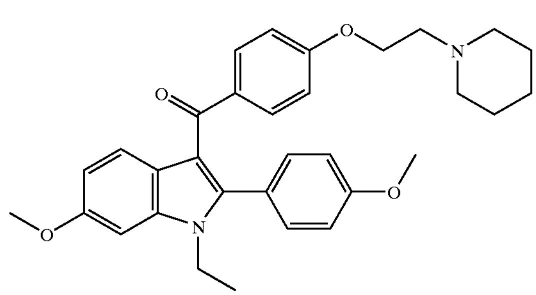 | I:NPY Y1<br>WO-96.12489<br>Ref 3, 12, 13, 14, 15, 16, 17 |

-continued

| Compound | Structure | Mode of Action References |
|---|---|---|
| F42 | 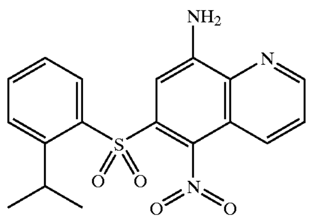 | I:NPY Y1<br>U.S. Pat. No. 5552422<br>Ref 17, 18, 19, 20 |
| F43 | 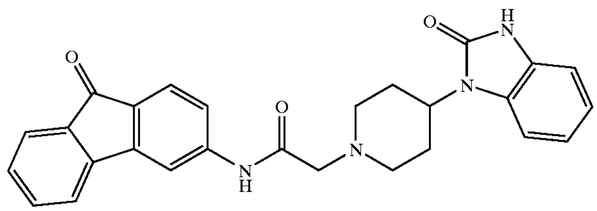 | I:NPY Y5<br>WO-98/35957<br>Ref 3 |
| F44 | Chiral | I:NPY Y1<br>Ref 21, 22 |
| F45 | 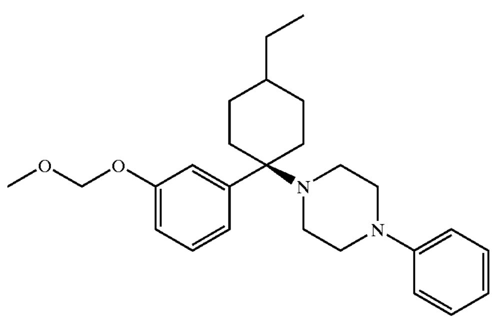 | I:NPY Y1<br>WO-96/14307<br>Ref 3 |
| F46 | For formula, see reference | I:NPY Y1<br>Ref 24 |
| F47a | Chiral | I:NPY Y1<br>WO-94/17035<br>Ref 3, 17, 25, 26 |

-continued

| Compound | Structure | Mode of Action References |
|---|---|---|
| F47b | For formula, see reference | I:NPY Y1<br>Ref 3, 12, 13, 14, 15, 16, 17 |
| F48 | 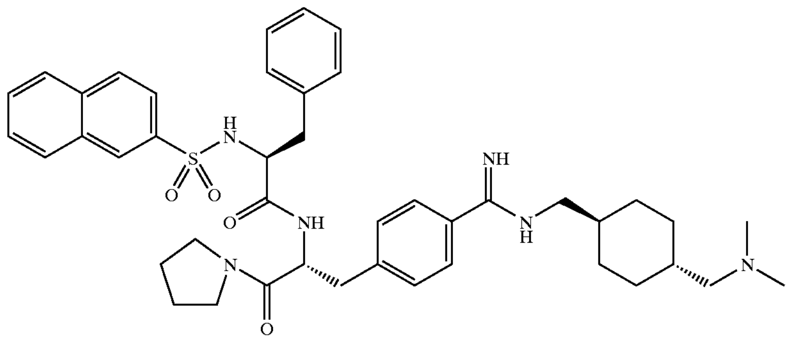 | I:NPY Y1<br>EP-0614911<br>Ref 27 |
| F49 | 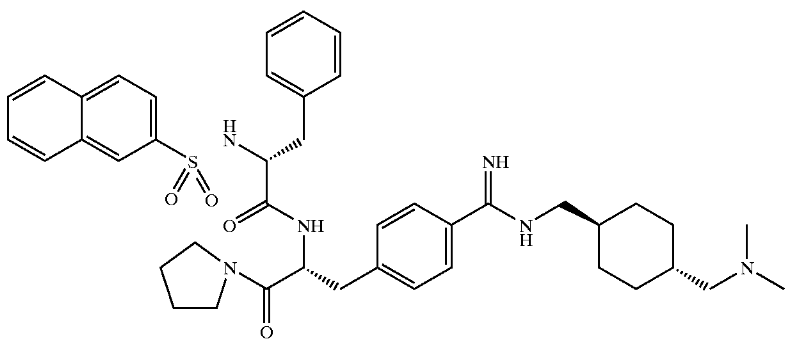 | I:NPY Y1<br>EP-0614911<br>Ref 27 |
| F50 | 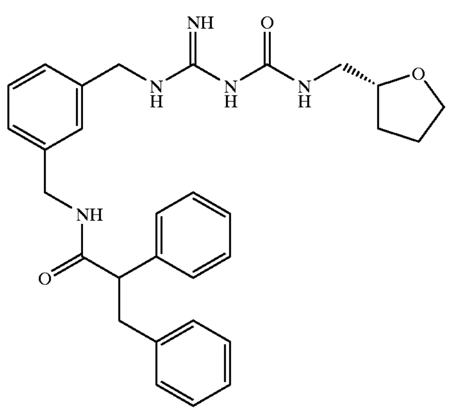 | I:NPY Y1<br>Ref 28 |
| F51 | 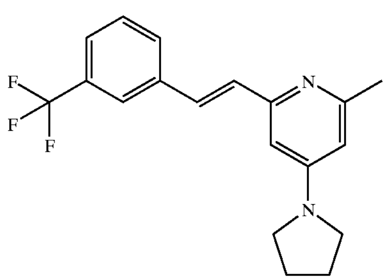 | I:NPY Y5<br>WO-98/40356 |

-continued

| Compound | Structure | Mode of Action References |
|---|---|---|
| F52 | 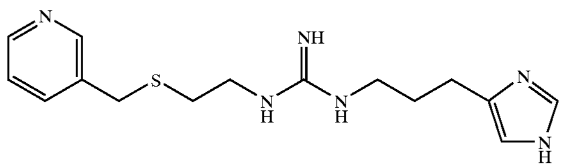 | I:NPY<br>EP-0448765 |
| F53 | 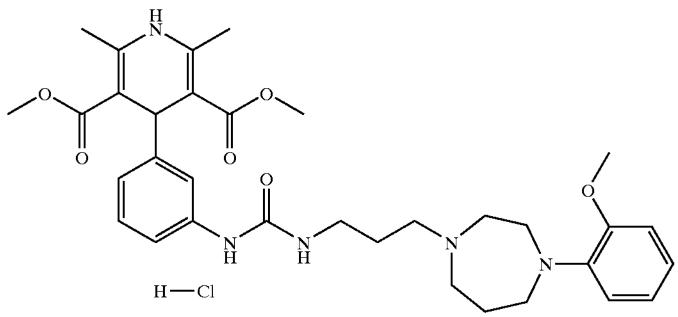 | I:NPY Y1<br>EP-0747356 |
| F54 | 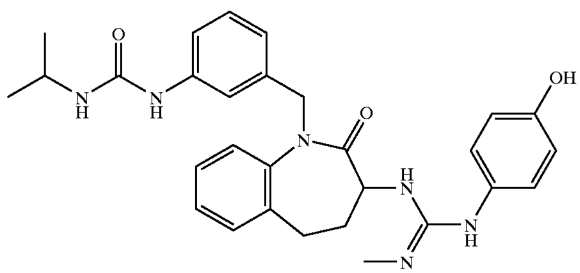 | I:NPY Y1<br>WO-98/35941 |
| F55 | 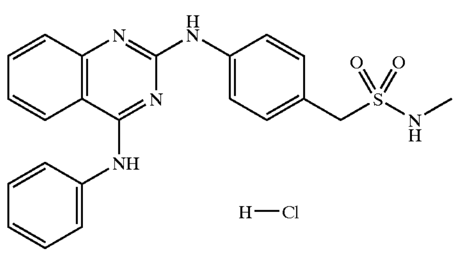 | I:NPY Y5<br>WO-97/46250 |
| F56 | 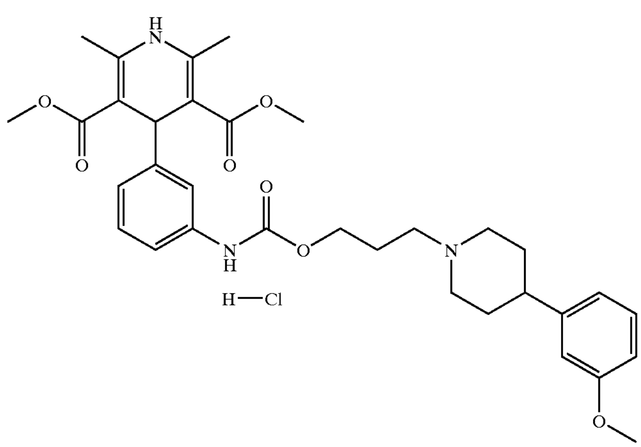 | I:NPY Y1<br>EP-0747357 |

VIP (Vasoactive Intestinal Peptide: Sequence No. 8)

According to one aspect of the present invention, a $P_{cAMP}$ target is VIP (Sequence No. 8) or one of its associated receptors. Current classification/nomenclature refers to these as VPAC1 (Sequence No. 9), VPAC2 (Sequence No. 10) and PACAP.

Nucleotide sequences and amino acid sequences for VIP (Sequence No. 8) and its receptors are available in the literature. Some sequences are presented in the Sequence Listings provided herein.

We have shown that VPAC1 (Sequence No. 9) and VPAC2 (Sequence No. 10) are present in human and rabbit vagina. PACAP was absent from both rabbit and human vagina.

VIP (Sequence No. 8) is a major endogenous neurotransmitter released during sexual arousal that is responsible for nerve-induced vaginal vasodilation of the vascular beds located in the vaginal wall. These vasodilatory effects are mediated by adenylate cyclase activation and cAMP production. Without wishing to be bound by theory, this effect may be mediated via VIP receptor subtypes $VPAC_1$ (Sequence No. 9), $VPAC_2$ (Sequence No. 10) or PACAP (pituitary adenylate cyclase-activating peptide) receptors. $VPAC_2$ (Sequence No. 10) and PACAP receptors are most widely expressed in the CNS and the receptors despite being expressed in the pituitary, appears to have no widespread biological function.

The agent of the present invention could potentiate VIP (Sequence No. 8) and/or act as a VIP (Sequence No. 8) mimetic or analogue thereof. The agent would then potentiate and/or mimic the vasorelaxant effects of endogenous VIP (Sequence No. 8) released during sexual arousal. The agent may also have an additive effect on VIP(Sequence No. 8)-induced relaxations of vaginal smooth muscle. Clinically this will lead to FSAD treatment, though increased vaginal lubrication via vaginal wall engorgement and compliance. In this embodiment, the mimetic or analogue would not have, however, the adverse properties of VIP (Sequence No. 8) as discussed supra.

Background teachings on VIP (Sequence No. 8) and it associated receptors are presented by Victor A. McKusick et al on http://www3.ncbi.nlm.nih.gov/Omim/searchomim.htm. The following text concerning VIP (Sequence No. 8) has been extracted from that source.

"Vasoactive intestinal peptide (VIP), a 28-amino acid peptide originally isolated from porcine duodenum, is present not only in gastrointestinal tissues but also in neural tissues, possibly as a neurotransmitter, and exhibits a wide variety of biological actions. Because VIP shows similarities to glucagon, secretin and gastric inhibitory peptide (GIP), it has been considered a member of the glucagon-secretin family. The primary translation product of the mRNA encoding VIP (prepro-VIP) has a molecular weight of 20 daltons. By cloning the DNA sequence complementary to the mRNA coding for human VIP, Itoh et al. (1983) found that the VIP precursor contains not only VIP but also a novel peptide of 27 amino acids, designated PHM27, that has aminoterminal histidine and carboxyterminal methionine. It differs from PHI17 isolated from porcine intestine by 2 amino acids; PH127, as its designation indicates, has carboxyterminal isoleucine. Linder et al. (1987) isolated the human gene for VIP and PHM27 and studied its expression in various tissues of the rat. Heinz-Erian et al. (1985) suggested that deficient innovation of sweat glands of cystic fibrosis patients by the VIP neuropeptide might be a basic mechanism for the decreased water content and relative impermeability of the epithelium to chloride and other ions that characterize cystic fibrosis. To test this hypothesis, Gozes et al. (1987) took the 'candidate gene' approach. Bodner et al. (1985) had shown that VIP (Sequence No. 8) and PHM-27 are encoded by adjacent exons. Gozes et al. (1987) used the PHM-27-encoding genomic fragment to detect the presence of the VIP gene at 6q21-qter. Thus, they eliminated a defective VIP gene as a candidate for the primary cause of cystic fibrosis (which is coded by chromosome 7). By in situ hybridization techniques, Gozes et al. (1987) assigned the VIP gene to 6q24. This placed VIP in the region of MYB (189990), which has been mapped to 6q22. Gozes et al. (1987) investigated a functional relationship between the 2 genes in neuronal tissue. They observed a sharp peak of MYB mRNA in the hippocampus of 3-day-old rats, preceding the peak of VIP mRNA that occurs in this area at 8 days of age. Omary and Kagnoff (1987) found nuclear receptors for VIP in a human colonic adenocarcinoma cell line. Gotoh et al. (1988) assigned VIP to chromosome 6 by spot blot hybridization of a molecularly cloned fragment of the gene to sorted chromosomes. The localization was refined to 6q26–q27 by in situ hybridization."

As indicated, background teachings on VIP (Sequence No. 8) and it associated receptors are presented by Victor A. McKusick et al (ibid). The following text concerning VIPRL or VPAC1 (Sequence No. 9) has been extracted from that source.

"Vasoactive intestinal peptide (VIP; 192320; Sequence No. 8) is an octacosameric neuroendocrine mediator found predominantly in cholinergic presynaptic neurons of the central nervous system and in peripheral peptidergic neurons innervating diverse tissues. Of the many neuroendocrine peptides with immunologic functions, VIP is distinguished by its capacity to affect both B and T cells directly. Distinct subsets of neural, respiratory, gastrointestinal, and immune cells bear specific high-affinity receptors for VIP, which are associated with a guanine nucleotide-binding (G) protein capable of activating adenylate cyclase. Libert et al. (1991) obtained 4 new receptors of the G protein-coupled receptor family by selective amplification and cloning from thyroid cDNA. One of these, termed RDC1, was identified as the VIP receptor by Sreedharan et al. (1991). Libert et al. (1991) mapped the VIPR gene to 2q37 by in situ hybridization. Later information made it doubtful that the gene mapped to 2q37 was in fact the VIP receptor gene (Vassart, 1992). The sequence that was designated GPRN1 by Sreedharan et al. (1991) and mapped to 2q37 was found not to bind VIP by Wenger (1993). Sreedharan et al. (1995) isolated an authentic type I VIP receptor gene and by fluorescence in situ hybridization localized it to the 3p22 band in a region associated with small-cell lung cancer. By interspecific backcross analysis, Hashimoto et al. (1999) mapped the mouse Viprl gene to the distal region of chromosome 9, a region that shows homology of synteny with human chromosome 3p. Sreedharan et al. (1993) cloned a human intestinal VIP receptor gene; the deduced amino acid sequence shares 84% identity with the rat lung VIP receptor. Couvineau et al. (1994) isolated 2 VIPR cDNA clones from a human jejunal epithelial cell cDNA library. One encodes a VIP receptor ;consisting of 460 amino acids and having 7 putative transmembrane domains, as do other G protein-coupled receptors. The other encodes a 495-amino acid VIP receptor-related protein exhibiting 100% homology with the functional VIP receptor over the 428 amino acids at the C-terminal region, but containing a completely divergent 67-amino acid N-terminal domain. When expressed in COS-7 cells, the second protein did not bind radioiodinated VIP, although it was normally addressed at the plasma membrane as assessed by immunofluorescence studies. The type I VIP receptor, also termed type II PACAP receptor (see 102981 for another type of PACAP receptor), was found by Sreedharan et al. (1995) to span approximately 22 kb and to be comprised of 13 exons (ranging from 42 to 1,400 bp) and 12 introns (ranging from 0.3 to 6.1 kb). Sreedharan et al. (1995) also characterized the promoter and the 5-prime flanking region of the gene."

As indicated, background teachings on VIP (Sequence No. 8) and it associated receptors are presented by Victor A. McKusick et al (ibid). The following text concerning VIPR2 or VPAC2 (Sequence No. 10) has been extracted from that source.

"Vasoactive intestinal peptide (VIP; 192320) and pituitary adenylate cyclase activating polypeptide (PACAP; 102980) are homologous peptides that function as neurotransmitters and neuroendocrine hormones. While the receptors for VIP and PACAP share homology, they differ in their substrate specificities and expression patterns. See VIPRL (192321) and ADCYAP1R1(102981). Svoboda et al. (1994) performed low stringency PCR using primers based on sequences conserved among VIP receptors. They cloned the human VIP2 receptor gene from a lymphoblast cDNA library. This gene encoded a 438-amino acid polypeptide that shares 86% identity with the rat VIP2 receptor. They expressed the human VIP2 receptor in Chinese hamster ovary cells and found that it binds to PACAP-38, PACAP-27, VIP (Sequence No. 8), and helodermin, and that binding of the receptor to any of these peptides activates adenylate cyclase. Peptide binding was found to be inhibited by GTP. Adamou et al. (1995) cloned the VIP2 receptor gene from a human placenta cDNA library. Northern blotting revealed that VIPR2 is expressed as 2 transcripts of 4.6 kb and 2.3 kb at high levels in skeletal muscle and at lower levels in heart, brain, placenta, and pancreas. Mackay et al. (1996) used fluorescence in situ hybridization to map the VIPR2 gene to human chromosome 7q36.3. Further mapping with cell lines derived from patients with holoprosencephaly type 3 (HPE3; 142945) revealed that the VIPR2 gene lies within the HPE3 minimal critical region. Mackay et al. (1996) stated that although VIPR2 may contribute to the HPE3 phenotype, it is not the sole factor responsible."

AC (Adenylate Cyclase)

According to one aspect of the present invention, a $P_{cAMP}$ target is AC.

Nucleotide sequences and amino acid sequences for AC are available in the literature.

To confirm that VIP (Sequence No. 8) induces vasorelaxation via elevation of intracellular cAMP levels and consequent activation of adenylate cyclase we have measured vaginal cAMP concentrations during VIP (Sequence No. 8) stimulation and used forskolin, an adenylate cyclase activator, to mimic the effects of activating the cAMP/adenylate cyclase pathway.

In these studies, we found that VIP (Sequence No. 8) treatment and forskolin treatment elevate intracellular concentrations cAMP in isolated vaginal tissue.

We also found that forskolin increases vaginal blood flow in an animal model of sexual arousal.

Additionally we found that forskolin induces relaxation in isolated vagina.

Background teachings on AC are presented by Victor A. McKusick et al on http://www3.ncbi.nlm.nih.gov/Omim/searchomim.htm. The following text concerning AC has been extracted from that source.

"Adenylyl cyclase (EC 4.6.1.1) catalyzes the transformation of ATP into cyclic cAMP. The enzymatic activity is under the control of several hormones, and different polypeptides participate in the transduction of the signal from the receptor to the catalytic moiety. Stimulatory or inhibitory receptors (Rs and Ri) interact with G proteins (Gs and Gi) that exhibit GTPase activity and they modulate the activity of the catalytic subunit of the adenylyl cyclase. Parma et al. (1991) cloned a cDNA corresponding to human brain adenylyl cyclase, symbolized by them as HBAC1. By in situ hybridization to metaphase chromosomal spreads using the human brain cDNA probe, Stengel et al. (1992) showed that the gene is located on 8q24.2. A highly homologous gene, ADCY2 (103071), was assigned to 5p15.3 by the same method."

General Recombinant DNA Methodology Techniques

Although in general the techniques mentioned herein are well known in the art, reference may be made in particular to Sambrook et al., Molecular Cloning, A Laboratory Manual (1989) and Ausubel et al., Short Protocols in Molecular Biology (1999) $4^{th}$ Ed, John Wiley & Sons, Inc. PCR is described in U.S. Pat. No. 4,683,195, U.S. Pat. No. 4,800,195 and U.S. Pat. No. 4,965,188.

EXAMPLES

Figure 3:
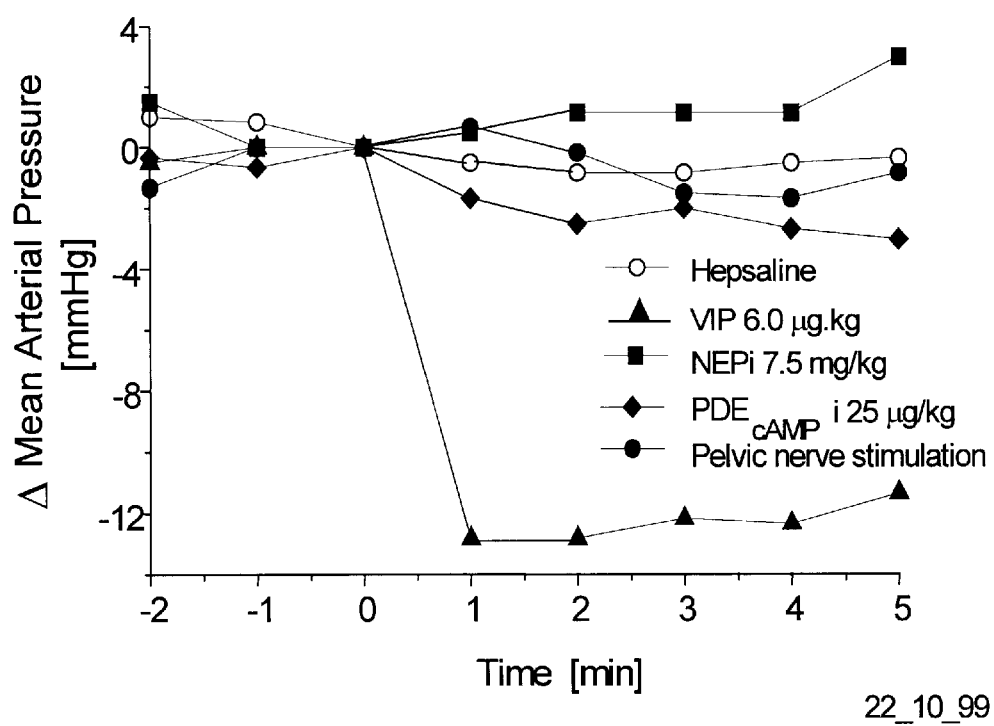
FIG. 3:—Vasoactive intestinal peptide (VIP; Sequence No. 8) reduces the mean arterial blood pressure in the anaesthetised rabbit model of sexual arousal. This graph illustrates the typical effects of the vasoactive agents and stimulation parameters used to investigate vagina blood flow on mean arterial pressure in an anaesthetised rabbit. These observed effects are typical of the trends seen in all animals tested. VIP (Sequence No. 8) induced a significant depression of mean arterial pressure whereas pelvic nerve stimulation, control infusions of Hepsaline or inhibitors of $PDE_{cAMP}$ or NEP (Sequence No. 1) have no effect on blood pressure. Note, the reduction in blood pressure associated with VIP (Sequence No. 8) infusions is also associated with a large increase in heart rate.
Figure 5:
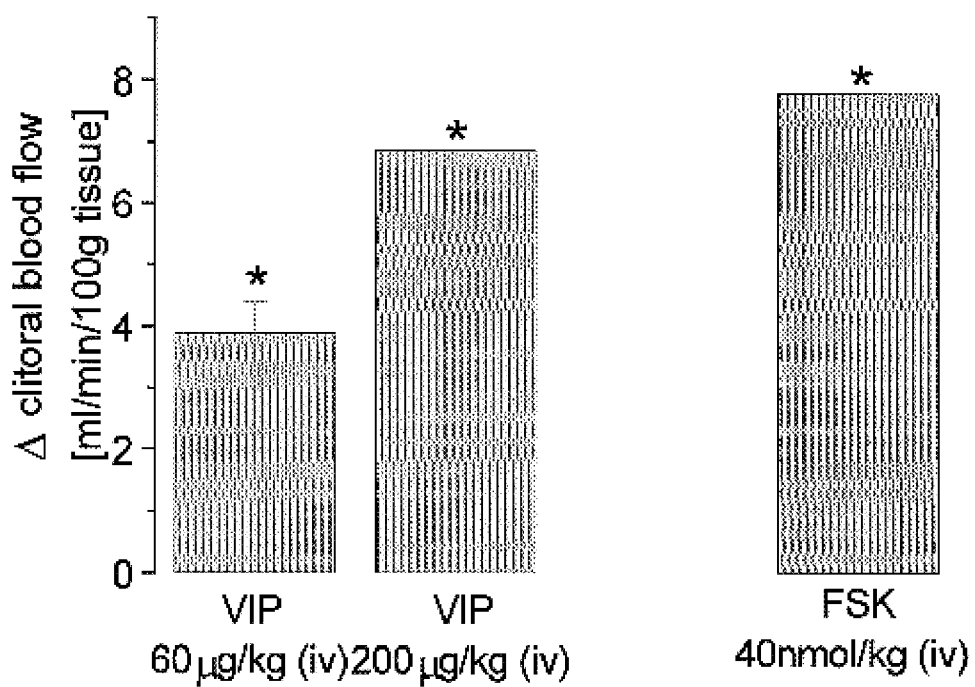
FIG. 5:—Infusion of VIP (Sequence No. 8) increases clitoral blood flow and activation of the cAMP/adenylate cyclase pathway mimics VIP (Sequence No. 8) mediated clitoral vasorelaxation in the anaesthetised rabbit model of sexual arousal. Infusion of VIP (Sequence No. 8)(60–200μg/kg) induces a concentration dependant increase in clitoral blood flow. A 115% increase in clitoral blood flow was observed after an iv infusion of 200 μg/kg VIP (Sequence No. 8). The effects of VIP (Sequence No. 8) on clitoral blood flow can be mimicked by an infusion of a cAMP mimetic forskolin (FSK, 40 nmol/kg iv bolus). A 156% increase in clitoral blood flow was observed after an iv infusion of 40 nmol/kg forskolin. All increases were significantly elevated from control infusions (Hepsaline). Note the amplitude of the response is similar to that induced by VIP (Sequence No. 8)(200 μg/kg, iv bolus) and comparable to those observed on vaginal blood flow in FIGS. 2 and 4. All changes were quantified using in vivo laser Doppler technologies and were significantly increased when compared to vehicle infusions (Hepsaline).
Figure 6:
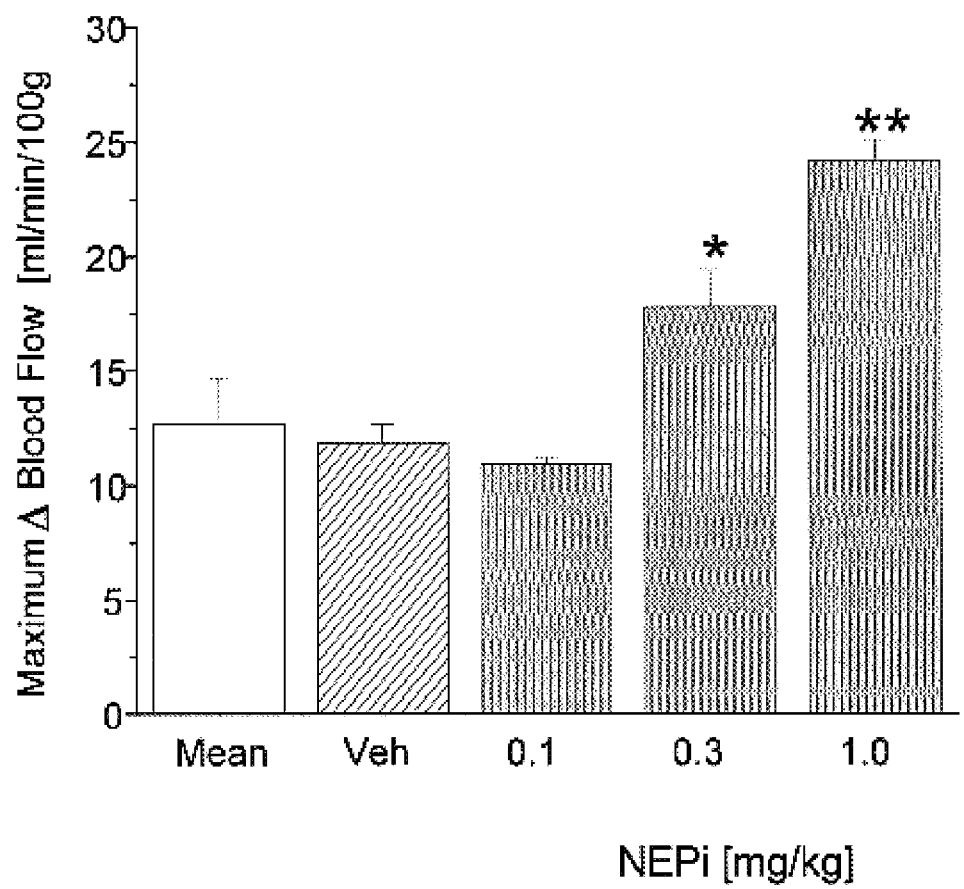
FIG. 6:—A selective inhibitor of NEP EC 3.4.24.11 (Sequence No. 1) enhances pelvic nerve stimulated (PNS) increases in vaginal blood flow in the anaesthetised rabbit model of sexual arousal. Repetitive PNS at 15 minute intervals induces reproducible increases in vaginal blood flow (White bar). Administration of a NEP inhibitor (Grey bar) enhanced the peak increase in vaginal blood flow induced by submaximal stimulation frequencies (eg 4 Hz) compared to increases observed during time matched control stimulations or vehicle controls (Hatched bar). The following dose dependant enhancements were observed—0.3 mg/kg iv induced a 40% increase and 1.0 mg/kg iv induced a 91% increase (mean n=3). The NEP inhibitor had no effect on basal (unstimulated) vaginal blood flow (Data not shown). All changes were monitored using laser Doppler technologies.
Figure 7:
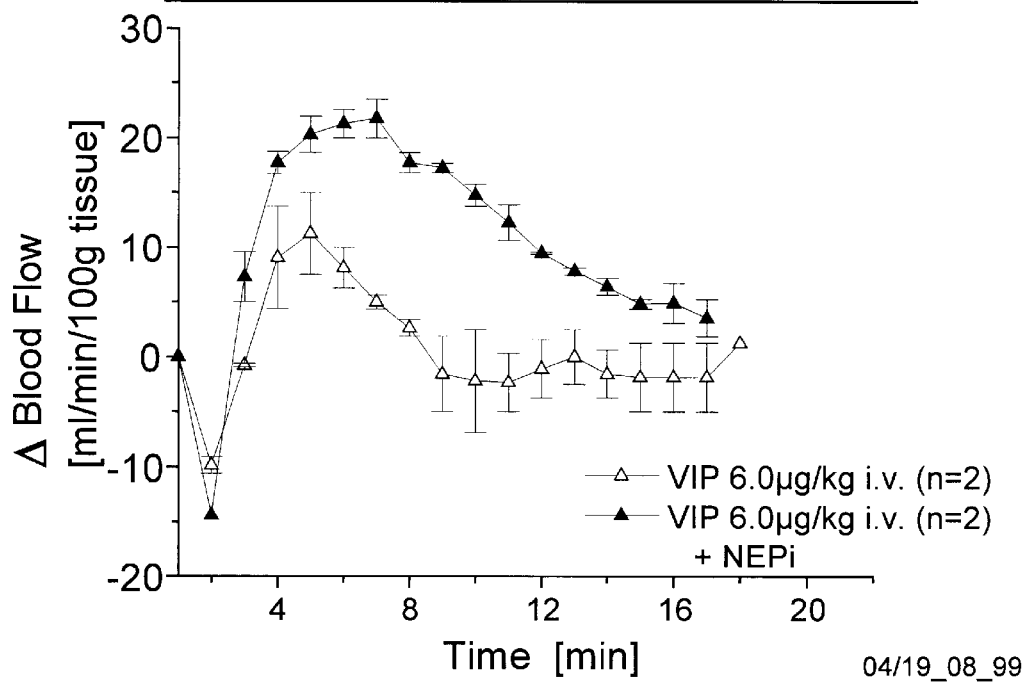
FIG. 7:—Selective inhibitors of NEP EC 3.4.24.11 (Sequence No. 1) enhance VIP(Sequence No. 8)-induced increases in vaginal blood flow in the anaesthetised rabbit model of sexual arousal. Repetitive infusions of VIP (Sequence No. 8) at 30 minute intervals induce reproducible increases in vaginal blood flow (See FIG. 2b). An NEP inhibitor both potentiates the amplitude and prolongs the duration of enhanced blood flow when these increases are induced by submaximal doses of VIP (Sequence No. 8) e.g. 6.0 μg/kg. At doses of VIP (Sequence No. 8) which induce maximal increases in vaginal blood flow eg 60 μg/kg, NEP inhibitors only potentiate the duration of enhanced vaginal blood flow. VIP(Sequence No. 8)-induced increase in the presence of a NEP inhibitor are shown as closed triangles whereas control VIP (Sequence No. 8) responses are shown as open triangles. A control infusion of Hepsaline has no effect on the amplitude of the responses. All changes were monitored using laser Doppler technologies.
Figure 7:
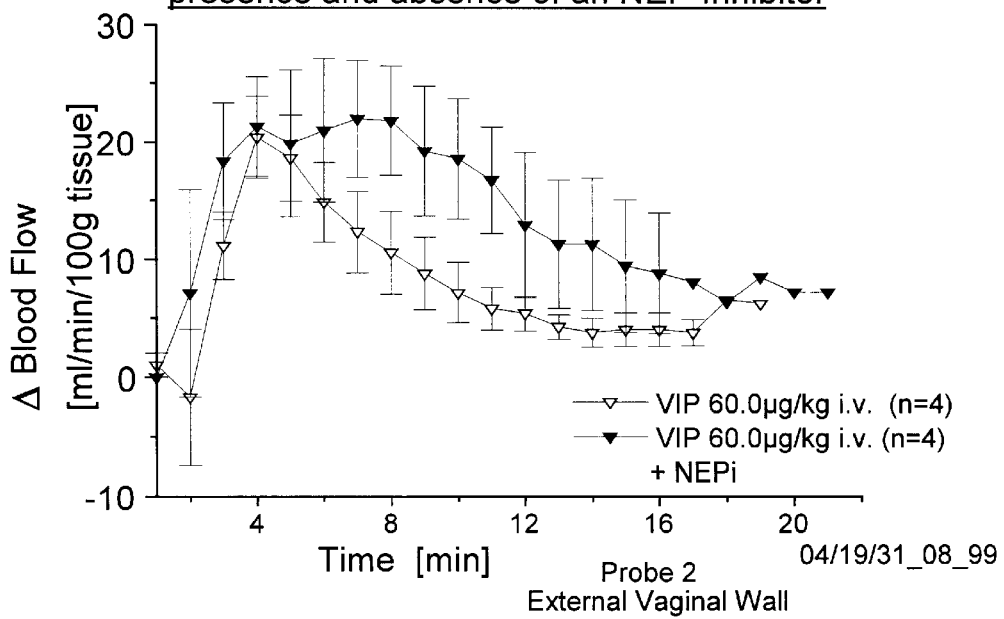
Figure 8:
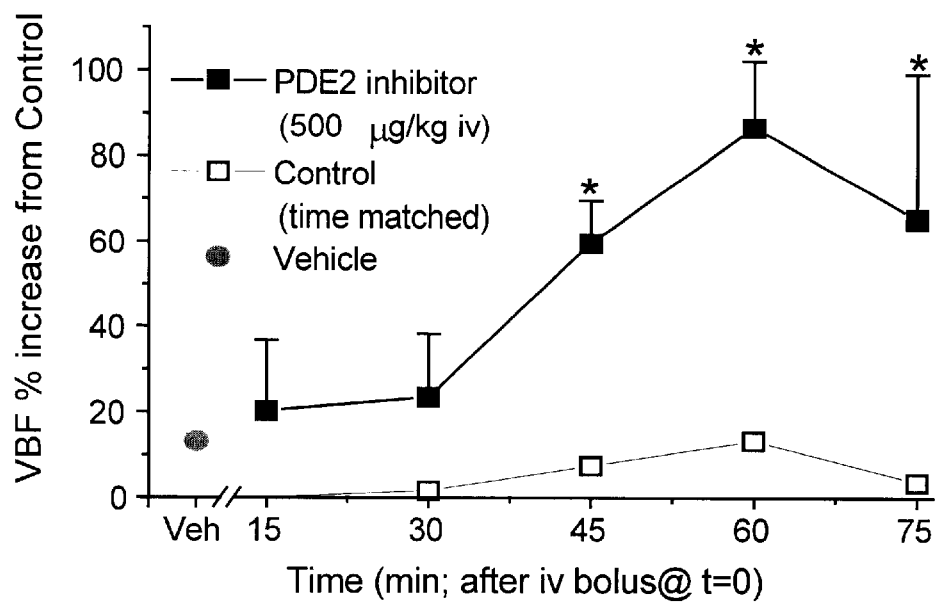
FIG. 8:—A selective inhibitor of $PDE_{cAMP}$ type 2 enhances pelvic nerve stimulated (PNS) increases in vaginal blood flow in the anaesthetised rabbit model of sexual arousal. Repetitive PNS at 15 minute intervals induces reproducible increases in vaginal blood flow (White squares). Administration of a $PDE_{cAMP}$ type 2 inhibitor enhanced the peak increase in vaginal blood flow in duced by submaximal stimulation frequencies (Black squares; at 4 Hz) compared to increases observed during time matched control stimulations (Open squares). An infusion of the PDE2 inhibitor (500 μg/kg) induced a 86.8±21.9% enhancement in vaginal blood flow (mean±sem n=2). All changes were monitored using laser Doppler technologies.
Figure 9:
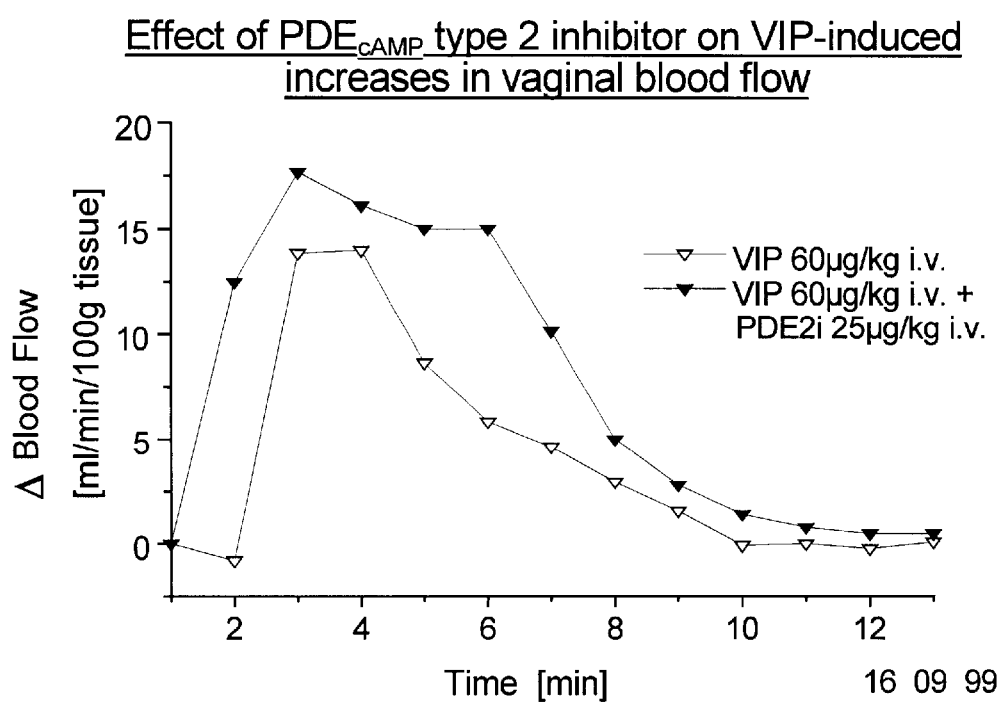
FIG. 9:—Selective inhibitors of $PDE_{cAMP}$ type 2 enhance VIP(Sequence No. 8)-induced increases in vaginal blood flow in the anaesthetised rabbit model of sexual arousal. Repetitive infusions of VIP (Sequence No. 8) at 30 minute intervals induce reproducible increases in vaginal blood flow (See FIG. 2b). A selective $PDE_{cAMP}$ type 2 inhibitor (25 μg/kg iv bolus) potentiates the duration of enhanced vaginal blood flow induced by VIP (Sequence No. 8)(60 μg/kg iv bolus). VIP(Sequence No. 8)-induced increases in the presence of a $PDE_{cAMP}$ inhibitor are shown as closed triangles whereas control VIP (Sequence No. 8) responses are shown as open triangles. A control infusion of Hepsaline had no effect on the amplitude of the responses. All changes were monitored using Laser Doppler technologies.
Figure 10:
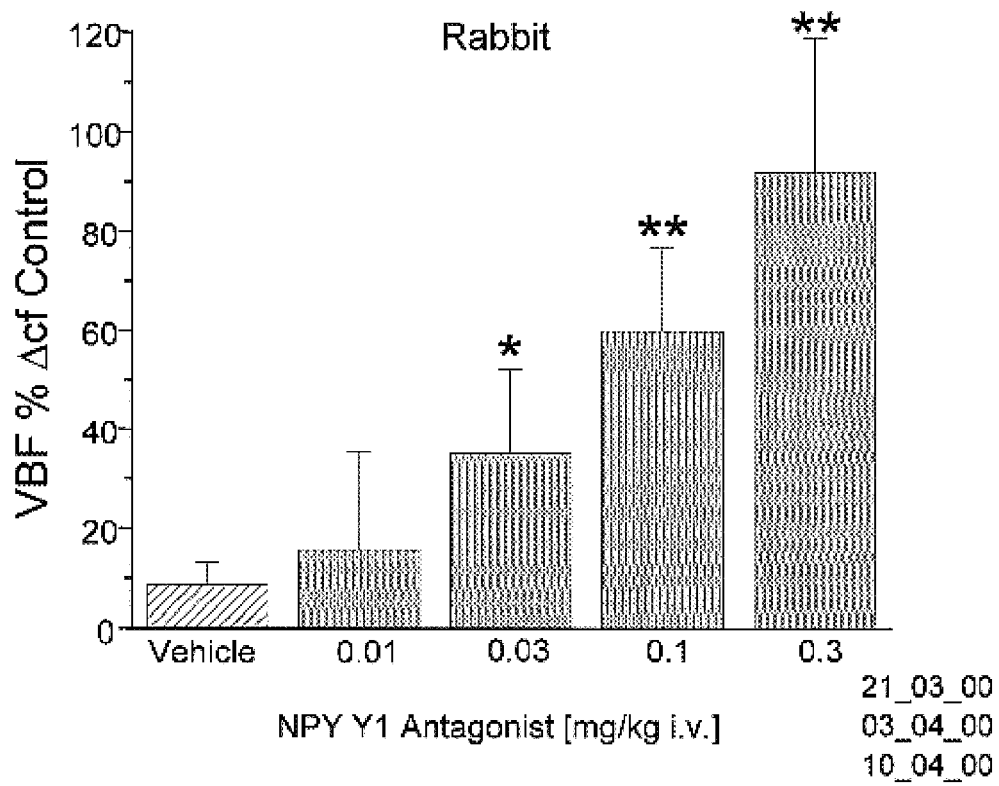
FIG. 10:—A selective antagonist of NPY Y1 receptors (Sequence No. 5) enhances pelvic nerve stimulated (PNS) increases in vaginal blood flow in the anaesthetised rabbit model of sexual arousal. Repetitive PNS at 15 minute intervals induces reproducible increases in vaginal blood flow (data not shown). Administration of a NPY Y1 antagonist (Grey bar) enhanced the peak increase in vaginal blood flow induced by submaximal stimulation frequencies (eg 4 Hz) compared to increases observed during time matched control stimulations or in vehicle controls (Hatched bar). The following dose dependant enhancements were observed—0.01 mg/kg iv induced a 15.8±19.6% increase; 0.03 mg/kg iv induced a 35.1±17.17% increase; 0.10 mg/kg iv induced a 60.1±16.9% increase and 0.3 mg/kg iv induced a 91.9±27.4% increase (mean±sem n=3). The NPY Y1 antagonist had no effect on basal (unstimulated) vaginal blood flow (Data not shown). All changes were monitored using laser Doppler technologies.
Figure 11:
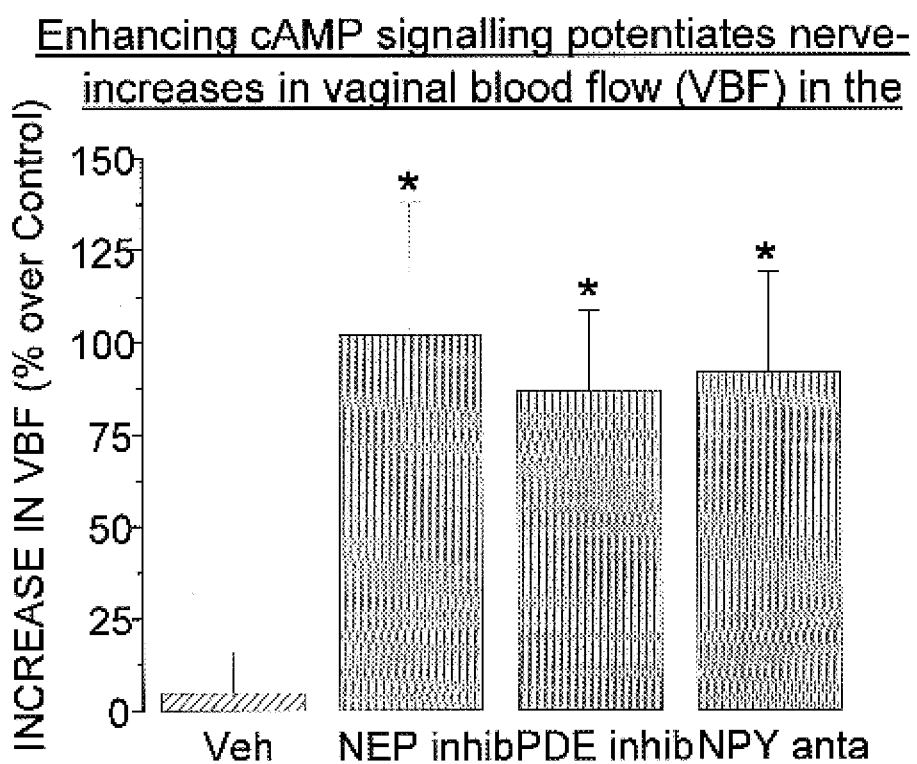
FIG. 11:—provides a summary graph for some of the data provided herein showing that the agents of the present invention are very useful in increasing vaginal blood flow by potentiating endogenous cAMP levels.

The present invention will now be described, by way of example only, in which reference is made to the following Figures:

FIG. 1 which is a graph;

FIG. 2 which is a graph;

FIG. 3 which is a graph;

FIG. 4 which is a graph;

FIG. 5 which is a graph;

FIG. 6 which is a graph;

FIG. 7 which is a graph;

FIG. 8 which is a graph;

FIG. 9 which is a graph;

FIG. 10 which is a graph;

FIG. 11 which is a graph; and

Figure 12:
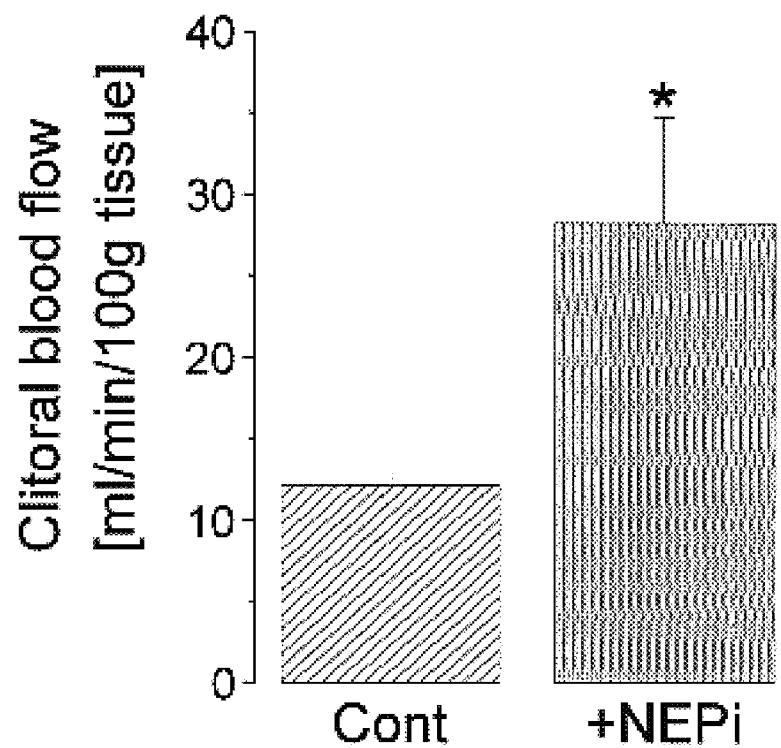
FIG. 12:—A selective inhibitor of NEP EC 3.4.24.11 (Sequence No.1) enhances pelvic nerve stimulated (PNS) increases in clitoral blood flow in the anaesthetised rabbit model of sexual arousal. Administration of a NEP inhibitor (Grey bar) enhanced the peak increase in clitoral blood flow induced by submaximal stimulation frequencies (eg 4 Hz) compared to increases observed during time matched control stimulations or vehicle controls (Hatched bar). The following dose dependant enhancements were observed—1.0 mg/kg iv induced a 131% increase (mean n=3). The NEP inhibitor had no effect on basal (unstimulated) clitoral blood flow. All changes were monitored using laser Doppler technologies.

FIG. 12 which is a graph.

AN ASSAY FOR MEASURING cAMP ACTIVITY/LEVELS

Measurement of cAMP from vaginal tissue samples using a Biotrak cAMP Enzymeimmunoassay (EIA) kit (Amersham Life Sciences RPN 225).

cAMP levels are measured by EIA in vaginal tissue samples. The EIA is based on competition between unlabelled cAMP and a fixed quantity of peroxidase labelled cAMP for a limited amount of cAMP specific antibody.

1. Materials

All materials are supplied by Amersham Life Science cAMP EIA kit (RPN 225) unless otherwise stated.

1.1 Microtitre plate—96 well plate coated with donkey anti-rabbit IgG.

1.2 Assay buffer—0.05M sodium acetate buffer pH5.8 containing 0.02% bovine serum albumin and 0.5% preservative upon reconstitution. The contents of the bottle are transferred to a graduated cylinder using 3×15 ml distilled water washes. The final volume is then adjusted to 500 ml.

1.3 cAMP standard (for acetylation method). cAMP at 10.24 pmol/ml in 0.05M acetate buffer pH5.8 containing 0.02% bovine serum albumin and 0.5% preservative upon reconstitution. Standard is dissolved in 2.5 ml of assay buffer for use.

1.4 Antiserum. Anti-cAMP antibody in 0.05M acetate buffer pH5.8 containing 0.02% bovine serum albumin and 0.5% preservative upon reconstitution. Prior to use, antibody is diluted with 11 ml assay buffer and mixed by gentle inversion to dissolve contents.

1.5 cAMP conjugate. cAMP horseradish peroxidase in 0.05M acetate buffer pH5.8 containing 0.02% bovine serum albumin and 0.5% preservative upon reconstitution. Prior to use, solution is diluted with 11 ml assay buffer and mixed by gentle inversion to dissolve contents.

1.6 Wash buffer 0.01M phosphate buffer pH7.5 containing 0.05% (v/v) Tween™ 20 upon reconstitution. The contents of the bottle are transferred to a graduated cylinder using 3×15 ml distilled water washes. The final volume is then adjusted to 500 ml.

1.7 TMB substrate. 3,3', 5,5'-tetramethylbenzidine (TMB)/hydrogen peroxide, in 20% (v/v) dimethylformamide. Ready for use.

1.8 Acetylation reagent. 2 ml acetic anhydride, 4 ml triethylamine, prepared as required.

1.9 Sulphuric acid (1M). 1M Sulphuric acid is prepared from an 18M stock (BDH). 1.11 ml of acid is added to 18.8 ml of distilled water.

2. Specific Equipment
   2.1 Disposable 5 ml glass test tubes
   2.2 Spectrophotometric plate reader (Spectra max 190)
   2.3 Microtitre plate shaker (Luckham R100)
3. Methods Tissue sample preparation. The tissues were treated with the relevant pretreatment in 5 ml samples of physiological salt solution eg agonists, cAMPmimetics etc. After treatment the samples were snap frozen in liquid nitrogen and then smashed using a hammer. The powder was scraped into a centrifuge tube and 1 ml of 0.5M ice cold perchloric acid (PCA) was added. The sample was vortex mixed and left on ice for 1 hr.

cAMP extraction from tissue samples. The samples were centrifuged at 10000 g for 5 min at 4° C. The supernatant was removed and placed in other centrifuge tubes. The pellet was keep for protein analysis at −80° C. The supernatant samples were then neutralised to pH-6 using $K_3PO_4$. Centrifuged at 10000 g for 5 min at 4° C. Recover supernatant and wash 4 times with 5 volumes (5 ml) of water saturated diethyl ether. The upper ether layer should be discarded after each wash. Transfer aqueous to into a short thin glass tube and dry under a steam of nitrogen at 60° C. Dissolve dried extract in 1 ml of assay buffer and store in refrigerator until required (or can be frozen).

Stock reagents are equilibrated to room temperature and working solutions then prepared.

cAMP standards are prepared in glass tubes labelled 2, 4, 8, 16, 32, 64, 128, 256, and 512 fmol. This is achieved by adding 1 ml of assay buffer to all tubes except the 512 fmol standard. 1 ml of acetylation standard (10.24 pmol/ml) is then added to the two top standards (256, and 512 fmol). The 256 fmol standard is vortexed and 1 ml transferred to the 128 fmol standard, his is continued until the 2 fmol standard where 1 ml of solution is disposed of. A zero standard tube is set up containing 1 ml of assay buffer.

Tissue extract samples are thawed on ice (if necessary) and diluted 1 in 100 (10 µl sample to 990 µl assay buffer) in labelled glass tubes.

The cAMP in all standards and samples is acetylated by the addition of 100 µl of acetylation reagent in a fume hood which is added down the side of the tube before immediately vortexing.

50 µl of all standards and samples are added to the appropriate wells of the 96 well plate, and 150 µl of assay buffer is added to non specific binding (NSB) wells.

100µl of antiserum is added to all wells except blanks (B) and NSB before incubating for 2 hours at 3–5° C.

After incubation, 100 µl of cAMP-peroxidase conjugate is added to all wells except B before a further 1 hour incubation at 3–5° C.

Plates are emptied by turning them upside down and blotting onto absorbent paper before washing each well four times with 400 µl of wash buffer. After each wash plates are re-blotted to ensure any residual wash buffer is removed. 200 µl TMB is then immediately dispensed into all wells.

Plates are put on a plate shaker for 30 minutes at room temperature before the addition of 100 µl of 1M sulphuric acid into all wells. The optical density is read on Spectra max 190 at 450 nm within 30 minutes.

4. Standards

With each assay the following standard tubes are set up:

4.1 Spiking a Standard in Assay Buffer

A known amount of cAMP is spiked into assay buffer to determine the efficiency of the assay. 70 pmol/ml of cAMP is added to assay buffer which is equivalent to 35 fmol/well in the assay, which is in the middle of the dose response curve.

To make up 1 ml of standard:—68.4 µl 52 fmol/well standard 931.6 µl Assay buffer 4. Effects of Compounds on Plate Standards are set up to determine whether the compound used in the functionalstudies has any effect on the 96 well plate or affects the binding of cAMP. These include:

Spiking the compound into assay buffer alone to assess the effects of the compound directly on the plate.

Spiking the compound into plasma containing basal levels of cAMP to assess the effects of the compound on the binding of cAMP to the plate. 5 nM concentrations of compound are spiked-into each standard. 5 nM is chosen because total drug levels at the end of infusion have in the past been approximately 150–300 nM. Samples are diluted 1:100 before being-assayed, therefore 5 nM allows for any larger than expected total drug concentrations at the end of infusion.

5. Calculations

The Spectra max plate reader reads the optical density (OD) at 450 nm.

The standard curve is generated by plotting the %B/Bo (y axis) against cAMP fmol/well (x axis) on Spectra max.

%B/BO (% bound) for each sample and standard is calculated as follows:—Bo=zero standard (see methods 3.2)

$$\% \; B/Bo = \frac{(\text{standard or sample } OD - NSB \; OD)}{(Bo \; OD - NSB \; OD)} \times 100$$

The fmol/well volume can then be read directly from the standard curve for each sample. Values are then converted to pmol/ml before taking the mean of each pair of samples.

Conversion of values from fmol/well to pmol/ml:

$$\text{fmol to pmol} = \text{divide by 1000}$$

$$\text{Volume in well} = 50\ \mu l\ \ldots\ \text{So}\frac{(\times 1000)}{50}$$

Sample is diluted 1/100, so overall=1×1000/1000×100/50=2
So all fmol/well values are multiplied by 2 to give pmol/ml

ANIMAL TEST MODEL

Potentiating the Effects of Cyclic Adenosine -3',5'-Monophosphate (cAMP) Results in Increases in Vaginal Blood Flow in the Anaesthetised Rabbit Model of Sexual Arousal

1.0 Aims

1. To develop and validate an animal model of female sexual arousal.
2. To identify the mechanism(s) responsible for the regulation of genital blood flow in the anaesthetised rabbit.
3. To identify potential approaches for, enhancement of vaginal and clitoral blood flow.
4. To investigate the mechanism(s) that underlie relaxation of vaginal smooth muscle and to identify potential approaches for enhancement of vaginal relaxation.

2.0 Introduction

The normal sexual arousal response consists of a number of physiological responses that are observed during sexual excitement. These changes such as vaginal, labial and clitoral engorgement result from increases in genital blood flow. Engorgement leads to increased vaginal lubrication via plasma transudation, increased vaginal compliance (relaxation of vaginal smooth muscle) and increases in vaginal and clitoral sensitivity.

Female sexual arousal disorder (FSAD) is a highly prevalent sexual disorder affecting up to 40% of pre-, per- and postmenopausal (±HRT) women. The primary consequence of FSAD is reduced genital engorgement or swelling which manifests itself as a lack of vaginal lubrication and a lack of pleasurable genital sensation. Secondary consequences include reduced sexual desire, pain during intercourse and difficulty in achieving orgasm. The most common cause of FSAD is decreased genital blood flow resulting in reduced vaginal, labial and clitoral engorgement. (Park, 1997; Goldstein, 1998; Berman, 1999a, Werbin, 1999).

As explained herein, the present invention provides a means for restoring or potentiating the normal sexual arousal response in women suffering from FSAD, by enhancing genital blood flow.

In our studies, we have identified cAMP (cyclic adenosine-3',5==-monophosphate) as a mediator of vaginal vasorelaxation using laser Doppler technology to measure small changes in genital blood flow. Using an inhibitor of VIP (Sequence No. 8) metabolism (a NEP EC3.4.24.11 (Sequence No. 1) inhibitor), we have also demonstrated that the increases in genital blood flow observed during pelvic nerve stimulation (ie sexual arousal) are mediated by VIP (Sequence No. 8). This has involved developing an animal model of sexual arousal and demonstrating that the data reflects the physiological changes observed during female sexual arousal. The model has then been used to identify and validate mechanisms that enhance genital blood flow eg. direct or indirect potentiation of cAMP-mediated vasorelaxation.

3.0 Methods

3.1 Anaesthetic Protocol

Female New Zealand rabbits (~2.5 kg) were premedicated with a combination of Medetomidine (Domitor®) 0.5 ml/kg i.m., and Ketamine (Vetalar®) 0.25 ml/kg i.m. whilst maintaining oxygen intake via a face mask. The rabbits were tracheotomised using a Portex™ uncuffed endotracheal tube 3 ID., connected to ventilator and maintained at a ventilation rate of 30–40 breaths per minute, with an approximate tidal volume of 18–20 ml, and a maximum airway pressure of 10 cm $H_2O$. Anaesthesia was then switched to Isoflurane and ventilation continued with $O_2$ at 2 l/min. The right marginal ear vein was cannulated using a 23G or 24G catheter, and Lactated Ringer solution perfused at 0.5 ml/min. The rabbit was maintained at 3% Isoflurane during invasive surgery, dropping to 2% for maintenance anaesthesia.

3.2 Cannulation of Vessels

The left groin area of the rabbit was shaved and a vertical incision was made approximately 5 cm in length along the thigh. The femoral vein and artery were exposed, isolated and then cannulated with a PVC catheter (17G) for the infusion of drugs and compounds. Cannulation was repeated for the femoral artery, inserting the catheter to a depth of 10 cm to ensure that the catheter reached the abdominal aorta. This arterial catheter was linked to a Gould system to record blood pressure. Samples for blood gas analysis were also taken via the arterial catheter. Systolic and diastolic pressures were measured, and the mean arterial pressure calculated using the formula (diastolic x2+systolic)+3. Heart rate was measured via the pulse oxymeter and Po-ne-mah data acquisition software system (Ponemah Physiology Platform, Gould Instrument Systems Inc).

3.3 Stimulation of the Pelvic Nerve

A ventral midline incision was made into the abdominal cavity. The incision was about 5 cm in length just above the pubis. The fat and muscle was bluntly dissected away to reveal the hypogastric nerve which runs down the body cavity. It was essential to keep close to the side curve of the pubis wall in order to avoid damaging the femoral vein and artery which lie above the pubis. The sciatic and pelvic nerves lie deeper and were located after further dissection on the dorsal side of the rabbit. Once the sciatic nerve is identified, the pelvic nerve was easily located. The term pelvic nerve is loosely applied; anatomy books on the subject fail to identify the nerves in sufficient detail. However, stimulation of the nerve causes an increase in vaginal and clitoral blood flow, and innervation of the pelvic region. The pelvic nerve was freed away from surrounding tissue and a Harvard bipolar stimulating electrode was placed around the nerve. The nerve was slightly lifted to give some tension, then the electrode was secured in position. Approximately 1 ml of light paraffin oil was placed around the nerve and electrode. This acts as a protective lubricant to the nerve and prevents blood contamination of the electrode. The electrode was connected to a Grass S88 Stimulator. The pelvic nerve was stimulated using the following parameters: −5V, pulse width 0.5 ms, duration of stimulus 10 seconds and a frequency range of 2 to 16 Hz. Reproducible responses were obtained when the nerve was stimulated every 15–20 minutes.

A frequency response curve was determined at the start of each experiment in order to determine the optimum frequency to use as a sub-maximal response, normally 4 Hz. The compound(s) to be tested were infused, via the femoral vein, using a Harvard 22 infusion pump allowing a continuous 15 minute stimulation cycle.

3.4 Positioning of the Laser Doppler Probes

A ventral midline incision was made, at the caudal end of the pubis, to expose the pubic area. Connective tissue was removed to expose the tunica of the clitoris, ensuring that the wall was free from small blood vessels. The external vaginal wall was also exposed by removing any connective tissue. One laser Doppler flow probe was inserted 3 cm into the vagina, so that half the probe shaft was still visible. A second probe was positioned so that it lay just above the external clitoral wall. The position of these probes was then adjusted until a signal was obtained. A second probe was placed just above the surface of a blood vessel on the external vaginal wall. Both probes were clamped in position.

Vaginal and clitoral blood flow was recorded either as numbers directly from the Flowmeter using Po-ne-mah data acquisition software (Ponemah Physiology Platform, Gould Instrument Systems Inc), or indirectly from Gould chart recorder trace. Calibration was set at the beginning of the experiment (0–125 ml/min/100 g tissue).

3.5 Infusion of Vasoactive Intestinal Peptide (VIP (Sequence No. 8))

The doses of VIP (Sequence No. 8)(Bachem, H-3775; Sequence No. 8) infused were 2.0, 6.0, 20.0, 60.0 µg/kg iv. and were infused in a volume of 0.5 ml of saline. VIP (Sequence No. 8) was infused using a Harvard 22 pump, infusing at 500 µl/min via a 3-way tap into the femoral vein. After VIP (Sequence No. 8) infusion, the catheter was flushed with heparinised saline (Hepsaline) so that no VIP was left in the catheter.

For experiments using VIP (Sequence No. 8) infusions, there was a need for an initial sensitising dose response curve (2–60 µg/kg), in order that reproducible responses could be obtained. An initial infusion of Hepsaline (50UI/ml) was infused to act as a negative control.

3.6 Infusion of Inhibitors

NEP (Neutral Endopeptidase EC3.4.24.11; Sequence No. 1) inhibitors, phosphodiesterase type 5 (PDE5) inhibitors and NPY Y1 antagonists were made up in saline or 5% glucose solution (200 µl 50% glucose in 1.8 ml water for injection). $PDE_{cAMP}$ inhibitors were dissolved in a 40% ethanol solution (200 µl 50% glucose in 1.8 ml water/ethanol for injection). The inhibitors and vehicle controls were infused at the same rate as VIP (Sequence No. 8). NEP inhibitors were left for 30 minutes prior to a VIP (Sequence No. 8) dose response curve, whilst NEP inhibitors, NPY Y1 receptor antagonists and $PDE_{cAMP}$ inhibitors were left for 15 minutes prior to pelvic nerve stimulation.

3.7 Measurement of Smooth Muscle Relaxation in Isolated Rabbit Vagina 3.7 (a). Rabbit vagina in vitro preparation:—Female New Zealand white rabbits (2.0–3.0 kg) were killed by cervical dislocation. The abdominal cavity was opened and the vagina excised. Tissue strips were mounted longitudinally in Wesley Co. 5 ml silanised organ chambers with braided silk sutures (6/0 gauge) at an initial resting tension of 1.5 g in Krebs bicarbonate buffer maintained at 37° C. and gassed with 95%$O_2$/5%$CO_2$. The upper ligature of each tissue strip was attached to a 10 g capacity force-displacement transducer and changes in isometric force were measured and recorded using a DART in vitro data capture system. Tissues were allowed to equilibrate for 1.5 hours and were regularly washed with Krebs.

3.7 (b). Vasoactive intestinal peptide-induced relaxation of rabbit vagina:

Each tissue was contracted using 1 µM bath concentration of phenylephrine. When the contractile response reached a stable plateau (~15 minutes), VIP (Sequence No. 8) was cumulatively added to the organ chamber at log units to produce concentrations from 0.1–100 nM. The relaxation responses were measured 5 minutes after the addition of each concentration of VIP (Sequence No. 8); maximum relaxation was achieved by this time. Tissues then received either a test agent (eg NEP or PDE inhibitor) or DMSO vehicle (time matched control).

3.7 (c). Analysis of Data for VIP (Sequence No. 8) Relaxation Experiments:

For each VIP (Sequence No. 8) concentration relaxation-response curve, the relaxation responses induced by VIP (Sequence No. 8) were expressed as a percentage of the maximum phenylephrine induced contraction. These values were then plotted against log VIP (Sequence No. 8) concentration and sigmoidal curves were fitted. For the purpose of curve fitting the minimum relaxation response was constrained to 0% and the maximum relaxation response was allowed to free fit. The concentration of VIP (Sequence No. 8) required to produce 50% relaxation of the phenylephrine contraction ($EC_{50\ PE}$) was determined.

3.7 (d). Electrical Field Stimulated Relaxation of Rabbit Vagina:

Rabbit vaginal strips were prepared as described in Section 3.7 (a). The tissue strips were mounted between two platinum electrodes placed at the top and bottom of the organ chamber approximately 4 cm apart. Each tissue was contracted using 1 µM bath concentration of phenylephrine. When the contractile response reached a stable plateau (15 minutes), the tissues underwent a pre-treatment electrical field stimulated (EFS) induced relaxation curve. This was performed between 40–60 volts using sequential frequencies of 2, 4, 8 and 16 Hz delivered as 10 second trains of 0.5 milli second pulse width. The tissues were allowed to return to base line pre-contractile tension between each frequency (5 minutes) and the size of the relaxation response recorded.

After completion of the pre-treatment EFS response curve, all tissues were washed for 15 minutes, allowing the tissues to return to the baseline tension. Tissues then received either a test agent (eg NEP or PDE inhibitor, nitric oxide synthase [NOS] inhibitor) or DMSO vehicle (time matched control). Tissues were re-contracted with phenylephrine (1 µM) 15 minutes after the addition of compound or vehicle and an EFS-induced relaxation response curve determined as described above.

For EFS experiments the Krebs was supplemented with atropine (10 µM) and guanethidine (150 µM) to abolish any cholinergic or adrenergic neuronal innervations of the vagina.

3.8 Measurement of cAMP Levels in Isolated Rabbit Vagina

Measurement of cAMP concentrations were made from vaginal tissue extracts using a Biotrak cAMP Enzyme immunoassay (EIA) kit (Amersham Life Sciences RPN 225). Isolated vaginal tissue samples were treated with test agents (eg forskolin or VIP. (Sequence No. 8)). After 5 minutes the samples were snap frozen using liquid nitrogen, homogenised and cAMP was extracted. cAMP levels are measured by EIA. The EIA is based on competition between unlabelled cAMP and a fixed quantity of peroxidase labelled cAMP for a limited amount of cAMP specific antibody.

3.9 Measurement of Phosphodiesterase (PDE) Activity in Isolated Rabbit Vagina

Human vaginal wall cytosol extracts were obtained from ABS Inc., Delaware (Age of donors 41 and 60 years old). The PDE isoenzymes were separated by Mono-Q anion exchange chromatography and characterised based upon their substrate selectivity, sensitivity to allosteric modulators and selective inhibitors. Western analysis using specific PDE isoenzyme antibodies was also performed to detect PDE expression in the human vagina.

All data are reported as mean±s.e.m. Significant changes were identified using Student's t-tests.

4.0 Results and Discussion

4.1 Animal Model of Sexual Arousal

In our studies, we have developed a robust reproducible model of the physiology of sexual arousal. Using this anaesthetised rabbit model, we are capable of measuring small changes in genital blood flow using Laser Doppler technology. Stimulation of the pelvic nerve is used to simulate the neuronal effects of sexual arousal.

We found that stimulation of the pelvic nerve induces frequency-dependent increases in vaginal and clitoral blood flow (See FIG. 1). The increases in vaginal blood flow are significant when recorded either on the intra- or extra-vaginal wall. Stimulation of the pelvic nerve at 2 Hz induced a mean maximum vaginal blood flow elevation of 10.3±1.8, at 4 Hz 20.0±4.6, 8 Hz 36.3±4.8 and 16 Hz 46.6±4.7 ml/min/100 g tissue (n=4); 15–20V, 0.5 ms, 10 s) and increases in clitoral blood flow of 14.7±3.6 at 2 Hz, 29.4±1.4 at 4 Hz and 69.7±2.1 at 8 Hz. These values are of similar amplitude to those previously observed in human studies and animal models of arousal (Berman, 1999a; Park, 1997).

We found that submaximal stimulation of the pelvic nerve results in reproducible increases in genital blood flow (eg stimulating 4 Hz every 15 minutes gave a mean increase of in vaginal blood flow of 8.50±0.10 ml/min/100 g tissue n=8 and a mean increase in clitoral blood flow of 13.65±0.86mi/min/100 g tissue n=11). This reproducibility is maintained for up to 5 hours. We can use the reproducibility of these responses to investigate a.) the identity of endogenous vasoactive agents/mechanisms which mediate genital engorgement, and b.) the influence of drugs which may be efficacious in enhancing vaginal and/or clitoral blood flow.

We found that there are no adverse cardiovascular effects associated with pelvic nerve stimulation in the anaesthetised rabbit (See FIG. 3).

Genital blood flow is increased during sexual arousal (Berman, 1999) via an increased arterial blood supply—the vaginal artery, the vaginal branch of the uterine artery, the internal pudendal artery and the middle branches of the middle rectal artery are all involved in supplying blood to the vagina and clitoris. The pelvic nerve which originates from S2/S4 spinal regions, innervates the female genitalia and has branches terminating in the lower vagina, clitoris and related blood vessels. By stimulating the pelvic nerve we can simulate the blood flow effects observed during sexual arousal i.e. an increase in arterial genital blood flow. Interestingly, the increased arterial blood flow is not mirrored by venous drainage allowing the capillary networks to become engorged with blood. Vaginal engorgement leads to vaginal lubrication, via increased plasma transudation and this is one of the first pelvic responses observed during sexual stimulation. The neurotransmitters that are released upon pelvic nerve stimulation or during sexual arousal are currently unidentified. Nerves containing neuropeptides and other neurotransmilter candidates that innervate the vasculature and microvasculature of the vagina and clitoris have been identified immunohistochemically. These studies indicate that calcitonin gene-related peptide (CGRP), neuropeptide Y (NPY; Sequence No. 4), nitric oxide synthase (NOS), substance P and vasoactive intestinal peptide (VIP; Sequence No. 8) are all present in the nerves that innervate the human vagina and clitoris (Hoyle, 1996; Burnett, 1997; Hauser-Kronberger, 1999).

4.2 Validation of the Anaesthetised Rabbit Model of Sexual Arousal

In order to translate blood flow data generated using this model to those observed in a human model of sexual arousal, we directly compared our data with vaginal blood flow and cardiovascular data generated in pre-clinical studies.

Figure 2A:
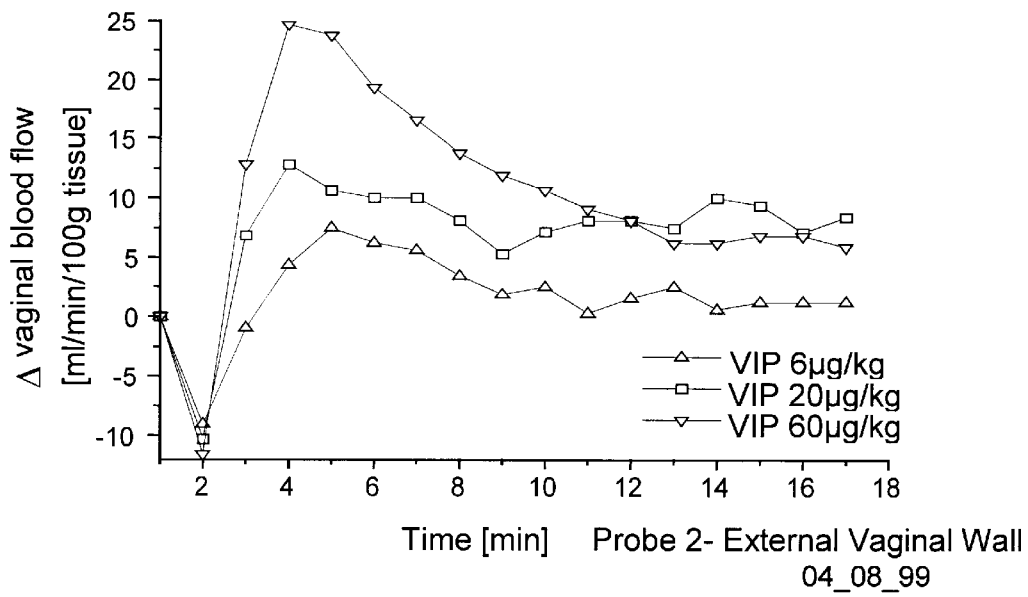
FIG. 2a illustrates how vaginal blood flow is increased in a concentration dependent manner by infusions of VIP (Sequence No. 8)(intravenous bolus).

We found that VIP (Sequence No. 8) infusion has the following effects in rabbit model of sexual arousal:

Exogenous VIP (Sequence No. 8)(iv bolus) induces significant concentration-dependent increases in vaginal blood flow (See FIG. 2a). These increases are significantly elevated above basal blood flow values when recorded either on the intra- or extra-vaginal wall. Vaginal blood flow was significantly increased by 24.7±3.6 ml/min/100 g tissue with an intravenous administration of VIP (Sequence No. 8)(60 µg/kg). The blood flow remained elevated above basal for about 11 minutes post-infusion. Lower doses induced smaller increases eg 6.0 g/kg, elevated blood flow by 7.5±1.3 ml/min/100 g tissue and blood flow was elevated for 7 minutes post-infusion.

Figure 2B:
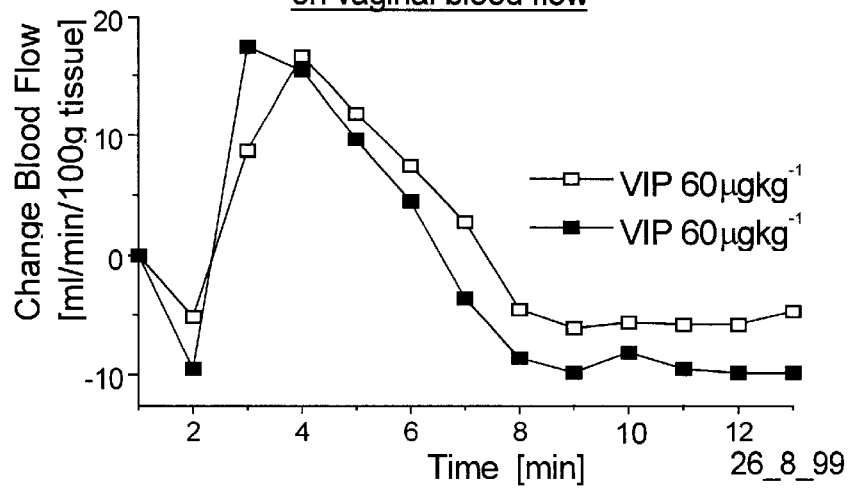
FIG. 2b demonstrates that 2 repetitive infusions of VIP (Sequence No. 8) produce similar increases in blood flow. Note the duration of the response is also similar. All changes were monitored using laser Doppler technologies.

Repetitive infusions of similar doses of VIP (Sequence No. 8)(iv at 30 minute intervals) induce significant reproducible increases in vaginal blood flow (See FIG. 2b).

VIP (Sequence No. 8)(iv) significantly increases heart rate and decreases mean arterial blood pressure (See FIG. 3). At 6.0 µg/kg VIP (Sequence No. 8)(iv) caused significant reduction in mean arterial blood pressure of 13.2±0.7 mm Hg and a significant increase in heart rate of 16±4 beats per minute.

This animal model directly reflects the clinical data observed upon infusion of VIP (Sequence No. 8) into health volunteers ie increased vaginal blood flow, suppressed blood pressure and elevated heart rate. Therefore this model can be used to investigate the mechanism(s) that underlie physiological changes that occur during sexual arousal and additionally to validate novel approaches for the enhancement of vaginal blood flow and hence treatment of FSAD.

4.3 VIP(Sequence No. 8)-induces Changes in Vaginal Blood Flow Via Stimulation of the cAMP/adenylate Cyclase Pathway Ottesen and co-workers demonstrated that VIP (Sequence No. 8) induces increases in vaginal blood flow and lubrication in healthy volunteers. However the mechanism by which VIP (Sequence No. 8) exerts it's effects are unclear. In the literature, there are plenty of examples of VIP (Sequence No. 8) signalling through different second messenger systems including cGMP/guanylate cyclase (Ashur-Fabian, 1999), carbon monoxide/heme oxygenase (Fan, 1998) and cAMP/adenylate cyclase (Schoeffler, 1985; Gu, 1992; Foda, 1995). This is exemplified by a recent report which describes how the relaxant effects of VIP (Sequence No. 8) in the uterine artery can be explained by the release of nitric oxide (Jovanovic, 1998). Interestingly there is also evidence for VIP (Sequence No. 8) modulating NO/cGMP in male urogenital function (Kim, 1994) and there is direct evidence that treatment of human vaginal smooth muscles cell cultures, with VIP (Sequence No. 8)(0.5 µM) fails to elevate cAMP levels (Traish, 1999 ibid).

In this study we have shown that VIP (Sequence No. 8) induces vasorelaxation via elevation of intracellular cAMP levels. By conducting a series of functional experiments we have measured blood flow and smooth muscle relaxation in addition to biochemically measuring intracellular cAMP concentrations. We have used forskolin, an activator of adenylate cyclase or cAMPmimetic, to mimic the effects of activating the cAMP/adenylate cyclase pathway. VIP (Sequence No. 8) and forskolin have identical effects on the physiological arousal effects on vaginal blood flow and relaxation.

Figure 4A:
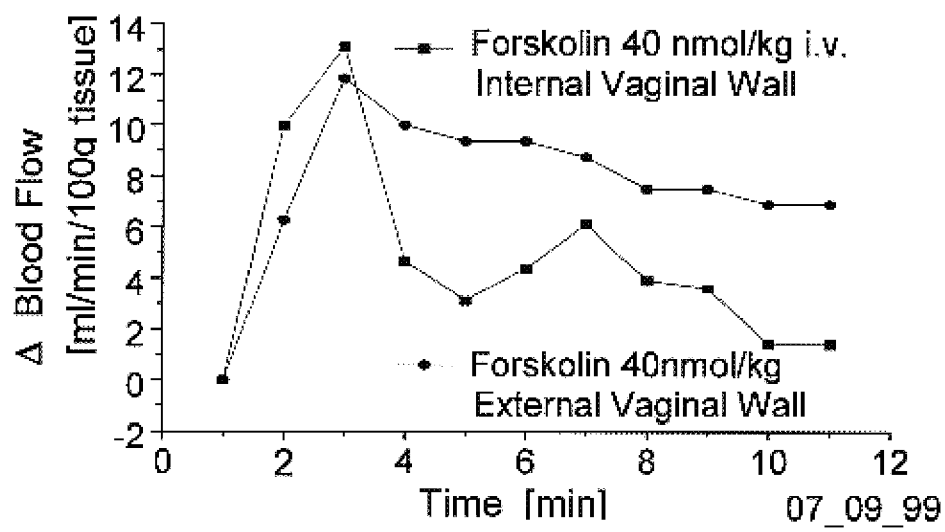
FIG. 4a illustrates that an infusion of forskolin (40 nmol/kg iv bolus, a cAMPmimetic) induces significant increases in vaginal blood flow. Note the amplitude and duration of the response is similar to that induced by VIP (Sequence No. 8)(20.0 μg/kg, iv bolus). Interestingly, the effects on blood flow have a longer duration of action on the external vaginal wall. All changes were monitored using laser Doppler technologies.

VIP (Sequence No. 8)(20 µg/kg) and forskolin (40 nmol/kg) induces significant increases in vaginal blood flow 13.2 and 12.7 ml/min/100 mg tissue respectively (See FIGS. 2a and 4a). These changes in amplitude induced by VIP (Sequence No. 8) and forskolin were not significantly different. These increases are significantly elevated above basal blood flow values when recorded either on the intra- or extra-vaginal wall.

Figure 4B:
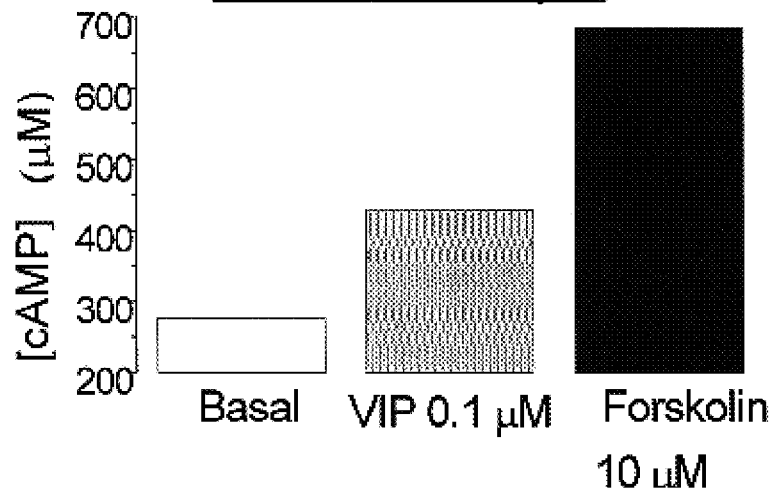
FIG. 4b demonstrates that both VIP (Sequence No. 8)(0.1 μM) and forskolin (10 μM) significantly elevate intracellular concentrations of cAMP above basal levels in the rabbit vagina.

VIP (Sequence No. 8)(0.1 μM) and forskolin (10 μM) both significantly increased intracellular concentrations cAMP above basal levels in isolated vaginal tissue (See FIG. 4b).

VIP (Sequence No. 8)(0.1 μM) and forskolin (10 μM) elevate basal concentrations from 276 nM by 156% and 238% respectively. The differences in these percentages reflects the difference in concentrations of VIP (Sequence No. 8) and forskolin used eg VIP (Sequence No. 8) at a concentration of 0.1 μM relaxes precontracted isolated vagina by circa 80% where as 10 μM forskolin is sufficient to completely relax isolated tissue.

Figure 4C:
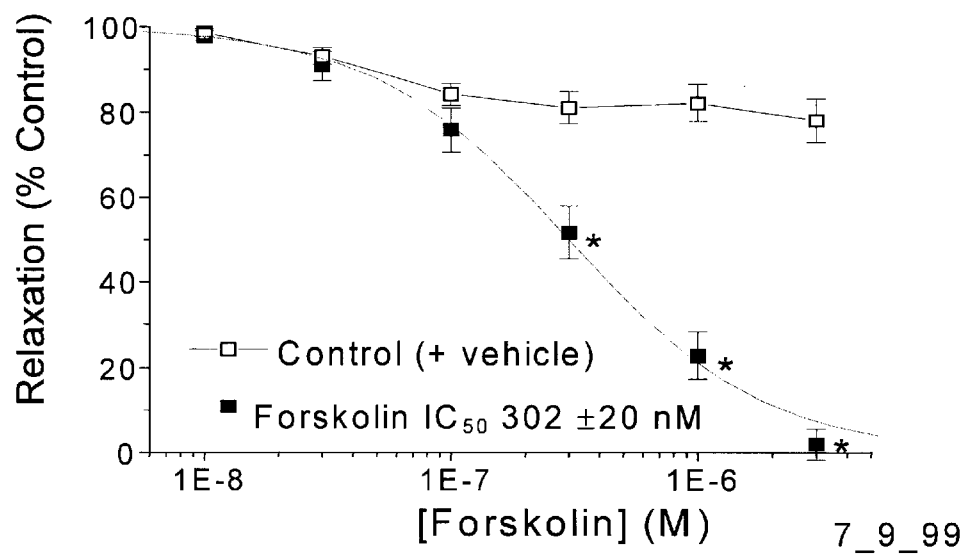
FIG. 4c shows that forskolin induces potent relaxations of precontracted (1 μM phenylephrine) rabbit vaginal strips with an $IC_{50}$~300 nM. All changes were quantified using in vivo laser Doppler technologies, biochemical cAMP enzyme immunoassay or by in vitro tissue relaxation.

Additionally we showed that VIP (Sequence No. 8) and forskolin induces relaxation in isolated vaginal tissue with $EC_{50}$ values of 18.8±0.6 nM and 320±20 nM respectively (See FIG. 4c).

These data establish that VIP (Sequence No. 8) induces vaginal vasorelaxation via the cAMP/adenylate cyclase pathway, hence this model can be used to investigate whether pelvic nerve stimulation, i.e. sexual arousal, leads to the release of VIP (Sequence No. 8)/activation of the cAMP/adenylate cyclase pathway. In addition, approaches to enhance vaginal blood flow during sexual arousal, eg by directly or indirectly enhancing cAMP signalling, can also be investigated.

4.4 cAMP is the Mediator of Vaginal Vasorelaxation

The neurotransmitter and second messenger candidates responsible for increases in vaginal blood flow during sexual arousal are currently unidentified. Todate, workers have focused on the nitric oxide (NO)/cGMP pathway. In accordance with the present invention, we have demonstrated that:—1.) the cAMP/adenylate cyclase pathway mediates VIP(Sequence No. 8)-induced increases in vaginal blood flow; 2.) VIP (Sequence No. 8) a the endogenous neurotransmitter released during sexual arousal and 3.) endogenously released VIP (Sequence No. 8) induces it's vasorelaxant effects via elevation of cAMP.

The neurotransmitter responsible for vaginal wall relaxation is currently unidentified. We have shown that VIP (Sequence No. 8) a the neurotransmitter release upon stimulation of the pelvic nerve and that cAMP mediates the VIP(Sequence No. 8)-mediated vasorelaxation. Agents that prevent the metabolism of VIP (Sequence No. 8) or directly enhance cAMP signalling enhance pelvic nerve stimulated increases in vaginal blood flow eg NEP-inhibitors or PDE-$_{cAMP}$ inhibitors respectively (see following sections).

In our studies, we have found that we can exclude a role for NO in VIP(Sequence No. 8)-induced vaginal relaxation. A potent and selective PDE type 5 inhibitor has a minimal effect on VIP(Sequence No. 8yinduced-relaxations of isolated vaginal smooth muscle (30% enhancement of VIP (Sequence No. 8)-induced relaxations; See table 1).

Table 1 illustrated the percentage enhancement of the $ECM_{50}$ for VIP(Sequence No. 8)-induced relaxations of precontracted vaginal smooth muscle (1 μM phenylephrine). Selective inhibitors of $PDE_{cAMP}$ types 1, 2, 3 and 4 all significantly potentiated VIP(Sequence No. 8)-mediated relaxations whereas a selective inhibitor of $PDE_{cGMP}$ type 5 or vehicle control had no effect on VIP(Sequence No. 8)-mediated relaxations.

TABLE 1

Enhancement of VIP (Sequence No. 8) mediated relaxation of isolated rabbit vagina.

| PDE inhibitor at selective dose | Percentage enhancement of VIP(Sequence No. 8)-induced relaxation |
|---|---|
| $PDE_{cAMP}$ type 1 | 210% |
| $PDE_{cAMP}$ type 2 | 130% |
| $PDE_{cAMP}$ type 3 | 220% |
| $PDE_{cAMP}$ type 4 | 160% |
| $PDE_{cAMP}$ type 5 | No effect (30%) |
| Control - vehicle | No effect |

We have shown that VIP (Sequence No. 8) is also the endogenous NANC (non-adrenergic, non-cholinergic) neurotransmitter partially responsible for EFS-induced relaxations of isolated vaginal smooth muscle. A high dose of a nitric oxide synthase inhibitor (L-NOARG, 300 μM) only inhibits 50% of EFS-induced relaxations. A NEP inhibitor (1 μM), which will prevent NEP-induced metabolism of VIP (Sequence No. 8) and hence enhance VIP (Sequence No. 8) signalling, enhances the non-nitric oxide NANC relaxation induced by EFS. We have shown that both NO and VIP (Sequence No. 8) regulate smooth muscle tone in the vaginal wall. Therapeutically it will be possible to enhance relaxations of vaginal smooth muscle with agents that enhance NO/cGMP and/or VIP/cAMP mediated signalling 4.5 VIP (Sequence No. 8) Induces Clitoral Vasorelaxation Via the cAMP Pathway The neurotransmitter and second messenger candidates responsible for increases in clitoral blood flow during sexual arousal are currently unidentified. In line with current research into vaginal blood flow, work has speculated and focused on the nitric oxide (NO)/cGMP pathway. There are no reports that VIP (Sequence No. 8) plays a role in mediating clitoral blood flow/engorgement although VIP (Sequence No. 8) containing neurones have been visualised in clitoral tissue (Hauser-Kronberger et al., 1999).

In this study we demonstrate that:

1. Infusion of VIP (Sequence No. 8) increases clitoral blood flow
2. The cAMP/adenylate cyclase pathway mediates VIP (Sequence No. 8)-induced increases in clitoral blood flow
3. VIP (Sequence No. 8) is an endogenous clitoral neurotransmitter that is released during sexual arousal:
   1. Infusion of VIP (Sequence No. 8)(60–200 μg/kg, iv bolus) induces a concentration dependant increase in clitoral blood flow (FIG. 5). A 115% increase in clitoral blood flow was observed after an iv infusion of 200 μg/kg VIP (Sequence No. 8). This was significantly elevated from control infusions (Hepsaline).
   2. The effects of VIP (Sequence No. 8) on clitoral blood flow can be mimicked by an infusion of a cAMP mimetic forskolin (40 nmol/kg iv bolus, FIG. 5). A 156% increase in clitoral blood flow was observed after an iv infusion of 40 nmol/kg forskolin. This was significantly elevated from control infusions (Hepsaline). Note the amplitude of the response is similar to that induced by VIP (Sequence No. 8)(200 μg/kg, iv bolus) and comparable to those observed on vaginal blood flow in FIGS. 2 and 4.
   3. Selective inhibitors of NEP EC 3.4.24.11 (Sequence No. 1) at clinically relevant doses significantly enhance pelvic nerve stimulated increases in clitoral blood flow (See FIG. 12). A NEP inhibitor enhanced the peak increase in clitoral blood flow by up to 131% compared to vehicle control increases.

These data establish that VIP (Sequence No. 8) is capable of increasing clitoral blood flow/vasorelaxation and that this can be mimicked by activation of the cAMP/adenylate cyclase pathway. The finding that an inhibitor of NEP EC3.4.24.11 (Sequence No.1)(responsible for VIP (Sequence No. 8) metabolism) enhances pelvic nerve stimulated increase in clitoral blood flow demonstrates that VIP (Sequence No. 8) is a neurotransmitter that is released during pelvic nerve stimulation/sexual arousal.

4.6 Genital Blood Flow is Enhanced by Pharmacological Agents That Directly or Indirectly Elevate cAMP Levels FSAD is associated with and may result from reduced genital blood flow. Potential approaches to treat this disorder revolve around enhancing genital blood flow. Having established that cAMP is the mediator of genital vasorelaxation and that elevations of cAMP result from neuronally released VIP (Sequence No. 8), we believe that if cAMP signalling is enhanced, then as a consequence genital blood flow will be increased, hence restoring genital blood flow to normal levels and treating FSAD.

In a highly preferred aspect, we chose three targets to directly or indirectly enhance cAMP-mediated vasorelaxation—$PDE_{cAMP}$ inhibitors, eg $PDE_{cAMP}$ type 2 inhibitors, NEP (EC 3.4.24.11; Sequence No. 1) inhibitors and neuropeptide Y Y1 (NPY Y1) receptor antagonists.

4.6.1 Neutral Endopeptidase (NEP EC 3.4.24.11; Sequence No. 1) Inhibitors

NEP EC 3.4.24.11 (Sequence No. 1) metabolises VIP (Sequence No. 8) and hence terminates VIP(Sequence No. 8)-mediated biological activity. NEP inhibitors will potentiate the endogenous vasorelaxant effect of VIP (Sequence No. 8) released during arousal. This will have the clinical effect of enhancing genital engorgement.

There have been no previous literature reports of NEP EC3.4.24.11 (Sequence No. 1) localisation or of it's functional role in vaginal tissue or a role in sexual arousal.

Selective inhibitors of NEP EC 3.4.24.11 (Sequence No. 1) at clinically relevant doses significantly enhance pelvic nerve stimulated increases in vaginal blood flow (See FIG. 6).

A NEP inhibitor enhanced the peak increase in vaginal blood flow by up to 53% compared to time matched control increases. This enhancement of submaximal stimulation frequencies (eg 4 Hz), was dose dependant eg 0.1 mg/kg iv induced a 35.0±7.6% increase; 0.3 mg/kg iv induced a 42.6.0±27.7% increase and 1.0 mg/kg iv induced a 52.8±32.5% increase. NEP inhibitors had no effect on basal (unstimulated) vaginal blood flow. Hence, the agents of the present invention enhance arousal, by potentiating cAMP signalling, rather than induce arousal in the absence of sexual desire ie by direct increasing cAMP signalling.

Selective inhibitors of NEP EC 3.4.24.11 (Sequence No. 1) at clinically relevant doses significantly enhance pelvic nerve stimulated increases in clitoral blood flow (See FIG. 12). A NEP inhibitor enhanced the peak increase in clitoral blood flow by up to 131% compared to vehicle control increases. NEP inhibitors had no effect on basal (unstimulated) vaginal blood flow. This further supports our believe that the agents of the present invention will enhance arousal, by potentiating cAMP signalling, rather than induce arousal in the absence of sexual desire i.e. by direct increasing cAMP signalling.

Selective inhibitors of NEP EC 3.4.24.11 (Sequence No. 1), at clinically relevant doses, enhance VIP(Sequence No. 8)-induced increases in vaginal blood flow when compared to time-matched controls. At submaximal doses of VIP (Sequence No. 8)(eg. 6.0 μg/kg) a significant potentiation in both the peak increase (95±6%) and prolongation of the duration of the enhancement (circa 140%—from 7 to in excess of 17 minutes; See FIG. 7). NEP inhibitors significantly prolong the duration of VIP(Sequence No. 8)-induced elevation of vaginal blood flow when given in combination with dose of VIP (Sequence No. 8) that produce maximal flow increases (circa 80% increase in duration—11 to 20 minutes). NEP inhibitors at clinically relevant-doses significantly enhance VIP(Sequence No. 8)-induced and nerve-mediated relaxations in isolated tissue. The $EC_{50}$ for VIP (Sequence No. 8) is significantly reduced from 18.8±0.6 nM to 2.9±0.3 nM in the presence of a selective NEP inhibitor (1 μM). The effect of the NEP inhibitor is concentration dependent.

NEP EC 3.4.24.11 (Sequence No. 1) mRNA message and protein is expressed and has been identified in human and rabbit vagina by Northern and Western analyses.

4.6.2 Phosphodiesterase (PDE) Inhibitors cAMP is degraded by cAMP-hydrolysing PDEs ie. $PDE_{cAMP}$. $PDE_{cAMP}$ inhibitors will potentiate the endogenous vasorelaxant effect of cAMP released during arousal. This should have the clinical effect of enhancing vaginal engorgement.

There are no literature reports of $PDE_{cAMP}$ localisation or of a functional role of these isozymes in vaginal tissue or a role in sexual arousal. We have shown by PDE profiling of human and rabbit vagina that the following $PDE_{cAMP}$ 1, 2, 3, 4, 7 & 8 isozymes are present. Inhibitors of these $PDE_{cAMP}$ represent potential agents to enhance vaginal blood flow and/or relax vaginal smooth muscle.

A selective inhibitor of $PDE_{cAMP}$ type 2 inhibitor at clinically relevant doses significantly enhances pelvic nerve stimulated increases in vaginal blood flow (See FIG. 8). A $PDE_{cAMP}$ type 2 inhibitor (500 μg/kg; iv) enhanced the peak increase in vaginal blood flow by 86.8±21.9% compared to increases observed during time matched control (@ 4 Hz).

A selective $PDE_{cAMP}$ type 2 inhibitor significantly enhanced the duration of VIP (Sequence No. 8)(60 μg/kg)-induced increases in peak vaginal blood flow by over 100% (measured at 50% amplitude; See FIG. 9). The selective $PDE_{cAMP}$ type 2 inhibitor significantly enhances the peak increase in blood flow induced by VIP(Sequence No. 8)-stimulation (circa 15±3% [200 μg/kg]) and significantly enhanced the duration of VIP(Sequence No. 8)-induced increases in peak vaginal blood flow by over 100% (measured at 50% amplitude; See FIG. 8). The selective $PDE_{cAMP}$ type 2 inhibitor significantly enhances the peak increase in blood flow induced by pelvic nerve stimulation (circa 15±3% [200 μg/kg] at 4 Hz).

$PDE_{cAMP}$ inhibitors enhance VIP(Sequence No. 8)-induced relaxations of precontracted isolated vaginal smooth muscle (1 μM phenylephrine; See Table 1). Selective inhibitors of $PDE_{cAMP}$ types 1, 2, 3 and 4 all significantly potentiated VIP(Sequence No. 8)-mediated relaxations. (210% @ 76 nM, 130% @ 8 nM, 220% @ 3.4 μM and 160% @ 686 nM potentiation of VIP (Sequence No. 8) $EC_{50}$ values) These inhibitors were administered at dose known to be selective for the particular $PDE_{cAMP}$ of interest. A selective inhibitor of $PDE_{cGMP}$ type 5 or vehicle control had no viable effect on VIP(Sequence No. 8)-mediated relaxations.

4.6.3 NPY Y1 Receptor Antagonists

NPY (Sequence No. 4) exerts an inhibitory influence over VIP(Sequence No. 8)-mediated vasorelaxation and NPY Y1 receptor antagonists will facilitate the vasorelaxant effect of endogenous VIP (Sequence No. 8) released during arousal. This will have the clinical effect of enhancing vaginal engorgement.

There are no literature reports of NPY receptor localisation or of a functional role for these receptors in vaginal tissue or a role in sexual arousal.

NPY receptor expression studies have identified by Northern and Western analyses that NPY $Y_1$ $Y_2$ and $Y_5$ receptor subtypes (Sequence Nos. 5, 6 and 7 respectively) are present in human and rabbit vagina.

Selective inhibitors of NPY Y1 (Sequence No. 5) at clinically relevant doses significantly enhance pelvic nerve stimulated increases in vaginal blood flow (See FIG. 10). An NPY Y1 antagonist enhanced the peak increase in vaginal blood flow by up to 92% compared to time matched control increases. This enhancement of submaximal stimulation frequencies (eg 4 Hz), was dose dependant eg 0.01 mg/kg iv induced a 15.8±19.6% increase; 0.03 mg/kg iv induced a 35.1±17.17% increase; 0.10 mg/kg iv induced a 60.1±16.9% increase and 0.3 mg/kg iv induced a 91.9±27.4% increase (mean±sem n=3). NPY Y1 antagonists had no effect on basal (unstimulated) vaginal blood flow. This reinforces our view that they will enhance arousal, by potentiating cAMP signalling, rather than induce arousal in the absence of sexual desire ie by direct increasing cAMP signalling.

4.7 Effects of Agents That Enhance cAMP or Increase Vaginal Blood Flow on the Mean Arterial Blood Pressure in the Anaesthetised Rabbit In the search for an oral therapy for FSAD it is desirable that there are no associated adverse cardiovascular effects eg effect on blood pressure or heart rate. In our studies, we have found that infusions of VIP (Sequence No. 8) significantly reduce mean arterial blood pressure (See FIG. 3) and significantly increased heart rate. Hence, in a highly preferred aspect, the agent is not VIP. Pelvic nerve stimulation and inhibitors of $PDE_{cAMP}$ and NEP (Sequence No. 1) however had no effect on blood pressure. At 6.0 μg/kg VIP (Sequence No. 8)(iv), caused a significant reduction in mean arterial blood pressure of 13.2±0.7 mm Hg and a significant increase in heart rate of 16±4 beats per minute. At higher doses such as 60.0 μg/kg VIP (Sequence No. 8)(iv) caused significant reduction in mean arterial blood pressure of 14.7±1.37 mm Hg and this was associated with a significant increase in heart rate of 111±30 beats per minute which then increased mean arterial blood pressure by 8.5±1.4 mm Hg.

COMPOUNDS TESTED

A series of compounds mentioned above were tested in accordance with the present invention and were found to be effective in accordance with the present invention—i.e. they can act as $P_{cAMP}$ in order to treat FSD, in particular FSAD. These compounds included:

Compound of Formula Ia ("FIa")—viz 5-[4-(diethylamino)benzyl]-1-methyl-3-propyl-6,7-dihydro-1H-pyrazolo[4,3-d]pyrimidin-7-one. FIa may be prepared according to the teachings of EP-A-0911333 (Example 50 thereof).

Compound of Formula II ("FII")—viz 9-(1-acetyl-4-phenylbutyl)-2-[(3,4-dimethoxyphenyl)methyl]-1,9-dihydro-6H-purin-6-one. FII may be prepared according to the teachings of EP-A-0771799 (Example 100 thereof).

Compound of Formula III ("FIII")—viz Milrinone. FIII is a commercially available product.

Compound of Formula IV ("FIV")—viz Rolipram. FIV is a commercially available product.

Compound of Formula V ("FV")—viz cyclohexanecarboxylic acid, 3-[[[1-(2-carboxy-4-pentenyl)cyclopentyl]carbonyl]amino]-,1-ethyl ester. FV may be prepared according to the teachings of EP-A-0274234 (Example 300 thereof.

Compound of Formula VI ("FVI")—viz cyclohexanecarboxylic acid, 3-[[[1-(2-carboxy-4-pentenyl)cyclopentyl]carbonyl]amino]-. FVI may be prepared according to the teachings of EP-A-0274234 (Example 379 thereof.

In particular, FIa, FII, FIII and FIV are $PDE_{cAMP}$ inhibitors. FIa is a I:PDEI, FII is a I:PDEII, FIII is a I:PDEIII and FIV is a I:PDEIV.

The data for these compounds are presented above in the previous Example sections—for example see Table I.

As is evident, these $PDE_{cAMP}$ inhibitors enhance VIP (Sequence No. 8)-induced relaxations of isolated tissue.

FII—which is a selective I:PDEII—enhances VIP (Sequence No. 8)-induced increases in vaginal blood flow at clinically relevant doses.

FII also enhances pelvic nerve stimulated increases in vaginal blood flow at clinically relevant doses.

FV and FVI are selective inhibitors of NEP EC 3.4.24.11 (Sequence No. 1).

The data presented above in the previous Example sections are for FVI. However, similar results were obtained for FV.

As is evident, FV and FVI enhance VIP(Sequence No. 8)-induced increases in vaginal blood flow at clinically relevant doses.

FV and FVI also enhance pelvic nerve stimulated increases in vaginal blood flow at clinically relevant doses.

FV and FVI also enhance VIP(Sequence No. 8)-induced and nerve-mediated relaxations of isolated tissue at clinically relevant doses.

Additional compounds that were tested and that proved to be effective included:

2-[(1-{[(1-benzyl-6-oxo-1,6-dihydro-3-pyridinyl)amino]carbonyl}cyclopentyl)methyl]-4-methoxybutanoic acid (F57)

2-{[1-({[3-(2-oxo-1-pyrrolidinyl)propyl]amino}carbonylcyclopentyl]-methyl}-4-phenylbutanoic acid (F58)

(+)-2-[1-({[2-(hydroxymethyl)-2,3-dihydro-1H-inden-2-yl]amino}carbonyl)cyclopentyl]-methyl}4-phenylbutanoic acid (F59)

2-[(1-{[(5-methyl-1,3,4-thiadiazol-2-yl)amino]carbonyl}cyclopentyl)methyl]-4-phenylbutanoic acid (F60)

cis-3-(2-methoxyethoxy)-2-[(1-{[(4-{[(phenylsulfonyl)amino]carbonyl}cyclohexyl)-amino]carbonyl}cyclopentyl)methyl]propanoic acid (F61)

(+)-2-{[1-({[2-(hydroxymethyl)-2,3-dihydro-1H-inden-2-yl]amino}carbonyl)cyclopentyl]-methyl}pentanoic acid (F62)

(+)-2-[(1-{[(5-ethyl-1,3,4-thiadiazol-2-yl)amino]carbonyl}cyclopentyl)methyl]pentanoic acid (F63)

2-({1-[(3-benzylanilino)carbonyl]cyclopentyl}methyl)pentanoic acid (F64)

2-[(1-{[(1-benzyl-6-oxo-1,6-dihydro-3-pyridinyl)amino]carbonyl}cyclopentyl)methyl]-pentanoic acid (F65)

2-{[1-({[(1R,3S,4R)4-(aminocarbonyl)-3-butylcyclohexyl]amino}carbonyl)-cyclopentyl]methyl}pentanoic acid (F66)

Each of compounds F57–66 is an I:NEP.

Synthesis of Compounds F57–66

In the following commentary, the Preparation Examples are the synthesis of intermediates; whereas the Examples are the synthesis of the respective, compounds of the present invention.

Example 1

2-[(1-{[(1-Benzyl-6-oxo-1,6-dihydro-3-pyridinyl) amino]carbonyl}cyclopentyl)methyl]4-methoxybutanoic Acid (F57)

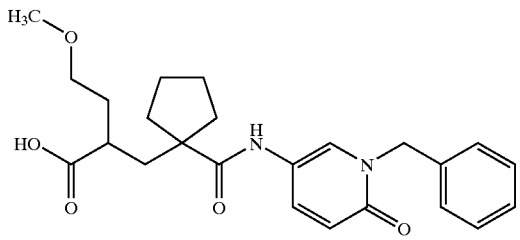

A mixture of the benzyl ester from preparation 1 (1/62) (850 mg, 1.64 mmol), and 5% palladium on charcoal (250 mg) in 40% aqueous ethanol (21 ml), was hydrogenated at 30 psi and room temperature for 30 minutes. The reaction mixture was filtered through Hyflo®, and the filtrate evaporated under reduced pressure. The residual foam was purified by column chromatography on silica gel using dichloromethane:methanol (97:3) as eluant to give the title compound as a white foam, 550 mg, 79%; $^1$H NMR (DMSO-$d_6$, 300 MHz) δ: 1.24–2.17 (m, 12H), 2.18–2.31 (m, 1H), 3.07 (s, 3H), 3.21 (t, 2H), 5.08 (s, 2H), 6.63 (d, 1H), 7.23–7.41 (m, 5H), 7.72 (d, 1H), 8.24 (s, 1H). Anal. Found: C, 67.46; H, 7.18; N, 6.24. $C_{24}H_{30}N_2O_5$ requires C, 67.58; H, 7.09; N, 6.57%.

Example 2

2-{[1-({[3-(2-oxo-1-Pyrrolidinyl)propyl] amino}carbonylcyclopentyl]-methyl}4-phenylbutanoic Acid. (F58)

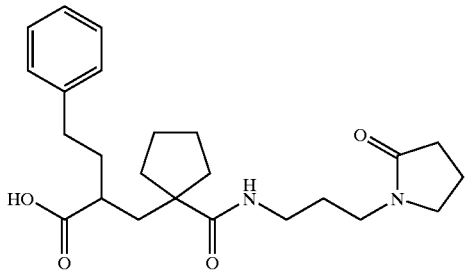

A mixture of the benzyl ester from preparation 3 (3/67) (780 mg, 1.55 mmol) and 10% palladium on charcoal (100 mg) in ethanol:water (90:10 by volume), (30 ml) was hydrogenated at room temperature under 60psi $H_2$ pressure for 1.5 hours. The catalyst was filtered off, and the filtrate evaporated under reduced pressure to provide the title compound as a white foam, 473 mg, 74%; $^1$H NMR (CDCl$_3$, 300MHz) d: 1.26–1.77 (m, 10H), 1.78–2.46 (m, 11H), 2.49–2.70 (m, 2H), 2.95–3.36 (m, 4H), 6.92–7.38 (m, 5H); Anal. Found: C, 64.05; H, 7.73; N, 6.22. $C_{24}H_{34}N_2O_4$;0.75$H_2O$ requires C, 65.88; H, 7.83; N, 6.40%.

Example 3

(+)-2-{[1-({[2-(Hydroxymethyl)-2,3-dihydro-1H-inden-2-yl]amino}carbonyl)cyclopentyl]-methyl}-4-phenylbutanoic Acid (F59)

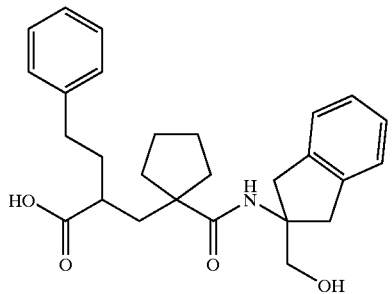

2-{[1-({[2-(Hydroxymethyl)-2,3-dihydro-1H-inden-2-yl]amino}carbonyl)cyclopentyl]-methyl}4-phenylbutanoic acid (WO 9110644) may be purified by standard HPLC procedures using an AD column and hexane:isopropanol-:trifluoroacetic acid (70:30:0.2) as eluant, to give the title compound of example 3, 99.5% ee; $[α]_D$=+9.1° (c=1.76 in ethanol)

Example 4

2-[(1-{[(5-Methyl-1,3,4-thiadiazol-2-yl)amino] carbonyl}cyclopentyl)methyl]-4-phenylbutanoic Acid (F60)

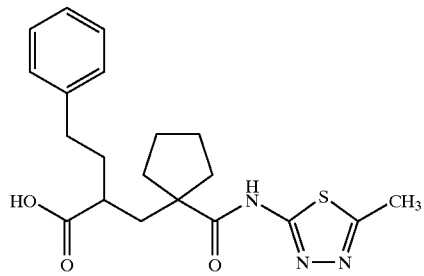

A mixture of the benzyl ester from preparation 4 (4/70) (187 mg, 0.39 mmol) and 10% palladium on charcoal (80 mg) in ethanol (20 ml) was hydrogenated at 60 psi for 18 hours. Tlc analysis showed starting material remaining, so additional 10% palladium on charcoal (100 mg) was added, and the reaction continued for a further 5 hours. Tlc analysis again-showed starting material remaining, so additional catalyst (100 mg) was added, and hydrogenation continued for 18 hours. The mixture was filtered through Arbocel®, and the filtrate concentrated under reduced pressure, and azeotroped with dichloromethane. The crude product was purified by chromatography on silica gel using a Biotage® column, and dichloromethane:methanol (95:5) as eluant to afford the title compound as a clear oil, 80 mg, 53%; $^1$H NMR (CDCl$_3$, 300 MHz) δ: 1.51–1.89 (m, 9H), 2.03 (m, 1H), 2.20 (m, 1H), 2.40 (m, 2H), 2.60 (m, 5H), 7.15–7.30 (m, 5H); LRMS: m/z 387.8 (MH$^+$).

Example 5

Cis-3-(2-Methoxyethoxy)-2-[(1-{[(4-{[(phenylsulfonyl)amino]carbonyl}cyclohexyl)-amino]carbonyl}cyclopentyl)methyl]propanoic Acid (F61)

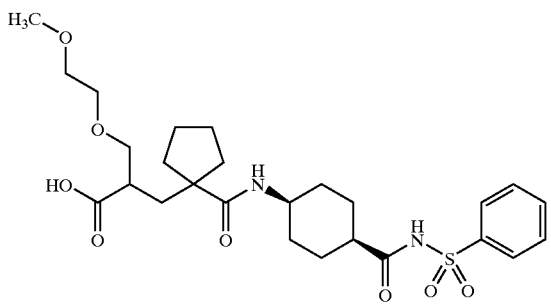

A solution of the tert-butyl ester from preparation 8 (8/66) (446 mg, 0.75 mmol) in dichloromethane (5 ml) and trifluoroacetic acid (5 ml) was stirred at room temperature for 18 hours. The reaction mixture was concentrated under reduced pressure, and the residue azeotroped with dichloromethane, then toluene, and finally ether, to afford the title compound as a white foam, 385 mg, 95%; $^1$H NMR (CDCl$_3$, 400 MHz) δ: 1.48–2.17 (m, 18H), 2.40 (s, 1H), 2.66 (s, 1H), 3.37 (s, 3H), 3.50 (m, 6H), 3.94 (s, 1H), 6.10 (d, 1H), 6.59 (s, 1H), 7.55 (t, 2H), 7.61 (m, 1H), 8.02 (d, 2H), 9.11 (s, 1H); Anal. Found: C, 54.88; H, 6.90; N, 5.04. C$_{26}$H$_{38}$N$_2$O$_8$S;1.7H$_2$O requires C, 57.97; H, 7.11; N, 5.20%.

Example 6

(+)-2-{[1-({[2-(Hydroxymethyl)-2,3-dihydro-1H-inden-2-yl]amino}carbonyl)cyclopentyl]-methyl}pentanoic Acid (F62)

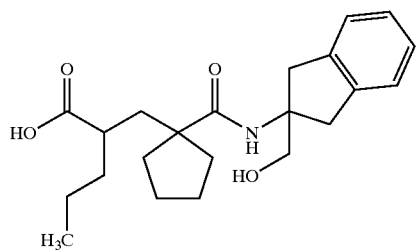

2-{[1-({[2-(Hydroxymethyl)-2,3-dihydro-1H-inden-2-yl]amino}carbonyl)cyclopentyl]-methyl}pentanoic acid (WO 9110644) was further purified by HPLC using an AD column and hexane:isopropanol:trifluoroacetic acid (90:10:0.1) as eluant, to give the title compound of example 6, 99% ee, [α]$_D$=+10.4° (c=0.067, ethanol).

Example 7

(+)-2-[(1-{[(5-Ethyl-1,3,4-thiadiazol-2-yl)amino]carbonyl}cyclopentyl)methyl]pentanoic Acid (F63)

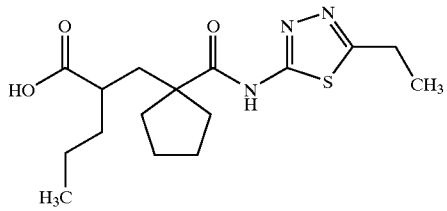

The acid from Preparation 18 (18/ex4) (824 mg) was further purified by HPLC using an AD column and using hexane:iso-propanol:trifluoroacetic acid (85:15:0.2) as eluant to give the title compound of example 7 as a white foam, 386 mg, 99% ee, $^1$H NMR (CDCl$_3$, 400 MHz) δ: 0.90 (t, 3H), 1.38 (m, 6H), 1.50–1.79 (m, 9H), 2.19 (m, 1H), 2.30 (m, 1H), 2.44 (m, 1H), 2.60 (m, 1H), 2.98 (q, 2H), 12.10–12.27 (bs, 1H); LRMS: m/z 338 (MH-); and [α]$_D$=+3.80°(c=0.1, methanol)

Example 8

2-({1-[(3-Benzylanilino)carbonyl]cyclopentyl}methyl)pentanoic Acid (F64)

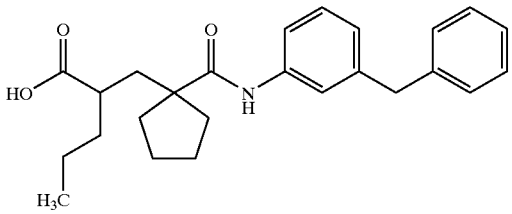

A mixture of the benzyl ester from preparation 10 (10/53) (1.3 mg, 2.47 mmol) and 5% palladium on charcoal (130 mg) in water (10 ml) and ethanol (40 ml) was hydrogenated at 30 psi and room temperature for 2 hours. The reaction mixture was filtered through Arbocel®, the filtrate concentrated under reduced pressure, and the residue triturated with dichloromethane. The residual gum was triturated with ether, then hexane, and dried at 50° C., to give the title compound as a solid, 0.79 g, 81%; $^1$H NMR (CDCl$_3$, 300 MHz) δ: 0.95 (t, 3H), 1.24–1.51 (m, 3H), 1.58–1.80 (m, 7H), 1.88 (dd, 1H), 2.15 (m, 2H), 2.24 (m, 1H), 2.48 (m, 1H), 4.00 (s, 2H), 6.98 (d, 1H), 7.24 (m, 6H), 7.40 (m, 3H); Anal. Found: C, 75.48; H, 7.76; N, 3.59. C$_{25}$H$_{31}$NO$_3$;0.25H$_2$O requires C, 75.44; H, 7.98; N, 3.51%.

Example 9

2-[(1-{[(1-Benzyl-6-oxo-1,6-dihydro-3-pyridinyl)amino]carbonyl}-cyclopentyl)methyl]-pentanoic Acid (F65)

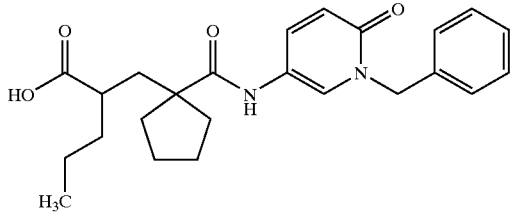

The title compound was obtained as a white foam in 51% yield from the benzyl ester from preparation 13 (13/56), following a similar procedure to that described in Preparation 19 (19/ex21), except, the product was purified by column chromatography on silica gel, using ethyl acetate as eluant; $^1$H NMR (CDCl$_3$, 300 MHz) δ: 0.96 (t, 3H), 1.28–1.80 (m, 12H), 2.01 (m, 1H), 2.30–2.52 (m, 2H), 5.02 (dd, 2H), 6.60 (d, 1H), 7.27 (m, 5H), 7.70 (s, 1H), 8.34 (s, 1H); Anal. Found: C, 69.52; H, 7.41; N, 6.51. C$_{24}$H$_{30}$N$_2$O$_4$;0.25H$_2$O requires C, 69.45; H, 7.41; N, 6.75.

Example 10

2-{[1-({[(1R,3S,4R)4-(aminocarbonyl)-3-butylcyclohexyl]amino}carbonyl)-cyclopentyl]methyl}pentanoic Acid (F66)

Compounds of formula ic, i.e. Compounds of general formula i where r$^1$ is propyl, where prepared from the corresponding tert-butyl ester, following a similar procedure to that described in Preparation 14 (14/ex1).

(Ic)

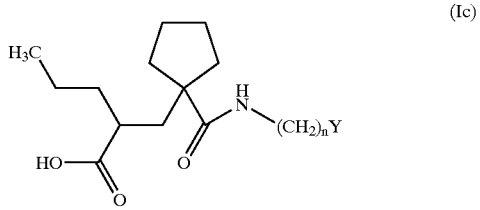

Preparation 1 (1/62)

Benzyl 2-[(1-{[(1-benzyl-6-oxo-1,6-dihydro-3-pyridinyl)amino]carbonyl}clopentyl)-methyl]-4-methoxybutanoate

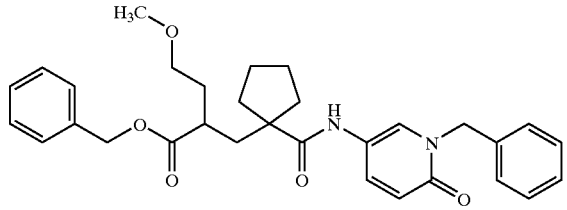

Oxalyl chloride (0.26 ml, 3.0 mmol) was added to an ice-cooled solution of 1-{2-[(benzyloxy)carbonyl]-4-methoxybutyl}cyclopentanecarboxylic acid (EP 274234) (1.0 g, 3.0 mmol) and N,N-dimethylformamide (2 drops) in dichloromethane (20 ml), and the reaction stirred at room temperature for 2 hours. The solution was concentrated under reduced pressure and the residue azeotroped with dichloromethane (3×10 ml). The product was dissolved in dichloromethane (20 ml), then cooled in an ice-bath. The amine from preparation 2 (2/28) (600 mg, 3 mmol) and N-methylmorpholine (0.6 ml, 5.45 mmol) were added and the reaction stirred at room temperature for 18 hours. The reaction mixture was concentrated under reduced pressure, and partitioned between water and ether. The organic layer was washed with hydrochloric acid (2N), sodium bicarbonate solution, then water, dried (MgSO$_4$) and evaporated under reduced pressure. The residual green solid was purified by medium pressure column chromatography on silica gel using ethyl acetate:hexane (90:10) as eluant to afford the title compound, 880 mg, 57%; $^1$H NMR (CDCl$_3$, 300 MHz) δ: 1.37–2.28 (m, 12H), 2.46–2.64 (m, 1H), 3.20 (s, 3H), 3.31 (m, 2H), 4.97 (dd, 2H), 5.08 (dd, 2H), 6.57 (d, 1H), 7.12 (m, 1H), 7.18–7.48 (m, 10H), 8.08 (d, 1H).

Preparation 2 (2/28)

5-Amino-1-benzyl-2(1H)-pyridinone

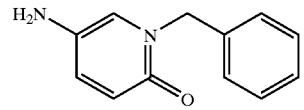

A mixture of 1-benzyl-5-nitro-1H-pynrdin-2-one (Justus Liebigs Ann. Chem. 484; 1930; 52) (1.0 g, 4.35 mmol), and granulated tin (3.5 g, 29.5 mmol) in concentrated hydrochloric acid (14ml) was heated at 90° C. for 1.5 h ours. The cooled solution was diluted with water, neutralised using sodium carbonate solution, and extracted with ethyl acetate (250 ml in total). The combined organic extracts were filtered, dried (MgSO$_4$), and evaporated under reduced pressure to give the title compound as a pale green solid, (turned blue with time), 440 mg, 51%; $^1$H NMR (CDCl$_3$, 250 MHz) δ: 4.12–447 (bs, 2H), 5.00 (s, 2H), 6.31 (d, 1H), 6.86 (s, 1H), 7.07 (m, 1H), 7.14–7.42 (m, 5H).

Preparation 3 (3/67)

Benzyl 2-{[1-({[3-(2-Oxo-1-pyrroidinyl)propyl]amino}carbonylcyclopentyl]-methyl}-4-phenylbutanoate

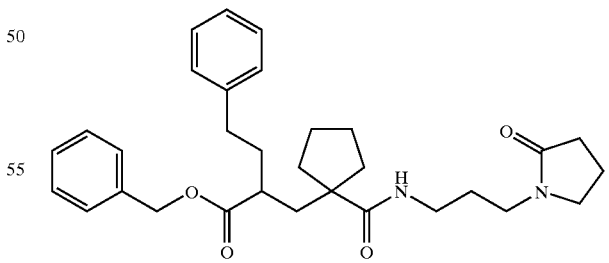

1-3-Dimethylaminopoyl)-3-ethylcarbodiimide (hydrochloride (1.06 g, 5.53 mmol), 1-hydroxybenzotriazole hydrate (0.60 g, 4.44 mmol) and 4-methylmorpholine (0.56 g, 5.54 mmol) were added sequentially to a cooled solution of 1-{2-[(benzyloxy)carbonyl]4-phenylbutyl}cyclopentanecarboxylic acid (EP 274234) (1.5 g, 3.94 mmol) in dry dichloromethane (15 ml) at room temperature, followed by N-(3-aminopropyl)-2-pyrrolidinone (0.56 g, 3.94 mmol), and the reaction stirred at room temperature for 18 hours. The mixture was washed with water, 2N hydrochloric acid, saturated aqueous sodium bicarbonate solution, and then dried (MgSO$_4$) and evaporated under reduced pressure. The residual yellow oil was purified by column chromatography on silica gel using ethyl acetate:pentane (50:50) as the eluant to provide the title compound as a clear gum, 800 mg, 40%; $^1$H NMR (CDCl$_3$, 300 MHz) d: 1.37–2.20 (m, 16H), 2.34–2.58 (m, 5H), 2.92–3.46 (m, 6H), 5.07 (d, 1H), 5.18 (d, 1H), 6.98–7.47 (m, 10H).

Preparation 4 (4/70)

Benzyl 2-[(1-{[(5-methyl-1,3,4-thiadiazol-2-yl)amino]carbonyl}cyclopentyl)methyl]-4-phenylbutanoate

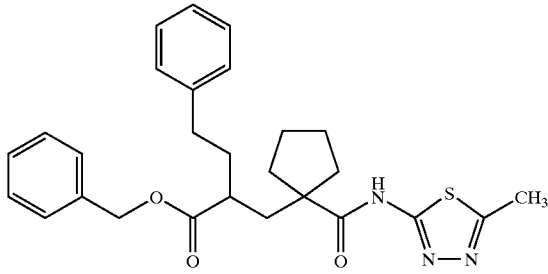

The title compound was obtained as a clear oil in 74% yield from 1-{2-[(benzyloxy)carbonyl]-4-phenylbutyl}cyclopentane-carboxylic acid (EP 274234) and 2-amino-5-methyl-1,3,4-thiadiazole, following a similar procedure to that described in preparation 5 (5/68); $^1$H NMR (CDCl$_3$, 400 MHz) δ: 1.58–1.76 (m, 7H), 1.83–1.98 (m, 3H), 2.03 (m, 1H), 2.20 (m, 1H), 2.35 (m, 1H), 2.44 (m, 3H), 2.65 (s, 3H), 5.02 (dd, 2H), 7.00 (d, 2H), 7.15 (m, 1H), 7.19 (m, 2H), 7.35 (m, 5H); LRMS: m/z 478.7 (MH$^+$).

Preparation 5 (5/68)

Benzyl 2-{[1-({[3-(methylamino)-3-oxopropyl]amino}carbonyl)cyclopentyl]methyl}-4-phenylbutanoate

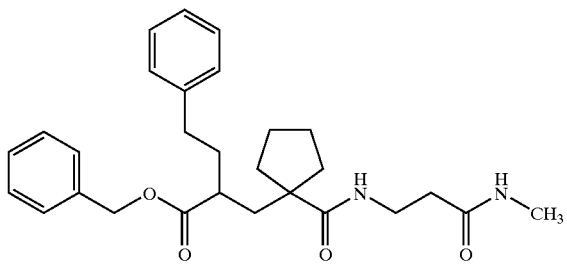

1-(3-Dimethylaminopropyl)-3-ethylcarbodiimide hydrochloride (122 mg, 0.64 mmol), 1-hydroxybenzotriazole hydrate (86 mg, 0.64 mmol) and 4-methylmorpholine (173 μl, 1.59 mmol) were added sequentially to a cooled solution of 1-{2-[(benzyloxy)carbonyl]4-phenylbutyl}cyclopentane-carboxylic acid (EP 274234) (202 mg, 0.53 mmol) in N,N-dimethylformamide (5 ml) at room temperature, followed by the amine hydrochloride from preparation 6 (6/23) (146 mg, 1.06 mmol), and the reaction stirred at 90° C. for 18 hours. The cooled solution was concentrated under reduced pressure and the residue partitioned between water (20 ml) and ethyl acetate (100 ml). The layers were separated, the organic phase washed with water (3×30 ml), brine (25 ml) dried (MgSO$_4$), and evaporated under reduced pressure to give a clear oil. The crude product was purified by column chromatography on silica gel using dichloromethane:methanol (98:2) as eluant to afford the title compound as a colourless oil, 162 mg, 67%; $^1$H NMR (CDCl$_3$, 400 MHz) δ: 1.38–1.53 (m, 2H), 1.53–1.96 (m, 8H), 2.02 (m, 2H), 2.27 (t, 2H), 2.46 (m, 3H), 2.76 (d, 3H), 3.44 (m, 2H), 5.13 (s, 2H), 5.79 (bs, 1H), 6.38 (m, 1H), 7.06 (d, 2H), 7.18 (m, 1H), 7.22 (m, 2H), 7.38 (m, 5H); LRMS: m/z 465.5 (MH$^+$).

Preparation 6 (6/23)

3-Amino-N-methylpropanamide Hydrochloride

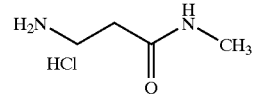

A mixture of the benzyl carbamate from preparation 7 (7/13) (7.92 g, 33.5 mmol) and 5% palladium on charcoal (800 mg) in ethanol (300 ml) was hydrogenated at 50 psi and room temperature for 4 hours. The reaction mixture was filtered through Arbocel®, washing through with ethanol, and 1N hydrochloric acid (36.9 ml, 36.9 mmol) was added to the combined filtrate. This solution was evaporated under reduced pressure and the residue azeotroped with dichloromethane to afford the title compound as a colourless foam, 4.66 g, $^1$H NMR (DMSOd$_6$, 300 MHz) δ: 2.46 (t, 2H), 2.60 (s, 3H), 2.95 (m, 2H), 7.98–8.16 (m, 2H).

Preparation 7 (7/13)

Benzyl 3-(methylamino)-3-oxopropylcarbamate

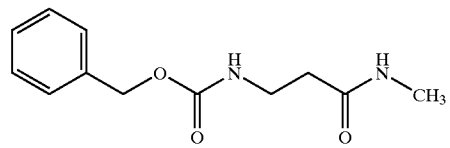

A mixture of N-[(benzyloxy)carbonyl]-β-alanine (10 g, 44.8 mmol), methylamine hydrochloride (3.33 g, 49.28 mmol), 1-hydroxybenzotriazole hydrate (6.05 g, 44.8 mmol), 1-(3-dimethylaminopropyl)-3-ethylcarbodiimide hydrochloride (10.3 g, 53.76 mmol) and N-methylmorpholine (11.33 ml, 103 mmol) in dichloromethane (200 ml) was stirred at room temperature for 18 hours. The resulting precipitate was filtered off to give the desired product as a colourless foam, and the filtrate evaporated under reduced pressure. The residue was purified by column chromatography on silica gel using an elution gradient of ethyl acetate-:hexane (90:10 to 100:0) to give additional product, 7.96 g, 75% in total; $^1$H NMR (CDCl$_3$, 300 MHz) δ: 2.42 (t, 2H), 2.80 (s, 3H), 3.50 (m, 2H), 5.21 (s, 2H), 5.49 (bs, 1H), 5.63 (bs, 1H), 7.36 (m, 5H); Anal. Found: C, 60.68; H, 7.00; N, 11.95. $C_{12}H_{16}N_2O_3$ requires C, 61.00; H, 6.83; N, 11.86%.

Preparation 8 (8/66)

Cis-tert-Butyl 3-(2-Methoxyethoxy)-2-[(1-{[(4-{[(phenylsulfonyl)amino]carbonyl}-cyclohexyl)amino]-carbonyl}cyclopentyl)methyl]proanoate

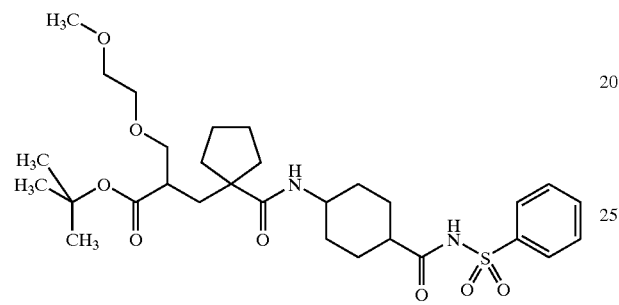

N,N'-Dicyclohexylcarbodiimide (1 99 mg, 0.97 mmol), 4-dimethylaminopyridine (118 mg, 0.97 mmol) and benzenesulphonamide (152 mg, 0.97 mmol) were added to an ice-cooled solution of the acid from preparation 9 (9/63) (400 mg, 0.878 mmol) in dichloromethane (12 ml) and N,N-dimethylformamide (0.5 ml), and the reaction stirred at room temperature for 20 hours. The mixture was concentrated under reduced pressure and the residue suspended in cold ethyl acetate. The resulting insoluble material was filtered off, the filtrate washed with hydrochloric acid (1N), and water, then dried (MgSO$_4$) and evaporated under reduced pressure. The crude product was purified by column chromatography on silica gel using an elution gradient of dichloromethane:methanol (95:5 to 90:10) to afford the title compound as a white foam, 480 mg, 92%; $^1$H NMR (CDCl$_3$, 400 MHz) δ: 1.44 (s, 9H), 1.63 (m, 13H), 1.80 (m, 2H), 1.88 (m, 1H), 1.98 (m, 2H), 2.36 (m, 1H), 2.57 (m, 1H), 3.38 (s, 3H), 3.40 (m, 1H), 3.51 (t, 2H), 3.58 (m, 3H), 3.95 (m, 1H), 5.92 (d, 1H), 7.56 (m, 2H), 7.62 (m, 1H), 8.05 (d, 2H), 8.75 (bs, 1H); LRMS: m/z 618 (MNa$^+$).

Preparation 9 (9/63)

4-{[(1-{3-tert-Butoxy-2-[(2-methoxyethoxy)methyl]-3-oxopropyl}cyclopentyl)-carbonyl]amino}cyclohexanecarboxylic Acid

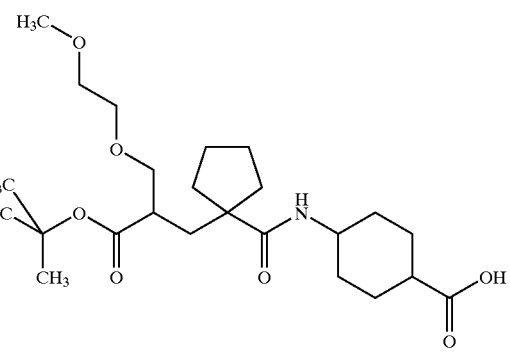

A mixture of benzyl 4-{[(1-{3-tert-butoxy-2-[(2-methoxyethoxy)methyl]-3-oxopropyl}cyclopentyl)carbonyl]amino}cyclohexanecarboxylate (EP 274234), and 10% palladium on charcoal (250 mg) in water (10 ml) and ethanol (50 ml) was hydrogenated at 50 psi and room temperature for 18 hours. The reaction mixture was filtered through Solkafloc®, the filtrate concentrated under reduced pressure and the residue azeotroped with toluene (3×) and then dichloromethane (3×), to give the title compound, 2.0 g, 96%; $^1$H NMR (CDCl$_3$, 300 MHz) δ: 1.48 (s, 9H), 1.53–1.84 (m, 14H), 1.94–2.10 (m, 5H), 2.60 (m, 2H), 3.40 (s, 3H), 3.41–3.63 (m, 5H), 3.96 (m, 1H), 5.90 (bd, 1H).

Preparation 10 (10/53)

Preparation 10 (10/53)

The following compound:

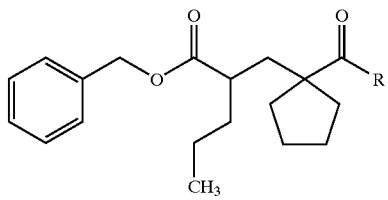

where:

| Prep | R | Yield (%) | Data |
|---|---|---|---|
| 10 (10/53)[1] | ![NH-CH2-phenyl-phenyl] | 90 | $^1$H NMR(CDCl$_3$, 300MHz)δ: 0.84(t, 3H), 1.24(m, 2H), 1.40–1.76(m, 7H), 1.84(dd, 1H), 1.98(m, 1H), 2.19(dd, 1H), 2.28(m, 1H), 2.56(m, 1H), 3.98(s, 2H), 4.99(dd, 2H), 6.98(d, 1H), 7.19–7.42(m, 15H). |

[1] = dichloromethane used as the column eluant was prepared from the acid chloride from preparation 11 (11/3) and the appropriate amine, following a similar procedure to that described in preparation 12 (12/52).

Preparation 11 (11/3)

Benzyl 2-{[1-(chlorocarbonyl)cyclopentyl]methyl}pentanoate

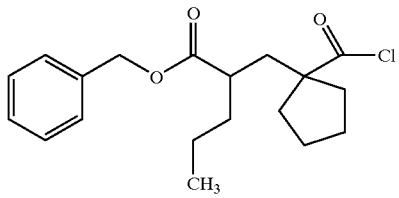

Oxalyl chloride (1.15 ml, 13.2 mmol) was added to an ice-cooled solution of 1-{2-[(benzyloxy)carbonyl]pentyl}cyclopentanecarboxylic acid (EP 274234) (2.0 g, 6.3 mmol) in dry dichloromethane (20 ml), and the solution stirred at room temperature for 2 hours. The reaction mixture was concentrated under reduced pressure and the residue azetroed with dichloromethane (3×), to give the title compound as a golden oil, 2.1 g; $^1$H NMR (CDCl$_3$, 300 MHz) δ: 0.88 (t, 3H), 1.28 (m, 2H), 1.43 (m, 2H), 1.63 (m, 6H), 2.00 (m, 1H), 2.08–2.35 (m, 3H), 2.44 (m, 1H), 5.15 (s, 2H), 7.28 (m, 5H).

Preparation 12 (12/52)

Benzyl 2-({1-[(3-pyridinylamino)carbonyl]cyclopentyl}methyl)pentanoate

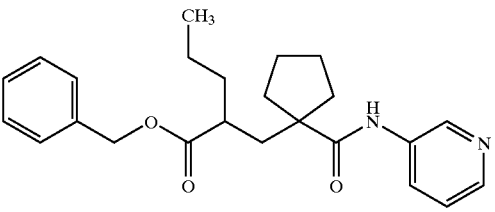

Triethylamine (0.11 ml, 0.78 mmol) was added to a mixture of the acid chloride from preparation 11 (11/3) (200 mg, 0.60 mmol) and 2-aminopyridine (61 mg, 0.65 mmol) in dichloromethane (3 ml), and the reaction stirred at room temperature for 16 hours. The mixture was evaporated under reduced pressure, the residue partitioned between sodium bicarbonate solution (5 ml) and ethyl acetate (20 ml), and the layers separated. The organic phase was dried (MgSO$_4$), and evaporated under reduced pressure to give a gum. The crude product was purified by column chromatography on silica gel using ethyl acetate as eluant, to afford the title compound, 130 mg; $^1$H NMR (CDCl$_3$, 400 MHz) δ: 0.82 (t, 3H), 1.21 (m, 3H), 1.40 (m, 1H), 1.43–1.72 (m, 6H), 1.81 (d, 1H), 1.98 (m, 1H), 2.18 (m, 1H), 2.24 (m, 1H), 2.46 (m, 1H), 4.98 (m, 2H), 7.20–7.38 (m, 6H), 7.42 (s, 1H), 8.06 (d, 1H), 8.35 (d, 1H), 8.56 (s, 1H).

Preparation 13 (13/56)

---

Preparation 13 (13/56)

The following compound:

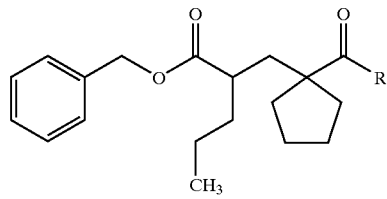

where:

| Prep | R | Yield (%) | Data |
|---|---|---|---|
| 13 (13/56)[2] | ![R group: 1-benzyl-2-oxo-1,2-dihydropyridin-5-yl amino] | 53 | $^1$H NMR(CDCl$_3$, 300MHz)δ: 0.84(t, 3H), 1.25(m, 2H), 1.27–1.99(m, 10H), 2.07–2.30 (m, 2H), 2.47(m, 1H), 4.99(s, 2H), 5.10(dd, 2H), 6.59(d, 1H), 7.15(d, 1H), 7.34(m, 11H), 8.10(s, 1H). |

[2] = N-methylmorpholine was used as the base was prepared from the acid chloride from preparation 11 (11/3) and the appropriate amine, following a similar procedure to that described in preparation 12 (12/52).

Preparation 14 (14/ex 1)

2-({1-[(1,3-Benzodioxol-5-ylamino)carbonyl]cyclopentyl}methyl)pentanoic Acid

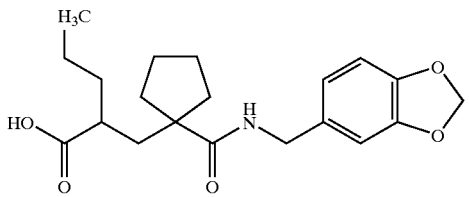

Trifluoroacetic acid (5 ml) was added to a solution of the tert-butyl ester from preparation 15 (15/34) (130 mg, 0.31 mmol) in dichloromethane (5 ml), and the solution stirred at room temperature for 4 hours. The reaction mixture was concentrated under reduced pressure and the residue azeotroped with toluene and dichloromethane to afford the title compound as a clear oil, 112 mg, $^1$H NMR (CDCl$_3$, 400 MHz) δ 0.83 (t, 3H), 1.22–1.40 (m, 3H), 1.50–1.72 (m, 8H), 1.95 (m, 1H), 2.10 (m, 2H), 2.19 (m, 1H), 4.30 (m, 2H), 5.93 (s, 2H), 5.99 (bs, 1H), 6.74 (m, 3H); LRMS: m/z 380 (MH$^-$).

Preparation 15 (15/34)

The following compound:

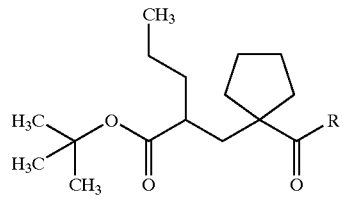

where

| Prep | R | Starting amine | Yield (%) | Data |
|---|---|---|---|---|
| 15 (15/34) | 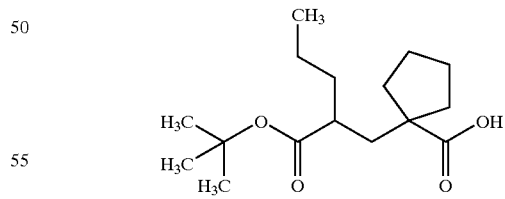 | Piperonylamine | 88 | $^1$H NMR(CDCl$_3$, 400MHz)δ: 0.85(t, 3H), 1.26(m, 4H), 1.42(s, 9H), 1.46(m, 2H), 1.59–1.75(m, 5H), 1.95(m, 2H), 2.06(m, 1H), 2.22(m, 1H), 4.26(dd, 1H), 4.39(dd, 1H), 5.95(m, 3H), 6.78(m, 3H). LRMS: m/z 418.3(MH$^+$) | was prepared from the acid from preparation 16 (16/1) and the appropriate amine compound, following a similar procedure to that described in preparation 17 (17/33).

Preparation 16 (16/1) cl 1-[2-(tert-Butoxycarbonyl)-4-pentyl]-cyclopentane Carboxylic Acid A mixture of 1-[2-(tert-butoxycarbonyl)-4-pentenyl]-cyclopentane carboxylic acid (EP 274234) (23 g, 81.5 mmol) and 10% palladium on charcoal (2 g) in dry ethanol (200 ml) was hydrogenated at 30 psi and room temperature for 18 hours. The reaction mixture was filtered through Arbocel®, and the filtrate evaporated under reduced pressure to give a yellow oil. The crude product was purified by column chromatography on silica gel, using ethyl acetate-:pentane (40:60) as the eluant, to provide the desired product as a clear oil, 21 g, 91%; ¹H NMR (CDCl₃, 0.86 (t, 3H), 1.22–1.58 (m, 15H), 1.64 (m, 4H), 1.78 (dd, 1H), 2.00–2.18 (m, 3H), 2.24 (m, 1H); LRMS: m/z 283 (M-H)⁻.

Preparation 17 (17/33)

tert-Butyl 2-{[1-({[1-(Hydroxymethyl)cyclopentyl]amino}carbonyl)-cyclopentyl]methyl}Pentanoate

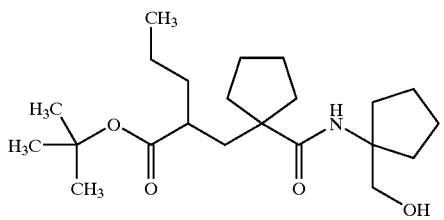

1-(3-Dimethylaminopropyl)-3-ethylcarbodiimide hydrochloride (41 mg, 0.21 mmol), 1-hydroxybenzotriazole hydrate (27 mg, 0.2 mmol), N-methylmorpholine (35 μl, 0.31 mmol) and finally 1-amino-1-cyclopentanemethanol (25 mg, 0.22 mmol) were added to a solution of the acid from preparation 16 (16/1) (150 mg, 0.53 mmol) in N,N-dimethylformamide (3 ml), and the reaction stirred at 90° C. for 18 hours. The cooled solution was diluted with ethyl acetate (90 ml), washed with water (3×25 ml), and brine (25 ml), then dried (MgSO₄) and evaporated under reduced pressure. The crude product was purified by chromatography on silica gel, using ethyl acetate:pentane (30:70) as the eluant to afford the title compound, 38 mg, 57%; ¹H NMR (CDCl₃, 400 MHz) δ: 0.88 (t, 3H), 1.29 (m, 3H), 1.41–1.78 (m, 26H), 1.78–1.98 (m, 4H), 2.04 (m, 1H), 2.26 (m, 1H), 3.59 (dd, 1H), 3.70 (dd, 1H), 4.80 (t, 1H), 5.81 (s, 1H); LRMS: m/z 380 (MH⁻).

Preparation 18 (18/ex.4)

A compound of the formula shown below was prepared from the corresponding tert-butyl ester following a similar procedure to that described in Preparation 14 (14/ex.1).

| Ex | N | R | Yield | Data |
|---|---|---|---|---|
| 18 (18/ex. 4)³ | 0 | [thiazole-CH₃ group] | 86 | ¹H NMR(CDCl₃, 400MHz)δ: 0.92(t, 3H), 1.35(t, 3H), 1.25–1.80(m, 11H), 2.20–2.50(m, 4H), 2.95(q, 2H), 12.10(bs, 1H). LRMS: m/z 339.8(MH⁺) Anal. Found: C, 56.46; H, 7.46; N, 12.36. C₁₆H₂₅N₃O₃S requires C, 56.62; H, 7.44; N, 12.37%. |

³= recrystallised from ether

Preparation 19 (19/ex.21)

2-({1-[(3-Benzylanilino)carbonyl]cyclopentyl}methyl)pentanoic Acid

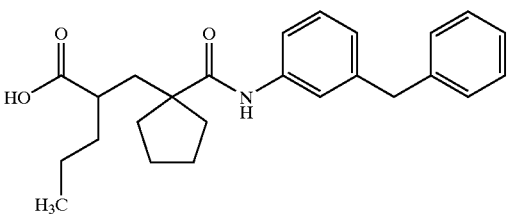

A mixture of the benzyl ester from preparation 10 (10/53) (1.3 mg, 2.47 mmol) and 5% palladium on charcoal (130 mg) in water (10 ml) and ethanol (40 ml) was hydrogenated at 30 psi and room temperature for 2 hours. The reaction mixture was filtered through Arbocel®, the filtrate concentrated under reduced pressure, and the residue triturated with dichloromethane. The residual gum was triturated with ether, then hexane, and dried at 50° C., to give the title compound as a solid, 0.79 g, 81%; ¹H NMR (CDCl₃, 300 MHz) δ: 0.95 (t, 3H), 1.24–1.51 (m, 3H), 1.58–1.80 (m, 7H), 1.88 (dd, 1H), 2.15 (m, 2H), 2.24 (m, 1H), 2.48 (m, 1H), 4.00 (s, 2H), 6.98 (d, 1H), 7.24 (m, 6H), 7.40 (m, 3H); Anal. Found: C, 75.48; H, 7.76; N, 3.59. C₂₅H₃₁NO₃;0.25H₂O requires C, 75.44; H, 7.98; N, 3.51%.

ACE ASSAY

The Preparation and Assay of Soluble Angiotensin Converting Enzyme (ACE), From Porcine and Human Kidney Cortex Soluble ACE activity is obtained from the kidney cortex and assayed by measuring the rate of cleavage of the ACE substrate Abz-Gly-p-nitro-Phe-Pro-OH to generate its fluorescent product, Abz-Gly.

1. Materials
   All water is double de ionised.
   1.1 Human Kidney IIAM (Pennsylvania. U.S.A.) or UK Human Tissue Bank (UK HTB)
   1.2 Porcine kidney ACE Sigma (A2580)
   1.3 Homogenisation buffer-1
   100 mM Mannitol and 20 mM Tris @ pH 7.1 2.42 g Tris (Fisher TtP630/60) is diluted in 1 liter of water and the pH adjusted to 7.1 using 6M HCl at room temperature. To this 18.22 g Mannitol (Sigma M-9546) is added.
   1.4 Homogenisation buffer-2
   100 mM Mannitol, 20 mM Tris @ pH7.1 and 10 mM MgCl₂6H₂O (Fisher M0600/53) To 500 ml of the homogenisation buffer 1 (1.4) 1.017 g of MgCl₂ is added.
   1.5 Tris buffer (ACE buffer).
   50 mM Tris and 300 mM NaCl @ pH 7.4 50 ml of 50 mM Tris pH 7.4 (Sigma T2663) and 17.52 g NaCl (Fisher S/3160/60) are made up to 1000 ml in water.
   1.6 Substrate (Abz-D-Gly-p-nitro-Phe-Pro-OH) (Bachem M-1100)
   ACE substrate is stored as a powder at −20° C. A 2 mM stock is made by gently re-suspending the substrate in ACE buffer, this must not be vortexed or sonicated. 400 μl aliquots of the 2 mM stock are stored at −20° C. for up to one month.
   1.7 Total product
   Samples corresponding to 100% substrate to product conversion are included on the plate to enable the % substrate turnover to be determined (see calculations). The total product is generated by incubating 1 ml of 2 mM substrate with 20 µl of enzyme stock for 24 hours at 37° C.
1.8 Stop solution.
   0.5M EDTA (Promega CAS[6081/92/6]) is diluted 1:250 in ACE buffer to make a 2 mM solution.
1.9 Dimethyl sulphoxide (DMSO).
1.10 Magnesium Chloride-MgCl$_2$.6H$_2$O (Fisher M0600/53).
1.11 Black 96 well flat bottom assay plates (Costar 3915 or Packard).
1.12 Topseal A (Packard 6005185).
1.13 Centrifuge tubes
2. Specific Equipment
2.1 Sorvall RC-5B centrifuge (SS34 GSA rotor, pre-cooled to 4° C.).
2.2 Braun miniprimer mixer.
2.3 Beckman CS-6R centrifuge.
2.4 BMG Fluostar Galaxy.
2.5 Wesbart 1589 shaking incubator.
3. Methods
3.1 Tissue Preparation
3.3 Human ACE is obtained from the kidney cortex using a method adapted from Booth, A. G. & Kenny, A. J. (1974) Biochem. J. 142, 575–581.
   3.3 Frozen kidneys are allowed to thaw at room temperature and the cortex is dissected away from the medulla.
3.4 The cortex is finely chopped and homogenised in approximately 10 volumes of homogenisation buffer-1 (1.4) using a Braun miniprimer (2.2).
3.5 Magnesium chloride (1.11) (20.3 mg/gm tissue) is added to the homogenate and stirred in an ice-water bath for 15 minutes.
3.6 The homogenate is centrifuged at 1,500 g (3,820 rpm) for 12 minutes in a Beckman centrifuge (2.3) before removing the supernatant to a fresh centrifuge tube and discarding the pellet.
3.7 The supernatant is centrifuged at 15,000 g (12,100 rpm) for 12 minutes in a Sovall centrifuge (2.1) and the supernatant is discarded.
3.8 The pale pink layer on the top of the remaining pellet is removed and re-suspended in homogenisation buffer-2 (1.5) (5 ml buffer per 1 g tissue).
3.9 The suspension is centrifuged at 2,200 g (4,630 rpm) for 12 minutes in a Beckman centrifuge before discarding the pellet.
3.10 The supernatant is centrifuged at 15,000 g (12,100 rpm) for 12 minutes using the Sorvall centrifuge and the supernatant is discarded.
3.11 The final pellet is resuspended in homogenisation buffer-2 (0.5 ml buffer per 1 g tissue). A homogenous suspension is obtained using a Braun miniprimer. This is then frozen down in 100 µl aliquots to be assayed for NEP (Sequence No. 1) activity.
4.0 Determination of Ace Activity
   The activity of the previously aliquoted ACE is measured by its ability to cleave the ACE specific peptide substrate. Porcine ACE (1.2) is defrosted and resuspended in ACE buffer (1.6) at 0.004U/µl, this is frozen down in 50 µl aliquots.
4.1 A 4% DMSO/ACE buffer solution is made (4 mls DMSO in 96 mls ACE buffer).
4.2 Substrate (1.7), total product (1.8) and enzyme (1.1, 1.2, 1.3), are left on ice to thaw.
4.3 50 µl of 4% DMSO/ACE buffer solution is added to each well.
4.4 The 2 mM substrate stock is diluted 1:100 to make a 20 µM solution. 00 µl of 20 µM substrate is added to each well (final concentration in the assay 10 µM).
4.5 50 µl of a range of enzyme dilutions is added to initiate the reaction (usually 1:100, 1:200, 1:400, 1:800, 1:1600, and 1:3200 are used). 50 µl of ACE buffer is added to blank wells.
4.6 The 2 mM total product is diluted 1:200 to make 10 µM solution. 200 µl 10 µM product is added to the first four wells of a new plate.
4.7 Plates are incubated at 37° C. in a shaking incubator for 60 minutes.
4.8 The enzyme reaction is stopped by the addition of 100 µl 2 mM EDTA in ACE buffer and incubated at 37° C. in a shaking incubator for 20 minutes before being read on the BMG Fluostar Galaxy (ex320/em420).
5. Ace Inhibiting Assay
5.1 Substrate, total product, and enzyme stocks are left on ice to thaw.
5.2 Compound stocks are made up in 100% DMSO and diluted 1:25 in ACE buffer to give a 4% DMSO solution. All further dilutions are carried out in a 4% DMSO/ACE buffer solution (4 mls DMSO in 96 mls ACE buffer).
5.3 50 µl of compound, in duplicate, is added to the 96 well plate and 50 µl of 4% DMSO/ACE buffer is added to control and blank wells.
5.4 Steps 5.2 and 5.3 can be carried out either by hand or using the Packard multiprobe robots.
5.5 The 2 mM substrate stock is diluted 1:100 in ACE buffer to make a 20 µM solution (10 µM final concentration in the assay) (110 µl of 2 mM substrate added to 10.89 ml buffer is enough for 1 late).
5.6 The enzyme stock is diluted in ACE buffer, as determined from activity checks (4.0).
5.7 The 2 mM total product stock is diluted 1:200 in ACE buffer to make a 10 µM solution. 200 µl is added to the first four wells of a separate plate.
5.8 The 0.5 mM EDTA stock is diluted 1:250 to make a 2 mM stock (44 µl EDTA to 10.96 ml ACE buffer).
5.9 To each well of the 96 well plate the following reagents are added:

TABLE 1

Reagents added to 96 well plate.

| | Compound/ DMSO | Tris Buffer | Substrate | ACE enzyme | Total product |
|---|---|---|---|---|---|
| Samples | 2 µl compound | 50 µl | 100 µl | 50 µl | None |
| Controls | 2 µl DMSO | 50 µl | 100 µl | 50 µl | None |
| Blanks | 2 µl DMSO | 100 µl | 100 µl | None | None |
| Totals | 2 µl DMSO | None | None | None | 200 µl |

5.10 50 µl of the highest concentration of each compound used in the assay is added in duplicate to the same 96 well plate as the totals (5.7). 150 µl of ACE buffer is added to determine any compound fluorescence.
5.11 The reaction is initiated by the addition of the ACE enzyme before incubating at 37° C. for 1 hour in a shaking incubator.
5.12 The reaction is stopped by the addition of 100 µl 2 mM EDTA and incubated at 37° C. for 20 minutes in a shaking incubator, before being read on the BMG Fluostar Galaxy (ex320/em420).
6. Calculations
   The activity of the ACE enzyme is determined in the presence and absence of compound and expressed as a percentage. FU=Fluorescence units
(i) % Control activity (turnover of enzyme):

Mean FU of controls−Mean FU of blanks/×100 Mean FU of totals−Mean FU of blanks (ii) % Activity with inhibitor:

Mean FU of compound−Mean FU of blanks/×100 Mean FU of totals−Mean FU of blanks (iii) Activity expressed as % of control:

% Activity with inhibitor×100% Control activity

OR Mean FU of compound−Mean FU of blanks×100 Mean FU of controls−Mean FU of blanks (iv) % Inhibition=100−% control (v) For fluorescent compounds the mean FU of blanks containing compound (5.10) is deducted from the mean FU of compound values used to calculate the % Activity.

A sigmoidal dose-response curve is fitted to the % activities (% of control) vs compound concentration and $IC_{50}$ values calculated using LabStats fit-curve in Excel.

CONCLUSIONS

We have developed an animal model that reflects the physiological arousal response observed during female sexual arousal and directly reflects the clinical data obtained in human volunteers. The model uses Laser Doppler technologies to record small changes in vaginal and clitoral blood flow induced by pelvic nerve stimulation or vasoactive neurotransmitters. During sexual arousal, there is an increase in genital blood flow resulting from increased innervation from the pelvic nerve. The pelvic nerve-stimulated increase in vaginal and clitoral blood flow, observed in the animal model, represents the endogenous vascular effects observed during female sexual arousal—i.e. engorgement. Therefore this model can be used to firstly, identify the mechanisms involved in the regulation of vaginal and clitoral blood flow and secondly, to validate novel approaches for the enhancement of genital blood flow.

This study has successfully used a combination of in vivo, in vitro and biochemical techniques to show that VIP (Sequence No. 8) mediates genital blood flow and to identify cAMP as the mediator/second messenger regulating genital vasorelaxation (and vaginal wall relaxation). Using this animal model we have demonstrated that infusion fusion of VIP (Sequence No. 8) induces increases in vaginal and clitoral blood flow. Using an inhibitor of VIP (Sequence No. 8) metabolism (e.g. a NEP EC3.4.24.11 (Sequence No. 1) inhibitor), we have also demonstrated that the increases in genital blood flow observed during pelvic nerve stimulation (ie sexual arousal) is mediated by VIP (Sequence No. 8). We have shown that VIP(Sequence No. 8)-mediated increases in genital blood flow result from elevation of tissue cAMP, whereas previously VIP (Sequence No. 8) had been shown to increase vaginal blood flow in healthy volunteers but the cellular mechanism was not identified. Additionally, we have demonstrated that genital blood flow can be enhanced directly with a cAMPmimetic or indirectly by elevating cAMP concentrations with a $PDE_{cAMP}$ type 2 inhibitor or an NPY Y1 receptor antagonist.

The major cause of FSAD is decreased genital blood flow and this manifests itself as reduced vaginal, labial and clitoral engorgement. Treatment of women with FSAD is achievable by restoration of the normal sexual arousal response. This can be achieved by enhancing genital blood flow. Our approach for the treatment of FSAD will be to enhance genital blood flow thereby potentiating vaginal engorgement/lubrication and clitoral engorgement/sensitivity by either directly or indirectly potentiating endogenous cAMP signalling eg with an inhibitor of NEP (EC 3.4.24.11; Sequence No. 1), a cAMP-hydrolysing PDE inhibitor or a NPY receptor antagonist. This will have the overall effect of restoring or potentiating the normal arousal response with no cardiovascular side effects. Sexual arousal/engorgement will be enhanced, rather than simply being induced in the absence of sexual drive, which may be the case with some exogenously administered vasoactive agents eg VIP (Sequence No. 8).

In summary therefore, the present invention relates to inter alia:

A pharmaceutical composition for use (or when in use) in the treatment of FSD, preferably FSAD; the pharmaceutical composition comprising an agent capable of potentiating cAMP in the sexual genitalia of a female suffering from FSD, preferably FSAD; wherein the agent is optionally admixed with a pharmaceutically acceptable carrier, diluent or excipient.

Use of an agent in the manufacture of a medicament for the treatment of FSD, preferably FSAD; wherein the agent is capable of potentiating cAMP in the sexual genitalia of a female suffering from FSD, preferably FSAD.

A method of treating a female (such as a female suffering from FSD, preferably FSAD); the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient.

For these embodiments, preferably the agent is at least one or more of: an I:PDE, an I:NEP, an I:NPY.

In a highly preferred embodiment, the present invention relates to inter alia:

A pharmaceutical composition for use (or when in use) in the treatment of FSD, preferably FSAD; the pharmaceutical composition comprising an agent capable of potentiating cAMP in the sexual genitalia of a female suffering from FSD, preferably FSAD; wherein the agent is optionally admixed with a pharmaceutically acceptable carrier, diluent or excipient; and wherein said agent is delivered orally.

Use of an agent in the manufacture of a medicament for the treatment of FSD, preferably FSAD; wherein the agent is capable of potentiating cAMP in the sexual genitalia of a female suffering from FSD, preferably FSAD; and wherein said agent is delivered orally.

A method of treating a female (such as a female suffering from FSD, preferably FSAD); the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient; and wherein said agent is delivered orally.

For these embodiments, preferably the agent is at least one or more of: an I:PDE, an I:NEP, an I:NPY.

In an additional highly preferred embodiment, the present invention relates to inter alia:

A pharmaceutical composition for use (or when in use) in the treatment of FSD, preferably FSAD; the pharmaceutical composition comprising an agent capable of potentiating cAMP in the sexual genitalia of a female suffering from FSD, preferably FSAD; wherein the agent is optionally admixed with a pharmaceutically acceptable carrier, diluent or excipient; and wherein said agent potentiates endogenous cAMP.

Use of an agent in the manufacture of a medicament for the treatment of FSD, preferably FSAD; wherein the agent is capable of potentiating cAMP in the sexual genitalia of a female suffering from FSD, preferably FSAD; and wherein said agent potentiates endogenous cAMP.

A method of treating a female (such as a female suffering from FSD, preferably FSAD); the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient; and wherein said agent potentiates endogenous cAMP.

For these embodiments, preferably the agent is at least one or more of: an I:PDE, an I:NEP, an I:NPY.

In a further highly preferred embodiment, the present invention relates to inter alia:

A pharmaceutical composition for use (or when in use) in the treatment of FSD, preferably FSAD; the pharmaceutical composition comprising an agent capable of potentiating cAMP in the sexual genitalia of a female suffering from FSD, preferably FSAD; wherein the agent is optionally admixed with a pharmaceutically acceptable carrier, diluent or excipient; and wherein said agent is delivered orally and wherein said agent potentiates endogenous cAMP.

Use of an agent in the manufacture of a medicament for the treatment of FSD, preferably FSAD; wherein the agent is capable of potentiating cAMP in the sexual genitalia of a female suffering from FSD, preferably FSAD; and wherein said agent is delivered orally and wherein said agent potentiates endogenous cAMP.

A method of treating a female (such as a female suffering from FSD, preferably FSAD); the method comprising delivering to the female an agent that is capable of potentiating cAMP in the sexual genitalia; wherein the agent is in an amount to cause potentiation of cAMP in the sexual genitalia of the female; wherein the agent is optionally admixed with a pharmaceutically acceptable carrier, diluent or excipient; and wherein said agent is delivered orally and wherein said agent potentiates endogenous cAMP.

For these embodiments, preferably the agent is at least one or more of: an I:PDE, an I:NEP, an I:NPY.

For these embodiments, preferably the agent is at least one or more of: an I:PDE2, an I:NEP wherein said NEP is EC 3.4.24.11(Sequence No. 1), an I:NPY1.

For these embodiments, preferably the agent is at least one or more of: a selective I:PDE2, a selective I:NEP wherein said NEP is EC 3.4.24.11 (Sequence No. 1), a selective I:NPY1. All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

General Text References

Ashur-Fabian, O., Perl, O., Lilling, G., et al. (1999). SNV, a lipophilic superactive VIP analog, acts through cGMP to promote neuronal survival. *Peptides*, 20, 629–633.

Berman, J. R., Berman, L. & Goldstein, I. (1999). Female sexual dysfunction: Incidence, pathophysiology, evaluation, and treatment options. *Urology*, 54, 385–391.

Berman, J., Goldstein, I., Werbin, T. et al. (1999a). Double blind placebo controlled study with crossover to assess effect of sildenafil on physiological parameters of the female sexual response. *J. Urol.*, 161, 805.

Burnett, A, Calvin, D., Silver, R. et al. (1997). Immunohistochemical description of nitric oxide synthase isoforms in human clitoris. *J. Urol.*, 158, 75–78.

Diagnostic and statistical manual of mental disorders-IV, American Psychiatric Association: Washington, DC., 1987, pp 493–518.

Fan, Y. P., Chakder, S. & Ratton, S. (1998). Inhibitory effect of zinc protoporphyrin IX on lower esophageal sphincter smooth muscle relaxation by vasoactive intestinal polypeptide and other receptor agonists. *J. Pharmacol. Exp. Ther.*, 285, 468–474.

Foda, H. D., Sharaf, H. H., Absood, A. et al. (1995). Pituitary adenylate cyclase-activating peptide (PACAP), a VIP-like peptide, has prolonged airway smooth muscle relaxant activity. *Peptides*, 16, 1057–1061.

Frank, E., Anderson, C. & Rubinstein, D. (1978). Frequency of sexual dysfunction in "normal" couples. *N. Engl. J. Med.*, 229, 111–115.

Goldstein, I. & Berman, J. R. (1998). Vasculogenic female sexual dysfunction: vaginal engorgement and clitoral erectile insufficiency syndromes. *Int. J. Impot. Res.*, 10, S84–S90.

Gu, Z. F., Jensen, R. T. & Maton, P. N. (1992). A primary role for protein kinase A in smooth muscle relaxation induced by adrenergic agonists and neuropeptides. *Am. J. Physiol.*, 263, G360–G364.

Hauser-Kronberger, C., Cheung, A., Hacker, G. et al. (1999). Peptidergic innervation of the human clitoris. *Peptides*, 20, 539–543.

Hoyle, C. H. V., Stones, R. W., Robson, T. et al. (1996). Innervation of vasculature and microvasculature of the human vagina by NOS and neuropeptide containing nerves. *J. Anat.*, 188, 633–644.

Ingenhoven, N. & Beck-Sickinger, A. G. (1997). Flourescent labelled analogues of neuropeptide Y for the characterisation of cells expressing NPY receptor subtypes. *J. Recept. Signal Transduct Res.*, 17, 407–418.

Jovanovic, A., Jovanovic, S., Tulic,. I. et al. (1998). Predominant role for nitric oxide in the relaxation induced by vasoactive intestinal polypeptide in human uterine artery. *Mol. Human Reprod.*, 4, 71–76.

Kaplan, H. S. (1974). The New Sex Therapy. London, Bailliere Tindall.

Kaplan, S. A., Reis, R. B., Kohm, I. J. et al. (1999). Safety and efficacy of sildenafil in postmenopausal women with sexual dysfunction. *Urology*, 53, 481486.

Kim, Y. C., Choi, H. K., Ahn, Y. S., et al. (1994). The effect of vasoactive intestinal polypeptide (VIP) on rabbit cavemosal smooth muscle contractility. *J. Androl.*, 15, 392–739.

Laan, E. & Everaerd, W. (1998). Physiological measures of vaginal vasocongestion. *Int. J. Impot. Res.*, 10, S107–S110.

Leiblum, S. R. (1998). Definition and classification of female sexual disorders. *Int. J. Impotence Res.*, 10, S104–S106.

Levin, R. J. (1980). The physiology of sexual function in women. *Clin. Obstet. Gynecol.*, 7, 213–252.

Levin, R. J. (1991). VIP, vagina, clitoral and preurethral glans: An update on female genital arousal. *Exp. Clin. Endocrinol.*, 98, 61–69.

Levin, R. J. (1992). The mechanisms of human female sexual arousal. *Ann. Rev. Sex Res.*, 3, 148.

Levin, R. J. & Wagner, G. (1986). TRH and vaginal blood flow-effects in concious women and anaesthetised sheep. *J. Physiol.*, 373, 83P.

Lundberg, J. M., Modin, A. & Malmstrom, R. E. (1996). Recent developments with neuropeptide Y receptor antagonists. *Trends. Pharmacol. Sci.*, 17, 301–304.

Masters, W. H., Johnson, V. E. Human Sexual Response. Little, Brown: Boston, 1996.

Ottesen, B., Gerstenberg, T., Ulrichsen, H. et al. (1983). Vasoactive intestinal polypeptide (VIP) increases vaginal blood flow and inhibits smooth muscle activity in women. *Eur. J. Clin. Invest.*, 13, 321–324.

Oltesen, B., Wagner, G. & Fahrenkrug, J. Peptide innervation of the sexual organs. In: Handbook of Sexology, Vol. 6, The Pharmacological and Endocrinology of Sexual Function, Sitsen, J. M. A. (eds), Amsterdam: Elsevier Science Publishers (1988), chapter 4, pp 66–97.

Ottensen, B., Pedersen, B., Nielsen, J. et al. (1987). Vasoactive intestinal polypeptide (VIP) provokes vaginal lubrication in normal women. *Peptides*, 8, 797–800.

Park, K., Goldstein, I., Andry, C., et al. (1997). Vasculogenic female sexual dysfunction: The hemodynamic basis for vaginal engorgement insufficiency and clitoral erectile insufficiency. *Int. J. Impotence Res.*, 9, 27–37.

Rosen, R., Taylor, J., Leiblum, S. et al. (1993). Prevalence of sexual dysfunction in women: results of a survey of 329 women in an outpatient gynecological clinic. *J. Sex Marital Ther.*, 19, 171–188.

Schiavi, R. C. & Seagraves, R. T. (1995). The biology of sexual function. *Psychiat. Clin. North. Am.*, 18, 7–23.

Schoeffter, P. & Stoclet, J. C. (1985). Effect of vasoactive intestinal polypeptide (VIP) on cyclic AMP level and relaxation in rat isolated aorta. *Eur. J. Pharmacol.*, 109, 275–279.

Serradeil-Le Gal, C., Valette, G., Rouby, P. E. et al. (1995). SR 120819A, an orally-active and selective neuropeptide Y Y1 receptor antagonist. *FEBS Letters*, 3, 192–196.

Sjoberg, I. (1992). The vagina: Morphological, functional and ecological aspects. *Acta Obst. Gynecol. Scand.*, 71, 84–85.

Spector, I. P. & Carey, M. P. (1990). Incidence and prevalence of sexual dysfunctions: a critical review of the empirical literature. *Arch. Sex. Behav.*, 19, 389–408.

Wagner, G. (1992). Aspects of genital physiology and pathology. *Sem. Neurol.*, 12, 87–97.

Werbin, T., Salimpour, P., Berman, L., et al. (1999). Effect of sexual stimulation and age on genital blood flow in women with sexual stimulation. *J. Urol.*, 161, 688.

Wincze, J. P., Albert, A. & Bansal, S. (1993). Sexual arousal in diabetic females: Physiological and self-report measures. *Arch. Sex Behav.*, 22, 587–601.

Wieland, H. A., Willim, K. D., Entzeroth, M. et al. (1995). Subtype selectivity and antagonist profile of the non-peptide Y1 receptor antagonist BIBP 3226. *J. Pharmacol Exp Ther.*, 275, 143–9.

References for the PDE Section

Han, P.; Fletcher, C. F.; Copeland, N. G.; Jenkins, N. A.; Yaremko, L. M.; Michaeli, T.: Assignment of the mouse Pde7A gene to the proximal region of chromosome 3 and of the human PDE7A gene to chromosome 8q13. Genomics 48: 275–276, 1998.

2. Michaeli, T.; Bloom, T. J.; Martins, T.; Loughney, K.; Ferguson, K.; Riggs, M.; Rodgers, L.; Beavo, J. A.; Wigler, M. : Isolation and characterization of a previously undetected human cAMP phosphodiesterase by complementation of cAMP phosphodiesterase-deficient Saccharomyces cerevisiae. J. Biol. Chem. 268: 12925–12932, 1993.

3. Milatovich, A.; Bolger, G.; Michaeli, T.; Francke, U. : Chromosome localizations of genes for five cAMP-specific phosphodiesterases in man and mouse. Somat. Cell Molec. Genet. 20: 75–86, 1994.

4. Rosman, G. J.; Martins, T. J.; Sonnenburg, W. K.; Beavo, J. A.; Ferguson, K.; Loughney, K.: Isolation and characterization of human cDNAs encoding a cGMP-stimulated 3-prime,5-prime-cyclic nucleotide phosphodiesterase. Gene 191: 89–95, 1997.

References for the NEP (Sequence No. 1) Section

1. Barker, P. E.; Shipp, M. A.; D'Adamio, L.; Masteller, E. L.; Reinherz, E. L. The common acute lymphoblastic leukemia antigen gene maps to chromosomal region 3(q21–q27). J. Immun. 142: 283–287,1989.

2. D'Adamio, L.; Shipp, M. A.; Masteller, E. L.; Reinherz, E. L. : Organization of the gene encoding common acute lymphoblastic leukemia antigen (neutral endopeptidase 24.11): multiple miniexons and separate 5-prime untranslated regions. Proc. Nat. Acad. Sci. 86: 7103–7107, 1989.

3. Letarte, M.; Vera, S.; Tran, R.; Addis, J. B. L.; Onizuka, R. J.; Quackenbush, E. J.; Jongeneel, C. V.; McInnes, R. R.: Common acute lymphocytic leukemia antigen is identical to neutral endopeptidase. J. Exp. Med. 168: 1247–1253, 1988.

4. Shipp, M. A.; Vijayaraghavan, J.; Schmidt, E. V.; Masteller, E. L.; D'Adamio, L.; Hersh, L. B.; Reinherz, E. L.: Common acute lymphoblastic leukemia antigen (CALLA) is active neutral endopeptidase 24.11 ('enkephalinase'): direct evidence by cDNA transfection analysis. Proc. Nat. Acad. Sci. 86: 297–301, 1989.

5. Tran-Paterson, R.; Willard, H. F.; Letarte, M.: The common acute lymphoblastic leukemia antigen (neutral endopeptidase—3.4.24.11) gene is located on human chromosome 3. Cancer Genet. Cytogenet. 42: 129–134, 1989.

References for the NPY (Sequence No. 4) Section

1. Allen, J. M.; Bloom, S. R. : Neuropeptide Y: a putative neurotransmilter. Neurochem. Int. 8: 1–8, 1986.

2. Bahary, N.; Zorich, G.; Pachter, J. E.; Leibel, R. L.; Friedman, J. M.: Molecular genetic linkage maps of mouse chromosomes 4 and 6. Genomics 11: 3347, 1991.

3. Baker, E.; Hort, Y. J.; Ball, H.; Sutherland, G. R.; Shine, J.; Herzog, H.: Assignment of the human neuropeptide Y gene to chromosome 7p15.1 by nonisotopic in situ hybridization. Genomics 26: 163–164, 1995.

4. Carr, L. G.; Foroud, T.; Bice, P.; Gobbett, T.; Ivashina, J.; Edenberg, H.; Lumeng, L.; Li, T. K.: A quantitative trait locus for alcohol consumption in selectively bred rat lines. Alcohol Clin. Exp. Res. 22: 884–887, 1998.

5. Dockray, G. J.: Neuropeptide Y: in search of a function. Neurochem. Int. 8: 9–11, 1986.

6. Erickson, J. C.; Clegg, K. E.; Palmiter, R. D.: Sensitivity to leptin and susceptibility to seizures of mice lacking neuropeptide Y. Nature 381: 415421, 1996. PubMed ID: 8632796.
7. Erickson, J. C.; Hollopeter, G.; Palmiter, R. D.: Attenuation of the obesity syndrome of ob/ob mice by the loss of neuropeptide Y. Science 274: 1704–1706, 1996.
8. Karvonen, M. K.; Pesonen, U.; Koulu, M.; Niskanen, L.; Laakso, M.; Rissanen, A.; Dekker, J. M.; 't Hart, L. M.; Valve, R.; Uusitupa, M. I.: Association of a leucine(7)-to-proline(7) polymorphism in the signal peptide of neuropeptide Y with high serum cholesterol and LDL cholesterol levels. Nature Med. 4: 1434–1437, 1998.
9. Maccarrone, C.; Jarrott, B.: Neuropeptide Y: a putative neurotransmitter. Neurochem. Int. 8: 13–22, 1986.
10. Meisler, M. H.; Spence, J. E.; Dixon, J. E.; Caldwell, R. M.; Minth, C. D.; Beaudet, A. L.: Exclusion of close linkage between the loci for-cystic fibrosis and neuropeptide Y on human chromosome 7. Cytogenet. Cell Genet. 44: 175–176,1987.
11. Minth, C. D.; Andrews, P. C.; Dixon, J. E.: Characterization, sequence, and expression of the cloned human neuropeptide Y gene. J. Biol. Chem. 261: 11974–11979, 1986.
12. Minth, C. D.; Bloom, S. R.; Polak, J. M.; Dixon, J. E.: Cloning, characterization, and DNA sequence of a human cDNA encoding neuropeptide tyrosine. Proc. Nat. Acad. Sci. 81: 45774581, 1984.
13. Takeuchi, T.; Gumucio, D.; Eddy, R.; Meisler, M.; Minth, C.; Dixon, J.; Yamada, T.; Shows, T.: Assignment of the related pancreatic polypeptide (PPY) and neuropeptide Y (NPY) genes to regions on human chromosomes 17 and 7. (Abstract) Cytogenet. Cell Genet. 40: 759 only, 1985.
14. Takeuchi, T.; Gumucio, D. L.; Yamada, T.; Meisler, M. H.; Minth, C. D.; Dixon, J. E.; Eddy, R. E.; Shows, T. B.: Genes encoding pancreatic polypeptide and neuropeptide Y are on human chromosomes 17 and 7. J. Clin. Invest. 77: 1038–1041, 1986.
15. Terenghi, G.; Polak, J. M.; Hamid, Q.; O'Brien, E.; Denny, P.; Legon, S.; Dixon, J.; Minth, C. D.; Palay, S. L.; Yasargil, G.; Chan-Palay, V.: Localization of neuropeptide Y mRNA in neurons of human cerebral cortex by means of in situ hybridization with a complementary RNA probe. Proc. Nat. Acad. Sci. 84: 7315–7318, 1987.
16. Thiele, T. E.; Marsh, D. J.; Ste. Marie, L.; Bernstein, I. L.; Palmiter, R. D.: Ethanol consumption and resistance are inversely related to neuropeptide Y levels. Nature 396: 366–369, 1998.
17. Uusitupa, M. I. J.; Karvonen, M. K.; Pesonen, U.; Koulu, M.: Neuropeptide Y: a novel link between the neuroendocrine system and cholesterol metabolism. Ann. Med. 30: 508–510, 1998.

References for the NPYR1 (Sequence No. 5) Section

1. Herzog, H.; Baumgartner, M.; Vivero, C.; Selbie, L. A.; Auer, B.; Shine, J.: Genomic organization, localization, and allelic differences in the gene for the human neuropeptide Y Y1 receptor. J. Biol. Chem. 268: 6703–6707, 1993.
2. Herzog, H.; Darby, K.; Ball, H.; Hort, Y.; Beck-Sickinger, A.; Shine, J.: Overlapping gene structure of the human neuropeptide Y receptor subtypes Y1 and Y5 suggests coordinate transcriptional regulation. Genomics 41: 315–319, 1997.
3. Herzog, H.; Hort, Y. J.; Ball, H. J.; Hayes, G.; Shine, J.; Selbie, L. A.: Cloned human neuropeptide Y receptor couples to two different second messenger systems. Proc. Nat. Acad. Sci. 89: 5794–5798, 1992.
4. Larhammar, D.; Blomqvist, A. G.; Yee, F.; Jazin, E.; Yoo, H.; Wahlestedt, C.: Cloning and functional expression of a human neuropeptide Y/peptide YY receptor of the Y1 type. J. Biol. Chem. 267: 10935–10938, 1992.
5. Lutz, C. M.; Frankel, W. N.; Richards, J. E.; Thompson, D. A.: Neuropeptide Y receptor genes on human chromosome 4q31–q32 map to conserved linkage groups on mouse chromosomes 3 and 8. Genomics 41: 498–500, 1997.

References for the NPYR2 (Sequence No. 6) Section

1. Ammar, D. A.; Eadie, D. M.; Wong, D. J.; Ma, Y.-Y.; Kolakowski, L. F., Jr.; Yang-Feng, T. L.; Thompson, D. A.: Characterization of the human type 2 neuropeptide Y receptor gene (NPY2R) and localization to the chromosome 4q region containing the type 1 neuropeptide Y receptor gene. Genomics 38: 392–398, 1996.
2. Gerald, C.; Walker, M. W.; Vaysse, P. J.-J.; He, C.; Branchek, T. A.; Weinshank, R. L.: Expression cloning and pharmacological characterization of a human hippocampal neuropeptide Y/peptide YY Y2 receptor subtype. J. Biol. Chem. 270: 26758–26761, 1995.
3. Lutz, C. M.; Frankel, W. N.; Richards, J. E.; Thompson, D. A.: Neuropeptide Y receptor genes on human chromosome 4q31–q32 map to conserved linkage groups on mouse chromosomes 3 and 8. Genomics 41: 498–500, 1997.
4. Rose, P. M.; Fernandes, P.; Lynch, J. S.; Frazier, S. T.; Fisher, S. M.; Kodukula, K.; Kienzle, B.; Seethala, R.: Cloning and functional expression of a cDNA encoding a human type 2 neuropeptide Y receptor. J. Biol. Chem. 270: 22661–22664, 1995.

References for the VIP (Sequence No. 8) Section

1. Bodner, M.; Fridkin, M.; Gozes, I.: Coding sequences for vasoactive intestinal peptide and PHM-27 peptide are located on two adjacent exons in the human genome. Proc. Nat. Acad. Sci. 82: 3548–3551, 1985.
2. Gotoh, E.; Yamagami, T.; Yamamoto, H.; Okamoto, H.: Chromosomal assignment of human VIP/PHM-27 gene to 6q26–q27 region by spot blot hybridization and in situ hybridization. Biochem. Int. 17: 555–562, 1988.
3. Gozes, I.; Avidor, R.; Yahav, Y.; Katznelson, D.; Croce, C. M.; Huebner, K.: The gene encoding vasoactive intestinal peptide is located on human chromosome 6p21–6qter. Hum. Genet. 75: 41–44, 1987.
4. Gozes, I.; Nakai, H.; Byers, M.; Avidor, R.; Weinstein, Y.; Shani, Y.; Shows, T. B.: Sequential expression in the nervous system of C-MYB and VIP genes, located in human chromosomal region 6q24. Somat. Cell Molec. Genet. 13: 305–313, 1987.
5. Heinz-Erian, P.; Dey, R. D.; Flux, M.; Said, S. I.: Deficient vasoactive intestinal peptide innervation in sweat glands of cystic fibrosis patients. Science 229: 1407–1408, 1985.
6. Itoh, N.; Obata, K.; Yanaihara, N.; Okamoto, H.: Human preprovasoactive intestinal polypeptide contains a novel PHI-27-like peptide, PHM-27. Nature 304: 547–549, 1983.
7. Linder, S.; Barkhem, T.; Norberg, A.; Persson, H.; Schalling, M.; Hokfelt, T.; Magnusson, G.: Structure and expression of the gene encoding the vasoactive intestinal peptide precursor. Proc. Nat. Acad. Sci. 84: 605–609, 1987.
8. Omary, M. B.; Kagnoff, M. F.: Identification of nuclear receptors for VIP on a human colonic. adenocarcinoma cell line. Science 238: 1578–1581, 1987.

References for the AC Section

1. Parma, J.; Stengel, D.; Gannage, M.-H.; Poyard, M.; Barouki, R.; Hanoune, J.: Sequence of a human brain adenylyl cyclase partial cDNA: evidence for a consensus cyclase domain. Biochem. Biophys. Res. Commun. 179: 455–462, 1991.
2. Stengel, D.; Parma, J.; Gannage, M.-H.; Roeckel, N.; Mattei, M.-G.; barouki, R.; Hanoune, J.: Different chromosomal localization of two adenylyl-cyclase genes expressed in human brain. Hum. Genet. 90: 126–130, 1992.

References for the VPAC1 (Sequence No. 9) Section

1. Couvineau, A.; Rouyer-Fessard, C.; Darmoul, D.; Maoret, J.-J.; Carrero, I.; Ogier-Denis, E.; Laburthe, M.: Human intestinal VIP receptor: cloning and functional expression of two cDNA encoding proteins with different N-terminal domains. Biochem. Biophys. Res. Commun. 200: 769–776, 1994.
2. Hashimoto, H.; Nishino, A.; Shintani, N.; Hagihara, N.; Copeland, N. G.; Jenkins, N. A.; Yamamoto, K.; Matsuda, T.; Ishihara, T.; Nagata, S.; Baba, A.: Genomic organization and chromosomal location of the mouse vasoactive intestinal polypeptide 1 (VPAC-1) receptor. Genomics 58: 90–93, 1999.
3. Libert, F.; Passage, E.; Parmentier, M.; Simons, M.-J.; Vassart, G.; Mattei, M.-G. Chromosomal mapping of A1 and A2 adenosine receptors, VIP receptor, and a new subtype of serotonin receptor. Genomics 11: 225–227, 1991.
4. Sreedharan, S. P.; Huang, J.-X.; Cheung, M.-C.; Goetzl, E. J.: Structure, expression, and chromosomal localization of the type I human vasoactive intestinal peptide receptor gene. Proc. Nat. Acad. Sci. 92: 2939–2943, 1995.
5. Sreedharan, S. P.; Patel, D. R.; Huang, J.-X.; Goetzl, E. J.: Cloning and functional expression of a human neuroendocrine vasoactive intestinal peptide receptor. Biochem. Biophys. Res. Commun. 193: 546–553, 1993.
6. Sreedharan, S. P.; Robichon, A.; Peterson, K. E.; Goetzl, E. J.: Cloning and expression of the human vasoactive intestinal peptide receptor. Proc. Nat. Acad. Sci. 88: 49864990, 1991.
7. Vassart, G.: Personal Communication. Brussels, Belgium, Jan. 15, 1992. 8. Wenger, G. D.: Personal Communication. Columbus, Ohio, Aug. 3, 1993.

References for the VPAC2 (Sequence No. 10) Section

1. Adamou, J. E.; Aiyar, N.; Van Horn, S.; Elshourbagy, N. A.: Cloning and functional characterization of the human vasoactive intestinal peptide (VIP)-2 receptor. Biochem. Biophys. Res. Commmun. 209: 385–392, 1995.
2. Mackay, M.; Fantes, J.; Scherer, S.; Boyle, S.; West, K.; Tsui, L.-C.; Belloni, E.; Lutz, E.; Van Heyningen, V.; Harmar, A. J.: Chromosomal localization in mouse and human of the vasoactive intestinal peptide receptor type 2 gene: a possible contributor to the holoprosencephaly 3 phenotype. Genomics 37: 345–353, 1996.
3. Svoboda, M.; Tastenoy, M.; Van Rampelbergh, J.; Goossens, J.-F.; De Neef, P.; Waelbroeck, M.; Robberecht, P.: Molecular cloning and functional characterization of a human VIP receptor from SUP-T1 lymphoblasts. Biochem. Biophy. Res. Commun. 205: 1617–1624, 1994.

Abbreviations

FSD=female sexual dysfunction
FSAD=female sexual arousal disorder
cAMP=cyclic adenosine-3',5'-monophosphate
cGMP=cyclic guanosine-3',5'-monophosphate
$P_{cAMP}$=potentiator of cAMP
$P_{cGMP}$=potentiator of cGMP
$A_{cAMP}$=activator of cAMP
$A_{cGMP}$=activator of cGMP
$AM_{cAMP}$ adverse modulator of cAMP
$AM_{cGMP}$=adverse modulator of cGMP
$I_{cAMP}$=inhibitor of cAMP
$I_{cGMP}$=inhibitor of cGMP
$I{:}I_{cAMP}$=inhibitor of an inhibitor of cAMP
$I{:}I_{cGMP}$=inhibitor of an inhibitor of cGMP
$I{:}AM_{cAMP}$=inhibitor of an adverse modulator of cAMP
$I{:}AM_{cGMP}$=inhibitor of an adverse modulator of cGMP
$U{:}A_{cAMP}$=upregulator of activator of cAMP
$U{:}A_{cGMP}$=upregulator of activator of cGMP
AC=adenylate cyclase
A:AC=activator of AC
NEP=neutral endopeptidase (Sequence No. 1)
I:NEP=inhibitor of NEP
VIP=vasoactive intestinal peptide (Sequence No. 8)
VIPr=receptor of VIP (may be expressed as VIPR)
$VIP_n$=receptor sub-type of VIP (such as VIPR1, VIPR2)
A:VIPr=activator of VIPr
A:$VIP_n$ activator of $VIP_n$
I:VIPr=inhibitor of VIPr
I:$VIP_n$ inhibitor of $VIP_n$
I:I:VIPr=inhibitor of an inhibitor of VIPr
I:I:$VIP_n$=inhibitor of an inhibitor of $VIP_n$
PDE=phosphodiesterase
PDEn=PDE family (e.g. PDE1 (Sequence No. 2), PDE2 (Sequence No. 3) etc.)
$PDE_{cAMP}$=cAMP hydrolysing PDE
$PDE_{cGMP}$=cGMP hydrolysing PDE
I:PDE=inhibitor of a PDE
I:$PDE_{cAMP}$=inhibitor of a cAMP hydrolysing PDE
I:$PDE_{cAMP}$=inhibitor of a cAMP hydrolysing PDE family
NPY=neuropeptide Y (Sequence No. 4)
NPYr=receptor of NPY (may be expressed as NPYR)
NPY $Y_n$=$Y_n$ receptor sub-type of NPY (e.g. NPY $Y_1$) (e.g. NPYR1)
I:NPY=inhibitor of NPY
I:NPY $Y_n$=inhibitor of NPY $Y_n$ (where n denotes NPY receptor subtype)
kDa=kilodalton
bp=base pair
kb=kilobase pair Within the scientific literature up to 1993, examples of the assessment of oral bioavailability in conscious dogs are available from the attached articles:

1. Bristol Myers Squibb for the oral antibiotic cefprozil:— Absolute Bioavailability of Cefprozil after Oral Administration in Beagles (Barbhaiya et al., 1992, Antimicrobial Agents and Chemotherapy, vol 36, pp 25 687–689).
2. Carlo Erba for the anti-tumor agent iododoxorubicin:— Pharmacokinetics of Iododoxorubicin in the Rat, Dog, and Monkey (Edwards et al., 1991, Drug Metabolism and Disposition, Vol 19, pp 938–945).
3. Eli Lilly for the experimental CNS antiischemic agent LY256548:—Pharmacokinetics of a Novel Butylated Hydroxytoluene-Thiazolidinone CNS Antiischemic Agent LY256548 in Rats, Mice, Dogs, and Monkeys (Ruterbories and Lindstrom, 1990, Drug Metabolism and Disposition, vol 18, pp 674–679).

4. Wellcome for the folate antagonist piritrexim:—The Disposition and Metabolism of [$^{14}$C]Piritrexim in Dogs after Intravenous and Oral Administration (Woolley et al., 1991, Drug Metabolism and Disposition, vol 19, pp 1139–1146).
5. ICI for the antiandrogen casodex:—The Pharmacokinetics of Casodex in Laboratory Animals (Cockshott et al., 1991, Xenobiotica, vol 21, pp 1347–1355).
6. Glaxo for the calcium antagonist lacidipine:—Absorption, Distribution and Excretion of Lacidipine, a Dihydropyridine Calcium Antagonist, in Rat and Dog (Pettegatti et al., 1990, Xenobiotica, 1990, vol 20, pp 765–777).
7. Fujisawa for the aldose reductase inhibitor zenarestat:—Absorption, Distribution and Excretion of Zenarestat, a New Aldose Reductase Inhibitor, in Rats and Dogs (Tanaka et al., 1992, Xenobiotica, vol 22, pp 57–64).

In the above examples use of conscious mice, rats and monkeys are also cited for the assessment of oral bioavailability.

We claim:

1. A method for treating female sexual arousal disorder comprising the step of orally delivering to a female suffering from female sexual arousal disorder an agent in an amount to cause potentiation of cAMP in the sexual genitalia of the female; wherein the agent is optionally admixed with a pharmaceutically acceptable carrier, diluent or excipient, and the agent a phosphodiesterase 2 inhibitor.

2. The method according to claim 1 wherein the agent is a mediator of genital vasorelaxation.

3. The method according to claim 1 or 2 wherein said cAMP is endogenous cAMP.

4. The method according to claim 1 or 2 wherein the agent is delivered before or during sexual stimulation.

5. The method according to claim 2 wherein the agent is a mediator of vaginal or clitoral vasorelaxation.

6. A method for treating female sexual arousal disorder comprising the step of orally delivering to a female suffering from female sexual arousal disorder a phosphodiesterase 2 inhibitor in an amount to cause potentiation of cAMP in the sexual genitalia of said female; wherein said phosphodiesterase 2 inhibitor is admixed with a pharmaceutically acceptable carrier, diluent or excipient.

7. The method according to claim 6 wherein said phosphodiesterase 2 inhibitor is a mediator of genital vasorelaxation.

8. The method according to claim 7 wherein said phosphodiesterase 2 inhibitor is a mediator of vaginal or clitoral vasorelaxation.

9. The method according to claim 6 wherein said cAMP is endogenous cAMP.

10. The method according to claim 6 wherein said phosphodieteras 2 inhibitor is delivered before or during sexual stimulation.

11. A method for treating a female sexual arousal disorder comprising the step of potentiating in vivo cAMP in female sexual genitalia with an orally administered phosphodiesterase inhibitor, wherein said phosphodiesterase inhibitor directly potentiates cAMP according to an assay method comprising the step of determining whether said phosphodiesterase 2 inhibitor directly potentiates cAMP; wherein a potentiation of cAMP in the presence of said inhibitor is indicative that said inhibitor is useful in the treatment of said female sexual arousal disorder.

12. A method for treating female sexual arousal disorder in a female suffering from female sexual arousal disorder comprising the step of orally delivering to a female suffering from female sexual arousal disorder a therapeutically effective amount of a phosphodiesterase 2 inhibitor, wherein said phosphodiesterase 2 inhibitor is optionally admixed with a pharmaceutically acceptable carrier, diluent or excipient.

13. The method of claim 12 wherein said inhibitor has a $K_i$ value of less than about 100 nM.

14. The method of claim 12 wherein said inhibitor has a $K_i$ value of less than about 75 nM.

15. The method of claim 12 wherein said inhibitor has a $K_i$ value of less than about 50 nM.

16. The method of claim 12 wherein said inhibitor has a $K_i$ value of less than about 25 nM.

17. The method of claim 12 wherein said inhibitor has a $K_i$ value of less than about 20 nM.

18. The method of claim 12 wherein said inhibitor has a $K_i$ value of less than about 15 nM.

19. The method of claim 12 wherein said inhibitor has a $k_i$ value of less than 10 nM.

20. The method of claim 12 wherein said inhibitor has a $K_i$ value of less than about 5 nM.

21. The method of claim 12 wherein said inhibitor has a $K_i$ selective effect on the genitalia of the female.

22. The method of claim 12 wherein in the absence of sexual stimulation said inhibitor has no or a negligible effect in causing an increase in genital blood flow in said female.

23. The method of claim 12 wherein said inhibitor is in an amount to cause potentiation of endogenous cAMP.

24. The method of claim 12 wherein said inhibitor is used in combination with one or more other pharmaceutically active agents.

* * * * *

SEQUENCE LISTING

<160> NUMBER OF SEQ ID NOS: 20

<210> SEQ ID NO 1
<211> LENGTH: 743
<212> TYPE: PRT
<213> ORGANISM: Homo sapiens

<400> SEQUENCE: 1

```
Met Asp Ile Thr Asp Ile Asn Thr Pro Lys Pro Lys Lys Gln Arg
  1               5                  10                  15

Trp Thr Pro Leu Glu Ile Ser Leu Ser Val Leu Val Leu Leu Leu Thr
                 20                  25                  30

Ile Ile Ala Val Thr Met Ile Ala Leu Tyr Ala Thr Tyr Asp Asp Gly
             35                  40                  45

Ile Cys Lys Ser Ser Asp Cys Ile Lys Ser Ala Ala Arg Leu Ile Gln
 50                      55                      60

Asn Met Asp Ala Thr Thr Glu Pro Cys Thr Asp Phe Phe Lys Tyr Ala
 65                  70                      75                  80

Cys Gly Gly Trp Leu Lys Arg Asn Val Ile Pro Glu Thr Ser Ser Arg
                 85                      90                      95

Tyr Gly Asn Phe Asp Ile Leu Arg Asp Glu Leu Glu Val Val Leu Lys
                100                 105                 110

Asp Val Leu Gln Glu Pro Lys Thr Glu Asp Ile Val Ala Val Gln Lys
            115                 120                 125

Ala Lys Ala Leu Tyr Arg Ser Cys Ile Asn Glu Ser Ala Ile Asp Ser
130                 135                 140

Arg Gly Gly Glu Pro Leu Leu Lys Leu Leu Pro Asp Ile Tyr Gly Trp
145                 150                 155                 160

Pro Val Ala Thr Glu Asn Trp Glu Gln Lys Tyr Gly Ala Ser Trp Thr
                165                 170                 175

Ala Glu Lys Ala Ile Ala Gln Leu Asn Ser Lys Tyr Gly Lys Lys Val
                180                 185                 190

Leu Ile Asn Leu Phe Val Gly Thr Asp Asp Lys Asn Ser Val Asn His
            195                 200                 205

Val Ile His Ile Asp Gln Pro Arg Leu Gly Leu Pro Ser Arg Asp Tyr
    210                 215                 220

Tyr Glu Cys Thr Gly Ile Tyr Lys Glu Ala Cys Thr Ala Tyr Val Asp
225                 230                 235                 240

Phe Met Ile Ser Val Ala Arg Leu Ile Arg Gln Glu Arg Leu Pro
                245                 250                 255

Ile Asp Glu Asn Gln Leu Ala Leu Glu Met Asn Lys Val Met Glu Leu
            260                 265                 270

Glu Lys Glu Ile Ala Asn Ala Thr Ala Lys Pro Glu Asp Arg Asn Asp
        275                 280                 285
```

-continued

```
Pro Met Leu Leu Tyr Asn Lys Met Thr Leu Ala Gln Ile Gln Asn Asn
    290                 295                 300
Phe Ser Leu Glu Ile Asn Gly Lys Pro Phe Ser Trp Leu Asn Phe Thr
305                 310                 315                 320
Asn Glu Ile Met Ser Thr Val Asn Ile Ser Ile Thr Asn Glu Glu Asp
                325                 330                 335
Val Val Val Tyr Ala Pro Glu Tyr Leu Thr Lys Leu Lys Pro Ile Leu
                340                 345                 350
Thr Lys Tyr Ser Ala Arg Asp Leu Gln Asn Leu Met Ser Trp Arg Phe
            355                 360                 365
Ile Met Asp Leu Val Ser Ser Leu Ser Arg Thr Tyr Lys Glu Ser Arg
370                 375                 380
Asn Ala Phe Arg Lys Ala Leu Tyr Gly Thr Thr Ser Glu Thr Ala Thr
385                 390                 395                 400
Trp Arg Arg Cys Ala Asn Tyr Val Asn Gly Asn Met Glu Asn Ala Val
                405                 410                 415
Gly Arg Leu Tyr Val Glu Ala Ala Phe Ala Gly Glu Ser Lys His Val
            420                 425                 430
Val Glu Asp Leu Ile Ala Gln Ile Arg Glu Val Phe Ile Gln Thr Leu
        435                 440                 445
Asp Asp Leu Thr Trp Met Asp Ala Glu Thr Lys Lys Arg Ala Glu Glu
450                 455                 460
Lys Ala Leu Ala Ile Lys Glu Arg Ile Gly Tyr Pro Asp Asp Ile Val
465                 470                 475                 480
Ser Asn Asp Asn Lys Leu Asn Asn Glu Tyr Leu Glu Leu Asn Tyr Lys
                485                 490                 495
Glu Asp Glu Tyr Phe Glu Asn Ile Ile Gln Asn Leu Lys Phe Ser Gln
            500                 505                 510
Ser Lys Gln Leu Lys Lys Leu Arg Glu Lys Val Asp Lys Asp Glu Trp
        515                 520                 525
Ile Ser Gly Ala Ala Val Val Asn Ala Phe Tyr Ser Ser Gly Arg Asn
530                 535                 540
Gln Ile Val Phe Pro Ala Gly Ile Leu Gln Pro Pro Phe Phe Ser Ala
545                 550                 555                 560
Gln Gln Ser Asn Ser Leu Asn Tyr Gly Gly Ile Gly Met Val Ile Gly
                565                 570                 575
His Glu Ile Thr His Gly Phe Asp Asp Asn Gly Arg Asn Phe Asn Lys
            580                 585                 590
Asp Gly Asp Leu Val Asp Trp Trp Thr Gln Gln Ser Ala Ser Asn Phe
        595                 600                 605
Lys Glu Gln Ser Gln Cys Met Val Tyr Gln Tyr Gly Asn Phe Ser Trp
610                 615                 620
Asp Leu Ala Gly Gly Gln His Leu Asn Gly Ile Asn Thr Leu Gly Glu
625                 630                 635                 640
Asn Ile Ala Asp Asn Gly Gly Leu Gly Gln Ala Tyr Arg Ala Tyr Gln
                645                 650                 655
Asn Tyr Ile Lys Lys Asn Gly Glu Glu Lys Leu Leu Pro Gly Leu Asp
            660                 665                 670
Leu Asn His Lys Gln Leu Phe Phe Leu Asn Phe Ala Gln Val Trp Cys
        675                 680                 685
Gly Thr Tyr Arg Pro Glu Tyr Ala Val Asn Ser Ile Lys Thr Asp Val
690                 695                 700
```

```
His Ser Pro Gly Asn Phe Arg Ile Ile Gly Thr Leu Gln Asn Ser Ala
705                 710                 715                 720

Glu Phe Ser Glu Ala Phe His Cys Arg Lys Asn Ser Tyr Met Asn Pro
                725                 730                 735

Glu Lys Lys Cys Arg Val Trp
            740

<210> SEQ ID NO 2
<211> LENGTH: 3181
<212> TYPE: DNA
<213> ORGANISM: Homo sapiens

<400> SEQUENCE: 2
```

| | | | | | |
|---|---|---|---|---|---|
| gcaagtcaga | aagtcagatg | gatataactg | atatcaacac | tccaaagcca | aagaagaaac    60 |
| agcgatggac | tccactggag | atcagcctct | cggtccttgt | cctgctcctc | accatcatag   120 |
| ctgtgacaat | gatcgcactc | tatgcaacct | acgatgatgg | tatttgcaag | tcatcagact   180 |
| gcataaaatc | agctgctcga | ctgatccaaa | acatggatgc | caccactgag | ccttgtacag   240 |
| acttttttcaa | atatgcttgc | ggaggctggt | tgaaacgtaa | tgtcattccc | gagaccagct   300 |
| cccgttacgg | caactttgac | attttaagag | atgaactaga | agtcgttttg | aaagatgtcc   360 |
| ttcaagaacc | caaaactgaa | gatatagtag | cagtgcagaa | agcaaaagca | ttgtacaggt   420 |
| cttgtataaa | tgaatctgct | attgatagca | gaggtggaga | acctctactc | aaactgttac   480 |
| cagacatata | tgggtggcca | gtagcaacag | aaaactggga | gcaaaaatat | ggtgcttctt   540 |
| ggacagctga | aaaagctatt | gcacaactga | attctaaata | tgggaaaaaa | gtccttatta   600 |
| atttgtttgt | tggcactgat | gataagaatt | ctgtgaatca | tgtaattcat | attgaccaac   660 |
| ctcgacttgg | cctcccttct | agagattact | atgaatgcac | tggaatctat | aaagaggctt   720 |
| gtacagcata | tgtggatttt | atgatttctg | tggccagatt | gattcgtcag | gaagaaagat   780 |
| tgcccatcga | tgaaaaccag | cttgctttgg | aaatgaataa | agttatggaa | ttggaaaaag   840 |
| aaattgccaa | tgctacggct | aaacctgaag | atcgaaatga | tccaatgctt | ctgtataaca   900 |
| agatgacatt | ggcccagatc | caaaataact | tttcactaga | gatcaatggg | aagccattca   960 |
| gctggttgaa | tttcacaaat | gaaatcatgt | caactgtgaa | tattagtatt | acaaatgagg  1020 |
| aagatgtggt | tgtttatgct | ccagaatatt | taaccaaact | taagcccatt | cttaccaaat  1080 |
| attctgccag | agatcttcaa | aatttaatgt | cctggagatt | cataatggat | cttgtaagca  1140 |
| gcctcagccg | aacctacaag | gagtccagaa | atgctttccg | caaggccctt | tatggtacaa  1200 |
| cctcagaaac | agcaacttgg | agacgttgtg | caaactatgt | caatgggaat | atggaaaatg  1260 |
| ctgtggggag | gctttatgtg | gaagcagcat | ttgctggaga | gagtaaacat | gtggtcgagg  1320 |
| atttgattgc | acagatccga | gaagttttta | ttcagacttt | agatgacctc | acttggatgg  1380 |
| atgccgagac | aaaaaagaga | gctgaagaaa | aggccttagc | aattaaagaa | aggatcggct  1440 |
| atcctgatga | cattgtttca | aatgataaca | aactgaataa | tgagtacctc | gagttgaact  1500 |
| acaaagaaga | tgaatacttc | gagaacataa | ttcaaaattt | gaaattcagc | caaagtaaac  1560 |
| aactgaagaa | gctccgagaa | aaggtggaca | agatgagtgg | ataagtggag | cagctgtag   1620 |
| tcaatgcatt | ttactcttca | ggaagaaatc | agatagtctt | cccagccggc | attctgcagc  1680 |
| ccccccttctt | tagtgcccag | cagtccaact | cattgaacta | tggggcatc | ggcatggtca  1740 |
| taggacacga | aatcacccat | ggcttcgatg | acaatgcag | aaactttaac | aaagatggag  1800 |
| acctcgttga | ctggtggact | caacagtctg | caagtaactt | taaggagcaa | tcccagtgca  1860 |

-continued

```
tggtgtatca gtatggaaac ttttcctggg acctggcagg tggacagcac cttaatggaa    1920
ttaatacact gggagaaaac attgctgata atggaggtct tggtcaagca tacagagcct    1980
atcagaatta tattaaaaag aatggcgaag aaaaattact tcctggactt gacctaaatc    2040
acaaacaact atttttcttg aactttgcac aggtgtggtg tggaacctat aggccagagt    2100
atgcggttaa ctccattaaa acagatgtgc acagtccagg caatttcagg attattggga    2160
ctttgcagaa ctctgcagag ttttcagaag cctttcactg ccgcaagaat tcatacatga    2220
atccagaaaa gaagtgccgg gtttggtgat cttcaaaaga agcattgcag cccttggcta    2280
gacttgccaa caccacagaa atggggaatt ctctaatcga agaaaatggg ccctagggg     2340
tcactgtact gacttgaggg tgattaacag agagggcacc atcacaatac agataacatt    2400
aggttgtcct agaaagggtg tggagggagg aagggggtct aaggtctatc aagtcaatca    2460
tttctcactg tgtacataat gcttaatttc taaagataat attactgttt atttctgttt    2520
ctcatatggt ctaccagttt gctgatgtcc ctagaaaaca atgcaaaacc tttgaggtag    2580
accaggattt ctaatcaaaa gggaaaagaa gatgttgaag aatacagtta ggcaccagaa    2640
gaacagtagg tgacactata gtttaaaaca cattgcctaa ctactagttt ttacttttat    2700
ttgcaacatt tacagtcctt caaaatcctt ccaaagaatt cttatacaca ttggggcctt    2760
ggagcttaca tagtttaaa ctcattttg ccatacatca gttattcatt ctgtgatcat     2820
ttattttaag cactcttaaa gcaaaaaatg aatgtctaaa attgttttt gttgtacctg     2880
ctttgactga tgctgagatt cttcaggctt cctgcaattt tctaagcaat ttcttgctct    2940
atctctcaaa acttggtatt tttcagagat ttatataaat gtaaaaataa taattttat     3000
atttaattat taactacatt tatgagtaac tattattata ggtaatcaat gaatattgaa    3060
gtttcagctt aaaataaaca gttgtgaacc aagatctata aagcgatata cagatgaaaa    3120
tttgagacta tttaaactta taaatcatat tgatgaaaag atttaagcac aaactttagg    3180
g                                                                    3181
```

<210> SEQ ID NO 3
<211> LENGTH: 535
<212> TYPE: PRT
<213> ORGANISM: Homo sapiens

<400> SEQUENCE: 3

```
Met Gly Ser Ser Ala Thr Glu Ile Glu Glu Leu Glu Asn Thr Thr Phe
 1               5                  10                  15

Lys Tyr Leu Thr Gly Glu Gln Thr Glu Lys Met Trp Gln Arg Leu Lys
            20                  25                  30

Gly Ile Leu Arg Cys Leu Val Lys Gln Leu Glu Arg Gly Asp Val Asn
        35                  40                  45

Val Val Asp Leu Lys Lys Asn Ile Glu Tyr Ala Ala Ser Val Leu Glu
    50                  55                  60

Ala Val Tyr Ile Asp Glu Thr Arg Arg Leu Leu Asp Thr Glu Asp Glu
65                  70                  75                  80

Leu Ser Asp Ile Gln Thr Asp Ser Val Pro Ser Glu Val Arg Asp Trp
                85                  90                  95

Leu Ala Ser Thr Phe Thr Arg Lys Met Gly Met Thr Lys Lys Lys Pro
            100                 105                 110

Glu Glu Lys Pro Lys Phe Arg Ser Ile Val His Ala Val Gln Ala Gly
        115                 120                 125

Ile Phe Val Glu Arg Met Tyr Arg Lys Thr Tyr His Met Val Gly Leu
```

```
            130                 135                 140
Ala Tyr Pro Ala Ala Val Ile Val Thr Leu Lys Asp Val Asp Lys Trp
145                 150                 155                 160
Ser Phe Asp Val Phe Ala Leu Asn Glu Ala Ser Gly Glu His Ser Leu
                165                 170                 175
Lys Phe Met Ile Tyr Glu Leu Phe Thr Arg Tyr Asp Leu Ile Asn Arg
            180                 185                 190
Phe Lys Ile Pro Val Ser Cys Leu Ile Thr Phe Ala Glu Ala Leu Glu
        195                 200                 205
Val Gly Tyr Ser Lys Tyr Lys Asn Pro Tyr His Asn Leu Ile His Ala
    210                 215                 220
Ala Asp Val Thr Gln Thr Val His Tyr Ile Met Leu His Thr Gly Ile
225                 230                 235                 240
Met His Trp Leu Thr Glu Leu Glu Ile Leu Ala Met Val Phe Ala Ala
                245                 250                 255
Ala Ile His Asp Tyr Glu His Thr Gly Thr Thr Asn Asn Phe His Ile
            260                 265                 270
Gln Thr Arg Ser Asp Val Ala Ile Leu Tyr Asn Asp Arg Ser Val Leu
        275                 280                 285
Glu Asn His His Val Ser Ala Ala Tyr Arg Leu Met Gln Glu Glu Glu
    290                 295                 300
Met Asn Ile Leu Ile Asn Leu Ser Lys Asp Asp Trp Arg Asp Leu Arg
305                 310                 315                 320
Asn Leu Val Ile Glu Met Val Leu Ser Thr Asp Met Ser Gly His Phe
                325                 330                 335
Gln Gln Ile Lys Asn Ile Arg Asn Ser Leu Gln Gln Pro Glu Gly Ile
            340                 345                 350
Asp Arg Ala Lys Thr Met Ser Leu Ile Leu His Ala Ala Asp Ile Ser
        355                 360                 365
His Pro Ala Lys Ser Trp Lys Leu His Tyr Arg Trp Thr Met Ala Leu
    370                 375                 380
Met Glu Glu Phe Phe Leu Gln Gly Asp Lys Glu Ala Glu Leu Gly Leu
385                 390                 395                 400
Pro Phe Ser Pro Leu Cys Asp Arg Lys Ser Thr Met Val Ala Gln Ser
                405                 410                 415
Gln Ile Gly Phe Ile Asp Phe Ile Val Glu Pro Thr Phe Ser Leu Leu
            420                 425                 430
Thr Asp Ser Thr Glu Lys Ile Val Ile Pro Leu Ile Glu Glu Ala Ser
        435                 440                 445
Lys Ala Glu Thr Ser Ser Tyr Val Ala Ser Ser Thr Thr Ile Val
    450                 455                 460
Gly Leu His Ile Ala Asp Ala Leu Arg Arg Ser Asn Thr Lys Gly Ser
465                 470                 475                 480
Met Ser Asp Gly Ser Tyr Ser Pro Asp Tyr Ser Leu Ala Ala Val Asp
                485                 490                 495
Leu Lys Ser Phe Lys Asn Asn Leu Val Asp Ile Ile Gln Gln Asn Lys
            500                 505                 510
Glu Arg Trp Lys Glu Leu Ala Ala Gln Glu Ala Arg Thr Ser Ser Gln
        515                 520                 525
Lys Cys Glu Phe Ile His Gln
    530                 535
```

<210> SEQ ID NO 4

<211> LENGTH: 2008
<212> TYPE: DNA
<213> ORGANISM: Homo sapiens

<400> SEQUENCE: 4

```
gaattctgat gtgcttcagt gcacagaaca gtaacagatg agctgctttt ggggagagct      60
tgagtactca gtcggagcat catcatgggg tctagtgcca cagagattga agaattggaa     120
aacaccactt ttaagtatct tacaggagaa cagactgaaa aaatgtggca gcgcctgaaa     180
ggaatactaa gatgcttggt gaagcagctg gaaagaggtg atgttaacgt cgtcgactta     240
aagaagaata ttgaatatgc ggcatctgtg ctggaagcag tttatatcga tgaaacaaga     300
agacttctgg atactgaaga tgagctcagt gacattcaga ctgactcagt cccatctgaa     360
gtccgggact ggttggcttc tacctttaca cggaaaatgg ggatgacaaa aagaaaacct     420
gaggaaaaac caaaatttcg gagcattgtg catgctgttc aagctggaat ttttgtggaa     480
agaatgtacc gaaaaacata tcatatggtt ggtttggcat atccagcagc tgtcatcgta     540
acattaaagg atgttgataa atggtctttc gatgtatttg ccctaaatga agcaagtgga     600
gagcatagtc tgaagtttat gatttatgaa ctgtttacca gatatgatct tatcaaccgt     660
ttcaagattc ctgtttcttg cctaatcacc tttgcagaag ctttagaagt tggttacagc     720
aagtacaaaa atccatatca caatttgatt catgcagctg atgtcactca aactgtgcat     780
tacataatgc ttcatacagg tatcatgcac tggctcactg aactggaaat tttagcaatg     840
gtctttgctg ctgccattca tgattatgag catacaggga caacaaacaa ctttcacatt     900
cagacaaggt cagatgttgc cattttgtat aatgatcgct ctgtccttga gaatcaccac     960
gtgagtgcag cttatcgact tatgcaagaa gaagaaatga atatcttgat aaatttatcc    1020
aaagatgact ggagggatct tcggaaccta gtgattgaaa tggttttatc tacagacatg    1080
tcaggtcact tccagcaaat taaaaatata agaaacagtt tgcagcagcc tgaagggatt    1140
gacagagcca aaaccatgtc cctgattctc cacgcagcag acatcagcca cccagccaaa    1200
tcctggaagc tgcattatcg gtggaccatg gcccctaatgg aggagttttt cctgcaggga    1260
gataaagaag ctgaattagg gcttccattt tccccacttt gtgatcggaa gtcaaccatg    1320
gtggcccagt cacaaatagg tttcatcgat ttcatagtag agccaacatt ttctcttctg    1380
acagactcaa cagagaaaat tgttattcct cttatagagg aagcctcaaa agccgaaact    1440
tcttcctatg tggcaagcag ctcaaccacc attgtgtgggt tacacattgc tgatgcacta    1500
agacgatcaa atacaaaagg ctccatgagt gatgggtcct attccccaga ctactccctt    1560
gcagcagtgg acctgaagag tttcaagaac aacctggtgg acatcattca gcagaacaaa    1620
gagaggtgga agagttagc tgcacaagaa gcaagaacca gttcacagaa gtgtgagttt    1680
attcatcagt aaacaccttt aagtaaaacc tcgtgcatgg tggcagctct aatttgacca    1740
aaagacttgg agattttgat tatgcttgct ggaaatctac cctgtcctgt gtgagacagg    1800
aaatctattt ttgcagattg ctcaataagc atcatgagcc acataaataa cagctgtaaa    1860
ctccttaatt caccgggctc aactgctacc gaacagattc atctagtggc tacatcagca    1920
ccttgtgctt tcagatatct gtttcaatgg cattttgtgg catttgtctt taccgagtgc    1980
caataaattt tctttgagca aaaaaaaa                                       2008
```

<210> SEQ ID NO 5
<211> LENGTH: 941
<212> TYPE: PRT
<213> ORGANISM: Homo sapiens

```
<400> SEQUENCE: 5

Met Gly Gln Ala Cys Gly His Ser Ile Leu Cys Arg Ser Gln Gln Tyr
 1               5                  10                  15

Pro Ala Ala Arg Pro Ala Glu Pro Arg Gly Gln Gln Val Phe Leu Lys
             20                  25                  30

Pro Asp Glu Pro Pro Pro Pro Gln Pro Cys Ala Asp Ser Leu Gln
         35                  40                  45

Asp Ala Leu Leu Ser Leu Gly Ser Val Ile Asp Ile Ser Gly Leu Gln
     50                  55                  60

Arg Ala Val Lys Glu Ala Leu Ser Ala Val Leu Pro Arg Val Glu Thr
 65                  70                  75                  80

Val Tyr Thr Tyr Leu Leu Asp Gly Glu Ser Gln Leu Val Cys Glu Asp
                 85                  90                  95

Pro Pro His Glu Leu Pro Gln Glu Gly Lys Val Arg Glu Ala Ile Ile
             100                 105                 110

Ser Gln Lys Arg Leu Gly Cys Asn Gly Leu Gly Phe Ser Asp Leu Pro
         115                 120                 125

Gly Lys Pro Leu Ala Arg Leu Val Ala Pro Leu Ala Pro Asp Thr Gln
    130                 135                 140

Val Leu Val Met Pro Leu Ala Asp Lys Glu Ala Gly Ala Val Ala Ala
145                 150                 155                 160

Val Ile Leu Val His Cys Gly Gln Leu Ser Asp Asn Glu Glu Trp Ser
                165                 170                 175

Leu Gln Ala Val Glu Lys His Thr Leu Val Ala Leu Arg Arg Val Gln
            180                 185                 190

Val Leu Gln Gln Arg Gly Pro Arg Glu Ala Pro Arg Ala Val Gln Asn
        195                 200                 205

Pro Pro Glu Gly Thr Ala Glu Asp Gln Lys Gly Gly Ala Ala Tyr Thr
    210                 215                 220

Asp Arg Asp Arg Lys Ile Leu Gln Leu Cys Gly Glu Leu Tyr Asp Leu
225                 230                 235                 240

Asp Ala Ser Ser Leu Gln Leu Lys Val Leu Gln Tyr Leu Gln Gln Glu
                245                 250                 255

Thr Arg Ala Ser Arg Cys Cys Leu Leu Leu Val Ser Glu Asp Asn Leu
            260                 265                 270

Gln Leu Ser Cys Lys Val Ile Gly Asp Lys Val Leu Gly Glu Glu Val
        275                 280                 285

Ser Phe Pro Leu Thr Gly Cys Leu Gly Gln Val Val Glu Asp Lys Lys
    290                 295                 300

Ser Ile Gln Leu Lys Asp Leu Thr Ser Glu Asp Val Gln Gln Leu Gln
305                 310                 315                 320

Ser Met Leu Gly Cys Glu Leu Gln Ala Met Leu Cys Val Pro Val Ile
                325                 330                 335

Ser Arg Ala Thr Asp Gln Val Val Ala Leu Ala Cys Ala Phe Asn Lys
            340                 345                 350

Leu Glu Gly Asp Leu Phe Thr Asp Glu Asp Glu His Val Ile Gln His
        355                 360                 365

Cys Phe His Tyr Thr Ser Thr Val Leu Thr Ser Thr Leu Ala Phe Gln
    370                 375                 380

Lys Glu Gln Lys Leu Lys Cys Glu Cys Gln Ala Leu Leu Gln Val Ala
385                 390                 395                 400

Lys Asn Leu Phe Thr His Leu Asp Asp Val Ser Val Leu Leu Gln Glu
```

-continued

```
                405                 410                 415
Ile Ile Thr Glu Ala Arg Asn Leu Ser Asn Ala Glu Ile Cys Ser Val
                420                 425                 430

Phe Leu Leu Asp Gln Asn Glu Leu Val Ala Lys Val Phe Asp Gly Gly
            435                 440                 445

Val Val Asp Asp Glu Ser Tyr Glu Ile Arg Ile Pro Ala Asp Gln Gly
    450                 455                 460

Ile Ala Gly His Val Ala Thr Thr Gly Gln Ile Leu Asn Ile Pro Asp
465                 470                 475                 480

Ala Tyr Ala His Pro Leu Phe Tyr Arg Gly Val Asp Asp Ser Thr Gly
                485                 490                 495

Phe Arg Thr Arg Asn Ile Leu Cys Phe Pro Ile Lys Asn Glu Asn Gln
            500                 505                 510

Glu Val Ile Gly Val Ala Glu Leu Val Asn Lys Ile Asn Gly Pro Trp
        515                 520                 525

Phe Ser Lys Phe Asp Glu Asp Leu Ala Thr Ala Phe Ser Ile Tyr Cys
    530                 535                 540

Gly Ile Ser Ile Ala His Ser Leu Leu Tyr Lys Lys Val Asn Glu Ala
545                 550                 555                 560

Gln Tyr Arg Ser His Leu Ala Asn Glu Met Met Met Tyr His Met Lys
                565                 570                 575

Val Ser Asp Asp Glu Tyr Thr Lys Leu Leu His Asp Gly Ile Gln Pro
            580                 585                 590

Val Ala Ala Ile Asp Ser Asn Phe Ala Ser Phe Thr Tyr Thr Pro Arg
        595                 600                 605

Ser Leu Pro Glu Asp Asp Thr Ser Met Ala Ile Leu Ser Met Leu Gln
    610                 615                 620

Asp Met Asn Phe Ile Asn Asn Tyr Lys Ile Asp Cys Pro Thr Leu Ala
625                 630                 635                 640

Arg Phe Cys Leu Met Val Lys Lys Gly Tyr Arg Asp Pro Pro Tyr His
                645                 650                 655

Asn Trp Met His Ala Phe Ser Val Ser His Phe Cys Tyr Leu Leu Tyr
            660                 665                 670

Lys Asn Leu Glu Leu Thr Asn Tyr Leu Glu Asp Ile Glu Ile Phe Ala
        675                 680                 685

Leu Phe Ile Ser Cys Met Cys His Asp Leu Asp His Arg Gly Thr Asn
    690                 695                 700

Asn Ser Phe Gln Val Ala Ser Lys Ser Val Leu Ala Ala Leu Tyr Ser
705                 710                 715                 720

Ser Glu Gly Ser Val Met Glu Arg His His Phe Ala Gln Ala Ile Ala
                725                 730                 735

Ile Leu Asn Thr His Gly Cys Asn Ile Phe Asp His Phe Ser Arg Lys
            740                 745                 750

Asp Tyr Gln Arg Met Leu Asp Leu Met Arg Asp Ile Ile Leu Ala Thr
        755                 760                 765

Asp Leu Ala His His Leu Arg Ile Phe Lys Asp Leu Gln Lys Met Ala
    770                 775                 780

Glu Val Gly Tyr Asp Arg Asn Asn Lys Gln His His Arg Leu Leu Leu
785                 790                 795                 800

Cys Leu Leu Met Thr Ser Cys Asp Leu Ser Asp Gln Thr Lys Gly Trp
                805                 810                 815

Lys Thr Thr Arg Lys Ile Ala Glu Leu Ile Tyr Lys Glu Phe Phe Ser
            820                 825                 830
```

```
Gln Gly Asp Leu Glu Lys Ala Met Gly Asn Arg Pro Met Glu Met Met
            835                 840                 845

Asp Arg Glu Lys Ala Tyr Ile Pro Glu Leu Gln Ile Ser Phe Met Glu
        850                 855                 860

His Ile Ala Met Pro Ile Tyr Lys Leu Leu Gln Asp Leu Phe Pro Lys
865                 870                 875                 880

Ala Ala Glu Leu Tyr Glu Arg Val Ala Ser Asn Arg Glu His Trp Thr
                885                 890                 895

Lys Val Ser His Lys Phe Thr Ile Arg Gly Leu Pro Ser Asn Asn Ser
            900                 905                 910

Leu Asp Phe Leu Asp Glu Glu Tyr Glu Val Pro Asp Leu Asp Gly Thr
        915                 920                 925

Arg Ala Pro Ile Asn Gly Cys Cys Ser Leu Asp Ala Glu
    930                 935                 940

<210> SEQ ID NO 6
<211> LENGTH: 4240
<212> TYPE: DNA
<213> ORGANISM: Homo sapiens

<400> SEQUENCE: 6
```

| | | | | | |
|---|---|---|---|---|---|
| cagcagagct | ggattggggt | gttgagtcca | ggctgagtag | ggggcagccc | actgctcttg | 60 |
| gtccctgtgc | ctgctggggg | tgccctgccc | tgaactccag | gcagcgggga | cagggcgagg | 120 |
| tgccacctta | gtctggctgg | ggaggcggac | gatgaggagt | gatggggcag | gcatgcggcc | 180 |
| actccatcct | ctgcaggagc | cagcagtacc | cggcagcgcg | accggctgag | ccgcggggcc | 240 |
| agcaggtctt | cctcaagccg | gacgagccgc | cgccgccgcc | gcagccatgc | gccgacagcc | 300 |
| tgcaggacgc | cttgctgagt | ctgggctctg | tcatcgacat | ttcaggcctg | caacgtgctg | 360 |
| tcaaggaggc | cctgtcagct | gtgctccccc | gagtggaaac | tgtctacacc | tacctactgg | 420 |
| atggtgagtc | ccagctggtg | tgtgaggacc | ccccacatga | gctgcccccag | gaggggaaag | 480 |
| tccgggaggc | tatcatctcc | cagaagcggc | tgggctgcaa | tgggctgggc | ttctcagacc | 540 |
| tgccagggaa | gcccttggcc | aggctggtgg | ctccactggc | tcctgatacc | caagtgctgg | 600 |
| tcatgccgct | agcggacaag | gaggctgggg | ccgtggcagc | tgtcatcttg | gtgcactgtg | 660 |
| gccagctgag | tgataatgag | gaatggagcc | tgcaggcggt | ggagaagcat | accctggtcg | 720 |
| ccctgcggag | ggtgcaggtc | ctgcagcagc | gcgggcccag | ggaggctccc | cgagccgtcc | 780 |
| agaacccccc | ggaggggacg | gcggaagacc | agaagggcgg | ggcggcgtac | accgaccgcg | 840 |
| accgcaagat | cctccaactg | tgcggggaac | tctacgacct | ggatgcctct | tcccctgcagc | 900 |
| tcaaagtgct | ccaatacctg | cagcaggaga | cccgggcatc | ccgctgctgc | ctcctgctgg | 960 |
| tgtcggagga | caatctccag | ctttcttgca | aggtcatcgg | agacaaagtg | ctcggggaag | 1020 |
| aggtcagctt | tcccttgaca | ggatgcctgg | gccaggtggt | ggaagacaag | aagtccatcc | 1080 |
| agctgaagga | cctcacctcc | gaggatgtac | aacagctgca | gagcatgttg | ggctgtgagc | 1140 |
| tgcaggccat | gctctgtgtc | cctgtcatca | gccgggccac | tgaccaggtg | gtggccttgg | 1200 |
| cctgcgcctt | caacaagcta | gaaggagact | tgttcaccga | cgaggacgag | catgtgatcc | 1260 |
| agcactgctt | ccactacacc | agcaccgtgc | tcaccagcac | cctggccttc | cagaaggaac | 1320 |
| agaaactcaa | gtgtgagtgc | caggctcttc | tccaagtggc | aaagaacctc | ttcacccacc | 1380 |
| tggatgacgt | ctctgtcctg | ctccaggaga | tcatcacgga | ggccagaaac | ctcagcaacg | 1440 |
| cagagatctg | ctctgtgttc | ctgctggatc | agaatgagct | ggtggccaag | gtgttcgacg | 1500 |

```
ggggcgtggt ggatgatgag agctatgaga tccgcatccc ggccgatcag ggcatcgcgg    1560
gacacgtggc gaccacgggc cagatcctga acatccctga cgcatatgcc catccgcttt    1620
tctaccgcgg cgtggacgac agcaccggct tccgcacgcg caacatcctc tgcttcccca    1680
tcaagaacga gaaccaggag gtcatcggtg tggccgagct ggtgaacaag atcaatgggc    1740
catggttcag caagttcgac gaggacctgg cgacggcctt ctccatctac tgcggcatca    1800
gcatcgccca ttctctccta tacaaaaaag tgaatgaggc tcagtatcgc agccacctgg    1860
ccaatgagat gatgatgtac cacatgaagg tctccgacga tgagtatacc aaacttctcc    1920
atgatgggat ccagcctgtg gctgccattg actccaattt tgcaagtttc acctataccc    1980
ctcgttccct gcccgaggat gacacgtcca tggccatcct gagcatgctg caggacatga    2040
atttcatcaa caactacaaa attgactgcc cgaccctggc ccggttctgt ttgatggtga    2100
agaagggcta ccgggatccc ccctaccaca actggatgca cgccttttct gtctcccact    2160
tctgctacct gctctacaag aacctggagc tcaccaacta cctcgaggac atcgagatct    2220
ttgccttgtt tatttcctgc atgtgtcatg acctggacca cagaggcaca aacaactctt    2280
tccaggtggc ctcgaaatct gtgctggctg cgctctacag ctctgagggc tccgtcatgg    2340
agaggcacca ctttgctcag gccatcgcca tcctcaacac ccacggctgc aacatctttg    2400
atcatttctc ccggaaggac tatcagcgca tgctggatct gatgcgggac atcatcttgg    2460
ccacagacct ggcccaccat ctccgcatct tcaaggacct ccagaagatg gctgaggtgg    2520
gctacgaccg aaacaacaag cagcaccaca gacttctcct ctgcctcctc atgacctcct    2580
gtgacctctc tgaccagacc aagggctgga agactacgag aaagatcgcg gagctgatct    2640
acaaagaatt cttctcccag ggagacctgg agaaggccat gggcaacagg ccgatggaga    2700
tgatggaccg ggagaaggcc tatatccctg agctgcaaat cagcttcatg gagcacattg    2760
caatgcccat ctacaagctg ttgcaggacc tgttccccaa agcggcagag ctgtacgagc    2820
gcgtggcctc caaccgtgag cactggacca aggtgtccca agttcacc atccgcggcc     2880 tcccaagtaa caactcgctg gacttcctgg atgaggagta cgaggtgcct gatctggatg    2940
gcactagggc ccccatcaat ggctgctgca gccttgatgc tgagtgatcc cctccaggac    3000
acttccctgc ccaggccacc tcccacagcc ctccactggt ctggccagat gcactgggaa    3060
cagagccacg ggtcctgggt cctagaccag gacttcctgt gtgaccctgg acaagtacta    3120
ccttcctggg cctcagcttt ctcgtctgta taatggaagc aagacttcca acctcacgga    3180
gactttgtaa tttgcttctc tgagagcaca ggggtgacca atgagcagtg ggccctactc    3240
tgcacctctg accacacctt ggcaagtctt tcccaagcca ttctttgtct gagcagcttg    3300
atggtttctc cttgccccat ttctgcccca ccagatcttt gctcctttcc ctttgaggac    3360
tcccacccct tgggtctcca ggatcctcat ggaagggaa ggtgagacat ctgagtgagc    3420
agagtgtggc atcttggaaa cagtccttag ttctgtggga ggactagaaa cagccgcggc    3480
gaaggccccc tgaggaccac tactatactg atggtgggat tgggacctgg gggatacagg    3540
ggccccagga agaagctggc cagaggggca gctcagtgct ctgcagagag gggccctggg    3600
gagaagcagg atgggattga tgggcaggag ggatccccgc actgggagac aggcccaggt    3660
atgaatgagc cagccatgct tcctcctgcc tgtgtgacgc tgggcgagtc tcttcccctg    3720
tctgggccaa acagggagcg ggtaagacaa tccatgctct aagatccatt ttagatcaat    3780
gtctaaaata gctctatggc tctgcggagt cccagcagag gctatggaat gtttctgcaa    3840
```

-continued

| | |
|---|---|
| ccctaaggca cagagagcca accctgagtg tctcagaggc cccctgagtg ttccccttgg | 3900 |
| cctgagcccc ttacccattc ctgcagccag tgagagacct ggcctcagcc tggcagcgct | 3960 |
| ctcttcaagg ccatatccac ctgtgccctg gggcttggga daccccatag ccgggactc | 4020 |
| ttgggtcagc ccgccactgg cttctctctt tttctccgtt tcattctgtg tgcgttgtgg | 4080 |
| ggtgggggag gggggtccacc tgccttacct ttctgagttg cctttagaga gatgcgtttt | 4140 |
| tctaggactc tgtgcaactg tcgtatatgg tcccgtgggc tgaccgcttt gtacatgaga | 4200 |
| ataaatctat ttctttctac caaaaaaaaa aaaaaaaaa | 4240 |

<210> SEQ ID NO 7
<211> LENGTH: 97
<212> TYPE: PRT
<213> ORGANISM: Homo sapiens

<400> SEQUENCE: 7

```
Met Leu Gly Asn Lys Arg Leu Gly Leu Ser Gly Leu Thr Leu Ala Leu
 1               5                  10                  15

Ser Leu Leu Val Cys Leu Gly Ala Leu Ala Glu Ala Tyr Pro Ser Lys
            20                  25                  30

Pro Asp Asn Pro Gly Glu Asp Ala Pro Ala Glu Asp Met Ala Arg Tyr
        35                  40                  45

Tyr Ser Ala Leu Arg His Tyr Ile Asn Leu Ile Thr Arg Gln Arg Tyr
    50                  55                  60

Gly Lys Arg Ser Ser Pro Glu Thr Leu Ile Ser Asp Leu Leu Met Arg
65                  70                  75                  80

Glu Ser Thr Glu Asn Val Pro Arg Thr Arg Leu Glu Asp Pro Ala Met
                85                  90                  95

Trp
```

<210> SEQ ID NO 8
<211> LENGTH: 551
<212> TYPE: DNA
<213> ORGANISM: Homo sapiens

<400> SEQUENCE: 8

| | |
|---|---|
| acccatccg ctggctctca cccctcggag acgctcgccc gacagcatag tacttgccgc | 60 |
| ccagccacgc ccgcgcgcca gccaccatgc taggtaacaa gcgactgggg ctgtccggac | 120 |
| tgaccctcgc cctgtccctg ctcgtgtgcc tgggtgcgct ggccgaggcg taccctcca | 180 |
| agccggacaa cccgggcgag gacgcaccag cggaggacat ggccagatac tactcggcgc | 240 |
| tgcgacacta catcaacctc atcaccaggc agagatatgg aaaacgatcc agcccagaga | 300 |
| cactgatttc agacctcttg atgagagaaa gcacagaaaa tgttcccaga actcggcttg | 360 |
| aagaccctgc aatgtggtga tgggaaatga gacttgctct ctggccttt cctattttca | 420 |
| gcccatattt catcgtgtaa aacgagaatc cacccatcct accaatgcat gcagccactg | 480 |
| tgctgaattc tgcaatgttt tcctttgtca tcattgtata tatgtgtgtt taaataaagt | 540 |
| atcatgcatt c | 551 |

<210> SEQ ID NO 9
<211> LENGTH: 384
<212> TYPE: PRT
<213> ORGANISM: Homo sapiens

<400> SEQUENCE: 9

Met Asn Ser Thr Leu Phe Ser Gln Val Glu Asn His Ser Val His Ser

```
  1               5                    10                   15
Asn Phe Ser Glu Lys Asn Ala Gln Leu Leu Ala Phe Glu Asn Asp Asp
                20                  25                  30

Cys His Leu Pro Leu Ala Met Ile Phe Thr Leu Ala Leu Ala Tyr Gly
        35                  40                  45

Ala Val Ile Ile Leu Gly Val Ser Gly Asn Leu Ala Leu Ile Ile Ile
    50                  55                  60

Ile Leu Lys Gln Lys Glu Met Arg Asn Val Thr Asn Ile Leu Ile Val
65                  70                  75                  80

Asn Leu Ser Phe Ser Asp Leu Leu Val Ala Ile Met Cys Leu Pro Phe
                85                  90                  95

Thr Phe Val Tyr Thr Leu Met Asp His Trp Val Phe Gly Glu Ala Met
            100                 105                 110

Cys Lys Leu Asn Pro Phe Val Gln Cys Val Ser Ile Thr Val Ser Ile
            115                 120                 125

Phe Ser Leu Val Leu Ile Ala Val Glu Arg His Gln Leu Ile Ile Asn
        130                 135                 140

Pro Arg Gly Trp Arg Pro Asn Asn Arg His Ala Tyr Val Gly Ile Ala
145                 150                 155                 160

Val Ile Trp Val Leu Ala Val Ala Ser Ser Leu Pro Phe Leu Ile Tyr
                165                 170                 175

Gln Val Met Thr Asp Glu Pro Phe Gln Asn Val Thr Leu Asp Ala Tyr
            180                 185                 190

Lys Asp Lys Tyr Val Cys Phe Asp Gln Phe Pro Ser Asp Ser His Arg
        195                 200                 205

Leu Ser Tyr Thr Thr Leu Leu Leu Val Leu Gln Tyr Phe Gly Pro Leu
    210                 215                 220

Cys Phe Ile Phe Ile Cys Tyr Phe Lys Ile Tyr Ile Arg Leu Lys Arg
225                 230                 235                 240

Arg Asn Asn Met Met Asp Lys Met Arg Asp Asn Lys Tyr Arg Ser Ser
                245                 250                 255

Glu Thr Lys Arg Ile Asn Ile Met Leu Leu Ser Ile Val Val Ala Phe
            260                 265                 270

Ala Val Cys Trp Leu Pro Leu Thr Ile Phe Asn Thr Val Phe Asp Trp
        275                 280                 285

Asn His Gln Ile Ile Ala Thr Cys Asn His Asn Leu Leu Phe Leu Leu
    290                 295                 300

Cys His Leu Thr Ala Met Ile Ser Thr Cys Val Asn Pro Ile Phe Tyr
305                 310                 315                 320

Gly Phe Leu Asn Lys Asn Phe Gln Arg Asp Leu Gln Phe Phe Phe Asn
                325                 330                 335

Phe Cys Asp Phe Arg Ser Arg Asp Asp Asp Tyr Glu Thr Ile Ala Met
            340                 345                 350

Ser Thr Met His Thr Asp Val Ser Lys Thr Ser Leu Lys Gln Ala Ser
        355                 360                 365

Pro Val Ala Phe Lys Lys Ile Asn Asn Asn Asp Asp Asn Glu Lys Ile
    370                 375                 380
```

<210> SEQ ID NO 10
<211> LENGTH: 2624
<212> TYPE: DNA
<213> ORGANISM: Homo sapiens
<220> FEATURE:
<221> NAME/KEY: misc_feature
<222> LOCATION: (1622)..(1624)

<223> OTHER INFORMATION: n is uncertain

<400> SEQUENCE: 10

```
attgttcagt tcaagggaat gaagaattca gaataatttt ggtaaatgga ttccaatatc      60
gggaataaga ataagctgaa cagttgacct gctttgaaga acatactgt ccatttgtct     120
aaaataatct ataacaacca aaccaatcaa atgaattca acattatttt cccaggttga     180
aaatcattca gtccactcta atttctcaga gaagaatgcc cagcttctgg cttttgaaaa     240
tgatgattgt catctgccct tggccatgat atttaccta gctcttgctt atggagctgt     300
gatcattctt ggtgtctctg gaaacctggc cttgatcata atcatcttga aacaaaagga     360
gatgagaaat gttaccaaca tcctgattgt gaacctttcc ttctcagact tgcttgttgc     420
catcatgtgt ctccccttta catttgtcta cacattaatg gaccactggg tctttggtga     480
ggcgatgtgt aagttgaatc cttttgtgca atgtgtttca atcactgtgt ccatttctc     540
tctggttctc attgctgtgg aacgacatca gctgataatc aaccctcgag ggtggagacc     600
aaataataga catgcttatg taggtattgc tgtgatttgg gtccttgctg tggcttcttc     660
tttgccttc ctgatctacc aagtaatgac tgatgagccg ttccaaaatg taacacttga     720
tgcgtacaaa gacaaatacg tgtgctttga tcaatttcca tcggactctc ataggttgtc     780
ttataccact ctcctcttgg tgctgcagta ttttggtcca ctttgtttta tatttatttg     840
ctacttcaag atatatatac gcctaaaaag gagaaacaac atgatggaca agatgagaga     900
caataagtac aggtccagtg aaaccaaaag aatcaatatc atgctgctct ccattgtggt     960
agcatttgca gtctgctggc tccctcttac catctttaac actgtgtttg attggaatca    1020
tcagatcatt gctacctgca accacaatct gttattcctg ctctgccacc tcacagcaat    1080
gatatccact tgtgtcaacc ccatattta tgggttcctg aacaaaaact tccagagaga    1140
cttgcagttc ttcttcaact tttgtgattt ccggtctcgg gatgatgatt atgaaacaat    1200
agccatgtcc acgatgcaca cagatgtttc caaaacttct ttgaagcaag caagcccagt    1260
cgcatttaaa aaaatcaaca acaatgatga taatgaaaaa atctgaaact acttatagcc    1320
tatggtcccg gatgacatct gtttaaaaac aagcacaacc tgcaacatac tttgattacc    1380
tgttctccca aggaatgggg ttgaaatcat ttgaaaatga ctaagatttt cttgtcttgc    1440
tttttttactg cttttgttgt agtgtcataa ttacatttgg aacaaaaggt gtgggctttg    1500
gggtcttctg gaaatagttt tgaccagaca tctttgaagt gcttttgtgt aatttatgca    1560
tataatataa agacttttat actgtactta ttggaatgaa atttctttaa agtattacga    1620
tnnnctgact tcagaagtac ctgccatcca atacggtcat tagattgggt catcttgatt    1680
agattagatt agattagatt gtcaacagat tgggccatcc ttactttatg ataggcatca    1740
ttttagtgtg ttacaatagt aacagtatgc aaaagcagca ttcaggagcc gaaagatagt    1800
cttgaagtca ttcagaagtg gtttgaggtt tctgtttttt ggtggttttt gtttgttttt    1860
tttttttttc accttaaggg aggctttcat ttcctcccga ctgattgtca cttaaatcaa    1920
aatttaaaaa tgaataaaaa gacatacttc tcagctgcaa atattatgga gaattgggca    1980
cccacaggaa tgaagagaga aagcagctcc ccaacttcaa aaccattttg gtacctgaca    2040
acaagagcat tttagagtaa ttaatttaat aaagtaaatt agtattgctg caaatagcta    2100
aattatattt atttgaattg atggtcaaga gattttccat tttttttaca gactgttcag    2160
tgtttgtcaa gcttctggtc taatatgtac tcgaaagact ttccgcttac aatttgtaga    2220
aacacaaata tcgttttcca tacagcagtg cctatatagt gactgatttt aactttcaat    2280
```

-continued

```
gtccatcttt caaaggaagt aacaccaagg tacaatgtta aaggaatatt cactttacct    2340
agcagggaaa aatacacaaa aactgcagat acttcatata gcccatttta acttgtataa    2400
actgtgtgac ttgtggcgtc ttataaataa tgcactgtaa agattactga atagttgtgt    2460
catgttaatg tgcctaattt catgtatctt gtaatcatga ttgagcctca gaatcatttg    2520
gagaaactat attttaaaga acaagacata cttcaatgta ttatacagat aaagtattac    2580
atgtgtttga ttttaaaagg gcggacattt tattaaaatc aagg                    2624
```

<210> SEQ ID NO 11
<211> LENGTH: 381
<212> TYPE: PRT
<213> ORGANISM: Homo sapiens

<400> SEQUENCE: 11

```
Met Gly Pro Ile Gly Ala Glu Ala Asp Glu Asn Gln Thr Val Glu Glu
 1               5                  10                  15

Met Lys Val Glu Gln Tyr Gly Pro Gln Thr Thr Pro Arg Gly Glu Leu
                20                  25                  30

Val Pro Asp Pro Glu Pro Glu Leu Ile Asp Ser Thr Lys Leu Ile Glu
            35                  40                  45

Val Gln Val Val Leu Ile Leu Ala Tyr Cys Ser Ile Ile Leu Leu Gly
        50                  55                  60

Val Ile Gly Asn Ser Leu Val Ile His Val Ile Lys Phe Lys Ser
 65                  70                  75                  80

Met Arg Thr Val Thr Asn Phe Phe Ile Ala Asn Leu Ala Val Ala Asp
                85                  90                  95

Leu Leu Val Asn Thr Leu Cys Leu Pro Phe Thr Leu Thr Tyr Thr Leu
            100                 105                 110

Met Gly Glu Trp Lys Met Gly Pro Val Leu Cys His Leu Val Pro Tyr
        115                 120                 125

Ala Gln Gly Leu Ala Val Gln Val Ser Thr Ile Thr Leu Thr Val Ile
    130                 135                 140

Ala Leu Asp Arg His Arg Cys Ile Val Tyr His Leu Glu Ser Lys Ile
145                 150                 155                 160

Ser Lys Arg Ile Ser Phe Leu Ile Ile Gly Leu Ala Trp Gly Ile Ser
                165                 170                 175

Ala Leu Leu Ala Ser Pro Leu Ala Ile Phe Arg Glu Tyr Ser Leu Ile
            180                 185                 190

Glu Ile Ile Pro Asp Phe Glu Ile Val Ala Cys Thr Glu Lys Trp Pro
        195                 200                 205

Gly Glu Glu Lys Ser Ile Tyr Gly Thr Val Tyr Ser Leu Ser Ser Leu
    210                 215                 220

Leu Ile Leu Tyr Val Leu Pro Leu Gly Ile Ile Ser Phe Ser Tyr Thr
225                 230                 235                 240

Arg Ile Trp Ser Lys Leu Lys Asn His Val Ser Pro Gly Ala Ala Asn
                245                 250                 255

Asp His Tyr His Gln Arg Arg Gln Lys Thr Thr Lys Met Leu Val Cys
            260                 265                 270

Val Val Val Phe Ala Val Ser Trp Leu Pro Leu His Ala Phe Gln
        275                 280                 285

Leu Ala Val Asp Ile Asp Ser Gln Val Leu Asp Leu Lys Glu Tyr Lys
    290                 295                 300

Leu Ile Phe Thr Val Phe His Ile Ile Ala Met Cys Ser Thr Phe Ala
```

```
                305                 310                 315                 320
Asn Pro Leu Leu Tyr Gly Trp Met Asn Ser Asn Tyr Arg Lys Ala Phe
                    325                 330                 335

Leu Ser Ala Phe Arg Cys Glu Gln Arg Leu Asp Ala Ile His Ser Glu
            340                 345                 350

Val Ser Val Thr Phe Lys Ala Lys Lys Asn Leu Glu Val Arg Lys Asn
        355                 360                 365

Ser Gly Pro Asn Asp Ser Phe Thr Glu Ala Thr Asn Val
    370                 375                 380

<210> SEQ ID NO 12
<211> LENGTH: 1200
<212> TYPE: DNA
<213> ORGANISM: Homo sapiens

<400> SEQUENCE: 12
caagtggacc tgtactgaaa atgggtccaa taggtgcaga ggctgatgag aaccagacag      60
tggaagaaat gaaggtggaa caatacgggc cacaaacaac tcctagaggt gaactggtcc     120
ctgaccctga gccagagctt atagatagta ccaagctgat tgaggtacaa gttgttctca     180
tattggccta ctgctccatc atcttgcttg gggtaattgg caactccttg gtgatccatg     240
tggtgatcaa attcaagagc atgcgcacag taaccaactt tttcattgcc aatctggctg     300
tgcagatctt tttggtgaac actctgtgtc taccgttcac tcttacctat accttaatgg     360
gggagtggaa aatgggtcct gtcctgtgcc acctggtgcc ctatgcccag ggcctggcag     420
tacaagtatc cacaatcacc ttgacagtaa ttgccctgga ccggcacagg tgcatcgtct     480
accacctaga gagcaagatc tccaagcgaa tcagcttcct gattattggc ttggcctggg     540
gcatcagtgc cctgctggca gtcccctgg ccatcttccg ggagtattcg ctgattgaga     600
tcatcccgga ctttgagatt gtggcctgta ctgaaaagtg gcctggcgag agaagagca     660 tctatggcac tgtctatagt ctttcttcct tgttgatctt gtatgttttg cctctgggca     720
ttatatcatt ttcctacact cgcatttgga gtaaattgaa gaaccatgtc agtcctggag     780
ctgcaaatga ccactaccat cagcgaaggc aaaaaaccac caaatgctg gtgtgtgtgg     840 tggtggtgtt tgcggtcagc tggctgcctc tccatgcctt ccagcttgcc gttgacattg     900
acagccaggt cctggacctg aaggagtaca actcatctt cacagtgttc cacatcatcg     960
ccatgtgctc cacttttgcc aatcccttc tctatgctg gatgaacagc aactacagaa    1020
aggctttcct ctcggccttc cgctgtgagc agcggttgga tgccattcac tctgaggtgt    1080
ccgtgacatt caaggctaaa aagaacctgg aggtcagaaa gaacagtggc cccaatgact    1140
ctttcacaga ggctaccaat gtctaaggaa gctgtggtgt gaaaatgtat ggatgaattc    1200

<210> SEQ ID NO 13
<211> LENGTH: 445
<212> TYPE: PRT
<213> ORGANISM: Homo sapiens

<400> SEQUENCE: 13

Met Asp Leu Glu Leu Asp Glu Tyr Tyr Asn Lys Thr Leu Ala Thr Glu
1               5                   10                  15

Asn Asn Thr Ala Ala Thr Arg Asn Ser Asp Phe Pro Val Trp Asp Asp
            20                  25                  30

Tyr Lys Ser Ser Val Asp Asp Leu Gln Tyr Phe Leu Ile Gly Leu Tyr
        35                  40                  45
```

-continued

```
Thr Phe Val Ser Leu Leu Gly Phe Met Gly Asn Leu Ile Leu Met
 50                  55                  60

Ala Leu Met Lys Lys Arg Asn Gln Lys Thr Thr Val Asn Phe Leu Ile
 65                  70                  75                  80

Gly Asn Leu Ala Phe Ser Asp Ile Leu Val Val Leu Phe Cys Ser Pro
                     85                  90                  95

Phe Thr Leu Thr Ser Val Leu Leu Asp Gln Trp Met Phe Gly Lys Val
                 100                 105                 110

Met Cys His Ile Met Pro Phe Leu Gln Cys Val Ser Val Leu Val Ser
             115                 120                 125

Thr Leu Ile Leu Ile Ser Ile Ala Ile Val Arg Tyr His Met Ile Lys
 130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                 165                 170                 175

Phe His Ser Leu Val Glu Leu Gln Glu Thr Phe Gly Ser Ala Leu Leu
             180                 185                 190

Ser Ser Arg Tyr Leu Cys Val Glu Ser Trp Pro Ser Asp Ser Tyr Arg
         195                 200                 205

Ile Ala Phe Thr Ile Ser Leu Leu Val Gln Tyr Ile Leu Pro Leu
 210                 215                 220

Val Cys Leu Thr Val Ser His Thr Ser Val Cys Arg Ser Ile Ser Cys
225                 230                 235                 240

Gly Leu Ser Asn Lys Glu Asn Arg Leu Glu Glu Asn Glu Met Ile Asn
                 245                 250                 255

Leu Thr Leu His Pro Ser Lys Lys Ser Gly Pro Gln Val Lys Leu Ser
             260                 265                 270

Gly Ser His Lys Trp Ser Tyr Ser Phe Ile Lys Lys His Arg Arg Arg
         275                 280                 285

Tyr Ser Lys Lys Thr Ala Cys Val Leu Pro Ala Pro Glu Arg Pro Ser
 290                 295                 300

Gln Glu Asn His Ser Arg Ile Leu Pro Glu Asn Phe Gly Ser Val Arg
305                 310                 315                 320

Ser Gln Leu Ser Ser Ser Lys Phe Ile Pro Gly Val Pro Thr Cys
                 325                 330                 335

Phe Glu Ile Lys Pro Glu Glu Asn Ser Asp Val His Glu Leu Arg Val
             340                 345                 350

Lys Arg Ser Val Thr Arg Ile Lys Lys Arg Ser Arg Ser Val Phe Tyr
         355                 360                 365

Arg Leu Thr Ile Leu Ile Leu Val Phe Ala Val Ser Trp Met Pro Leu
 370                 375                 380

His Leu Phe His Val Val Thr Asp Phe Asn Asp Asn Leu Ile Ser Asn
385                 390                 395                 400

Arg His Phe Lys Leu Val Tyr Cys Ile Cys His Leu Leu Gly Met Met
                 405                 410                 415

Ser Cys Cys Leu Asn Pro Ile Leu Tyr Gly Phe Leu Asn Asn Gly Ile
             420                 425                 430

Lys Ala Asp Leu Val Ser Leu Ile His Cys Leu His Met
         435                 440                 445
```

<210> SEQ ID NO 14
<211> LENGTH: 1370
<212> TYPE: DNA

<213> ORGANISM: Homo sapiens

<400> SEQUENCE: 14

```
ccaagcagga ctataatatg gatttagagc tcgacgagta ttataacaag acacttgcca        60
cagagaataa tactgctgcc actcggaatt ctgatttccc agtctgggat gactataaaa       120
gcagtgtaga tgacttacag tattttctga ttgggctcta tacatttgta agtcttcttg       180
gctttatggg gaatctactt attttaatgg ctctcatgaa aaagcgtaat cagaagacta       240
cggtaaactt cctcataggc aatctggcct tttctgatat cttggttgtg ctgttttgct       300
cacctttcac actgacgtct gtcttgctgg atcagtggat gtttggcaaa gtcatgtgcc       360
atattatgcc ttttcttcaa tgtgtgtcag ttttggtttc aactttaatt ttaatatcaa       420
ttgccattgt caggtatcat atgataaaac atcccatatc taataattta acagcaaacc       480
atggctactt tctgatagct actgtctgga cactaggttt tgccatctgt tctcccttc        540
cagtgtttca cagtcttgtg gaacttcaag aaacatttgg ttcagcattg ctgagcagca       600
ggtatttatg tgttgagtca tggccatctg attcatacag aattgccttt actatctctt       660
tattgctagt tcagtatatt ctgcccttag tttgtcttac tgtaagtcat acaagtgtct       720
gcagaagtat aagctgtgga ttgtccaaca agaaaacag acttgaagaa atgagatga         780
tcaacttaac tcttcatcca tccaaaaaga gtgggcctca ggtgaaactc tctggcagcc       840
ataaatggag ttattcattc atcaaaaaac acagaagaag atatagcaag aagacagcat       900
gtgtgttacc tgctccagaa agaccttctc aagagaacca ctccagaata cttccagaaa       960
actttggctc tgtaagaagt cagctctctt catccagtaa gttcatacca ggggtcccca      1020
cttgctttga gataaaacct gaagaaaatt cagatgttca tgaattgaga gtaaaacgtt      1080
ctgttacaag aataaaaaag agatctcgaa gtgttttcta cagactgacc atactgatat      1140
tagtatttgc tgttagttgg atgccactac acctttttcca tgtggtaact gattttaatg    1200
acaatcttat ttcaaatagg catttcaagt tggtgtattg catttgtcat ttgttgggca      1260
tgatgtcctg ttgtcttaat ccaattctat atgggtttct taataatggg attaaagctg      1320
atttagtgtc ccttatacac tgtcttcata tgtaataatt ctcactgttt                 1370
```

<210> SEQ ID NO 15
<211> LENGTH: 170
<212> TYPE: PRT
<213> ORGANISM: Homo sapiens

<400> SEQUENCE: 15

```
Met Asp Thr Arg Asn Lys Ala Gln Leu Leu Val Leu Thr Leu Leu
 1               5                  10                  15

Ser Val Leu Phe Ser Gln Thr Ser Ala Trp Pro Leu Tyr Arg Ala Pro
                20                  25                  30

Ser Ala Leu Arg Leu Gly Asp Arg Ile Pro Phe Glu Gly Ala Asn Glu
            35                  40                  45

Pro Asp Gln Val Ser Leu Lys Glu Asp Ile Asp Met Leu Gln Asn Ala
        50                  55                  60

Leu Ala Glu Asn Asp Thr Pro Tyr Tyr Asp Val Ser Arg Asn Ala Arg
65                  70                  75                  80

His Ala Asp Gly Val Phe Thr Ser Asp Phe Ser Lys Leu Leu Gly Gln
                85                  90                  95

Leu Ser Ala Lys Lys Tyr Leu Glu Ser Leu Met Gly Lys Arg Val Ser
            100                 105                 110
```

| | | | | | | | | | | | | |
|---|---|---|---|---|---|---|---|---|---|---|---|---|
|Ser|Asn|Ile|Ser|Glu|Asp|Pro|Val|Pro|Val|Lys|Arg|His|Ser|Asp|Ala|
| |115| | | | |120| | | | |125| | | | |

Val Phe Thr Asp Asn Tyr Thr Arg Leu Arg Lys Gln Met Ala Val Lys
    130                 135                 140

Lys Tyr Leu Asn Ser Ile Leu Asn Gly Lys Arg Ser Ser Glu Gly Glu
145                 150                 155                 160

Ser Pro Asp Phe Pro Glu Glu Leu Glu Lys
            165                 170

<210> SEQ ID NO 16
<211> LENGTH: 1511
<212> TYPE: DNA
<213> ORGANISM: Homo sapiens

<400> SEQUENCE: 16

```
ggtcagctcc aaaacaatcc ggaacggcca gctccggggg agcacgactg ggcgagaggc      60
acagaaatgg acaccagaaa taaggcccag ctccttgtgc tcctgactct tctcagtgtg     120
ctcttctcac agacttcggc atggcctctt tacagggcac cttctgctct caggttgggt     180
gacagaatac cctttgaggg agcaaatgaa cctgatcaag tttcattaaa agaagacatt     240
gacatgttgc aaaatgcatt agctgaaaat gacacaccct attatgatgt atccagaaat     300
gccaggcatg ctgatggagt tttcaccagt gacttcagta aactcttggg tcaacttttct    360
gccaaaaagt accttgagtc tcttatggga aacgtgtta gcagtaacat ctcagaagac      420
cctgtaccag tcaaacgtca ctcagatgca gtcttcactg caactatac ccgccttaga      480
aaacaaatgg ctgtaaagaa atatttgaac tcaattctga atggaaagag gagcagtgag     540
ggagaatctc ccgactttcc agaagagtta gaaaatgat gaaaaagacc tttggagcaa      600
agctgatgac aacttcccag tgaattcttg aaggaaaatg atacgcaaca taattaaatt     660
ttagattcta cataagtaat tcaagaaaac aacttcaata tccaaaccaa ataaaaatat     720
tgtgttgtga atgttgtgat gtattctagc taatgtaata actgtgaagt ttacattgta     780
aatagtatt gagagttcta aattttgtct ttaactcata aaaagcctgc aatttcatat      840
gctgtatatc ctttctaaca aaaaaatata ttttaatgat aagtaatgct aggttaatcc     900
aattatatga gacgttttg gaagagtagt aatagagcaa aattgatgtg tttatttata      960
gagtgtactt aactattcag gagagtagaa cagataatca gtgtgtctaa atttgaatgt    1020
taagcagatg gaatgctgtg ttaaataaac ctcaaaatgt ctaagatagt aacaatgaag    1080
ataaaaagac attcttccaa aaagattttc agaaatatt atgtgttttcc atattttata   1140
ggcaacctttt attttaatg gtgttttaaa aaatctcaaa tttggattgc taatcaccaa    1200
aggctctctc ctgatagtct ttcagttaag gagaacgacc cctgcttctg acactgaaac    1260
ttccctttct gcttgtgtta agtatgtgta aaatgtgaag tgaatgaaac actcagttgt    1320
tcaataataa atatttttgc cataatgact cagaatattg ctttggtcat atgagcttcc    1380
ttctgtgaaa tacattttgg agacacaact attttttccaa ataattttta agaaatcaaa   1440
gagagaaaat aaagaccttg cttatgattg cagataaaaa aaaaaaaaaa aaaaaaaaa    1500
aaaaaaaaa a                                                          1511
```

<210> SEQ ID NO 17
<211> LENGTH: 170
<212> TYPE: PRT
<213> ORGANISM: Homo sapiens

<400> SEQUENCE: 17

```
Met Asp Thr Arg Asn Lys Ala Gln Leu Leu Val Leu Leu Thr Leu Leu
 1               5                  10                  15
Ser Val Leu Phe Ser Gln Thr Ser Ala Trp Pro Leu Tyr Arg Ala Pro
                20                  25                  30
Ser Ala Leu Arg Leu Gly Asp Arg Ile Pro Phe Glu Gly Ala Asn Glu
                35                  40                  45
Pro Asp Gln Val Ser Leu Lys Glu Asp Ile Asp Met Leu Gln Asn Ala
            50                  55                  60
Leu Ala Glu Asn Asp Thr Pro Tyr Tyr Asp Val Ser Arg Asn Ala Arg
 65                  70                  75                  80
His Ala Asp Gly Val Phe Thr Ser Asp Phe Ser Lys Leu Leu Gly Gln
                85                  90                  95
Leu Ser Ala Lys Lys Tyr Leu Glu Ser Leu Met Gly Lys Arg Val Ser
                100                 105                 110
Ser Asn Ile Ser Glu Asp Pro Val Pro Val Lys Arg His Ser Asp Ala
                115                 120                 125
Val Phe Thr Asp Asn Tyr Thr Arg Leu Arg Lys Gln Met Ala Val Lys
            130                 135                 140
Lys Tyr Leu Asn Ser Ile Leu Asn Gly Lys Arg Ser Ser Glu Gly Glu
145                 150                 155                 160
Ser Pro Asp Phe Pro Glu Glu Leu Glu Lys
                165                 170

<210> SEQ ID NO 18
<211> LENGTH: 1511
<212> TYPE: DNA
<213> ORGANISM: Homo sapiens

<400> SEQUENCE: 18
ggtcagctcc aaaacaatcc ggaacggcca gctccggggg agcacgactg ggcgagaggc     60
acagaaatgg acaccagaaa taaggcccag ctccttgtgc tcctgactct tctcagtgtg    120
ctcttctcac agacttcggc atggcctctt tacagggcac cttctgctct caggttgggt    180
gacagaatac cctttgaggg agcaaatgaa cctgatcaag tttcattaaa agaagacatt    240
gacatgttgc aaaatgcatt agctgaaaat gacacaccct attatgatgt atccagaaat    300
gccaggcatg ctgatggagt tttcaccagt gacttcagta aactcttggg tcaactttct    360
gccaaaaagt accttgagtc tcttatggga aacgtgtta gcagtaacat ctcagaagac    420
cctgtaccag tcaaacgtca ctcagatgca gtcttcactg acaactatac ccgccttaga    480
aaacaaatgc tgtaaagaa atatttgaac tcaattctga atggaaagag gagcagtgag    540
ggagaatctc ccgactttcc agaagagtta gaaaatgat gaaaaagacc tttggagcaa    600
agctgatgac aacttcccag tgaattcttg aaggaaaatg atacgcaaca taattaaatt    660
ttagattcta cataagtaat tcaagaaaac aacttcaata tccaaaccaa ataaaaatat    720
tgtgttgtga atgttgtgat gtattctagc taatgtaata actgtgaagt ttacattgta    780
aatagtattt gagagttcta aattttgtct ttaactcata aaaagcctgc aatttcatat    840
gctgtatatc ctttctaaca aaaaaatata ttttaatgat aagtaatgct aggttaatcc    900
aattatatga gacgttttg gaagagtagt aatagagcaa aattgatgtg tttatttata    960
gagtgtactt aactattcag gagagtagaa cagataatca gtgtgtctaa atttgaatgt   1020
taagcagatg gaatgctgtg ttaaataaac ctcaaaatgt ctaagatagt aacaatgaag   1080
ataaaaagac attcttccaa aaagattttc agaaatatt atgtgtttcc atatttata    1140
```

-continued

```
ggcaaccttt attttttaatg gtgttttaaa aaatctcaaa tttggattgc taatcaccaa    1200
aggctctctc ctgatagtct ttcagttaag gagaacgacc cctgcttctg acactgaaac    1260 ttcccttttct gcttgtgtta agtatgtgta aaatgtgaag tgaatgaaac actcagttgt    1320
tcaataataa atattttttgc cataatgact cagaatattg ctttggtcat atgagcttcc    1380
ttctgtgaaa tacattttgg agacacaact attttttccaa aataatttta agaaatcaaa    1440
gagagaaaat aaagaccttg cttatgattg cagataaaaa aaaaaaaaaa aaaaaaaaa    1500 aaaaaaaaaa a                                                          1511
```

<210> SEQ ID NO 19
<211> LENGTH: 438
<212> TYPE: PRT
<213> ORGANISM: Homo sapiens

<400> SEQUENCE: 19

```
Met Arg Thr Leu Leu Pro Ala Leu Leu Thr Cys Trp Leu Leu Ala
 1               5                  10                  15

Pro Val Asn Ser Ile His Pro Glu Cys Arg Phe His Leu Glu Ile Gln
            20                  25                  30

Glu Glu Glu Thr Lys Cys Thr Glu Leu Leu Arg Ser Gln Thr Glu Lys
        35                  40                  45

His Lys Ala Cys Ser Gly Val Trp Asp Asn Ile Thr Cys Trp Arg Pro
    50                  55                  60

Ala Asn Val Gly Glu Thr Val Thr Val Pro Cys Pro Lys Val Phe Ser
65                  70                  75                  80

Asn Phe Tyr Ser Lys Ala Gly Asn Ile Ser Lys Asn Cys Thr Ser Asp
                85                  90                  95

Gly Trp Ser Glu Thr Phe Pro Asp Phe Val Asp Ala Cys Gly Tyr Ser
           100                 105                 110

Asp Pro Glu Asp Glu Ser Lys Ile Thr Phe Tyr Ile Leu Val Lys Ala
       115                 120                 125

Ile Tyr Thr Leu Gly Tyr Ser Val Ser Leu Met Ser Leu Ala Thr Gly
   130                 135                 140

Ser Ile Ile Leu Cys Leu Phe Arg Lys Leu His Cys Thr Arg Asn Tyr
145                 150                 155                 160

Ile His Leu Asn Leu Phe Leu Ser Phe Ile Leu Arg Ala Ile Ser Val
               165                 170                 175

Leu Val Lys Asp Asp Val Leu Tyr Ser Ser Gly Thr Leu His Cys
           180                 185                 190

Pro Asp Gln Pro Ser Ser Trp Val Gly Cys Lys Leu Ser Leu Val Phe
       195                 200                 205

Leu Gln Tyr Cys Ile Met Ala Asn Phe Phe Trp Leu Leu Val Glu Gly
   210                 215                 220

Leu Tyr Leu His Thr Leu Leu Val Ala Met Leu Pro Pro Arg Arg Cys
225                 230                 235                 240

Phe Leu Ala Tyr Leu Leu Ile Gly Trp Gly Leu Pro Thr Val Cys Ile
               245                 250                 255

Gly Ala Trp Thr Ala Ala Arg Leu Tyr Leu Glu Asp Thr Gly Cys Trp
           260                 265                 270

Asp Thr Asn Asp His Ser Val Pro Trp Trp Val Ile Arg Ile Pro Ile
       275                 280                 285

Leu Ile Ser Ile Ile Val Asn Phe Val Leu Phe Ile Ser Ile Ile Arg
   290                 295                 300
```

```
Ile Leu Leu Gln Lys Leu Thr Ser Pro Asp Val Gly Gly Asn Asp Gln
305                 310                 315                 320

Ser Gln Tyr Lys Arg Leu Ala Lys Ser Thr Leu Leu Ile Pro Leu
            325                 330                 335

Phe Gly Val His Tyr Met Val Phe Ala Val Phe Pro Ile Ser Ile Ser
                340                 345                 350

Ser Lys Tyr Gln Ile Leu Phe Glu Leu Cys Leu Gly Ser Phe Gln Gly
            355                 360                 365

Leu Val Val Ala Val Leu Tyr Cys Phe Leu Asn Ser Glu Val Gln Cys
        370                 375                 380

Glu Leu Lys Arg Lys Trp Arg Ser Arg Cys Pro Thr Pro Ser Ala Ser
385                 390                 395                 400

Arg Asp Tyr Arg Val Cys Gly Ser Ser Phe Ser His Asn Gly Ser Glu
                405                 410                 415

Gly Ala Leu Gln Phe His Arg Ala Ser Arg Ala Gln Ser Phe Leu Gln
            420                 425                 430

Thr Glu Thr Ser Val Ile
            435
```

<210> SEQ ID NO 20
<211> LENGTH: 1640
<212> TYPE: DNA
<213> ORGANISM: Homo sapiens

<400> SEQUENCE: 20

```
cgggacgagg gggcggcccc cgcgctcggg gcgctcggct acagctgcgg ggcccgaggt      60
ctccgcgcac tcgctcccgg cccatgctgg aggcggcgga acccggggga cctaggacgg     120
aggcggcggg cgctgggcgg cccccggcac gctgagctcg ggatgcggac gctgctgcct     180
cccgcgctgc tgacctgctg gctgctcgcc cccgtgaaca gcattcaccc agaatgccga     240
tttcatctgg aaatacagga ggaagaaaca aaatgtacag agcttctgag gtctcaaaca     300
gaaaaacaca aagcctgcag tggcgtctgg acaacatca cgtgctggcg gcctgccaat      360
gtgggagaga ccgtcacggt gccctgccca aaagtcttca gcaatttta cagcaaagca     420
ggaaacataa gcaaaaactg tacgagtgac ggatggtcag agacgttccc agatttcgtc     480
gatgcctgtg gctacagcga cccggaggat gagagcaaga tcacgtttta tattctggtg     540
aaggccattt ataccctggg ctacagtgtc tctctgatgt ctcttgcaac aggaagcata     600
attctgtgcc tcttcaggaa gctgcactgc accaggaatt acatccacct gaacctgttc     660
ctgtccttca tcctgagagc catctcagtg ctggtcaagg acgacgttct ctactccagc     720
tctggcacgt tgcactgccc tgaccagcca tcctcctggg tgggctgcaa gctgagcctg     780
gtcttcctgc agtactgcat catggccaac ttcttctggc tgctggtgga ggggctctac     840
ctccacaccc tcctggtggc catgctcccc ctagaaggt gcttcctggc ctacctcctg     900
atcggatggg gcctccccac cgtctgcatc ggtgcatgga ctgcggccag gctctactta     960
gaagacaccg gttgctggga tacaaacgac cacagtgtgc cctggtgggt catacgaata    1020
ccgatttta tttccatcat cgtcaatttt gtccttttca ttagtattat acgaattttg    1080
ctgcagaagt taacatcccc agatgtcggc ggcaacgacc agtctcagta caagaggctg    1140
gccaagtcca cgctcctgct tatcccgctg ttcggcgtcc actacatggt gtttgccgtg    1200
tttcccatca gcatctcctc caaataccag atactgtttg agctgtgcct cggtcgttc    1260
cagggcctgg tggtggccgt cctctactgt ttcctgaaca gtgaggtgca gtgcgagctg    1320
```

```
aagcgaaaat ggcgaagccg gtgcccgacc ccgtccgcga gccgggatta cagggtctgc    1380
ggttcctcct tctcccacaa cggctcggag ggcgccctgc agttccaccg cgcgtcccga    1440
gcccagtcct tcctgcaaac ggagacctcg gtcatctagc cccaccctg cctgtcggac     1500 gcggcgggag gcccacggtt cggggcttct gcggggctga gacgccggct tcctccttcc    1560
agatgcccga gcaccgtgtc gggcaggtca gcgcggtcct gactccgtca agctggttgt    1620
ccactaaacc ccatacctgg                                                1640
```